US006150502A

United States Patent [19]

Strachan

[11] Patent Number: 6,150,502

[45] Date of Patent: Nov. 21, 2000

[54] POLYPEPTIDES EXPRESSED IN SKIN CELLS

[75] Inventor: Lorna Strachan, Cox Bay, New Zealand

[73] Assignee: Genesis Research & Development Corporation Limited, Parnell, New Zealand

[21] Appl. No.: 09/188,930

[22] Filed: Nov. 9, 1998

Related U.S. Application Data

[63] Continuation-in-part of application No. 09/069,726, Apr. 29, 1998, abandoned.

[51] Int. Cl.$^7$ .................................................... C07K 14/435

[52] U.S. Cl. ............................................ 530/350; 530/300

[58] Field of Search .................................... 530/350, 399, 530/300

[56] References Cited

PUBLICATIONS

George et al., Macromolecular Sequencing and Synthesis: Selected Methods and Applications, Schlesinger, ed., Alan R. Liss Inc., New York, pp. 127–149, 1988.
Bowie et al., Science 247:1306–1310, 1990.
Ngo et al., The Protein Folding Problem and tertiary Structure Prediction, Merz et al., eds., Birkhauser, Boston, pp. 492–495, 1994.
Wells, Biochemistry 29:8509–8517, 1990.
GenBank (ESTs) Accession No. AI412233, Feb. 1999.
GenBank (ESTs) Accession No. AA850731, Apr. 1998.
GenBank (ESTs) Accession No. AI299847, Jan. 1999.
GenBank (ESTs) Accession No. W97325, Jul. 1996.
GenBank (ESTs) Accession No. AA111146, Nov. 1996.
GenBank (ESTs) Accession No. AI037414, Jun. 1998.
GenBank (ESTs) Accession No. AI282114, Feb. 1999.
GenBank (ESTs) Accession No. AA865643, Apr. 1998.
GenBank (ESTs) Accession No. AI140104, Apr. 1999.
GenBank (ESTs) Accession No. AA726580, Jan. 1998.
GenBank (ESTs) Accession No. AA407924, Aug. 1998.
GenBank (ESTs) Accession No. AA498629, Jul. 1997.

*Primary Examiner*—Elizabeth Kemmerer
*Attorney, Agent, or Firm*—Ann W. Speckman; Janet Sleath

[57] ABSTRACT

Isolated polynucleotides encoding polypeptides expressed in mammalian skin cells are provided, together with expression vectors and host cells comprising such isolated polynucleotides. Methods for the use of such polynucleotides and polypeptides are also provided.

22 Claims, 5 Drawing Sheets

Stimulation of A431 cells with mu and huTR1

POLYPEPTIDES EXPRESSED IN SKIN CELLS

REFERENCE TO RELATED APPLICATIONS

This application is a continuation-in-part of U.S. application Ser. No. 09/069,726, filed Apr. 29,1998, now abandoned.

TECHNICAL FIELD OF THE INVENTION

This invention relates to polynucleotides encoding polypeptides, polypeptides expressed in skin cells, and their use in therapeutic methods.

BACKGROUND OF THE INVENTION

The skin is the largest organ in the body and serves as a protective cover. The loss of skin, as occurs in a badly burned person, may lead to death owing to the absence of a barrier against infection by external microbial organisms, as well as loss of body temperature and body fluids.

Skin tissue is composed of several layers. The outermost layer is the epidermis which is supported by a basement membrane and overlies the dermis. Beneath the dermis is loose connective tissue and fascia which cover muscles or bony tissue. The skin is a self-renewing tissue in that cells are constantly being formed and shed. The deepest cells of the epidermis are the basal cells, which are enriched in cells capable of replication. Such replicating cells are called progenitor or stem cells. Replicating cells in turn give rise to daughter cells called 'transit amplifying cells'. These cells undergo differentiation and maturation into keratinocytes (mature skin cells) as they move from the basal layer to the more superficial layers of the epidermis. In the process, keratinocytes become cornified and are ultimately shed from the skin surface. Other cells in the epidermis include melanocytes which synthesize melanin, the pigment responsible for protection against sunlight. The Langerhan cell also resides in the epidermis and functions as a cell which processes foreign proteins for presentation to the immune system.

The dermis contains nerves, blood and lymphatic vessels, fibrous and fatty tissue. Within the dermis are fibroblasts, macrophages and mast cells. Both the epidermis and dermis are penetrated by sweat, or sebaceous, glands and hair follicles. Each strand of hair is derived from a hair follicle. When hair is plucked out, the hair re-grows from epithelial cells directed by the dermal papillae of the hair follicle.

When the skin surface is breached, for example in a wound, the stem cells proliferate and daughter keratinocytes migrate across the wound to reseal the tissues. The skin cells therefore possess genes activated in response to trauma. The products of these genes include several growth factors, such as epidermal growth factor, which mediate the proliferation of skin cells. The genes that are activated in the skin, and the protein products of such genes, may be developed as agents for the treatment of skin wounds. Additional growth factors derived from skin cells may also influence growth of other cell types. As skin cancers are a disorder of the growth of skin cells, proteins derived from skin that regulate cellular growth may be developed as agents for the treatment of skin cancers. Skin derived proteins that regulate the production of melanin may be useful as agents which protect skin against unwanted effects of sunlight.

Keratinocytes are known to secrete cytokines and express various cell surface proteins. Cytokines and cell surface molecules are proteins which play an important role in the inflammatory response against infection and also in autoimmune diseases affecting the skin. Genes and their protein products that are expressed by skin cells may thus be developed into agents for the treatment of inflammatory disorders affecting the skin.

Hair is an important part of a person's individuality. Disorders of the skin may lead to hair loss. *Alopecia areata* is a disease characterized by the patchy loss of hair over the scalp. Total baldness is a side effect of drug treatment for cancer. The growth and development of hair are mediated by the effects of genes expressed in skin and dermal papillae. Such genes and their protein products may be usefully developed into agents for the treatment of disorders of the hair follicle.

New treatments are required to hasten the healing of skin wounds, to prevent the loss of hair, enhance the re-growth of hair or removal of hair, and to treat autoimmune and inflammatory skin diseases more effectively and without adverse effects. More effective treatments of skin cancers are also required. There thus remains a need in the art for the identification and isolation of genes encoding proteins expressed in the skin, for use in the development of therapeutic agents for the treatment of disorders including those associated with skin.

SUMMARY OF THE INVENTION

The present invention provides polypeptides expressed in skin cells, together with polynucleotides encoding such polypeptides, expression vectors and host cells comprising such polynucleotides, and methods for their use.

In specific embodiments, isolated polynucleotides are provided that comprise a DNA sequence selected from the group consisting of: (a) sequences recited in SEQ ID NO: 1–14, 45–48, 64–68, 77–89, 118, 119, 198–231, 239–249, and 254–274; (b) complements of the sequences recited in SEQ ID NO: 1–14, 45–48, 64–68, 77–89, 118, 119, 198–231, 239–249 and 254–274; (c) reverse complements of the sequences recited in SEQ ID NO: 1–14, 45–48, 64–68, 77–89, 118, 119, 198–231, 239–249 and 254–274; (d) reverse sequences of the sequences recited in SEQ ID NO: 1–14, 45–48, 64–68, 77–89, 118, 119, 198–231, 239–249 and 254–274; (e) sequences having a 99% probability of being the same as a sequence of (a)–(d); and (f) sequences having 50%, 75% or 90% identity to a sequence of (a)–(d).

In farther embodiments, the present invention provides isolated polypeptides comprising an amino acid sequence selected from the group consisting of: (a) sequences provided in SEQ ID NO: 120–197 and 275–348; and (b) sequences having 50%, 75% or 90% identity to a sequence provided in SEQ ID NO: 120–197 and 275–348, together with isolated polynucleotides encoding such polypeptides. Isolated polypeptides which comprise at least a functional portion of a polypeptide comprising an amino acid sequence selected from the group consisting of: (a) sequences provided in SEQ ID NO: 120–197 and 275–348; and (b) sequences having 50%, 75% of 90% identity to a sequence of SEQ ID NO: 120–197 and 275–348 are also provided.

In related embodiments, the present invention provides expression vectors comprising the above polynucleotides, together with host cells transformed with such vectors.

In a further aspect, the present invention provides a method of stimulating keratinocyte growth and motility, inhibiting the growth of epithelial-derived cancer cells, inhibiting angiogenesis and vascularisation of tumors, or modulating the growth of blood vessels in a subject, comprising administering to the subject a composition comprising an isolated polypeptide, wherein the polypeptide comprises an amino acid sequence selected from the group consisting of: (a) sequences provided in SEQ ID NO: 187, 196, 342 and 343; and (b) sequences having 50%, 75% or 90% identity to a sequence provided in SEQ ID NO: 187, 196, 342 and 343.

Methods for modulating skin inflammation in a subject are also provided, the methods comprising administering to the subject a composition comprising an isolated polypeptide, wherein the polypeptide comprises an amino acid sequence selected from the group consisting of: (a) sequences provided in SEQ ID NO: 338 and 347; and (b) sequences having 50%, 75% or 90% identity to a sequence provided in SEQ ID NO: 338 and 347.

In an additional aspect, the present invention provides methods for stimulating the growth of intestinal epithelial cells in a subject. Such methods comprise administering to the subject a composition comprising an isolated polypeptide including an amino acid sequence selected from the group consisting of: (a) sequences provided in SEQ ID NO: 129 and 348; and (b) sequences having 50%, 75% or 90% identity to a sequence provided in SEQ ID NO: 129 and 348.

In yet a further aspect, methods for inhibiting the binding of HIV-1 to leukocytes, for the treatment of an inflammatory disease or for the treatment of cancer in a subject are provided, the methods comprising administering to the subject a composition comprising an isolated polypeptide including an amino acid sequence selected from the group consisting of: (a) sequences provided in SEQ ID NO: 340, 344, 345 and 346; and (b) sequences having 50%, 75% or 90% identity to a sequence provided in SEQ ID NO: 340, 344, 345 and 346. As detailed below, the isolated polynucleotides and polypeptides of the present invention may be usefully employed in the preparation of therapeutic agents for the treatment of skin disorders.

The above-mentioned and additional features of the present invention, together with the manner of obtaining them, will be best understood by reference to the following more detailed description. All references disclosed herein are hereby incorporated by reference in their entirety as if each was incorporated individually.

BRIEF DESCRIPTION OF THE DRAWINGS

FIG. 3 shows the stimulation of growth of neonatal foreskin keratinocytes by muTR1a.

FIG. 4 shows the stimulation of growth of the transformed human keratinocyte cell line HaCaT by muTR1a and huTR1a.

FIG. 5 shows the inhibition of growth of the human epidermal carcinoma cell line A431 by muTR1a and huTR1a.

FIG. 6 shows the inhibition of IL-2 induced growth of concanavalin A-stimulated murine splenocytes by KS2a.

DETAILED DESCRIPTION OF THE INVENTION

Figure 1:
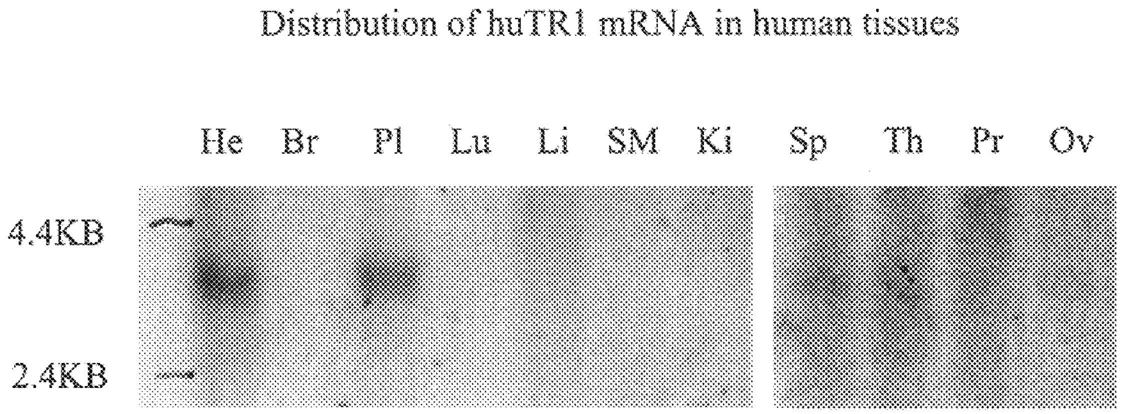
FIG. 1 shows the results of a Northern analysis of the distribution of huTR1 mRNA in human tissues. Key: He, Heart; Br, Brain; Pl, Placenta; Lu, Lung; Li, Liver; SM, Skeletal muscle; Ki, Kidney; Sp, Spleen; Th, Thymus; Pr, Prostate; Ov, Ovary.

In one aspect, the present invention provides polynucleotides that are isolatable from mammalian skin cells. As used herein, the term "polynucleotide" means a single or double-stranded polymer of deoxyribonucleotide or ribonucleotide bases and includes DNA and RNA molecules, both sense and anti-sense strands. The term comprehends cDNA, genomic DNA, recombinant DNA and wholly or partially synthesized nucleic acid molecules. A polynucleotide may consist of an entire gene, or a portion thereof. A gene is a DNA sequence that codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al. (1995), Antisense Techniques, *Methods in Enzymol.* 254(23): 363–375 and Kawasaki et al. (1996), *Artific. Organs* 20 (8): 836–848.

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All the polynucleotides provided by the present invention are isolated and purified, as those terms are commonly used in the art.

In specific embodiments, the polynucleotides of the present invention comprise a DNA sequence selected from the group consisting of sequences provided in SEQ ID NO: 1–119, 198–274, and variants of the sequences of SEQ ID NO: 1–119 and 198–274. Polynucleotides that comprise complements of such DNA sequences, reverse complements of such DNA sequences or reverse sequences of such DNA sequences, together with variants of such sequences, are also provided.

The definition of the terms "complement", "reverse complement" and "reverse sequence", as used herein, is best illustrated by the following example. For the sequence 5'AGGACC 3', the complement, reverse complement and reverse sequence are as follows:

| | |
|---|---|
| complement | 3' TCCTGG 5' |
| reverse complement | 3' GGTCCT 5' |
| reverse sequence | 5' CCAGGA 3'. |

In another aspect, the present invention provides isolated polypeptides encoded, or partially encoded, by the above polynucleotides. As used herein, the term "polypeptide" encompasses amino acid chains of any length, including full length proteins, wherein the amino acid residues are linked by covalent peptide bonds. The term "polypeptide encoded by a polynucleotide" as used herein, includes polypeptides encoded by a polynucleotide which comprises a partial isolated DNA sequence provided herein. In specific embodiments, the inventive polypeptides comprise an amino acid sequence selected from the group consisting of sequences provided in SEQ ID NO: 120–197, 275–348 and variants of such sequences.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NO: 120–197, 275–348 and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, T., *Proc. Natl. Acad. Sci. USA* 82:488–492, 1985). Sections of DNA sequence may also be removed using standard techniques to permit preparation of truncated polypeptides.

In general, the polypeptides disclosed herein are prepared in an isolated, substantially pure, form. Preferably, the polypeptides are at least about 80% pure, more preferably at least about 90% pure and most preferably at least about 99% pure. In certain preferred embodiments, described in detail below, the isolated polypeptides are incorporated into pharmaceutical compositions or vaccines for use in the treatment of skin disorders.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least about 50%, more preferably at least about 75% and most preferably at least about 90% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide or polypeptide sequences may be aligned, and percentage of identical nucleotides in a specified region may be determined against another polynucleotide or polypeptide, using computer algorithms that are publicly available. Two exemplary algorithms for aligning and identifying the similarity of polynucleotide sequences are the BLASTN and FASTA algorithms. The alignment and similarity of polypeptide sequences may be examined using the BLASTP and algorithm. BLASTX and FASTX algorithms compare nucleotide query sequences translated in all reading frames against polypeptide sequences. The BLASTN, BLASTP and BLASTX algorithms are available on the NCBI anonymous FTP server under /blast/executables/. The FASTA algorithm, set to the default parameters described in the documentation and distributed with the algorithm, may be used in the determination of polynucleotide variants. The readme files for FASTA and FASTX v1.0x that are distributed with the algorithms described the use of the algorithms and describe the default parameters. The use of the FASTA and FASTX algorithms is also described in W. R. Pearson and D. J. Lipman, "Improved Tools for Biological Sequence Analysis," PNAS 85:2444–2448 (1988) and W. R. Pearson, "Rapid and Sensitive Sequence Comparison with FASTP and FASTA," Methods in Enzymology 183:63–98 (1990).

The BLASTN algorithm version 2.0.4 [Feb. 24, 1998], set to the default parameters described in the documentation and distributed with the algorithm, is preferred for use in the determination of polynucleotide variants according to the present invention. The BLASTP algorithm version 2.0.4, set to the default parameters described in the documentation and distributed with the algorithm, is preferred for use in the determination of polypeptide variants according to the present invention. The use of the BLAST family of algorithms, including BLASTN, BLASTP and BLASTX is described in the publication of Altschul, Stephen F., et al. (1997), "Gapped BLAST and PSI-BLAST: new generation of protein database search programs", *Nucleic Acids Res.* 25:3389–3402.

The following running parameters are preferred for determination of alignments and similarities using BLASTN that contribute to the E values and percentage identity for polynucleotides: Unix running command with default parameters thus: blastall -p blastn-d embldb -e 10 -G 0 -E 0 -r 1 -v 30 -b 30 -i queryseq -o results; and parameters are: -p program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; -o BLAST report Output File [File Out] Optional. The following running parameters are preferred for determination of alignments and similarities using BLASTP that contribute to the E values and percentage identity for polypeptides: blastall -p blastp -d swissprotdb -e 10-G 1-E 11 -r 1 -v 30 -b 30 -i queryseq -o results; and the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The percentage similarity of a polynucleotide or polypeptide sequence is determined by aligning polynucleotide and polypeptide sequences using the appropriate algorithm, namely BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage similarity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23 nucleotide hit includes 21 identical nucleotides, one gap and one different nucleotide. The percentage identity of the queried polynucleotide to the hit in the EMBL database is thus 21/220 times 100, or 9.5%. The similarity of polypeptide sequences may be determined in a similar fashion.

The BLASTN and BLASTX algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SWISSPROT database.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being the same as the polypeptide of the present invention, measured as having an E value of 0.01 or less using the BLASTP algorithm set at the default parameters.

Variant polynucleotide sequences will generally hybridize to the recited polynucleotide sequences under stringent conditions. As used herein, "stringent conditions" refers to prewashing in a solution of 6× SSC, 0.2% SDS; hybridizing at 65° C., 6×SSC, 0.2% SDS overnight; followed by two washes of 30 minutes each in 1× SSC, 0.1% SDS at 65° C. and two washes of 30 minutes each in 0.2× SSC, 0.1% SDS at 65° C.

As used herein, the term "x-mer," with reference to a specific value of "x," refers to a polynucleotide or polypeptide, respectively, comprising at least a specified number ("x") of contiguous residues of: any of the polynucleotides provided in SEQ ID NO: 1–119 and 198–274; or any of the polypeptides set out in SEQ ID NO: 120–197 and 275–348. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1–119 and 198–274 or their variants. Polypeptides of the present invention comprehend polypeptides comprising at least a specified number of contiguous residues (x-mers) of any of the polypeptides identified as SEQ ID NO: 120–197 and 275–348. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide provided in SEQ ID NO: 1–119 and 198–274 or a variant of one of the polynucleotides provided in SEQ ID NO: 1–119 and 198–274. Polypeptides of the present invention include polypeptides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polypeptide provided in SEQ ID NO: 120–197 and 275–348, or a variant of one of the polynucleotides provided in SEQ ID NO: 120–197 and 275–348.

The inventive polynucleotides may be isolated by high throughput sequencing of cDNA libraries prepared from mammalian skin cells as described below in Example 1. Alternatively, oligonucleotide probes based on the sequences provided in SEQ ID NO: 1–119 and 198–274 can be synthesized and used to identify positive clones in either cDNA or genomic DNA libraries from mammalian skin cells by means of hybridization or polymerase chain reaction (PCR) techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art (see, for example, Mullis, et al., *Cold Spring Harbor Symp. Quant. Biol.,* 51:263, 1987; Erlich ed., *PCR Technology,* Stockton Press, NY, 1989; Maniatis et al., *Molecular Cloning—A Laboratory Manual,* Cold Spring Harbor Laboratory, Cold Spring Harbor, N.Y., 1989). Positive clones may be analyzed by restriction enzyme digestion, DNA sequencing or the like.

In addition, DNA sequences of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

Since the polynucleotide sequences of the present invention have been derived from skin, they likely encode proteins that have important role(s) in growth and development of skin, and in responses of skin to tissue injury and inflammation as well as disease states. Some of the polynucleotides contain sequences that code for signal sequences, or transmembrane domains, which identify the protein products as secreted molecules or receptors. Such protein products are likely to be growth factors, cytokines, or their cognate receptors. Several of the polypeptide sequences have more than 25% similarity to known biologically important proteins and thus are likely to represent proteins having similar biological functions.

In particular, the inventive polypeptides may have important roles in processes such as: induction of hair growth; differentiation of skin stem cells into specialized cell types; cell migration; cell proliferation and cell-cell interaction. The polypeptides may be important in the maintenance of tissue integrity, and thus be of importance in processes such as wound healing. The disclosed polypeptides may act as modulators of immune response, especially since immune cells are known to infiltrate skin during tissue insult causing growth and differentiation of skin cells. In addition, these polypeptides may be immunologically active, making them important therapeutic targets in a whole range of disease states not only within skin, but also in other tissues of the body. Antibodies to the polypeptides of the present invention and small molecule inhibitors related to the polypeptides of the present invention may also be used for modulating immune responses and for treatment of diseases according to the present invention.

In one aspect, the present invention provides methods for using one or more of the inventive polypeptides or polynucleotides to treat disorders in a patient. As used herein, a "patient" refers to any warm-blooded animal, preferably a human.

In this aspect, the polypeptide or polynucleotide is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated.

Alternatively, a vaccine or pharmaceutical composition of the present invention may contain DNA encoding one or more polypeptides as described above, such that the polypeptide is generated in situ. In such vaccines and pharmaceutical compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus-Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual. In general, the pharmaceutical compositions and vaccines may be administered by injection (e.g., intradermal, intramuscular, intravenous or subcutaneous), intranasally (e.g., by aspiration) or orally. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 $\mu$g per kg of host. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines derived from this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis* or *M. tuberculosis.* Suitable adjuvants are commercially available as, for example, Freund's Incomplete Adjuvant and Freund's Complete Adjuvant (Difco Laboratories, Detroit, Mi.), and Merck Adjuvant 65 (Merck and Company, Inc., Rahway, N.J.). Other suitable adjuvants include alum, biodegradable microspheres, monophosphoryl lipid A and Quil A.

The polynucleotides of the present invention may also be used as markers for tissue, as chromosome markers or tags, in the identification of genetic disorders, and for the design of oligonucleotides for examination of expression patterns using techniques well known in the art, such as the microarray technology available from Synteni (Palo Alto, Calif.). Partial polynucleotide sequences disclosed herein may be employed to obtain full length genes by, for example, screening of DNA expression libraries using hybridization probes or PCR primers based on the inventive sequences.

The polypeptides provided by the present invention may additionally be used in assays to determine biological activity, to raise antibodies, to isolate corresponding ligands or receptors, in assays to quantitatively determine levels of protein or cognate corresponding ligand or receptor, as anti-inflammatory agents, and in compositions for skin, connective tissue and/or nerve tissue growth or regeneration.

EXAMPLE 1

Isolation of cDNA Sequences From Skin Cell Expression Libraries

The cDNA sequences of the present invention were obtained by high-throughput sequencing of cDNA expression libraries constructed from specialized rodent or human skin cells as shown in Table 1.

TABLE 1

| Library | Skin cell type | Source |
|---|---|---|
| DEPA | dermal papilla | rat |
| SKTC | keratinocytes | human |
| HNFF | neonatal foreskin fibroblast | human |
| MEMS | embryonic skin | mouse |
| KSCL | keratinocyte stem cell | mouse |
| TRAM | transit amplifying cells | mouse |

These cDNA libraries were prepared as described below.

cDNA Library from Dermal Papilla (DEPA)

Dermal papilla cells from rat hair vibrissae (whiskers) were grown in culture and the total RNA extracted from these cells using established protocols. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library was then prepared from the mRNA by reverse transcriptase synthesis using a Lambda ZAP cDNA library synthesis kit (Stratagene).

cDNA Library from Keratinocytes (SKTC)

Keratinocytes obtained from human neonatal foreskins (Mitra, R and Nikoloff, B. in Handbook of Keratinocyte Methods p. 17–24, 1994) were grown in serum-free KSFM (BRL Life Technologies) and harvested along with differentiated cells ($10^8$ cells). Keratinocytes were allowed to differentiate by addition of fetal calf serum at a final concentration of 10% to the culture medium and cells were harvested after 48 hours. Total RNA was isolated from the two cell populations using TRIzol Reagent (BRL Life Technologies) and used to obtain mRNA using a Poly(A) Quik mRNA isolation kit (Stratagene). cDNAs expressed in differentiated keratinocytes were enriched by using a PCR-Select cDNA Subtraction Kit (Clontech, Palo Alto, Calif.). Briefly, mRNA was obtained from either undifferentiated keratinocytes ("driver mRNA") or differentiated keratinocytes ("tester mRNA") and used to synthesize cDNA. The two populations of cDNA were separately digested with Rsa I to obtain shorter, blunt-ended molecules. Two tester populations were created by ligating different adaptors at the cDNA ends and two successive rounds of hybridization were performed with an excess of driver cDNA. The adaptors allowed for PCR amplification of only the differentially expressed sequences which were then ligated into T-tailed pBluescript (Hadjeb, N. and Berkowitz, G. A. *BioTechniques* 20:20–22 1996), allowing for a blue/white selection of cells containing vector with inserts. White cells were isolated and used to obtain plasmid DNA for sequencing.

cDNA Library from Human Neonatal Fibroblasts (HNFF)

Human neonatal fibroblast cells were grown in culture from explants of human neonatal foreskin and the total RNA extracted from these cells using established protocols. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library was then prepared from the mRNA by reverse transcriptase synthesis using a Lambda ZAP cDNA library synthesis kit (Stratagene).

cDNA Library from Mouse Embryonic Skin (MEMS)

Embryonic skin was micro-dissected from day 13 post coitum Balb/c mice. Embryonic skin was washed in phosphate buffered saline and mRNA directly isolated from the tissue using the Quick Prep Micro mRNA purification kit (Pharmacia, Sweden). The mRNA was then used to prepare cDNA libraries as described above for the DEPA library.

cDNA Library From Mouse Stem Cells (KSCL) and Transit Amplifying (TRAM) Cells

Pelts obtained from 1–2 day post-partum neonatal Balb/c mice were washed and incubated in trypsin (BRL Life Technologies) to separate the epidermis from the dermis. Epidermal tissue was disrupted to disperse cells, which were then resuspended in growth medium and centrifuged over Percoll density gradients prepared according to the manufacturer's protocol (Pharmacia, Sweden). Pelleted cells were labelled using Rhodamine 123 (Bertoncello, I, Hodgson, G S and Bradley, T R *Exp Hematol.* 13:999–1006, 1985), and analysed by flow cytometry (Epics Elite Coulter Cytometry, Hialeah, Fla.). Single cell suspensions of rhodamine-labelled murine keratinocytes were then labelled with a cross reactive anti-rat CD29 biotin monoclonal antibody (Pharmingen, San Diego, Calif.; clone Ha2/5). Cells were washed and incubated with anti-mouse CD45 phycoerythrin conjugated monoclonal antibody (Pharmingen; clone 30F11.1, 10 ug/ml) followed by labelling with streptavidin spectral red (Southern Biotechnology, Birmingham, Ala.). Sort gates were defined using listmode data to identify four populations: CD29 bright rhodamine dull CD45 negative cells; CD29 bright rhodamine bright CD45 negative cells; CD29 dull rhodamine bright CD45 negative cells; and CD29 dull rhodamine dull CD45 negative cells. Cells were sorted, pelleted and snap frozen prior to storage at −80° C. This protocol was followed multiple times to obtain sufficient cell numbers of each population to prepare cDNA libraries. Skin stem cells and transit ampling cells are known to express CD29, the integrin β1 chain. CD45, a leucocyte specific antigen, was used as a marker for cells to be excluded in the isolation of skin stem cells and transit amplfying cells. Keratinocyte stem cells expel the rhodamine dye more efficiently than transit amplifying cells. The CD29 bright, rhodarnine dull, CD45 negative population (putative keratinocyte stem cells; referred to as KSCL) and the CD29 bright, rhodamine bright, CD45 negative population (keratinocyte transit amplifying cells; referred to as TRAM) were sorted and mRNA was directly isolated from each cell population using the Quick Prep Micro mRNA purification kit (Pharmacia, Sweden). The mRNA was then used to prepare cDNA libraries as described above for the DEPA library.

cDNA sequences were obtained by high-throughput sequencing of the cDNA libraries described above using a Perkin Elmer/Applied Biosystems Division Prism 377 sequencer.

EXAMPLE 2

Characterization of Isolated cDNA Sequences

The isolated cDNA sequences were compared to sequences in the EMBL DNA database using the computer algorithms FASTA and/or BLASTN. The corresponding predicted protein sequences (DNA translated to protein in each of 6 reading frames) were compared to sequences in the SwissProt database using the computer algorithms FASTX and/or BLASTP. Comparisons of DNA sequences provided in SEQ ID NO: 1–119 to sequences in the EMBL DNA database (using PASTA) and amino acid sequences provided in SEQ ID NO: 120–197 to sequences in the SwissProt database (using FASTX) were made as of Mar. 21, 1998. Comparisons of DNA sequences provided in SEQ ID NO: 198–274 to sequences in the EMBL DNA database (using BLASTN) and amino acid sequences provided in SEQ ID NO: 275–348 to sequences in the SwissProt database (using BLASTP) were made as of Oct. 7, 1998.

Isolated cDNA sequences and their corresponding predicted protein sequences, were computer analyzed for the presence of signal sequences identifying secreted molecules. Isolated cDNA sequences that have a signal sequence at a putative start site within the sequence are provided in SEQ ID NO: 1–44 and 198–238. The cDNA sequences of SEQ ID NO: 1–6 and 198–199, and their corresponding predicted amino acid sequences (SEQ ID NO: 120–125 and 275–276, respectively) were determined to have less than 75% identity (determined as described above)to sequences in the EMBL and SwissProt databases using the computer algorithms FASTA and FASTX respectively.

Further sequencing of the some of the isolated partial cDNA sequences resulted in the isolation of the full-length cDNA sequences provided in SEQ ID NO: 7–14 and 200–231. The corresponding predicted amino acid sequences are provided in SEQ ID NO: 126–133 and 277–308 respectively. Comparison of these sequences with those in the EMBL or SwissProt databases revealed less than 75% identity (determined as described above) to known sequences.

Comparison of the predicted amino acid sequences corresponding to the cDNA sequences of SEQ ID NO: 15–23 with those in the SwissProt database showed less than 75% identity (determined as described above) to known sequences. These predicted amino acid sequences are provided in SEQ ID NO: 134–142.

Further sequencing of some of the isolated partial cDNA sequences resulted in the isolation of full-length cDNA sequences provided in SEQ ID NO: 24–44 and 232–238. The corresponding predicted amino acid sequences are provided in SEQ ID NO: 143–163 and 309–315, respectively. These amino acid sequences were determined to have less than 75% identity (determined as described above) to known sequences in the SwissProt database.

Isolated cDNA sequences having less than 75% identity to known expressed sequence tags (ESTs) or to other DNA sequences in the public database, or whose corresponding predicted protein sequence showed less than 75% identity to known protein sequences, were computer analyzed for the presence of transmembrane domains coding for putative membrane-bound molecules. Isolated cDNA sequences that have either one or more transmembrane domain(s) within the sequence are provided in SEQ ID NO: 45–63 and 239–253. The cDNA sequences of SEQ ID NO: 45–48 and 239–249 and their corresponding predicted amino acid sequences (provided in SEQ ID NO: 164–167 and 316–326, respectively) were found to have less than 75% identity (determined as described above) to sequences in the EMBL and SwissProt databases.

Comparison of the predicted amino acid sequences corresponding to the cDNA sequences of SEQ ID NO: 49–63 and 250–253 with those in the SwissProt database showed less than 75% identity (determined as described above) to known sequences. These predicted amino acid sequences are provided in SEQ ID NO: 168–182 and 327–330.

Using automated search programs to screen against sequences coding for molecules reported to be of therapeutic and/or diagnostic use, some of the cDNA sequences isolated as described above in Example 1 were determined to encode predicted protein sequences that appear to be family members of known protein families. A family member is here defined to have at least 25% identity in the translated polypeptide to a known protein or member of a protein family. These cDNA sequences are provided in SEQ ID NO: 64–76 and 254–264 with the corresponding predicted amino acid sequences being provided in SEQ ID NO: 183–195 and 331–341, respectively. The cDNA sequences of SEQ ID NO: 64–68 and 254–264 show less than 75% identity (determined as described above) to sequences in the EMBL database. Similarly, the amino acid sequences of SEQ ID NO: 183–195 and 331–341 show less than 75% identity to sequences in the SwissProt database.

The likely utility for each of the proteins encoded by the DNA sequences of SEQ ID NO: 64–76 and 254–264, based on similarity to known proteins, is provided below:

TABLE 2

PUTATIVE FUNCTION OF NOVEL PROTEINS

| SEQ ID NO: | SIMILARITY TO KNOWN PROTEINS |
|---|---|
| 64 | Slit, a secreted molecule required for central nervous system development |
| 65 | Immunoglobulin receptor family. About 40% of leucocyte membrane polypeptides contain immunoglobulin superfamily domains |
| 66 | RIP protein kinase, a serine/threonine kinase that contains a death domain to mediate apoptosis |
| 67 | Extracellular protein with epidermal growth factor domain capable of stimulating fibroblast proliferation |
| 68 | Transforming growth factor alpha, a protein which binds epidermal growth factor receptor and stimulates growth and mobility of keratinocytes |
| 69 | DRS protein which has a secretion signal component and whose expression is suppressed in cells transformed by oncogenes |
| 70 | A33 receptor with immunoglobulin-like domains and is expressed in greater than 95% of colon tumours |
| 71 | Interleukin-12 alpha subunit, component of a cytokine that is important in the immune defense against intracellular pathogens. IL-12 also stimulates proliferation and differentiation of TH1 subset of lymphocytes |
| 72 | Tumour Necrosis Factor receptor family of proteins that are involved in the proliferation, differentiation and death of many cell types including B and T lymphocytes. |
| 73 | Epidermal growth factor family proteins which stimulate growth and mobility of keratinocytes and epithelial cells. EGF is involved in wound healing. It also inhibits gastric acid secretion. |
| 74 | Fibronectin Type III receptor family. The fibronectin III domains are found on the extracellular regions of cytokine receptors |
| 75 | Serine/threonine kinases (STK2_HUMAN) which participate in cell cycle progression and signal transduction |

TABLE 2-continued

PUTATIVE FUNCTION OF NOVEL PROTEINS

| SEQ ID NO: | SIMILARITY TO KNOWN PROTEINS |
|---|---|
| 76 | Immunoglobulin receptor family |
| 254 | Receptor with immunoglobulin-like domains and homology to A33 receptor which is expressed in greater than 95% of colon tumours |
| 255 | Epidermal growth factor family proteins which stimulate growth and mobility of keratinocytes and epithelial cells. EGF is involved in wound healing. It also inhibits gastric acid secretion. |
| 256 | Serine/threonine kinases (STK2_HUMAN) which participate in cell cycle progression and signal transduction |
| 257 | Contains protein kinase and ankyrin domains. Possible role in cellular growth and differentiation. |
| 258 | Notch family proteins which are receptors involved in cellular differentiation. |
| 259 | Extracellular protein with epidermal growth factor domain capable of stimulating fibroblast proliferation. |
| 260 | Fibronectin Type III receptor family. The fibronectin III domains are found on the extracellular regions of cytokine receptors. |
| 261 | Immunoglobulin receptor family |
| 262 | ADP/ATP transporter family member containing a calcium binding site. |
| 263 | Mouse CXC chemokine family members are regulators of epithelial, lymphoid, myeloid, stromal and neuronal cell migration and cancers, agents for the healing of cancers, neuro-degenerative diseases, wound healing, inflammatory autoimmune diseases like psoriasis, asthma, Crohns disease and as agents for the prevention of HIV-1 of leukocytes |
| 264 | Nucleotide-sugar transporter family member. |

These isolated sequences thus encode proteins that are likely to influence the growth, differentiation and activation of several cell types. They may usefully be developed as agents for the treatment and diagnosis of skin wounds, cancers, growth and developmental defects, and inflammatory disease.

The polynucleotide sequences of SEQ ID NO: 77–117 and 265–267 appear to be differentially expressed in either keratinocyte stem cells (KSCL) or in transit amplified cells (TRAM) on the basis of the number of times these sequences exclusively appear in either one of the above two libraries; more than 9 times in one and none in the other (Audic S. and Claverie J-M. *Genome Research,* 7:986–995, 1997). The sequences of SEQ ID NO: 77–89 and 265–267 were determined to have less than 75% identity to sequences in the EMBL and SwissProt databases using the computer algorithm PASTA, as described above. The proteins encoded by these polynucleotide sequences have utility as markers for identification and isolation of these cell types, and antibodies against these proteins may be usefully employed in the isolation and enrichment of these cells from complex mixtures of cells. Isolated polynucleotides and their corresponding proteins exclusive to the stem cell population can be used as drug targets to cause alterations in regulation of growth and differentiation of skin cells, or in gene targeting to transport specific therapeutic molecules to skin stem cells.

EXAMPLE 3

Isolationg and Characterization of the Human Homolog of MuTR1

The human homolog of muTR1 (SEQ ID NO: 68), obtained as described above in Example 1, was isolated by screening 50,000 pfu's of an oligo dT primed HeLa cell cDNA library. Plaque lifts, hybridization and screening were performed using standard molecular biology techniques (Sambrook, J., Fritsch, E. F. and Maniatis, T., eds. (1989) "Molecular Cloning: A Laboratory Manual," Second Ed. Cold Spring Harbor Laboratory Press, Cold Spring Harbor, N.Y.). The determined cDNA sequence of the isolated human homolog (huTR1) is provided in SEQ ID NO: 118, with the corresponding predicted amino acid sequence being provided in SEQ ID NO: 196. The library was screened using an [$\alpha^{32}$P]-dCTP labeled double stranded cDNA probe corresponding to nucleotides 1 to 459 of the coding region within SEQ ID NO: 118.

The polypeptide sequence of huTR1 has regions similar to Transforming Growth Factor-alpha, suggesting that this protein may function as an epidermal growth factor (EGF). This EGF-like protein may be expected to stimulate keratinocyte growth and motility, and to inhibit the growth of epithelial-derived cancer cells. This novel gene and its encoded protein may thus be developed as agents for the healing of wounds and regulators of epithelial-derived cancers.

Analysis of RNA transcripts by Northern Blotting

Northern analysis to determine the size and distribution of mRNA for huTR1 was performed by probing human tissue mRNA blots (Clontech) with a probe comprising nucleotides 93–673 of SEQ ID NO: 118, radioactively labelled with [$\alpha^{32}$P]-dCTP. Prehybridisation, hybridisation, washing and probe labelling were performed as described in Sambrook et al., *Ibid.* mRNA for huTR1 was 3.5–4 kb in size and was observed to be most abundant in heart and placenta, with expression at lower levels being observed in spleen, thymus prostate and ovary (FIG. 1).

The high abundance of mRNA for huTR1 in the heart and placenta indicates a possible role of huTR1 in the formation or maintenance of blood vessels, as heart and placental tissues have an increased abundance of blood vessels, and therefore endothelial cells, compared to other tissues in the body. This, in turn, suggests a possible role of huTR1 in angiogenesis and vascularisation of tumors. This is supported by the ability of Transforming Growth Factor-alpha and EGF to induce de novo development of blood vessels (Schreiber et al., (1986) *Science* 232:1250–1253) and stimulate DNA synthesis in endothelial cells (Schreiber et al., (1986) *Science,* 232:1250–1253), and their over-expression in a variety of human tumors.

Purification of muTR1 and huTR1

Polynucleotides 177–329 of muTR1 (SEQ ID NO: 268), encoding amino acids 53–103 of muTR1 (SEQ ID NO: 342), and polynucleotides 208–360 of huTR1 (SEQ ID NO: 269), encoding amino acids 54–104 of huTR1 (SEQ ID NO: 343), were cloned into the bacterial expression vector pProEX HT (BRL Life Technologies), which contains a bacterial leader sequence and N-terminal 6xHistidine tag. These constructs were transformed into competent XL1-Blue *E. coli* as described in Sambrook et al., *Ibid.*

Starter cultures of these recombinant XL1-Blue *E. coli* were grown overnight at 37° C. in Terrific broth containing 100 μg/ml ampicillin. This culture was spun down and used to inoculate 500 ml culture of terrific broth containing 100 μg/ml ampicillin. Cultures were grown until the $OD_{595}$ of the cells was between 0.4 and 0.8, whereupon IPTG was added to 1 mM. Cells were induced overnight and bacteria were harvested by centrifugation.

Both the polypeptide of muTR1 (SEQ ID NO: 342; referred to as muTR1a) and that of huTR1 (SEQ ID NO: 343; referred to as huTR1a) were expressed in insoluble inclusion bodies. In order to purify the polypeptides muTR1a and huTR1a, bacterial cell pellets were re-suspended in lysis buffer (20 mM Tris-HCl pH 8.0, 10 mM beta mercaptoethanol, 1 mM PMSF). To the lysed cells, 1% NP40 was added and the mix incubated on ice for 10 minutes. Lysates were further disrupted by sonication on ice at 95 W for 4×15 seconds and then centrifuged for 15 minutes at 14,000 rpm to pellet the inclusion bodies.

The resulting pellet was re-suspended in lysis buffer containing 0.5% w/v CHAPS and sonicated on ice for 5–10 seconds. This mix was stored on ice for 1 hour, centrifuged at 14,000 rpm for 15 minutes at 4° C. and the supernatant discarded. The pellet was once more re-suspended in lysis buffer containing 0.5% w/v CHAPS, sonicated, centrifuged and the supernatant removed as before. The pellet was re-suspended in solubilising buffer (6 M Guanidine HCl, 0.5 M NaCl, 20 mM Tris HCl, pH 8.0), sonicated at 95 W for 4×15 seconds and then centrifuged for 20 minutes at 14,000 rpm and 4° C. to remove debris. The supernatant was stored at 4° C. until use. Polypeptides muTR1a and huTR1a were purified by virtue of the N-terminal 6× Histidine tag contained within the bacterial leader sequence, using a Nickel-Chelating Sepharose column (Amersham Pharmacia, Uppsala, Sweden) and following the manufacturer's recommended protocol. In order to refold the proteins once purified, the protein solution was added to 5× its volume of refolding buffer (1 mM EDTA, 1.25 mM reduced glutathione, 0.25 mM oxidised glutathione, 20 mM Tris-HCl, pH 8.0) over a period of 1 hour at 4° C. The refolding buffer was stirred rapidly during this time, and stirring continued at 4° C. overnight. The refolded proteins were then concentrated by ultrafiltration using standard protocols.

Biological Activities of Polypeptides muTR1a and huTR1a muTR1 and huTR1 are novel members of the EGF family, which includes EGF, TGFα, epiregulin and others. These growth factors are known to act as ligands for the EGF receptor. The pathway of EGF receptor activation is well documented. Upon binding of a ligand to the EGF receptor, a cascade of events follows, including the phosphorylation of proteins known as MAP kinases. The phosphorylation of MAP kinase can thus be used as a marker of EGF receptor activation. Monoclonal antibodies exist which recognise the phosphorylated forms of 2 MAP kinase proteins—ERK1 and ERK2.

In order to examine whether purified polypeptides of muTR1a and huTR1a act as a ligand for the EGF receptor, cells from the human epidermal carcinoma cell line A431 (American Type Culture Collection, No. CRL-1555, Manassas Va., USA) were seeded into 6 well plates, serum starved for 24 hours and then stimulated with purified muTR1a or huTR1a for 5 min in serum free conditions. As a positive control, cells were stimulated in the same way with 10 to 100 ng/ml TGF-alpha or EGF. As a negative control, cells were stimulated with PBS containing varying amounts of LPS. Cells were immediately lysed and protein concentration of the lysates estimated by Bradford assay. 15 μg of protein from each sample was loaded onto 12% SDS-PAGE gels. The proteins were then transferred to PVDF membrane using standard techniques.

For western blotting, membranes were incubated in blocking buffer (10 mM Tris-HCl, pH 7.6, 100 mM NaCl, 0.1% Tween-20, 5% non-fat milk) for 1 hour at room temperature. Rabbit anti-Active MAP kinase pAb (Promega, Madison, Wis.) was added to 50 ng/ml in blocking buffer and incubated overnight at 4° C. Membranes were washed for 30 mins in blocking buffer minus non-fat milk before being incubated with anti rabbit IgG-HRP antibody, at a 1:3500 dilution in blocking buffer, for 1 hour at room temperature. Membranes were washed for 30 min in blocking buffer minus non-fat milk, then once for 5 min in blocking buffer minus non-fat milk and 0.1% Tween-20. Membranes were then exposed to ECL reagents for 2 min, and then autoradiographed for 5 to 30 min.

Figure 2:
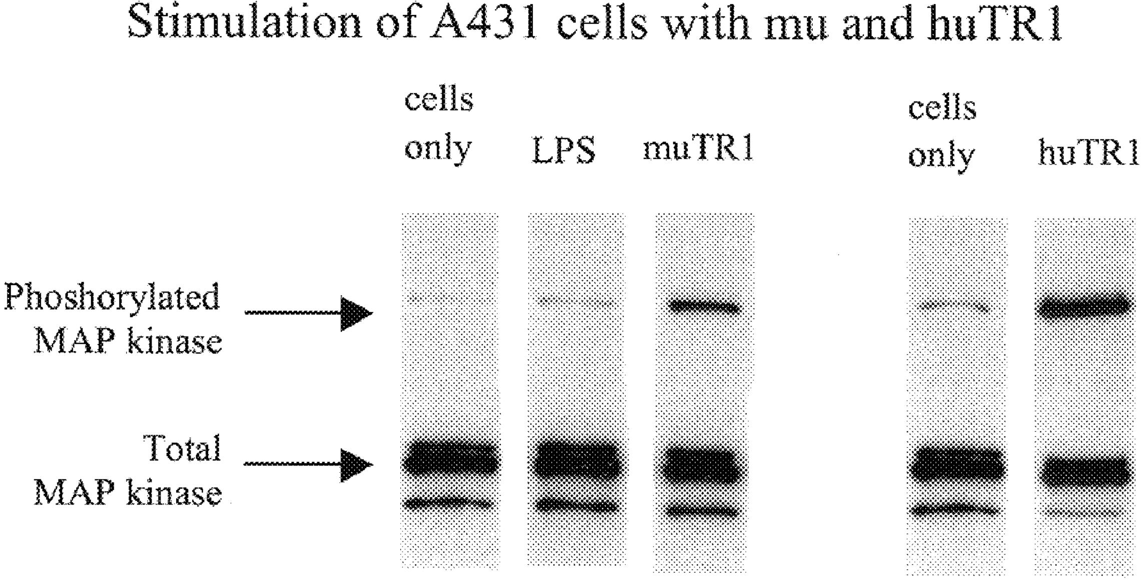
FIG. 2 shows the results of a MAP kinase assay of muTR1a and huTR1a. MuTR1a (500 ng/ml), huTR1a (100 ng/ml) or LPS (3 pg/ml) were added as described in the text.

As shown in FIG. 2, both muTR1a and huTR1a were found to induce the phosphorylation of ERK1 and ERK2 over background levels, indicating that muTR1 and huTR1 act as ligands for a cell surface receptor that activates the MAP kinase signaling pathway, possibly the EGF receptor.

Figure 3:
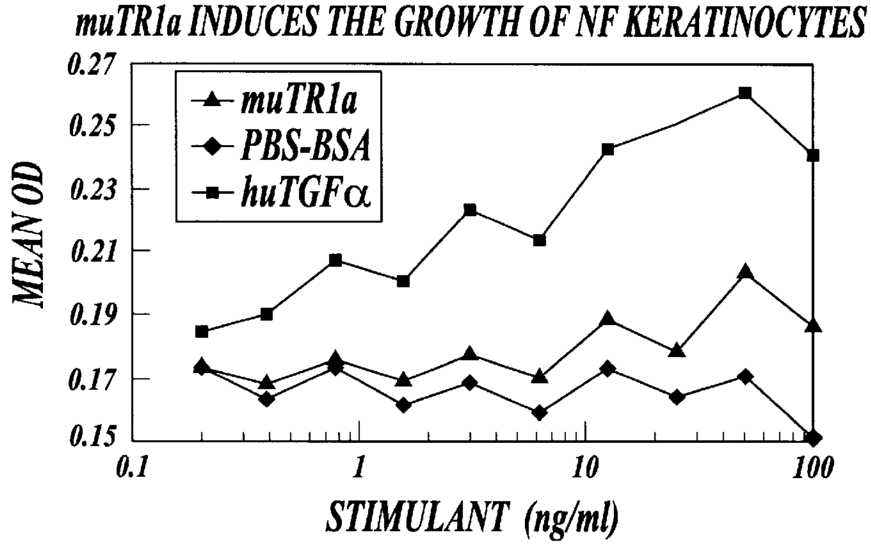

The ability of MuTR1a to stimulate the growth of neonatal foreskin (NF) keratinocytes was determined as follows. NF keratinocytes derived from surgical discards were cultured in KSFM (BRL Life Technologies) supplemented with bovine pituatary extract (BPE) and epidermal growth factor (EGF). The assay was performed in 96 well flat-bottomed plates in 0.1 ml unsupplemented KSFM. MuTR1a, human transforming growth factor alpha (huTGFα) or PBS-BSA were titrated into the plates and $1\times10^3$ NF keratinocytes were added to each well. The plates were incubated for 5 days in an atmosphere of 5% $CO_2$ at 37° C. The degree of cell growth was determined by MTT dye reduction as described previously (*J. Imm. Meth.* (1986) 93:157–165). As shown in FIG. 3, both muTR1a and the positive control human TGFα stimulated the growth of NF keratinocytes, whereas the negative control, PBS-BSA, did not.

Figure 4:
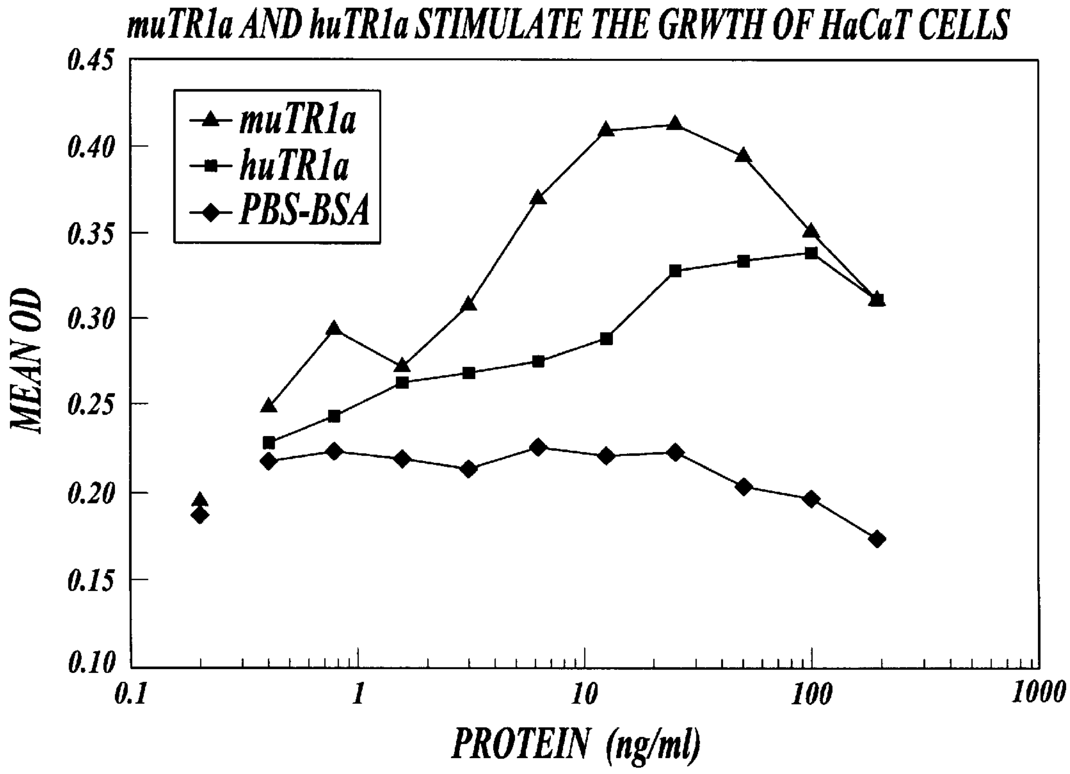

The ability of muTR1a and huTR1a to stimulate the growth of a transformed human keratinocyte cell line, HaCaT, was determined as follows. The assay was performed in 96 well flat-bottomed plates in 0.1 ml DMEM (BRL Life Technologies) supplemented with 0.2% FCS. MuTR1a, huTR1a and PBS-BSA were titrated into the plates and $1\times10^3$ HaCaT cells were added to each well. The plates were incubated for 5 days in an atmosphere containing 10% $CO_2$ at 37° C. The degree of cell growth was determined by MTT dye reduction as described previously (*J. Imm. Meth.* (1986) 93:157–165). As shown in FIG. 4, both muTR1a and huTR1a stimulated the growth of HaCaT cells, whereas the negative control PBS-BSA did not.

Figure 5:
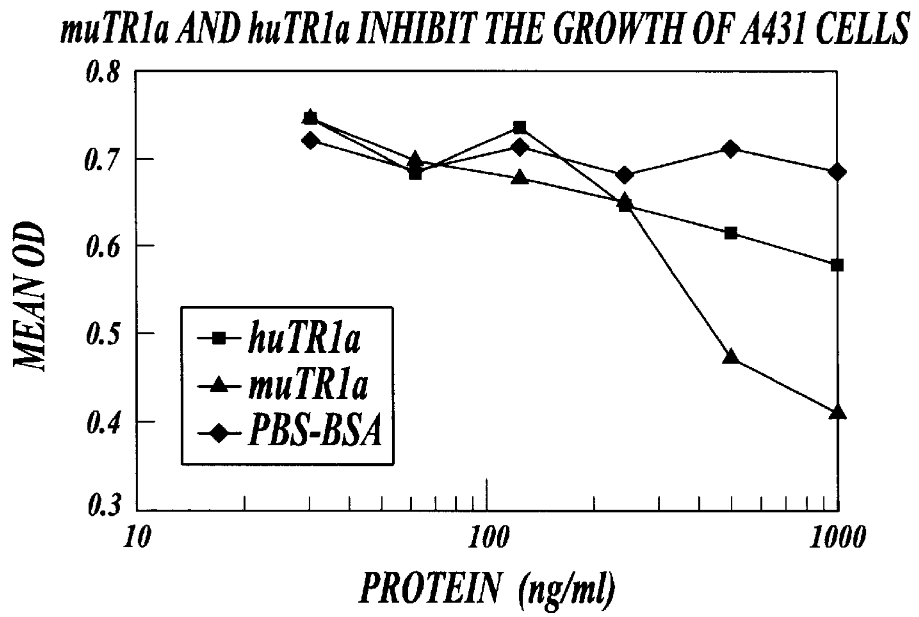

The ability of muTR1a and huTR1a to inhibit the growth of A431 cells was determined as follows. Polypeptides muTR1a (SEQ ID NO: 293) and huTR1a (SEQ ID NO: 294) and PBS-BSA were titrated as described previously (*J. Cell. Biol.* (1982) 93:1–4) and cell death determined using the MTT dye reduction as described previously (*J. Imm. Meth.* (1986) 93:157–165). Both muTR1a and huTR1a were found to inhibit the growth of A431 cells, whereas the negative control PBS-BSA did not (FIG. 5).

These results indicate that muTR1 and huTR1 may be expected to stimulate keratinocyte growth and motility, inhibit the growth of epithelial-derived cancer cells, and play a role in angiogenesis and vascularisation of tumors. This novel gene and its encoded protein may thus be developed as agents for the healing of wounds, angiogenesis and regulators of epithelial-derived cancers.

EXAMPLE 4

Identification, Isolation and Characterization of DP3

A partial cDNA fragment, referred to as DP3, was identified by differential display RT-PCR (modified from Liang P. and Pardee, A. B. *Science* 257:967–971, 1992) using mRNA from cultured rat dermal papilla and footpad fibroblast cells, isolated by standard cell biology techniques. This double stranded cDNA was labeled with [$\alpha^{32}$P]-dCTP and used to identify a full length DP3 clone by screening 400,000 pfi's of an oligo dT-primed rat dermal papilla cDNA library. The determined full-length cDNA sequence for DP3 is provided in SEQ ID NO: 119, with the corresponding amino acid sequence being provided in SEQ ID NO: 197. Plaque lifts, hybridization and screening were performed using standard molecular biology techniques.

EXAMPLE 5

Isolation and Characterization of the Human Homolog of MuKS1

Analysis of RNA Transcripts by Northern Blotting

Northern analysis to determine the size and distribution of mRNA for muKS1 (SEQ ID NO: 263) was performed by probing murine tissue mRNA blots with a probe consisting of nucleotides 268–499 of muKS1, radioactively labelled with [$\alpha^{32}$P]-dCTP. Prehybridisation, hybridisation, washing and probe labelling were performed as described in Sambrook et al., *Ibid.* mRNA for muKS1 was 1.6 kb in size and was observed to be most abundant in brain, lung, muscle and heart. Expression could also be detected in lower intestine, skin and kidney. No detectable signal was found in testis, spleen, liver, thymus, stomach.

Human Homologue of muKS1

MuKS1 (SEQ ID NO: 263) was used to search the EMBL database (Release 50 plus updates to June, 1998) to identify human EST homologues. The top three homologies were to the following ESTs: accession numbers AA643952, HS1301003 and AA865643. These showed 92.63% identity over 285 nucleotides, 93.64% over 283 nucleotides and 94.035% over 285 nucleotides, respectively. Frame shifts were identified in AA643952 and HS1301003 when translated. Combination of all three ESTs identified huKS1 (SEQ ID NO: 270) and translated polypeptide SEQ ID NO: 344. Alignment of muKS1 and huKS1 polypeptides indicated 95% identity over 96 amino acids.

Bacterial Expression and Purification of muKS1 and huKS1

Polynucleotides 269–502 of muKS1 (SEQ ID NO: 271), encoding amino acids 23–99 of polypeptide muKS1 (SEQ ID NO: 345), and polynucleotides 55–288 of huKS1 (SEQ ID NO: 272), encoding amino acids 19–95 of polypeptide huKS1 (SEQ ID NO: 346), were cloned into the bacterial expression vector pET-16b (Novagen, Madison, Wis.), which contains a bacterial leader sequence and N-terminal 6xHistidine tag. These constructs were transformed into competent XL1-Blue *E. coli* as described in Sambrook et al., *Ibid.*

Starter cultures of recombinant BL 21 (DE3) *E. coli* (Novagen) containing SEQ ID NO: 271 (muKS1a) and SEQ ID NO: 272 (huKS1a) were grown in NZY broth containing 100 μg/ml ampicillin (Gibco-BRL Life Technologies) at 37° C. Cultures were spun down and used to inoculate 800 ml of NZY broth and 100 μg/ml ampicillin. Cultures were grown until the $OD_{595}$ of the cells was between 0.4 and 0.8. Bacterial expression was induced for 3 hours with 1 mM IPTG. Bacterial expression produced an induced band of approximately 15 kDa for muKS1a and huKS1a.

MuKS1a and huKS1a were expressed in insoluble inclusion bodies. In order to purify the polypeptides, bacterial cell pellets were re-suspended in lysis buffer (20 mM Tris-HCl pH 8.0, 10 mM βMercaptoethanol, 1 mM PMSF). To the lysed cells, 1% NP-40 was added and the mix incubated on ice for 10 minutes. Lysates were further disrupted by sonication on ice at 95 W for 4×15 seconds and then centrifuged for 10 minutes at 18,000 rpm to pellet the inclusion bodies.

The pellet containing the inclusion bodies was re-suspended in lysis buffer containing 0.5% w/v CHAPS and sonicated for 5–10 seconds. This mix was stored on ice for 1 hour, centrifuged at 14000 rpm for 15 minutes at 4° C. and the supernatant discarded. The pellet was once more re-suspended in lysis buffer containing 0.5% w/v CHAPS, sonicated, centrifuged and the supernatant removed as before. The pellet was re-suspended in solubilising buffer (6 M guanidine HCl, 0.5 M NaCl, 20 mM Tris-HCl pH 8.0), sonicated at 95 W for 4×15 sec and centrifuged for 10 minutes at 18000 rpm and 4° C. to remove debris. The supernatant was stored at 4° C. MuKS1a and huKS1a were purified by virtue of the N-terminal 6× histidine tag contained within the bacterial leader sequence, using a Nickel-Chelating sepharose column (Amersham Pharmacia, Uppsala, Sweden) and following the manufacturer's protocol. Proteins were purified twice over the column to reduce endotoxin contamination. In order to re-fold the proteins once purified, the protein solution was dialysed in a 4M–2M urea gradient in 20 mM tris-HCl pH 7.5+10% glycerol overnight at 4° C. The protein was then further dialysed 2× against 2 litres of 20 mM tris-HCl pH 7.5+10% glycerol.

Injection of Bacterially Expressed muKS1a into Nude Mice

Two nude mice were anaesthetised intraperitoneally with 75 μl of 1/10 dilution of Hypnorm (Janssen Pharmaceuticals, Buckinghamshire, England) in phosphate buffered saline. 20 ug of bacterially expressed muKS1a (SEQ ID NO: 345) was injected subcutaneously in the left hind foot, ear and left hand side of the back. The same volume of phosphate buffered saline was injected in the same sites but on the right hand side of the same animal. Mice were left for 18 hours and then examined for inflammation. Both mice showed a red swelling in the ear and foot sites injected with the bacterially expressed protein. No obvious inflammation could be identified in either back site. Mice were culled and biopsies taken from the ear, back and foot sites and fixed in 3.7% formol saline. Biopsies were embedded, sectioned and stained with Haemotoxylin and eosin. Sites injected with muKS1a had a marked increase in polymorphonuclear granulocytes, whereas sites injected with phosphate buffered saline had a low background infiltrate of polymorphonuclear granulocytes.

Chemokines are a large superfamily of highly basic secreted proteins with a broad number of functions (Baggiolini et al., 1997, *Annu. Rev. Immunol.,* 15:675–705; Ward et al., 1998, *Immunity,* 9:1–11; Horuk, 1998, *Nature,* 393:524–525). The polypeptide sequences of muKS1 and huKS1 have similarity to CXC chemokines, suggesting that this protein will act like other CXC chemokines. The in vivo data from nude mice supports this hypothesis. This chemokine-like protein may therefore be expected to stimulate leukocyte, epithelial, stromal and neuronal cell migration, promote angiogenesis and vascular development, promote neuronal patterning, hemopoietic stem cell mobilization, keratinocyte and epithelial stem cell patterning and development, activation and proliferation of leukocytes, and promotion of migration in wound healing events. It has recently been shown that receptors to chemokines act as co-receptors for HIV-1 infection of CD4+ cells (Cairns et al., 1998, *Nature Medicine,* 4:563–568) and that high circulating levels of chemokines can render a degree of immunity to those exposed to the HIV virus (Zagury et al., 1998, *Proc. Natl. Acad. Sci. USA* 95:3857–3861). This novel gene and its encoded protein may thus be usefully employed as regulators of epithelial, lymphoid, myeloid, stromal and neuronal cells migration and cancers; as agents for the treatment of cancers, neuro-degenerative diseases, inflammatory autoimmune diseases such as psoriasis, asthma and Crohns disease; for use in wound healing; and as agents for the prevention of HIV-1 binding and infection of leukocytes.

EXAMPLE 6

Characterization of KS2

KS2 contains a transmembrane domain and may function as either a membrane-bound ligand or a receptor. Northern analysis indicated that the mRNA for KS2 was expressed in the mouse keratinocyte cell line, Pam212, consistent with the cDNA being identified in mouse keratinocytes.

Mammalian Expression

To express KS2, the extracellular domain was fused to the amino terminus of the constant domain of immunoglobulinG (Fc) that had a C-terminal 6×Histidine tag. This was performed by cloning polynucleotides 20–664 of KS2 (SEQ ID NO: 273), encoding amino acids 1–215 of polypeptide KS2 (SEQ ID NO: 347), into the mammalian expression vector pcDNA3 (Invitrogen, NV Leek, Netherlands), to the amino terminus of the constant domain of immunoglobulinG (Fc) that had a C-terminal 6×Histidine tag. This construct was transformed into competent XL1-Blue *E. coli* as described in Sambrook et al., *Ibid.* The Fc fusion construct of KS2a was expressed by transfecting Cos-1 cells in 5×T175 flasks with 180 μg of KS1a using DEAE-dextran. The supernatant was harvested after seven days and passed over a Ni-NTA column. Bound KS2a was eluted from the column and dialysed against PBS.

Figure 6:
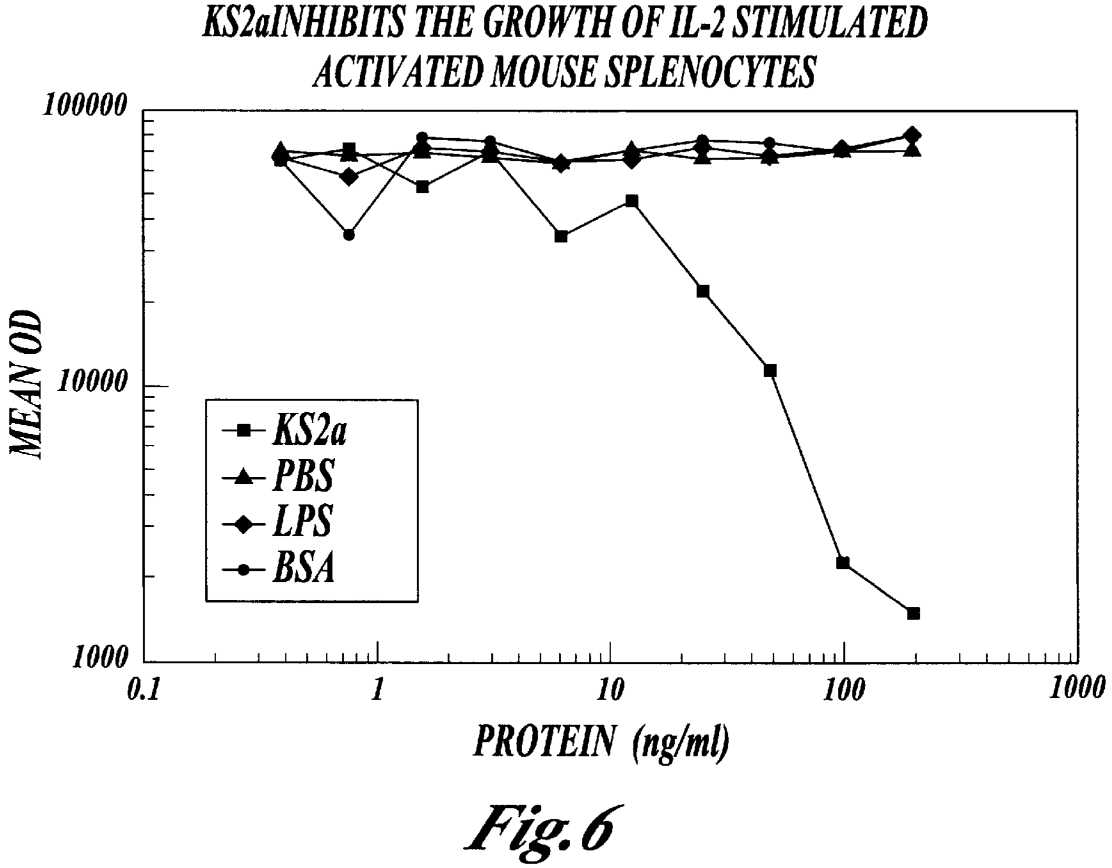

The ability of the Fc fusion polypeptide of KS2a to inhibit the IL-2 induced growth of concanavalin A stimulated murine splenocytes was determined as follows. A single cell suspension was prepared from the spleens of BALB/c mice and washed into DMEM (GIBCO-BRL) supplemented with 2 mM L-glutamine, 1 mM sodium pyruvate, 0.77 mM L-asparagine, 0.2 mM L-arganine, 160 mM penicillin G, 70 mM dihydrostreptomycin sulfate, $5\times10^{-2}$ mM beta mercaptoethanol and 5% FCS (cDMEM). Splenocytes ($4\times10^{6}$/ml) were stimulated with 2 ug/ml concanavalin A for 24 hrs at 37° C. in 10% $CO_2$. The cells were harvested from the culture, washed 3 times in cDMEM and resuspended in cDMEM supplemented with 10 ng/ml rhuIL-2 at $1\times10^{5}$ cells/ml. The assay was performed in 96 well round bottomed plates in 0.2 ml cDMEM. The Fc fusion polypeptide of KS2a, PBS, LPS and BSA were titrated into the plates and $1\times10^{4}$ activated T cells (0.1 ml) were added to each well. The plates were incubated for 2 days in an atmosphere containing 10% $CO_2$ at 37° C. The degree of proliferation was determined by pulsing the cells with 0.25 uCi/ml tritiated thymidine for the final 4 hrs of culture after which the cells were harvested onto glass fiber filtermats and the degree of thymidine incorporation determined by standard liquid scintillation techniques. As shown in FIG. 6, the Fc fusion polypeptide of KS2a was found to inhibit the IL-2 induced growth of concanavalin A stimulated murine splenocytes, whereas the negative controls PBS, BSA and LPS did not.

This data demonstrates that Ks2 is expressed in skin keratinocytes and inhibits the growth of cytokine induced splenocytes. This suggests a role for KS2 in the regulation of skin inflammation and malignancy.

EXAMPLE 7

Characterization of KS3

KS3 encodes a polypeptide of 40 amino acids (SEQ ID NO: 129). KS3 contains a signal sequence of 23 amino acids that would result in a mature polypeptide of 17 amino acids (SEQ ID NO: 348; referred to as KS3a).

Figure 7:
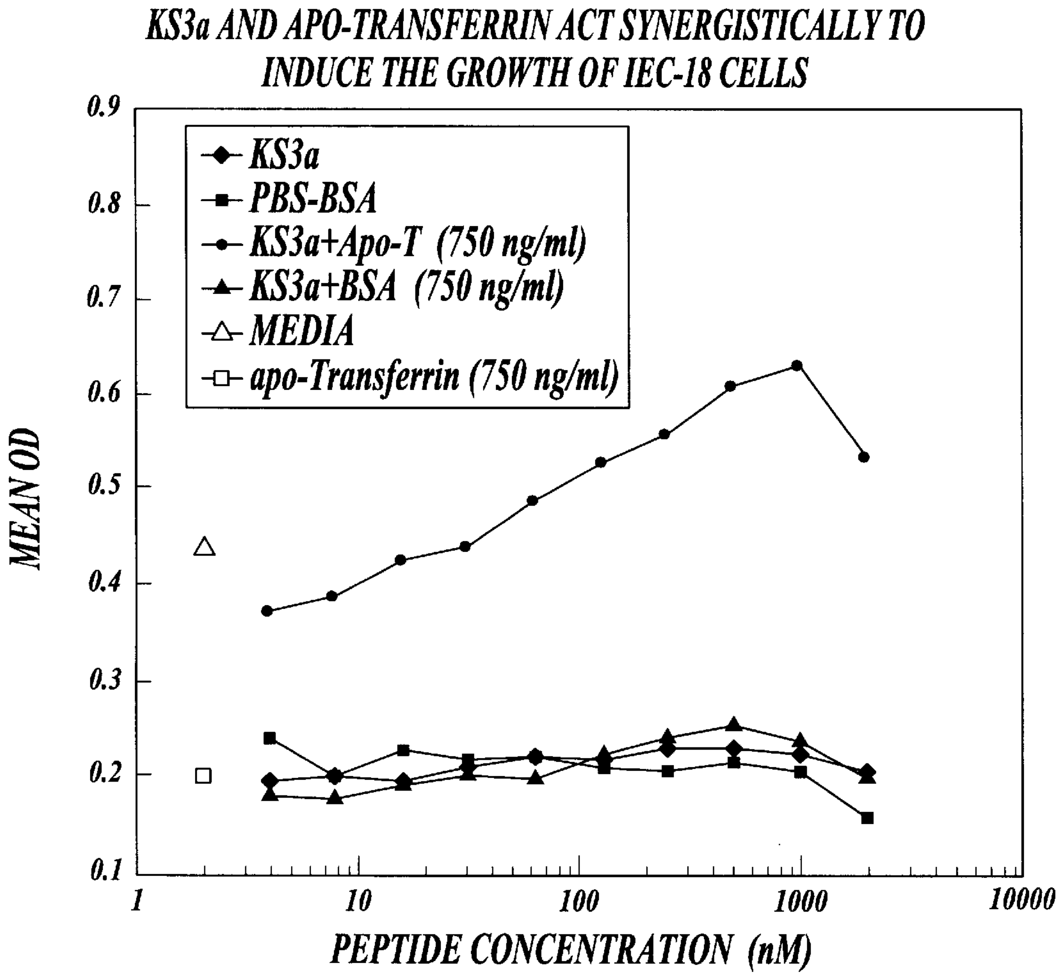
FIG. 7 shows the stimulation of growth of rat intestinal epithelial cells (IEC-18) by a combination of KS3a plus apo-transferrin.

KS3a was prepared synthetically (Chiron Technologies, Victoria, Australia) and observed to enhance transferrin-induced growth of the rat intestinal epithelial cells IEC-18 cells. The assay was performed in 96 well flat-bottomed plates in 0.1 ml DMEM (GIBCO-BRL Life Technologies) supplemented with 0.2% FCS. KS3a (SEQ ID NO: 348), apo-Transferrin, media and PBS-BSA were titrated either alone, with 750 ng/ml Apo-transferrin or with 750 ng/ml BSA, into the plates and $1\times10^{3}$ IEC-18 cells were added to each well. The plates were incubated for 5 days at 37° C. in an atmosphere containing 10% $CO_2$. The degree of cell growth was determined by MTT dye reduction as described previously (*J. Imm. Meth.* (1986) 93:157–165). As shown in FIG. 7, KS3a plus Apo-transferrin was found to enhance transferrin-induced growth of IEC-18 cells, whereas KS3a alone or PBS-BSA did not, indicating that KS3a and apo-Transferrin act synergistically to induce the growth of IEC-18 cells.

This data indicates that KS3 is epithelial derived and stimulates the growth of epithelial cells of the intestine. This suggests a role for KS3 in wound healing, protection from radiation- or drug-induced intestinal disease and integrity of the epithelium of the intestine.

SEQ ID NOS: 1–348 are set out in the attached Sequence Listing. The codes for polynucleotide and polypeptide sequences used in the attached Sequence Listing confirm to WIPO Standard ST.25 (1988), Appendix 2.

All references cited herein, including patent references and non-patent references, are hereby incorporated by reference in their entireties.

Although the present invention has been described in terms of specific embodiments, changes and modifications can be carried out without departing from the scope of the invention which is intended to be limited only by the scope of the appended claims.

What is claimed is:

1. An isolated polypeptide comprising an amino acid sequence provided in SEQ ID NO: 187.

2. An isolated polypeptide comprising an amino acid sequence selected from the group consisting of sequences having at least about a 99% probability of being the same as a sequence of SEQ ID NO: 187, 196, 342 or 343 as measured by computer algorithm BLASTP, wherein the polypeptide possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

3. An isolated polypeptide comprising an amino acid sequence having at least about 50% identity to a sequence provided in SEQ ID NO: 187 as measured by computer algorithm BLASTP, wherein the isolated polypeptide comprises at least a functional portion of a polypeptide having an amino acid sequence of SEQ ID NO: 187 and possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

4. An isolated polypeptide according to claim 3, wherein the amino acid sequence has at least about 75% identity to a sequence provided in SEQ ID NO: 187 as measured by computer algorithm BLASTP.

5. An isolated polypeptide according to claim 3 wherein the amino acid sequence has at least about 90% identity to a sequence provided in SEQ ID NO: 187 as measured by computer algorithm BLASTP.

6. An isolated polypeptide comprising at least a functional portion of a polypeptide having an amino acid sequence provided in SEQ ID NO: 187, wherein the isolated polypeptide possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

7. An isolated polypeptide comprising at least a functional portion of a polypeptide having an amino acid sequence selected from the group consisting of:

sequences having at least about a 99% probability of being the same as a sequence of SEQ ID NO: 187, 196, 342 or 343 as measured by computer algorithm BLASTP, wherein the isolated polypeptide possesses at least one property selected from the group consisting of:

(i) an ability to stimulate growth of keratinocytes;

(ii) an ability to induce phosphorylation of a MAP kinase; and (iii) an ability to inhibit growth of a human epidermal carcinoma cell line.

8. An isolated polypeptide comprising an amino acid sequence provided in SEQ ID NO: 196.

9. An isolated polypeptide comprising an amino acid sequence provided in SEQ ID NO: 342.

10. An isolated polypeptide comprising an amino acid sequence provided in SEQ ID NO: 343.

11. An isolated polypeptide comprising an amino acid sequence having at least about 50% identity to SEQ ED NO: 196, wherein the isolated polypeptide comprises at least a functional portion of a polypeptide having an amino acid sequence of SEQ ID NO: 196 and possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

12. An isolated polypeptide according to claim 11, wherein the amino acid sequence has at least about 75% identity to SEQ ID NO: 196 as measured by computer algorithm BLASTP.

13. An isolated polypeptide according to claim 11, wherein the amino acid sequence has at least about 90% identity to SEQ ID NO: 196 as measured by computer algorithm BLASTP.

14. An isolated polypeptide comprising an amino acid sequence having at least about 50% identity to SEQ ID NO: 342, wherein the isolated polypeptide comprises at least a functional portion of a polypeptide having an amino acid sequence of SEQ ID NO: 342 and possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

15. An isolated polypeptide according to claim 14, wherein the amino acid sequence has at least about 75% identity to SEQ ID NO: 342 as measured by computer algorithm BLASTP.

16. An isolated polypeptide according to claim 14, wherein the amino acid sequence has at least about 90% identity to SEQ ID NO: 342 as measured by computer algorithm BLASTP.

17. An isolated polypeptide comprising an amino acid sequence having at least about 50% identity to SEQ ID NO: 343, wherein the isolated polypeptide comprises at least a functional portion of a polypeptide having an amino acid sequence of SEQ ID NO: 343 and possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

18. An isolated polypeptide according to claim 17, wherein the amino acid sequence has at least about 75% identity to SEQ ID NO: 343 as measured by computer algorithm BLASTP.

19. An isolated polypeptide according to claim 17, wherein the amino acid sequence has at least about 90% identity to SEQ ID NO: 343 as measured by computer algorithm BLASTP.

20. An isolated polypeptide comprising at least a functional portion of a polypeptide having an amino acid sequence provided in SEQ ID NO: 196, wherein the isolated polypeptide possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

21. An isolated polypeptide comprising at least a functional portion of a polypeptide having an amino acid sequence provided in SEQ ID NO: 342, wherein the isolated polypeptide possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

22. An isolated polypeptide comprising at least a functional portion of a polypeptide having an amino acid sequence provided in SEQ ID NO: 343, wherein the isolated polypeptide possesses at least one property selected from the group consisting of:

(a) an ability to stimulate growth of keratinocytes;

(b) an ability to induce phosphorylation of a MAP kinase; and (c) an ability to inhibit growth of a human epidermal carcinoma cell line.

* * * * *

SEQUENCE LISTING

```
<160> NUMBER OF SEQ ID NOS: 348

<210> SEQ ID NO 1
<211> LENGTH: 696
<212> TYPE: DNA
<213> ORGANISM: Rat

<400> SEQUENCE: 1

aattcggcac gaggccgagg cgggcaggca ccagccagag cagctggcgg cagacagtcg     60

gaccgagaca gttggaccga gacagtcgaa cggtctaaca gggcctggct tgcctacctg    120

gcagctgcac ccggtccttt tcccagagct ggttctgtgg gtcaacatgg tcccctgctt    180
```

-continued

```
cctcctgtct ctgctgctac ttgtgaggcc tgcgcctgtg gtggcctact ctgtgtccct    240

cccggcctcc ttcctggagg aagtggcggg cagtggggaa gctgagggtt cttcagcctc    300

ttccccaagc ctgctgccgc cccggactcc agccttcagt cccacaccag ggaggaccca    360

gcccacagct ccggtcggcc ctgtgccacc caccaacctc ctggatggga tcgtggactt    420

cttccgccag tatgtgatgc tcattgcggt ggtgggctcg ctgacctttc tcatcatgtt    480

catagtctgc gcggcactca tcacgcgcca gaagcacaag gccacagcct actacccgtc    540

ctctttcccc gaaaagaagt atgtggacca gagagaccgg gctgggggc cccatgcctt    600

cagcgaggtc cctgacaggg cacctgacag ccggcaggaa gagggcctgg acttcttcca    660

gcagctccag gctgacattc tggcttgcta ctcaga                               696


<210> SEQ ID NO 2
<211> LENGTH: 475
<212> TYPE: DNA
<213> ORGANISM: Rat

<400> SEQUENCE: 2

cggtatcgat aagcttgata tcgaattcct gcaggtcgac actagtggat ccaaagaatt     60

cggcacgaga aaataaccaa ccaaacaaac tttcctcttc ccgctagaaa aaacaaattc    120

tttaaggatg gagctgctct actggtgttt gctgtgcctc ctgttaccac tcacctccag    180

gacccagaag ctgcccacca gagatgagga actttttcag atgcagatcc gggataaggc    240

attgtttcac gattcatccg tgattccaga tggagctgaa atcagcagtt acctatttag    300

agatacacct agaaggtatt tcttcatggt tgaggaagat aacaccccac tgtcagtcac    360

agtgacacct tgtgatgcgc ctttggaatg gaagcttagc ctccaggagc tgcctgagga    420

gtccagtgca gatgggtcag gtgacccaga accacttgac cagcagaagc agcag         475


<210> SEQ ID NO 3
<211> LENGTH: 381
<212> TYPE: DNA
<213> ORGANISM: Human
<220> FEATURE:
<221> NAME/KEY: unsure
<222> LOCATION: (19)...(19)

<400> SEQUENCE: 3

ctggagatcc tggggatcna ggtgatcccg gtagaaccag gcagatttgt tgtagatgac     60

tggctggtga ggttagtctt cgttccactg gacagggaaa gcttgaaact tgggctctgc    120

cgtccagaaa ggtttgtttt cagaagcact tccttttcct cactttcttt taatttcttc    180

ctttccatga atttacttat tggatccata atattatcat catttttagt tttgtcagat    240

ggagacacta cagcttctcc atcttccatg tcatcttcat ctgtgttaaa ccacatctct    300

tcttcatctt ctagtgtctg gcatctcttc gatatctgtg attcctcaaa atggaacgca    360

tactgtcaag tttgggggta a                                               381


<210> SEQ ID NO 4
<211> LENGTH: 311
<212> TYPE: DNA
<213> ORGANISM: Human

<400> SEQUENCE: 4

agcgtggtcg cggccgaggt actacagact ttgtgataag gctgaagctt ggggcatcgt     60

cctagaaacg gtggccacag ctggggttgt gacctcggtg gccttcatgc tcactctccc    120
```

-continued

```
gatcctcgtc tgcaaggtgc aggactccaa caggcgaaaa atgctgccta ctcagtttct    180

cttcctcctg ggtgtgttgg gcatctttgg cctcaccttc gccttcatca tcggactgga    240

cgggagcaca gggcccacac gcttcttcct ctttgggatc ctcttttcca tctgcttctc    300

ctgcctgctg g                                                         311


<210> SEQ ID NO 5
<211> LENGTH: 514
<212> TYPE: DNA
<213> ORGANISM: Mouse

<400> SEQUENCE: 5

ctggagctcg cgcgcctgca ggtcgacact agtggatcca aagcttaaaa gagactccac     60

ccactccagt agaccgggga ctaaaacaga aattctgaga aagcagcaag aagcagaaga    120

aatagctatt tcacagcagt aacagaagct acctgctata ataaagacct caacactgct    180

gaccatgatc agcccagcct ggagcctctt cctcatcggg actaaaattg ggctgttctt    240

ccaagtggca cctctgtcag ttgtggctaa atcctgtcca tctgtatgtc gctgtgacgc    300

aggcttcatt tactgtaacg atcgctctct gacatccatt ccagtgggaa ttccggagga    360

tgctacaaca ctctaccttc agaacaacca aataaacaat gttgggattc cttccgattt    420

gaagaacttg ctgaaagtac aaagaatata cctataccac aacagtttag atgaattccc    480

taccaacctt ccaaagtatg tcaaagagtt acat                                514


<210> SEQ ID NO 6
<211> LENGTH: 1059
<212> TYPE: DNA
<213> ORGANISM: Mouse

<400> SEQUENCE: 6

ggcacgagcc tgctgccctc ttgcagacag gaaagacatg gtctctgcgc ccggatccta     60

cagaagctca tggggagccc cagactggca gccttgctcc tgtctctccc gctactgctc    120

atcggcctcg ctgtgtctgc tcgggttgcc tgcccctgcc tgcggagttg gaccagccac    180

tgtctcctgg cctaccgtgt ggataaacgt tttgctggcc ttcagtgggg ctggttccct    240

ctcttggtga ggaaatctaa aagtcctcct aaatttgaag actattggag gcacaggaca    300

ccagcatcct tccagaggaa gctgctaggc agcccttccc tgtctgagga aagccatcga    360

atttccatcc cctcctcagc catctcccac agaggccaac gcaccaaaag ggcccagcct    420

tcagctgcag aaggaagaga acatctccct gaagcagggt cacaaaagtg tggaggacct    480

gaattctcct ttgatttgct gcccgaggtg caggctgttc gggtgactat tcctgcaggc    540

cccaaggcca gtgtgcgcct ttgttatcag tgggcactgg aatgtgaaga cttgagtagc    600

ccttttgata cccagaaaat tgtgtctgga ggccacactg tagacctgcc ttatgaattc    660

cttctgccct gcatgtgcat agaggcctcc tacctgcaag aggacactgt gaggcgcaaa    720

aagtgtccct tccagagctg gcctgaagct tatggctcag acttctggca gtcaatacgc    780

ttcactgact acagccagca caatcagatg gtcatggctc tgacactccg ctgcccactg    840

aaactggagg cctccctctg ctggaggcag gacccactca caccctgcga aacccttccc    900

aacgccacag cacaggagtc agaaggatgg tatatcctgg agaatgtgga cttgcacccc    960

cagctctgct ttaagttctc atttgaaaac agcagccacg ttgaatgtcc ccaccagagt   1020

ggctctctcc catcctggac tgtgagcatg gatacccag                          1059
```

-continued

<210> SEQ ID NO 7
<211> LENGTH: 861
<212> TYPE: DNA
<213> ORGANISM: Rat

<400> SEQUENCE: 7
gaattcggca cgagaggaga gaaagagaag tgtgcacaaa gaaacttgta ttattattaa 60
ttagcaccta gcttgtttgt gtctgataca ccaccaagta gtaattgttg aaaaaacgaa 120
gaagaaaaaa aaaaaacaaa aaaaccaaac agtgggtact caaataagat aggagaaaaa 180
tgagagaaca gacccagttc tcgacccttg cttctcaagg tcctcccacc aggctgccaa 240
agcaagatgg tgttgctctg atccagtcag tattcttttg actttttttt ttaatctcca 300
ggttttggtt caggctccca tattcatacc ctggctcatt tagctttccc tcatgttgtg 360
ggttcttctg tccctcaccc ccttactctc cccactgata ttcttcccag tcaagactgt 420
ggctctggaa gaaatatcca ccatttgcag agctgatgtt ctgtagatcg taatgttgaa 480
gcgctgggtg tcctggttgg cagaatcact cctgtattac tctggtacat aggtgtctcc 540
tgatagactc cctggcctta gtcatggggt gttttctaga ggcagactaa gacaggagtc 600
aaaaaagatt tagaggaagg agctgaggaa agaaagacag ttgtgggagg aaaatcaagt 660
tctactcagg atcccgagtg tttctgtaga tgtagattgg aatgtgtcca taacagagag 720
gccagtgaga gacatcccca aggacctgcc aggctttcct tcgctccagg aagacgcacc 780
atcactcaaa aggggtttcc tagaaagaaa gacaagtgac ttaaaaaatc tgccagtggg 840
ttcttgaagt catcgaacct a 861

<210> SEQ ID NO 8
<211> LENGTH: 398
<212> TYPE: DNA
<213> ORGANISM: Mouse

<400> SEQUENCE: 8
gtcaccagca aaggtggaaa caaattcttt gaaggactct gacagccctg ggtctccaag 60
gctgctggga ccagtcttag cctcttgtgg caagtggtag gaatgtgaat ctttgcgacc 120
agggggatca gaaatggggt ctcccatttc tggtgtctgc ccagtccttc caggtgggct 180
cttcgtagcc ctggggtgga ttttcctcct cttccacaga gatgcttttt ctctgcatac 240
catgtctgct ggtttcccat aatctccctc aaacccacac caccctccac tgaggctcag 300
ccccagagcc atgaaaactc ccaccagttt ccaggataga gtctggacag aactggggcc 360
ctggttgcca agtggtgaaa aaaggaatgg cccccctg 398

<210> SEQ ID NO 9
<211> LENGTH: 1060
<212> TYPE: DNA
<213> ORGANISM: mouse
<220> FEATURE:
<221> NAME/KEY: unsure
<222> LOCATION: (816)...(816)
<221> NAME/KEY: unsure
<222> LOCATION: (944)...(944)
<221> NAME/KEY: unsure
<222> LOCATION: (1035)...(1035)

<400> SEQUENCE: 9
agaacattcg agaatatgtt cggtggatga tgtattggat tgtctttgcg atcttcatgg 60
cagcagaaac cttcacagac atcttcattt cctggtccgg cccacggatt ggcaggccat 120
ggggttggga agggcctcac caccaccacc acctggcctc tggctcacac aaacccctcc 180

-continued

```
ccttgcttac acacaggttc ccgttttatt acgagttcaa gatggctttt gtgctgtggc    240

tgctctcacc ttacaccaag gggccagcc tgctttaccg aaagtttgtc cacccatccc    300

tatcccgcca tgagaaggag atcgacgcat gtatcgtgca ggcaaaggag cgcagctatg    360

aaaccatgct cagttttggg aagcggagcc tcaacatcgc tgcctcagct gctgtgcagg    420

ctgctaccaa gagtcaaggc gctctagctg gaaggctacg gagtttctct atgcaagacc    480

tgcgctctat ccctgacacc cctgtcccca cctaccaaga tcccctctac ctggaagacc    540

aggtaccccg acgtagaccc cctattggat accggccagg cggcctgcag ggcagtgaca    600

cagaggatga gtgttggtca gacaatgaga ttgtccccca gccacctgtt cggccccgag    660

agaagcctct aggccgcagc cagagccttc gggtggtcaa gaggaagcca ttgactcgag    720

agggcacctc acgctccctg aaggtccgaa cccggaaaaa ggccatgccc tcagacatgg    780

acagctagag tctgcagatt gaggccacct tacctntgga gccagcaggg gacctttcgc    840

tgctacacca gctaccgggg ttctgctccg tctggcttgt gcctaaatgg cacatggcgt    900

ggtaccctgc acagggagac attcactgta ccaaagcagc ccangcctgg ggcctattta    960

ttgccttcct ctgccttttg ctttctcaga catgggacca gagccccacc agtccctacc   1020

gacgaaacca aaagnccaac cagctgtgtt cattccttct                         1060
```

<210> SEQ ID NO 10
<211> LENGTH: 353
<212> TYPE: DNA
<213> ORGANISM: mouse

<400> SEQUENCE: 10

```
ggaaagtcat ctacctgctg gtggcctcca tcagagccgg gagatctcca ctgtgtgtat     60

ggagaccgca ttgatagctt actctcttcc tgaactacag gatgaaggcc atggctctga    120

gcctaggagc aagcccagtg cttgcttttc tcctctctgg gtacagtgat ggttaccaag    180

tgtgtagtag gttcggaagc aaagtgcctc agtttctgaa ctagaactac agctctgtct    240

gccttagcac agacaggcgt tgtctcattc ctctcacctg ccctacccat gcatgactcg    300

tccgcttatt gaggggcagg tgagtcatct gagatgctat ttgaaacatg aga           353
```

<210> SEQ ID NO 11
<211> LENGTH: 969
<212> TYPE: DNA
<213> ORGANISM: mouse

<400> SEQUENCE: 11

```
cggcacgaga gagtatgaag ccagagtctt agagaagtca ctgagaaaag aatccagaaa     60

caaagagacc gacaaggtga agctgacctg gagggaccga ttcccagcct atttcaccaa    120

tcttgtctcc atcatcttca tgatcgcagt gacatttgca atcgtcctcg gagttatcat    180

ctatagaatc tccacagctg cagccttggc catgaactcc tccccgtctg tgcggtccaa    240

catccgggtt acagtcacgg ccaccgctgt tatcatcaac ctcgtggtca tcattctgct    300

ggatgaagtt tacggctgca ttgccaggtg gctcaccaag attggtgagt gccatgtgca    360

ggacagcata ggcagcatgg gcctagggca gggccagcct tgaagtgggc agcctggtca    420

cagaactgtg gctagtccca acttcccctg gcctggcctg gctgtgagtg gctagcagct    480

ggcacagtca gtaccgtatg tctctcctca gaggtcccaa agacagagaa gagctttgag    540

gagaggctaa ccttcaaggc cttcctgctc aagtttgtga actcttacac tcccatcttc    600
```

-continued

```
tatgtcgcct tcttcaaagg ccggtttgtt ggtcggcccg gtgactacgt gtacatcttc    660

cgctctttcc ggatggagga gtgtgccccg ggcggctgcc tcatggagct ctgtatccag    720

ctgagcatca ttatgctggg caagcagcta atccagaaca atctcttcga gattggcatc    780

ccgaagatga aaaagttcat ccgctacctg aagctgcgca gacagagccc ctcagaccgt    840

gaagagtacg tgaagcggaa gcagcgctat gaggtggact tcaacctcga acctttcgcc    900

ggcctcacgc ccgagtacat ggaaatgatc attcagttcg gctttgtcac cctgtttgtt    960

gcgtccttc                                                            969
```

```
<210> SEQ ID NO 12
<211> LENGTH: 1411
<212> TYPE: DNA
<213> ORGANISM: mouse

<400> SEQUENCE: 12

ggcacgaggc aacttggaca ctaaagctag gtaccagcct gttagtttac atgagttcaa     60

aattcaggtc agggtctctg aaatggagtc tgaatttaaa agctttggcc tctcatgtga    120

ataatacata tgtcatgtgt catttgaata gtttcagtca cacacacttt gtatttctct    180

aagtgtaacg catgtgtagt gggtggttgt agtatgattt ctccgtcttt cttgtttgaa    240

tgtttggact tgtgcacgtg tgcacatgtg tgtgtgtgtg tgtgtgtgtg tgtgtgtgtg    300

tgtgtatttg ctcctgtggc tatgtgcatg tgccatgtgg gtgtgtgtgc ttgtgggggc    360

cagaggttag gtaccttcct ctatctctcc accctggtgg tttttgtttt gttttgtttt    420

gttttggacc aggtctatca ctgataagct aggttggatg gcttctgaga agagtctgcc    480

tctctgtccc cctgccccty ctccccccag ccctcaggtt acagataagt gccacaagtc    540

cttgtccttt caagtagcct ctagggatcc aggctcatat ccttgtgctt actgactgag    600

ccacctctca gctccctcag ccccgtttta cacgttaact ttgtctcctg tctatgcctg    660

ctctcttcag tgaccccttc cgttttcctt tcactctttt ctctgaatag atttgtgtgc    720

gagagactat tatcatatgg atgcataaat atcatctgca aagtcaatcg caggaaagac    780

ttagagtctc tttagcttta tgactgtaaa ggattccgct tcttgccatt gattcagctt    840

ttttgccatt gatcctttat tagagatcaa ttagagtcgt atacaaagac cttggctggg    900

ccctgagggt ctatctcagg ctaggccctg agggtctatc tcaggctagg ccctgagggt    960

ctatctcagg atagatggat ttaactgctt ttctcaagac gcttttactc tctcgttgaa   1020

ttctttttaa acttttaatt gacattgtac ttgcattctt atgggaaaca gggtgaccca   1080

cacacatgtg tacacaggta cacacacagt caggtcagca tagctggtat gttgttgttt   1140

atgttgggga cagtcagatt ggtattgttt ttgcactgtg ctgtggaaca ttggaaaacc   1200

ttatctgatg gtgaccctgt gcctactaac agccctcact aggatacatt ttggagtctc   1260

tggcaaccac aattttgctc tatttccatg agtccagcat ctctactact gcatagaagt   1320

aaaaaaaaaa aaaaaaaact cgagagtact tctagagcgg ccgcgggccc cccctcgagg   1380

tcgacggtat cgataagctt gatatcgaat t                                  1411
```

```
<210> SEQ ID NO 13
<211> LENGTH: 888
<212> TYPE: DNA
<213> ORGANISM: mouse

<400> SEQUENCE: 13

ggcacgagag gaccttgacc gacatccaga ccacgggacc cgactggatg tctcaccctg     60
```

-continued

```
cccctgcagg ccctgtccct tccaaaacag gcacttctgt cacaggatac tttttttttt    120

aacttaaatt tgcttggggg aggggagcag ttctagttcc atgaggcaca aatggaggtc    180

aaagagcaac ttgccgatgt ctcttctctc ctcccactgt gtgggtagta ggaattgaat    240

caggttatcg atcttggggc tgagccatct ctgtggccca cagagcactt atatgtggtt    300

acttgttgct ctcacattgt cagtgtacag cttggtggcc tttgtcactg gcatgctctg    360

tgacactgtt gtgataaaaa tgttgatgag tttacacaaa tctagtaaat tgaacccaag    420

agccaagtgt ggtggtgtac ccttaattcc agcactttgg gggcaagttc aggtagttct    480

ctgaatttga gagcctcctg gcccacatag tgagttccat ggctgcgtag ttgcaaaaga    540

acaccaacac ctttccccca caaatagaat tgtactgaag gtcacagtca gagaaagcat    600

agcaaggatg gctgctctga gcccctcctg tgcacttctg tagacctagc cccggtgtct    660

aaatggagtc tgattttagc acctgcactt gactgctgtg ctccaccctg acccgcctty    720

tcctgatccc agattgctag aactttgacc aaaatgggac ttaattggag ttgtgattgg    780

katgttcatt gatttaaagt gctctttaca ttttaaggaa actaaccctt tgggtaagaa    840

aaaaaaaaaa aaaaaaaaaa aaaaaaaaaa aaaaaaaaaa aaaaaaaa                 888
```

```
<210> SEQ ID NO 14
<211> LENGTH: 547
<212> TYPE: DNA
<213> ORGANISM: mouse

<400> SEQUENCE: 14

gaattcggca cgagcctaaa tgctgggatt aaaggcgtgc gccactactg ccaggctgtt     60

tttttttttt tttttttttt attaatgatc tgccagacaa agagatgtcc tttttggtgc    120

aaaagtcacc caatgcttga agtcactata tttgattagc tctgtaactg atacacaaat    180

aaaactttcc attatggata atacattatc tattattatt tatctcttgt tcatttttgc    240

aatttctgta cttgactccc agttgagtac aaggtgcctt tggtggtttt ccaaggatct    300

tgaggttaca tgaaattgct gatgatgtct gttgaaagca ttgtatggag gcctgaggta    360

tatttggcct gagagcagag tttttaaaat agagcctgct ggaaaagcta gctggagctt    420

ctgactactt tagaaaggca ctgtttgaag cacaggccat gaagtaagac ttgctttcta    480

gttaaattga ggttttttgt ttttttaagt cwttagtgta tagagatttc ctacattttt    540

tgtggtt                                                              547
```

```
<210> SEQ ID NO 15
<211> LENGTH: 318
<212> TYPE: DNA
<213> ORGANISM: Rat

<400> SEQUENCE: 15

ctgacatgaa gccccctaag acccaaagat tggttcctgc tgtgacatgc ctaccatgtg     60

gccacttctt catgtcctct ggcttgctct ggtctgtggc tctgttcaca ccaccctgtc    120

aaagtcagat gccaaaaaag ctgcctcaaa gacgctgctg gaaaagactc agttttcgga    180

taaacctgtc caagaccggg gtctggtggt gacggacatc aaagctgagg atgtggttct    240

tgaacatcgt agctactgct cagcaagggc tcgggagaga aactttgctg gagaggtcct    300

aggcatatgt cactccat                                                  318
```

```
<210> SEQ ID NO 16
```

-continued

<211> LENGTH: 856
<212> TYPE: DNA
<213> ORGANISM: Rat

<400> SEQUENCE: 16
gaattcggca cgagcggcac gagcggcccc gaagggggct gcacgggcga cttggcggcg 60
atggctcgag ctccggcggc gacgacggtg gccggaggcg gcggctcctc ctccttctcc 120
tcctgggctt gggcccggcg gtgatccgag ctggcggccg cggcccccck atgagactgt 180
tggcgggctg gctgtgcctg agcctggcgt ccgtgtggct ggcgcggarg atgtggacgc 240
tgcggagccc gctctcccgc tctctgtacg tgaacatgac tagcggccct ggcgggccag 300
cggcggccac cggcggcggg aaggacacgc accagtggta tgtgtgcaac agagagaaat 360
tatgcgaatc acttcagtct gtctttgttc agagttatct tgaccaagga acacagatct 420
tcttaaacaa cagcattgag aaatctggct ggctgtttat ccaactctat cattcttttg 480
tatcatctgt ttttaccctg tttatgtcta gaacatctat taacgggttg ctaggaagag 540
gctccatgtt tgtgttctca ccagatcagt ttcagagact gcttaaaatt aatccggact 600
ggaaaaccca tagacttctt gatttaggtg ctggagatgg agaagtcacg aaaatcatga 660
gccctcattt tgaagaaatt tatgccactg aactttctga aacaatgatc tggcagctcc 720
agaagaagaa atacagagtg cttggtataa atgaatggca gaatacaggg ttccagtatg 780
atgtcatcag ctgcttaaat ctgctggatc gctgtgatca gcctctgaca ttgttaaaag 840
atatcagaat gtcttg 856

<210> SEQ ID NO 17
<211> LENGTH: 349
<212> TYPE: DNA
<213> ORGANISM: Rat

<400> SEQUENCE: 17
ccaaagaatt cggcacgagg cggctcggga tggcggcccc catggaccgg acccatggtg 60
gccgggcagc ccgggcgctg cggcgggctc tggcgctggc ctcgctggcc gggctattgc 120
tgagcggcct ggcgggtgct ctccccaccc tcgggcccgg ctggcggcgc caaaaccccg 180
agccgccggc ctcccgcacc cgctcgctgc tgctggacgc cgcttcgggc cagctgcgcc 240
tggagtacgg cttccacccc gatgcggtgg cctgggctaa cctcaccaac gccatccgcg 300
agactgggtg ggcctatctg gacctgggca caaatggcag ctacaagtg 349

<210> SEQ ID NO 18
<211> LENGTH: 1057
<212> TYPE: DNA
<213> ORGANISM: Rat
<220> FEATURE:
<221> NAME/KEY: unsure
<222> LOCATION: (45)...(45)
<221> NAME/KEY: unsure
<222> LOCATION: (53)...(53)
<221> NAME/KEY: unsure
<222> LOCATION: (116)...(116)
<221> NAME/KEY: unsure
<222> LOCATION: (118)...(118)

<400> SEQUENCE: 18
cctgcaggaa gggtggcccc cagtatcggg tcccccaaaa ccctngcgtg aangacaggt 60
gtacctcccg cagagagtac atggagatca actgtcccag ggctgtaggg aaaagncngt 120
aatgggacac tccttcccgc tgcaggtcga cactagtgga tccaaagaat tcggcacgag 180

-continued

```
gcggaagcag ccgcaggtat ggcggctgcc atgccgctgg gtttatcgtt gctgttgctg    240
gtgctagtgg ggcagggctg ctgtggccgc gtggagggcc cacgcgacag cctgcgagag    300
gaactcgtta tcactccgct gccttccggc gacgtggccg ccacattcca gttccgcacg    360
cgttgggatt ccgatctgca gcgggaagga gtgtcccatt acaggctctt ccctaaagcc    420
ctgggacagt tgatctccaa gtactctctg cgggagctac acctgtcatt cacgcaaggc    480
ttttggagga cccgatactg gggccaccc ttcctgcagg ctccatcagg tgcagagctc     540
tgggtctggt tccaagacac tgtcacagat gtggataagt cttggaagga gctcagtaat    600
gtcctctcag ggatcttctg cgcgtccctc aacttcatcg actccaccaa taccgtcact    660
cccacagcct ccttcaaacc tctggggctg gccaatgaca ctgaccacta cttcctgcgc    720
tatgctgtgc tgccccggga ggtcgtctgc accgagaatc tcacgccgtg gaagaagctc    780
ctgccctgta gctccaaggc agggctgtcc gtgctactga aagcagatcg attgttccac    840
accagttacc actcccaggc agtgcatatc cggccaatct gcagaaatgc tcactgcacc    900
agtatctcct gggagctgag gcagaccctt tcagttgtct ttgatgcctt catcaccgga    960
caggggaaga aagaggcctg tccattggca tctcagagcc tagtttatgt ggacatcaca   1020
ggctacagcc aggacaacga aacactggag gtgagca                            1057
```

<210> SEQ ID NO 19
<211> LENGTH: 750
<212> TYPE: DNA
<213> ORGANISM: Rat

<400> SEQUENCE: 19

```
ggcacgagcg gcatctcaag ctgctgcaag caggactgag cactaccaga gcagcaacct     60
cggatggccc tggacgtggc acgcgcgggg cacagaggca agaagacttg atgaagcctc    120
tcttcccaac ccatatccag aaagaacgat ttagatgaca gtttttagaa aggtgaccac    180
catgatctcc tggatgctct tggcctgtgc ccttccgtgt gctgctgacc caatgcttgg    240
tgcctttgct cgcagggact tccagaaggg tggtcctcaa ctggtgtgca gtctgcctgg    300
tccccaaggc ccacctggcc ctccaggagc accaggatcc tcaggaatgg tgggaagaat    360
gggttttcct ggtaaggatg gccaagacgg ccaggacgga gaccgagggg acagtggaga    420
agaaggtcca cctggcagga caggcaaccg aggaaaacaa ggaccaaagg gcaaagctgg    480
ggccattggg agagcgggtc ctcgaggacc caagggggtc agtggtaccc ccgggaaaca    540
tggtataccg ggcaagaagg gacctaaggg caagaaaggg gaacctgggc tcccaggccc    600
ctgtagctgc ggcagtagcc gagccaagtc ggcctttccg gtggcggtaa ccaagagtta    660
cccacgtgag cgactgccca tcaagtttga caagattctg atgaatgagg gaggccacta    720
caatgcatcc agtggcaagt tcgtctgcag                                     750
```

<210> SEQ ID NO 20
<211> LENGTH: 849
<212> TYPE: DNA
<213> ORGANISM: Rat

<400> SEQUENCE: 20

```
gataatycgg sacgaggggc cgccgagtcc cgccgggtcg gtgtagctcg ctgccgacgc     60
tgcgacgctc gtgggtgccg tgttcggctt ttcctgtcta cttcagtgca ccgctgcagc    120
tccggcctcg ggtctgacgc gccacagcat ggcttccgct ttggaggagt tgcagaaaga    180
cctagaagag gtcaaagtgc tgctggaaaa gtccactagg aaaagactac gtgatactct    240
```

-continued

```
tacaaatgaa aaatccaaga ttgagacgga actaaggaac aagatgcagc agaagtcaca    300
gaagaaacca gaatttgata atgaaaagcc agctgctgtg gttgctcctc ttacaacagg    360
gtacactgtg aaaatcagta attatggatg ggatcagtca gataagtttg tgaaaatcta    420
cattacttta actggagttc atcaggttcc tgctgagaat gtgcaagtac acttcacaga    480
gaggtcattt gatcttttgg taaaaaacct caatggcaag aattactcca tgattgtgaa    540
caatcttttg aaacctatct ctgtggaaag cagttcaaaa aaagtcaaga ctgatacagt    600
tattatccta tgtagaaaga aagcagaaaa cacacgatgg gactacttaa ctcaggtgga    660
aaaagaatgc aaagagaaag aaaagccttc ctacgacact gaggcagatc ctagtgaggg    720
attaatgaat gttctaaaga aaatttatga agatggagat gatgacatga agcgaaccat    780
taataaagcg tgggtggaat cccgagagaa gcaagccagg gaagacacag aattcctgca    840
gcccggggg                                                            849
```

<210> SEQ ID NO 21
<211> LENGTH: 312
<212> TYPE: DNA
<213> ORGANISM: Human

<400> SEQUENCE: 21

```
ttcgagcggc cgcccgggca ggtaccagca catgctgtgg tgatgctggt ttgtgttccc     60
acctcactca cactcagccc tggcatctcc tctcctggct ctgtttgagt ggcagcgtca    120
atggcctttc tgctctggag ctcgtccctg tggctgctga agtagtcttc ctcactaaca    180
gtagaggact cacagtcatg gggcttgcgc tctgccttgc ctctgcgggc atctctgggt    240
ccaggtccgc cttcctggga gtacctcggc cgcgaccaac gctaatcaag cttatcgata    300
ccgtcgacct cg                                                        312
```

<210> SEQ ID NO 22
<211> LENGTH: 1023
<212> TYPE: DNA
<213> ORGANISM: mouse

<400> SEQUENCE: 22

```
gcgcggcccg ggggactcac attccccggt ccccccctccg ccccacgcgg ctgggccatg     60
gacgccagat ggtgggcagt agtggtactc gccacactcc cttccttggg agcaggtgga    120
gagtcacccg aagcccctcc gcagtcctgg acacagctgt ggctcttccg cttcttgttg    180
aatgtagcgg gctatgccag ctttatggta cctggctacc tcctggtgca gtacttaaga    240
cggaagaact acctggagac aggcaggggt ctctgcttcc ccctggtgaa agcctgtgtg    300
tttggcaatg agcccaaggc tcctgatgag gttctcctgg ctccgcggac agagacagcg    360
gaatccaccc cgtcttggca ggtcctgaag ctggtcttct gtgcctcggg tctccaggtg    420
tcctatctga cttggggcat actgcaggaa agagtgatga ctggcagcta cggggccaca    480
gccacatcac caggagagca tttcacagac tcccagtttc tggtgctgat gaaccgtgtg    540
ctggcgctgg ttgtggcagg cctctactgt gtcctgcgca agcagccccg tcatggtgca    600
cccatgtacc ggtactcctt tgccagtctg tcaaatgtgc ttagcagctg gtgccagtat    660
gaagcactta agttcgtcag cttccctacc caggtgctgg cgaaggcctc caaggtgatc    720
cctgtcatga tgatgggaaa gctggtgtcc cggcgcagct atgaacactg ggaatacctg    780
actgccggcc tcatctccat tggagtgagc atgtttcttc tatccagtgg accagagcct    840
```

-continued

```
agaagctctc cagccaccac actctctggc ttggtcctac tggcaggcta tattgctttc    900

gacagcttca cctcaaattg gcaggatgcc ctgtttgcct ataagatgtc atcggtgcag    960

atgatgtttg gggtcaattt attctcctgt cttttcacag taggctcact actggaacag   1020

ggg                                                                 1023
```

<210> SEQ ID NO 23
<211> LENGTH: 997
<212> TYPE: DNA
<213> ORGANISM: mouse

<400> SEQUENCE: 23

```
ggcacgagga cttctgctag tacttgctcc tggcggtggc tgagcaaccg gtctcaccag     60

catgctctgc ctgtgcctgt atgtgcccat cgccggggcg gctcagactg agttccagta    120

ctttgagtcc aaggggcttc ctgccgagct gaaatccatc ttcaaactca gtgtctttat    180

cccctctcaa gagttctcca cataccgcca atggaagcag aaaattgtgc aagcaggtga    240

caaggacctt gatgggcaac tggactttga agagtttgta cattacctcc aagatcatga    300

gaaaaaactg aggctggtgt tcaagagtct ggacaaaaag aatgatggtc gaatcgatgc    360

tcaggagatc atgcagtccc tgcgggacct gggtgtcaag atctcggaac agcaggcgga    420

gaagattctt aagagcatgg ataagaatgg cacgatgacc atcgactgga acgagtggag    480

ggactaccac ctcctgcacc ctgtggagaa catcccggag atcatcctgt actggaagca    540

ctcgacgatc ttcgatgtcg gtgagaatct gacagtccca gatgagttca cagtggagga    600

gaggcagacg gggatgtggt ggaggcacct ggtggcagga ggtggggcag gggcagtttc    660

cagaacctgc actgcccccc tggacagact gaaggtgctc atgcaggtcc atgcctcccg    720

cagcaacaac atgtgcatcg taggtggatt cacacagatg attcgagaag gggagccaa     780

gtcactctgg cggggcaacg gcatcaatgt cctcaaaatt gcccctgagt cggccatcaa    840

attcatggca tatgagcaga tgaaacggct tgtcggtagt gatcaggaga cgctgaggat    900

ccacgaaagg cttgtggcag gctccttggc cggagccatt gcccagagta gcatctaccc    960

aatggaggtt ctgaagaccc gaatggccct gcggaaa                             997
```

<210> SEQ ID NO 24
<211> LENGTH: 529
<212> TYPE: DNA
<213> ORGANISM: Rat

<400> SEQUENCE: 24

```
aaagcttcca tcctcaacat gccactagtg acgacactct tctacgcctg cttctatcac     60

tacacggagt ccgaggggac cttcagcagt ccagtcaacc tgaagaaaac attcaagatc    120

ccagacagac agtatgtgct gacagccttg gctgcgcggg ccaagcttag agcctggaat    180

gatgtcgacg ccttgttcac cacaaagaac tggttgggtt acaccaagaa gagagcaccc    240

attggcttcc atcgagttgt ggaaattttg cacaagaaca gtgcccctgt ccagatattg    300

caggaatatg tcaatctggt ggaagatgtg gacacaaagt tgaacttagc cactaagttc    360

aagtgccatg atgttgtcat tgatacttgc cgagacctga aggatcgtca acagttgctt    420

gcatacagga gcaaagtaga taaaggatct gctgaggaag agaaaatcga tgtcatcctc    480

agcagctcgc aaattcgatg gaagaactaa ggttcttttg ctacccaga                529
```

<210> SEQ ID NO 25
<211> LENGTH: 1230

-continued

<212> TYPE: DNA
<213> ORGANISM: Rat

<400> SEQUENCE: 25

```
aagaattcgg cacgaggcca tggctggttg ggcgggggcc gagctctcgg tcctgaaccc     60
gctgcgtgcg ctgtggctgt tgctggccgc cgccttcctg ctcgcactgc tgctgcagct    120
ggcgcccgcc aggctgctac cgagctgcgc gctcttccag gacctcatcc gctacgggaa    180
gaccaagcag tccggctcgc ggcgccccgc cgtctgcagg gccttcgacg tccccaagag    240
gtacttttct cacttctacg tcgtctcagt gttatggaat ggctccctgc tctggttcct    300
gtctcagtct ctgttcctgg gagcgccgtt tccaagctgg ctttgggctt tgctcagaac    360
tcttggggtc acgcagttcc aagccctggg gatggagtcc aaggcttctc ggatacaagc    420
aggcgagctg gctctgtcta ccttcttagt gttggtgttc ctctgggtcc atagtcttcg    480
gagactcttc gagtgcttct acgtcagcgt cttctctaac acggccattc acgtcgtgca    540
gtactgtttc gggctggtct actatgtcct tgttggcctg accgtactga gccaagtgcc    600
catgaatgac aagaacgtgt acgctctggg gaagaatcta ctgctacaag ctcggtggtt    660
ccacatcttg ggaatgatga tgttcttctg gtcctctgcc catcagtata agtgccacgt    720
cattctcagc aatctcagga gaaataagaa aggtgtggtc atccactgcc agcacagaat    780
cccctttgga gactggttcg agtatgtgtc ttctgctaac tacctagcag agctgatgat    840
ctacatctcc atggctgtca ccttcgggct ccacaacgta acctggtggc tggtggtgac    900
ctatgtcttc ttcagccaag ccttgtctgc gttcttcaac cacaggttct acaaaagcac    960
atttgtgtcc tacccaaagc ataggaaagc tttcctcccg ttcttgtttt gaacaggctt   1020
tatggtgaag agcgcagccc aggtgacagg ttcccttcct cgagacgctg agacaggctg   1080
aagtacactt tctgcagctg gcgcccgcca ggctgctacc gagctgcgcg ctcttccagg   1140
acctcatccg ctacgggaag accaagcagt ccggctcgcg gcgccccgcc gtctgcagcc   1200
cgggggatcc actagttcta gagcgccgcc                                     1230
```

<210> SEQ ID NO 26
<211> LENGTH: 393
<212> TYPE: DNA
<213> ORGANISM: Rat

<400> SEQUENCE: 26

```
ggcagcaaga agcaacccgc aagctaggag tctgtcagcg agggcagggg ctgcctggtt     60
ggggtaggag tgggagcagg gccagcagga gggtctgagg aagccattca aagcgagcag    120
ctgggagagc tggggagccg ggaagggcct acagactaca agagaggatc ctggcgtctg    180
ggcctcctgg gtcatcacca tgaggccact tcttgccctg ctgcttctgg gtctggcatc    240
aggctctcct cctctggacg acaacaagat ccccagcctg tgtcccgggc agcccggcct    300
cccaggcaca ccaggccacc acggcagcca aggcctgcct ggccgtgacg gcctgatggc    360
cgcgacggtg cacccggagt ccgggagaga aac                                 393
```

<210> SEQ ID NO 27
<211> LENGTH: 778
<212> TYPE: DNA
<213> ORGANISM: Rat

<400> SEQUENCE: 27

```
ctgcaggtcg acactagtgg atccaaagat tcggcacgag ataaggcaca tttgcttcat     60
```

-continued

```
aaaataaaaa aaaaggaaat ttacttagcc gcatgtcagt cacccaaatt ttgagtgtac    120

aaatgaaatg gaaaacattt attacacaaa tttaattaca attctaggga ataaacatgc    180

aaatcagatg gagctcaatc tgcaggcgct gatcctctcc ccctggtttg cagtctgtgc    240

acctcctgga ttcgcccgcg accaggcagt cagaggcctg gctcttgcag gcaggaggat    300

cactgttgta aagaacagcg tcacatttag cgcatctggc gtagtagcag tttttaacac    360

tttgcgcagg tgcctccctt cccccacccg cgctttgtta ggtctacctc tctaaatctc    420

tgccttcctc gcacagtaag tgacctctcc atgacaaagg gcccccagac agcagttata    480

aatcaatgtg ttttgggttt gtttgtttgt ttgttttgtt ttaaagaaaa acccggccat    540

gcttggtggc acttgccttt aatagtagcg cttggtagac agaggcaagc ggttctctgt    600

aagttcaagg ccagcctggt ctacacagtg agaccgggtc tcaaaaacaa aacaacaaaa    660

aacaactcct attgaatcca ctacaggaag ggggggcgcg gatcactgtc tgcaaactaa    720

agtgacttga gctcctgtca cagcctttcc agcaagggca agcttcttta ttagttat      778
```

<210> SEQ ID NO 28
<211> LENGTH: 1123
<212> TYPE: DNA
<213> ORGANISM: Rat

<400> SEQUENCE: 28

```
gggccccccc tcgagtcgac gktatcgata agcttgatat cgaattcctg caggtcgaca     60

ctagtggatc caaagaattc ggcacgagcc tgaggcgact acggtgcggg tgccgggtgc    120

cgggtgccta cagcccccat cagcttcccc ggggagattc tgccgatttg tcacgagcca    180

tgctcaggag gcagctcgtc tggtggcacc tgctggcttt gcttttcctc ccattttgcc    240

tgtgtcaaga tgaatacatg gagtctccac aagctggagg actgccccca gactgcagca    300

agtgttgcca tggagattat ggattccgtg gttaccaagg gccccctgga cccccaggtc    360

ctcctggcat tccaggaaac catggaaaca atggaaataa cggagccact ggccacgaag    420

gggccaaggg tgagaaagga gacaaaggcg acctggggcc tcgaggggaa cgggggcagc    480

atggccccaa aggatagaag ggatacccag gggtgccacc agagctgcag attgcgttca    540

tggcttctct agcgactcac ttcagcaatc agaacagtgg cattatcttc agcagtgttg    600

agaccaacat tggaaacttc ttcgatgtca tgactggtag atttggggcc cccgtatcag    660

gcgtgtattt cttcaccttc agcatgatga agcatgagga cgtggaggaa gtgtatgtgt    720

accttatgca caatggtaac acggtgttca gcatgtacag ctatgaaaca aagggaaaat    780

cagatacatc cagcaaccat gcagtgctga agttggccaa aggagatgaa gtctggctaa    840

gaatgggcaa cggtgccctc catggggacc accagcgctt ctctaccttc gcaggctttc    900

tgctttttga aactaagtga tgaggaagtc aggatagctc catgctaagg gcgatttgta    960

ggtgagctag ggttgttagg atctgagggg tgttggagtt gggcttctct atggagtatt   1020

taactgttac attggtcaca ctgctactca ttctaatggc ataccaatta tgttggatac   1080

tttaggggct aggaagaata gaccacaagg taatattccc aga                     1123
```

<210> SEQ ID NO 29
<211> LENGTH: 849
<212> TYPE: DNA
<213> ORGANISM: Rat

<400> SEQUENCE: 29

```
aattcggcac gaggtgccct ccgccgggtc gggatggagc tgcctgccgt gaacttgaag     60
```

-continued

```
gttattctcc tggttcactg gctgttgaca acctggggct gcttggcgtt ctcaggctcc    120
tatgcttggg gcaacttcac tatcctggcc ctgggtgctg tgggctgtgg cccagcggga    180
ctctgttgat gccattggca tgtttcttgg tggcttggtt gccaccatct tcctggacat    240
tatctacatt agcatcttct actcaagcgt tgccgttggg gacactggcc gcttcagtgc    300
cggcatggcc atcttcagct tgctgctgca agcccttctc ctgctgcctc gtctaccaca    360
tgcaccgggc agcgaggggg tgagctcccg ctccgctcgg atttcttcgg accttctcag    420
gaacatagtg cctaccagac aattgactcg tcagactcac ctgcagaccc ccttgcaagc    480
ctggagaaca agggccaagc tgccccccgg gggtactgaa gctgtccctg gccgtcctgg    540
ggcccagcag gatgcttgtc accttcttta ctggacctac aatggggtat cctccattcc    600
ctgccacaga ggtggcctga gtcatgtgcc ctcggaggtc ccagctgaga agagcccagt    660
cctaattctc catgctgccc ctccattcaa gacacctgtt aaccccctggg ctagaactgt    720
ggttggtttc ttcccctcct ccccatcact ataacacaca accgccgagc tgtgcagagt    780
gttcagggcc atccaggcct tatgggccaa tgatcactgc ctctcaggct accccaaggt    840
gacccagcc                                                            849
```

<210> SEQ ID NO 30
<211> LENGTH: 1015
<212> TYPE: DNA
<213> ORGANISM: Rat
<220> FEATURE:
<221> NAME/KEY: unsure
<222> LOCATION: (545)...(545)

<400> SEQUENCE: 30

```
gaattcggca cgagggagca agaagcaacc cgaagctagg agtctgtcag cgagggcagg     60
ggctgcctgg ttggggtagg agtgggagca gggccagcag gagggtctga ggaagccatt    120
caaagcgagc agctgggaga gctggggagc cgggaagggc ctacagacta caagagagga    180
tcctggcgtc tgggcctcct gggtcatcac catgaggcca cttcttgccc tgctgcttct    240
gggtctggca tcaggctctc ctcctctgga cgacaacaag atccccagcc tgtgtcccgg    300
gcagcccggc ctcccaggca caccaggcca ccacggcagc caaggcctgc ctggccgtga    360
cggccgtgat ggccgcgacg gtgcacccgg agctccggga gagaaaggcg agggcgggag    420
accgggacta cctgggccac gtggggagcc cgggccgcgt ggagaggcag gacctgtggg    480
ggctatcggg cctgcggggg agtgctcggt gcccccacga tcagccttca gtgccaagcg    540
atcanagagc cgggtacctc cgccagccga cacaccccta cccttcgacc gtgtgctgct    600
caatgagcag ggacattacg atgccactac cggcaagttc acctgccaag tgcctggtgt    660
ctactacttt gctgtccatg ccactgtcta ccgggccagc ctacagtttg atcttgtcaa    720
aaatggccaa tccatagctt ctttcttcca gttttttggg gggtggccaa agccagcctc    780
gctctcaggg ggtgcgatgg tgaggctaga acctgaggac caggtatggg ttcaggtggg    840
tgtgggtgat tacattggca tctatgccag catcaaaaca gacagtacct tctctggatt    900
tctcgtctat tctgactggc acagctcccc agtcttcgct taaaatacag tgaacccgga    960
gctggcactt gctcctagtg gagggtgtga cattggtcca gcgcgcatac cagga        1015
```

<210> SEQ ID NO 31
<211> LENGTH: 452
<212> TYPE: DNA
<213> ORGANISM: Human

-continued

<400> SEQUENCE: 31

```
ttcgagcggc cgcccgggca ggttgaaact ttagaaagaa gagccgggag gatgtattgg     60
ttgttaggaa aatgtaggct accagtagaa aatgacattc tctattaata agatctgagg    120
tgcgacacac ataattgtcc caatttttaa gattgatggg gagcatgaag cattttttta    180
atgtgttggc aggccccatt aaatgcataa actgcatagg actcatgtgg tctgaatgta    240
ttttagggct ttctgggaat tgtcttgaca gagaacctca gctggacaaa gcagccttga    300
tctgagtgag ctaactgaca caatgaaact gtcaggcatg tttctgctcc tctctctggc    360
tcttttctgc tttttaacag gtgtcttcag tcagggagga caggttgact gtggtgagtc    420
caggacacca aggcctactg cactcgggaa cc                                  452
```

<210> SEQ ID NO 32
<211> LENGTH: 434
<212> TYPE: DNA
<213> ORGANISM: mouse

<400> SEQUENCE: 32

```
accaccaagc agatggaatg ctggcacacc catgcacctg catggcgtca caggtggaag     60
attgttaaaa aattgacatc agaaatattt acagaaatag atacctgttt gaataaagtt    120
agagatgaaa tttttgctaa acttcaaccg aagcttagat gcacattagg tgacatggaa    180
agtcctgtgt ttgcacttcc tgtactgtta aagcttgaac cccatgttga aagcctcttt    240
acatattctt tttcttggaa ttttgaatgt tcccattgtg gacaccagta ccaaaacagg    300
tgtgtgaaga gtctggtcac ctttaccaat attgttcctg agtggcatcc actcaatgct    360
gcccattttg gtccatgtaa cagctgcaac agtaaatcac aaataagaaa aatggtgttg    420
gaaagagcgt cgcc                                                      434
```

<210> SEQ ID NO 33
<211> LENGTH: 903
<212> TYPE: DNA
<213> ORGANISM: mouse

<400> SEQUENCE: 33

```
ctgcaacaag gctgttggtt cctctccaat gggctccagt gaagggctcc tgggcctggg     60
ccctgggccc aatggtcaca gtcacctgct gaagacccca ctgggtggcc agaaacgcag    120
tttttcccac ctgctgccct cacctgagcc cagcccagag ggcagctacg tgggccagca    180
ctcccagggc ctcggcggcc actacgcgga ctcctacctg aagcggaaga ggattttcta    240
aggggtcgac accagagatg ctccaagggc ctgcaccaag ttgcttttgg gttttttctg    300
gtatttgtgt tttctgggat tttattttta ttattttttt taatgtcctt tctttgggta    360
atagagaaat ctctgcaaaa gactttgctg accaaccagc tggagctcaa ggaatgtggg    420
gtatctgggg ccacaccatt acctgtgggc ttgctcctgg agccaaaccc tgcagcctta    480
agagagaggg gcctgacctg ctctctttcc ctccctagct ccaggcctcc tctcctgcct    540
cgtcactcct gtgttctggc ctcttgagtg cctttggagg tgtctctgac ctgtgaggat    600
cagagacagt ccccgttttt aaacttcgac aattgacttt tatttccttt tctaattttt    660
attatttttt aaaacaacca ggatgattat cacatctact cccccatccg tccagaaaag    720
ccccaaattg attccttcag ggtctggcct gcccaggctc tattccacat gtgcaggttc    780
caacagctta accctattct cttcccagtc atctgctgca ggtatagctg tctcatgccc    840
```

-continued ctgcctgcct attctggcca gtaccctaag ccccaagatc tccagcccct gccccagtat 900
cct 903

<210> SEQ ID NO 34
<211> LENGTH: 1359
<212> TYPE: DNA
<213> ORGANISM: mouse
<220> FEATURE:
<221> NAME/KEY: unsure
<222> LOCATION: (644)...(644)

<400> SEQUENCE: 34
caaagaattc ggcacgagac cggcctcact atgtctgcca ttttcaattt tcagagtctg 60
ttgactgtaa tcttgctgct tatatgtaca tgtgcttata tccgatccct ggcacccagc 120
atcctggaca gaaataaaac tggactattg ggaatatttt ggaagtgtgc ccgaattggg 180
gaacgcaaga gtccttatgt cgccatatgc tgtatagtga tggccttcag catcctcttc 240
atacagtagc tttggaaact accagcatgt gcttgctatc agactgtaaa caaggacttg 300
cctccagaaa ataatgggaa gaatggttaa gccatttgtc tctgaacatg gaatgagata 360
aacttcaaga tgctgttctc tatttttatg ctattggacc aatgagctga atgaataatt 420
aagatgtaac agttcaatac acaggaatgt gattgtatcc atcaacctca gttctctcac 480
tccagtatta cattctgcaa atgtcattct gttgtgtcag gactgctttt cataaggttc 540
ttcgggcacg aagtagaaac ccagtggcaa attccaaggc tcctttgact agggcttcaa 600
aataatgtct tcacagaatg gtacctctag cgactgtcct attnttattg agaaaaaaac 660
ttgttctatt tttgttgttg ttactgttct tatggattgc attcatattt aaaccctttg 720
gattgctaac cagagtacct ctattcttgg caaattccgc agtttattac aggtgtttaa 780
agtattttaa acaaaactct gaatttcttt agttagccta agagttggct tctagtcaca 840
aagatacagc tgccacactg tgacgaagag caccttagaa agaaaagcag caagtgagcg 900
gtgagcaagt aagcaccgtg cagtcttcgt gcaagtaagc accgtgcagt cttcgttctc 960
tgtagtcttg tcttccaaat agaacgtcca tcgtagttac ccaaaggtgg tatttgtggt 1020
gttcttaatg cagtgcttta agtctagtgt atgttctgtc agcttgaact ggaatctctc 1080
ttgtaacttt gtaggttata aacatatctc atatctgctt tagtctgggt actatgctct 1140
aagtacattt cagctttgac acagaatgtg aatagacgaa tatcaaagga tacttacaag 1200
tttgtatcca acatttcttc aggttcagct gaaaatcagt tactgtttca aaacaaagag 1260
gaattaaatc ctagctgaaa actatacata gcatttatta attaattact gggtttaact 1320
gctcttttta aaagtttgaa aaaaaaaaaa aaaaactcg 1359

<210> SEQ ID NO 35
<211> LENGTH: 797
<212> TYPE: DNA
<213> ORGANISM: mouse

<400> SEQUENCE: 35
aattcggcac gaggctagtc gaatgtccgg gctgcggacg ctgctggggc tggggctgct 60
ggttgcgggc tcgcgcctgc cacgggtcat cagccagcag agtgtgtgtc gtgcaaggcc 120
catctggtgg ggaacacagc gccggggctc ggagaccatg gcgggcgctg cggtgaagta 180
cttaagtcag gaggaggctc aggccgtgga ccaagagctt tttaacgagt atcagttcag 240
cgtggatcaa ctcatggagc tggccgggtt gagctgtgcc acggctattg ccaaggctta 300

-continued

```
tccccccacg tctatgtcca agagtccccc gactgtcttg gtcatctgtg gccccggaaa    360

taacggaggg gatgggctgg tctgtgcgcg acacctcaaa ctttttggtt accagccaac    420

tatctattac cccaaaagac ctaacaagcc cctcttcact gggctagtga ctcagtgtca    480

gaaaatggac attcctttcc ttggtgaaat gcccccagag gatgggatgt agagaaggga    540

aaccctagcg gaatccaacc agacttactc atctcactga cggcacccaa gaagtctgca    600

actcacttta ctggccgata tcattacctt gggggtcgct ttgtaccacc tgctctagag    660

aagaagtacc agctgaacct gccatcttac cctgacacag agtgtgtcta ccgtctacag    720

taagggaggt gggtaggcag gattctcaat aaagacttgg tactttctgt cttgaaaaaa    780

aaaaaaaaaa aaactcg                                                    797
```

```
<210> SEQ ID NO 36
<211> LENGTH: 896
<212> TYPE: DNA
<213> ORGANISM: mouse

<400> SEQUENCE: 36

ttaaggtttt cagactttat ttcatggtat ttgacattga cacatactga gttagtaaca     60

agataccatg cagctccctc tagcctcgga tcaccgaagc aggaagaagg tcagactgcc    120

cccatcccag atttgcttag tttgtctccc aatgtgctgg actttaaaga cagggaatgg    180

agaagcagat ggatgcttca gtttcagtca tttttggctc tatagtgatc tctgccttcc    240

tgtacctgtc cttggctgga ccctgggcag taactgtcac tcagatgagg acgatcatca    300

ttacaatgga ccaactgagg gatgccctca tattagacca attaaaagtt gctgtgagtt    360

aaaccaggaa tgaccgcact tccacatcag aaatcaaaca aaatcaatgg ttgaagaaca    420

tggttaggag cctggctagg tatctttgag agatggatgc agctggctac tcaggcaggt    480

aagcaatgga ggtcagccac accctatcgt gatgcactcc ccatgttcag ggtaactgaa    540

gaagtgggta aggccagctg aaggccagtc agggcaactt agatgtagcc tggcttctac    600

ttccagcctc cggggacagg caaacacatt ttgggaagta agatgatgtc ccaattatta    660

tcagtttttt gatatcacag tattgtcaca gggagcactg gggtccaggg ctagcctggg    720

gtgaggctgg ccctcagcac acacaggaga gcagcttaag tgggacctaa aaaggaccca    780

atgttacttg gtttaatgaa ggccccctca accccaacag cccctcctgc tcagggacac    840

agttctcacc caattacaca ttaataacac acaaacagtg cctagcaatg ggccag        896
```

```
<210> SEQ ID NO 37
<211> LENGTH: 501
<212> TYPE: DNA
<213> ORGANISM: mouse

<400> SEQUENCE: 37

ctgcaggtcg acactagtgg atccaaagaa ttcggcacga gaatcatggc gccgtcgctg     60

tggaaggggc ttgtaggtgt cgggcttttt gccctagccc acgctgcctt ttcagctgcg    120

cagcatcgtt cttatatgcg actaacagaa aaggaagatg aatcattacc aatagatata    180

gttcttcaga cacttctggc ctttgcagtt acctgttatg gcatagttca tatcgcaggg    240

gagttcaaag acatggatgc cacttcagaa ttaaagaata agacatttga taccttaagg    300

aatcacccat ctttttatgt gtttaaccat cgtggtcgag tgctgttccg gccttcagat    360

gcaacaaatt cttcaaacct agatgcattg tcctctaata catcgttgaa gttacgaaag    420

tttgactcac tgcgccgtta agctttttac aaattaaata acaggacaga cacagaattg    480
```

-continued agtattggag tttggggtgt a 501

<210> SEQ ID NO 38
<211> LENGTH: 766
<212> TYPE: DNA
<213> ORGANISM: mouse

<400> SEQUENCE: 38
gcagcaccca gcgccaagcg caccaggcac cgcgacagac ggcaggagca cccatcgacg 60
ggcgtactgg agcgagccga gcagagcaga gagaggcgtg cttgaaaccg agaaccaagc 120
cgggcggcat cccccggccg ccgcacgcac aggccggcgc cctccttgcc tccctgctcc 180
ccaccgcgcc cctccggcca gcatgaggct cctggcggcc gcgctgctcc tgctgctcct 240
ggcgctgtgc gcctcgcgcg tggacgggtc caagtgtaag tgttcccgga aggggcccaa 300
gatccgctac agcgacgtga agaagctgga aatgaagcca aagtacccac actgcgagga 360
gaagatggtt atcgtcacca ccaaagagca tgtccaaggt accggggcca ggagcactgc 420
ctgcacccta agctgcagag caccaaacgc ttcatcaagt ggtacaatgc ctggaacgag 480
aagcgcaggg tctacgaaga atagggtgga cgatcatgga aagaaaaact ccaggccagt 540
tgagagactt cagcagagga ctttgcagat taaaataaaa gccctttctt tctcacaagc 600
ataagacaaa ttatatattg ctatgaagct cttcttacca gggtcagttt ttacatttta 660
tagctgtgtg tgaaaggctt ccagatgtga gatccagctc gcctgcgcac cagacttcat 720
tacaagtggc tttttgctgg gcggttggcg gggggcgggg ggacct 766

<210> SEQ ID NO 39
<211> LENGTH: 480
<212> TYPE: DNA
<213> ORGANISM: mouse

<400> SEQUENCE: 39
ggcacgagga agcctcttcc catggaagca cactctagga gagagaaggc ctctgggctc 60
cgcctggcct ggcattatga atgcagtggg gtcagtgtgt ggtggatgtg tgtactgggt 120
tggctttcct ttttagtttt tttacttttt agtttagttt gttcttttcc ttccccaata 180
aatcattctc acatgcttcc atgtttgttt ctgagaggtg ggggctcaaa tgtatagaaa 240
gtaggcccca gtccataagg aggtgtgaac acaccccctt actgcttatc acccatttga 300
caggaacgcc caggagggga gggggagggg aagaggtgag ttctgcacag tcggacattt 360
ctgttgcttt tgcatgttta atatagacgt tcctgtcgat ccttgggaga tcatggcctt 420
cagatatgca cacgaccttt gaattgtgcc tactaattat agcaggggac ttgggtaccc 480

<210> SEQ ID NO 40
<211> LENGTH: 962
<212> TYPE: DNA
<213> ORGANISM: mouse

<400> SEQUENCE: 40
ggcacgagat tagcggctcc tcagcccagc aaatcctcca ctcatcatgc ttcctcctgc 60
cattcatctc tctctcattc ccctgctctg catcctgatg agaaactgtt tggcttttaa 120
aaatgatgcc acagaaatcc tttattcaca tgtggttaaa cctgtcccgg cacaccccag 180
cagcaacagc accctgaatc aagccaggaa tggaggcagg catttcagta gcactggact 240
ggatcgaaac agtcgagttc aagtgggctg cagggaactg cggtccacca aatacatttc 300

-continued

```
ggacggccag tgcaccagca tcagccctct gaaggagctg gtgtgcgcgg gcgagtgctt    360

gcccctgccg gtgcttccca actggatcgg aggaggctac ggaacaaagt actggagccg    420

gaggagctct caggagtggc ggtgtgtcaa cgacaagacg cgcacccaga ggatccagct    480

gcagtgtcag gacggcagca cgcgcaccta caaaatcacc gtggtcacgg cgtgcaagtg    540

caagaggtac acccgtcagc acaacgagtc cagccacaac tttgaaagcg tgtcgccagc    600

caagcccgcc cagcaccaca gagagcggaa gagagccagc aaatccagca agcacagtct    660

gagctagacc tggactgact aggaagcatc tgctacccag atttgattgc ttggaagact    720

ctctctcgag cctgccattg ctctttcctc acttgaaagt atatgctttc tgctttgatc    780

aagcccagca ggctgtcctt ctctgggact agcttttcct ttgcaagtgt ctcaagatgt    840

aatgagtggt ttgcagtgaa agccaggcat cctgtagttt ccatcccctc cccatcccca    900

gtcatttctt taaaagcacc tgatgctgca ttctgttaca gtttaaaaaa aaaaaaaaaa    960

aa                                                                   962
```

<210> SEQ ID NO 41
<211> LENGTH: 794
<212> TYPE: DNA
<213> ORGANISM: mouse

<400> SEQUENCE: 41

```
ggcacgaggc tagtcgaatg tccgggctgc ggacgctgct ggggctgggg ctgctggttg     60

cgggctcgcg cctgccacgg gtcatcagcc agcagagtgt gtgtcgtgca aggcccatct    120

ggtggggaac acagcgccgg ggctcggaga ccatggcggg cgctgcggtg aagtacttaa    180

gtcaggagga ggctcaggcc gtggaccaag agctttttaa cgagtatcag ttcagcgtgg    240

atcaactcat ggagctggcc gggttgagct gtgccacggc tattgccaag gcttatcccc    300

ccacgtctat gtccaagagt cccccgactg tcttggtcat ctgtggcccc ggaaataacg    360

gaggggatgg gctggtctgt gcgcgacacc tcaaactttt tggttaccag ccaactatct    420

attaccccaa aagacctaac aagcccctct tcactgggct agtgactcag tgtcagaaaa    480

tggacattcc tttccttggt gaaatgcccc cagaggatgg gatgtagaga agggaaaccc    540

tagcggaatc caaccagact tactcatctc actgacggca cccaagaagt ctgcaactca    600

ctttactggc cgatatcatt accttggggg tcgctttgta ccacctgctc tagagaagaa    660

gtaccagctg aacctgccat cttaccctga cacagagtgt gtctaccgtc tacagtaagg    720

gaggtgggta ggcaggattc tcaataaaga cttggtactt tctgtcttga aaaaaaaaaa    780

aaaaaaaact cgag                                                      794
```

<210> SEQ ID NO 42
<211> LENGTH: 1152
<212> TYPE: DNA
<213> ORGANISM: mouse

<400> SEQUENCE: 42

```
ggcacgagct tctcagggcc tgccacccaa ataagtctgg ccctagcctc aactctctct     60

caggctgggc cacaggaagc tgctgactgg ccacttgaca ccctccccct aaagctaatg    120

tctgtgacta tagggaggtt agcacttttt ctaattggaa ttcttctctg tcctgtggcc    180

ccatccctca cccgctcttg gcctggacca gatacatgca gcctctttct ccagcacagc    240

ctttccctga gcctgaggtt agggcagagt ttagagggtg ggctaagtgt atgttttcat    300

gtatgcattc atgcctgtga gtgtgtggct tgctgtcgtg tcctctggga tcccaagcca    360
```

-continued cgcgggtctt ccctctgtag atgggtcctg ggttctatca cctgcttatt tatgtacgag 420
gttggggggt ggacccaggg tgggttgatt gtctctttgt aaggaagtat gtgtcggggg 480
tgacacgagg ctaagcccga gaaaccccgg gagacagcac tgcataagaa actggtttcc 540
magactgcag agggagctgc acttttgttt tgaccaaaaa caaaaaacaa aacaaaacaa 600
aaacaaaaca aaaataactc tgaagggcgg gaggataccc aagcctgatg cctgagagga 660
gtccctagac ttcagcaact ccgctgcgtg gcctgagccc agcgggaggg atggggagag 720
aattttttgg agtccgtgcc tgtggtgggc agtcctgagc cttcagctga agcagtgctt 780
tttggctgcc ctcacctcgc actacttgac cttgaggctc tgagtatctc ctgtgcacag 840
gagaagctcc tgcaccagaa agcaccaaar sccmtggcac cccatcttac tccactctcc 900
ccagggactc ccaggtggga actgctgtgg cagtgagctc agcccggaca gacactgcca 960
accctgtctc ctggcattgg gctccggctc tacctcccca agcagggcga ggccccgcct 1020
tctcagccta gcaccacctg tccccgagtc ttctcagctt gcccatcatt ctcggcgccc 1080
acacaggtga cagtcccaag tagataacct ccatgggaca agttgggtgt tgccttaccc 1140
gcctgcccag cc 1152

<210> SEQ ID NO 43
<211> LENGTH: 446
<212> TYPE: DNA
<213> ORGANISM: mouse

<400> SEQUENCE: 43
ggcacgagct tgagtctgga gtgctgcaaa taatagtatg cactatccct gcctggcatg 60
tttgtttgtt aatgtgcact ggtgttttgc ctggatgtgt atacttgtga agatgtcaga 120
actcctggag ctggagttag agacaatggt gagctgcctt gtggatgttg ggaattgaac 180
ccaggtcctc tggagaaata accagtgctc ttaaccacta agccatctca acagccccaa 240
attatttttt taataagttg cctcggtcat gttgtcttaa tcagagcgat agaaaagtaa 300
ctaatataga ttatttatga attcaggtgg cttaatggta tatgcatgaa ttagtagtaa 360
aacaagaact agggccagca agtggcttaa gggtgcctgc taaccatctc agccacctga 420
gttcagtctc caggaaccac acagtg 446

<210> SEQ ID NO 44
<211> LENGTH: 391
<212> TYPE: DNA
<213> ORGANISM: mouse

<400> SEQUENCE: 44
ggcacgagcc cacgtctatg ttcaccttcg ttgttctggt aatcaccatc gtcatctgtc 60
tctgccacgt ctgctttgga cacttcaaat acctcagtgc ccacaactac aagattgaac 120
acacagagac agatgccgtg agctccagaa gtaatggacg gccccccact gctggcgctg 180
tccccaaatc tgcgaaatac atcgctcagg tgctgcagga ctcagagggg gacggggacg 240
gagatggggc tcctgggagc tcaggcgatg agcccccatc gtcctcctcc caagacgagg 300
agttgctgat gcctcctgat ggcctcacgg acacagactt ccagtcatgc gaggacagcc 360
tcatagagaa tgagattcac cagtaagggg t 391

<210> SEQ ID NO 45
<211> LENGTH: 516
<212> TYPE: DNA

-continued

<213> ORGANISM: Rat

<400> SEQUENCE: 45
cctcctgtct ctgctgctac ttgtgaggcc tgcgcctgtg gtggcctact ctgtgtccct 60
cccggcctcc ttcctggagg aagtggcggg cagtggggaa gctgagggtt cttcagcctc 120
ttccccaagc ctgctgccgc cccggactcc agccttcagt cccacaccag ggaggaccca 180
gcccacagct ccggtcggcc ctgtgccacc caccaacctc ctggatggga tcgtggactt 240
cttccgccag tatgtgatgc tcattgcggt ggtgggctcg ctgacctttc tcatcatgtt 300
catagtctgc gcggcactca tcacgcgcca gaagcacaag gccacagcct actacccgtc 360
ctctttcccc gaaaagaagt atgtggacca gagagaccgg gctgggggc cccatgcctt 420 cagcgaggtc cctgacaggg cacctgacag ccggcaggaa gagggcctgg acttcttcca 480
gcagctccag gctgacattc tggcttgcta ctcaga 516

<210> SEQ ID NO 46
<211> LENGTH: 306
<212> TYPE: DNA
<213> ORGANISM: mouse

<400> SEQUENCE: 46
gtcaccagca aaggtggaaa caaattcttt gaaggactct gacagccctg ggtctccaag 60
gctgctggga ccagtcttag cctcttgtgg caagtggtag gaatgtgaat ctttgcgacc 120
agggggatca gaaatggggt ctcccatttc tggtgtctgc ccagtccttc caggtgggct 180
cttcgtagcc ctggggtgga ttttcctcct cttccacaga gatgcttttt ctctgcatac 240
catgtctgct ggtttcccaa aatctcccgc aaacccacac caccctccac tgaggctcag 300
ccccag 306

<210> SEQ ID NO 47
<211> LENGTH: 439
<212> TYPE: DNA
<213> ORGANISM: mouse

<400> SEQUENCE: 47
gaaaactcgc aggacgctca ctggacagct tgggcttttt tcagttgatt ttatggtttg 60
catctttctc tttctctttt tctgtttctt gttccccttt ccccttttcc tggtgagaaa 120
gcacatatta ctgagccatt gcaagcaatg ggaggggtcc acaatgacac acacacacac 180
acacacacac atacacatac acacaccccc gagacagtgc cagagctaac agcctacatg 240
tgtattttgg ccaaacttgg aaaataggtt tccttcttcg ttttgcttcc agccttttat 300
ttgcaagtga tcttccatgc agtatgaaac atgcagacag cactggagtg tggcaagagt 360
gagcttgccc cacaagtctc tcggggatgt tgtactcttg tgtgtgttta cagtatcatg 420
gctgttacat ctactggtc 439

<210> SEQ ID NO 48
<211> LENGTH: 159
<212> TYPE: DNA
<213> ORGANISM: mouse
<220> FEATURE:
<221> NAME/KEY: unsure
<222> LOCATION: (3)...(3)

<400> SEQUENCE: 48
cangtacgct cactggaaca gcttgggctt ttttcagttg attttatggt ttgcatcttt 60

-continued

```
ctctttctct ttttctgttt cttgttcccc tttccccttt tcctggtgag aaagcacata    120

ttactgagcc attgcaagca atgggagggg tccacaatg                           159


<210> SEQ ID NO 49
<211> LENGTH: 465
<212> TYPE: DNA
<213> ORGANISM: Rat

<400> SEQUENCE: 49

gtgccctccg ccgggtcggg atggagctgc ctgccgtgaa cttgaaggtt attctcctgg     60

ttcactggct gttgacaacc tggggctgct tggcgttctc aggctcctat gcttggggca    120

acttcactat cctggccctg ggtgctgtgg gctgtggccc agcgggactc tgttgatgcc    180

attggcatgt ttcttggtgg cttggttgcc accatcttcc tggacattat ctacattagc    240

atcttctact caagcgttgc cgttggggac actggccgct tcagtgccgg catggccatc    300

ttcagcttgc tgctgcaagc ccttctcctg ctgcctcgtc taccacatgc accgggcagc    360

gagggggtga gctcccgctc cgctcggatt tcttcggacc ttctcaggaa catagtgcct    420

accagacaat tgactcgtca gactcacctg cagacccccct tgcaa                   465


<210> SEQ ID NO 50
<211> LENGTH: 337
<212> TYPE: DNA
<213> ORGANISM: Rat
<220> FEATURE:
<221> NAME/KEY: unsure
<222> LOCATION: (42)...(42)
<221> NAME/KEY: unsure
<222> LOCATION: (52)...(52)
<221> NAME/KEY: unsure
<222> LOCATION: (55)...(55)
<221> NAME/KEY: unsure
<222> LOCATION: (62)...(62)
<221> NAME/KEY: unsure
<222> LOCATION: (76)...(76)
<221> NAME/KEY: unsure
<222> LOCATION: (144)...(144)
<221> NAME/KEY: unsure
<222> LOCATION: (171)...(171)
<221> NAME/KEY: unsure
<222> LOCATION: (273)...(273)
<221> NAME/KEY: unsure
<222> LOCATION: (319)...(319)
<221> NAME/KEY: unsure
<222> LOCATION: (325)...(325)

<400> SEQUENCE: 50

ctcgtgccga aatcggcaga gcgtcgctcc tgtgctgtgg gnctaagctg gncgnctgtg     60

gnatcgtcct cagcgnctgg ggagtgatca tgttgataat gctcgggata tttttcaatg    120

tccattctgc tgtggtaatt tagnatgtcc ccttcacaga gaaagatttt nagaacggcc    180

ctcagaacat atacaacctg tacgagcaag tcagctacaa ctgtttcatc gccgcgggcc    240

tctacctcct cctcgggggc ttctccttct gcnaagttcg tctcaataag cgcaaggaat    300

acatggtgcg ctagagcgna gtccnactct ccccatt                             337


<210> SEQ ID NO 51
<211> LENGTH: 371
<212> TYPE: DNA
<213> ORGANISM: Rat
<220> FEATURE:
<221> NAME/KEY: unsure
<222> LOCATION: (80)...(80)
<221> NAME/KEY: unsure
<222> LOCATION: (312)...(312)
```

-continued

<221> NAME/KEY: unsure
<222> LOCATION: (319)...(319)
<221> NAME/KEY: unsure
<222> LOCATION: (353)...(354)

<400> SEQUENCE: 51
gatgcgccct ggagccgact gggctgcggt ctgcgctttg tggccttcct ggcgaccgag 60
ctgctccctc ccttccagcn ggcgaattca gcccgacgag ctgtggcttt accggaaccc 120
gtacgtgaag gcggaatact tccccaccgg ccccatgttt gtcattgcct ttctcacccc 180
actgtccctg atcttcttcg ccaagtttct gaggaaagct gacgccgacc gacagcgagc 240
aagcctgcct cgctgccagc cttgccctag cgctaaatgg tgtctttacc aacatcataa 300
gactgatagt gngcaaggnc acgcccaaat tgcttctacc gagtgttccc cgnncgggat 360
tgcccattct t 371

<210> SEQ ID NO 52
<211> LENGTH: 228
<212> TYPE: DNA
<213> ORGANISM: Rat

<400> SEQUENCE: 52
ttccgcgggc gtcatgacgg ctgcggtgtt ctttggttgc gccttcatcg ccttcgggcc 60
cgcgctctcc ctttacgtct tcaccatcgc cactgatcct ttgcgagtca tcttcctcat 120
cgccggtgcc ttcttctggt tggtgtctct gctgctttcg tctgttttct ggttcctagt 180
gagagtcatc actgacaaca gagatggacc agtacagaat tacctgct 228

<210> SEQ ID NO 53
<211> LENGTH: 361
<212> TYPE: DNA
<213> ORGANISM: Human

<400> SEQUENCE: 53
cgtggacact gctgaggaat gataccgagt ggtaggtcag aagaagatgc tgtgaacacc 60
aggactttaa tcttatgctt gaaaatgcca gatgttgttc gggggacaac ttgtatcttt 120
ctagcagcag atctgtagtt tgtatagcct caacaacaat tttaaataag atggagaata 180
aattattgag gggactaggc tatatgcatt tgccttcatc cacccatgtt tattaagaat 240
cattgtgctt aataatacca agactaagca ccataaccaa gaaatactaa tgtaaagatt 300
gtttcttgtt tcaggaatgg ttaattcttc aacgttggta tgataatgat aacttgtttt 360
g 361

<210> SEQ ID NO 54
<211> LENGTH: 403
<212> TYPE: DNA
<213> ORGANISM: Human
<220> FEATURE:
<221> NAME/KEY: unsure
<222> LOCATION: (9)...(9)
<221> NAME/KEY: unsure
<222> LOCATION: (28)...(29)
<221> NAME/KEY: unsure
<222> LOCATION: (37)...(38)
<221> NAME/KEY: unsure
<222> LOCATION: (63)...(63)
<221> NAME/KEY: unsure
<222> LOCATION: (380)...(380)

<400> SEQUENCE: 54
ttgcgtggnc gcggccgagg tgtctgtnnc caggagnnct tcggcggctg ttgtgtcagt 60

-continued

```
ggnctgatcg cgatggggac aaaggcgcaa gtcgagagga aactgttgtg tctcttcata    120

ttggcgatcc tgttgtgctc cctggcattg ggcagtgtta cagtgcactc ttctgaacct    180

gaagtcagaa ttcctgagaa taatcctgtg aagttgtcct gtgcctactc gggcttttct    240

tctccccgtg tggagtggaa gtttgaccaa ggagacacca ccagactcgt ttgctataat    300

aacaagatca cagcttccta tgaggaccgg gtgaccttct tgccaactgg tatcaccttc    360

aagtccgtga cacgggaagn cactgggaca tacacttgta tgg                      403


<210> SEQ ID NO 55
<211> LENGTH: 413
<212> TYPE: DNA
<213> ORGANISM: Human

<400> SEQUENCE: 55

tagcgtggtc gcggccgagg tacgactcgg tgctcgccct gtccgcggcc ttgcaggcca     60

ctcgagccct aatggtggtc tccctggtgc tgggcttcct ggccatgttt gtggccacga    120

tgggcatgaa gtgcacgcgc tgtgggggag acgacaaagt gaagaaggcc cgtatagcca    180

tgggtggagg cataattttc atcgtggcag gtcttgccgc cttggtagct tgctcctggt    240

atggccatca gattgtcaca gacttttata accctttgat ccctaccaac attaagtatg    300

agtttggccc tgccatcttt attggctggg cagggtctgc cctagtcatc ctgggaggtg    360

cactgtctcc tgttcctgtc ctggggataa gagcagggct gggtacctgc ccg            413


<210> SEQ ID NO 56
<211> LENGTH: 452
<212> TYPE: DNA
<213> ORGANISM: Human

<400> SEQUENCE: 56

ttcgagcggc cgcccgggca ggttgaaact ttagaaagaa gagccgggag gatgtattgg     60

ttgttaggaa aatgtaggct accagtagaa aatgacattc tctattaata agatctgagg    120

tgcgacacac ataattgtcc caatttttaa gattgatggg gagcatgaag catttttta    180

atgtgttggc aggccccatt aaatgcataa actgcatagg actcatgtgg tctgaatgta    240

ttttagggct ttctgggaat tgtcttgaca gagaacctca gctggacaaa gcagccttga    300

tctgagtgag ctaactgaca caatgaaact gtcaggcatg tttctgctcc tctctctggc    360

tcttttctgc tttttaacag gtgtcttcag tcagggagga caggttgact gtggtgagtc    420

caggacacca aggcctactg cactcgggaa cc                                    452


<210> SEQ ID NO 57
<211> LENGTH: 190
<212> TYPE: DNA
<213> ORGANISM: Rat
<220> FEATURE:
<221> NAME/KEY: unsure
<222> LOCATION: (11)...(11)

<400> SEQUENCE: 57

ttcgcggccc ngtcgacggc attggcaaat agtcaaacct gggaagtaaa aagcaaaacc     60

aaaaacaaaa ccaaagaaac aaactaaaac aaaacaagaa aaaccaacat ttcttcaatt    120

cagtgtgcaa catatataaa acagaaatac taactctaca ggcagtatgt cgacgcggcc    180

gcgtattcgg                                                            190
```

-continued

<210> SEQ ID NO 58
<211> LENGTH: 413
<212> TYPE: DNA
<213> ORGANISM: mouse

<400> SEQUENCE: 58
ctgcaacaag gctgttggtt cctctccaat gggctccagt gaagggctcc tgggcctggg 60
ccctgggccc aatggtcaca gtcacctgct gaagacccca ctgggtggcc agaaacgcag 120
tttttcccac ctgctgccct cacctgagcc cagcccagag ggcagctacg tgggccagca 180
ctcccagggc ctcggcggcc actacgcgga ctcctacctg aagcggaaga ggattttcta 240
aggggtcgac accagagatg ctccaagggc ctgcaccaag ttgcttttgg gttttttctg 300
gtatttgtgt tttctgggat tttattttta ttattttttt taatgtcctt tctttgggta 360
atagagaaat ctctgcaaaa gactttgctg accaaccagc tggagctcaa gga 413

<210> SEQ ID NO 59
<211> LENGTH: 325
<212> TYPE: DNA
<213> ORGANISM: mouse
<220> FEATURE:
<221> NAME/KEY: unsure
<222> LOCATION: (213)...(213)
<221> NAME/KEY: unsure
<222> LOCATION: (223)...(223)
<221> NAME/KEY: unsure
<222> LOCATION: (227)...(227)
<221> NAME/KEY: unsure
<222> LOCATION: (243)...(243)

<400> SEQUENCE: 59
ggtatcaccc aggcccactt atccatctac agcgagtagt atggcggcct tccttgtaac 60
aggctttttc ttttctctct tcgtggtgct tgggatggaa cccagggctt tgtttaggcc 120
tgacaaggct ctgcccctga gctgtgccaa gcccacctcc ctctgtgtac aaagctcctt 180
tcttgggtga ccaacatctt cctgtctttg agnaaccagg ggncagnatg ggagccaccc 240
agnagttaat taaaccaggt tcatcgggag tttgctgaaa tgttaagcat actctgttct 300
agagagggag tgaagaaagg ggcca 325

<210> SEQ ID NO 60
<211> LENGTH: 372
<212> TYPE: DNA
<213> ORGANISM: mouse

<400> SEQUENCE: 60
ggccagcagg accgcggtca tgagcctctg caggtgtcaa caaggctcaa ggagcaggat 60
ggatctcgat gtggttaaca tgtttgtgat tgcgggtggg accctggcca ttccaatcct 120
ggcatttgtt gcgtctttcc tcctgtggcc ttcagcactg ataagaatct attattggta 180
ctggcggagg acactgggca tgcaagttcg ctacgcacac catgaggact atcagttctg 240
ttactccttc cggggcaggc caggacacaa gccatccatc cttatgctcc atggattctc 300
cgcacacaaa ggacatgtgg ctcagcgtgg ccaagttcct tcccgaaaga acctgcactt 360
tggctgtgtg ga 372

<210> SEQ ID NO 61
<211> LENGTH: 363
<212> TYPE: DNA
<213> ORGANISM: mouse
<220> FEATURE:
<221> NAME/KEY: unsure -continued

<222> LOCATION: (15)...(15)

<400> SEQUENCE: 61
gggcgcgcag gcggnaccgg tggcggcggg gctgctgctg gctaattggc acaggactgc 60
gggccgcgac atggactgtc ctgtgcagcc cgaattccag cctcgttgta gccaggcaca 120
ccaagagctt tccaccaaag aagcccctcc aagcactgac catgtctatt atggaccaca 180
gccccaccac cggggtggta acggtcattg tcatcctcat cgccatagct gccctggggg 240
gcttgatcct gggctgctgg tgctacctgc ggctgcagcg catcagccag tcagaggatg 300
aggagagcat cgtgggtgat ggcgagacaa aggagccctt ttactggtgc agtactctgc 360
taa 363

<210> SEQ ID NO 62
<211> LENGTH: 399
<212> TYPE: DNA
<213> ORGANISM: mouse

<400> SEQUENCE: 62
aagggtcctg aagtcagttg ttgcatcaaa tacttcattt ttggcttcaa tgtcatattt 60
tggtttttgg gaataacgtt tcttggaatc ggactgtggg cgtggaatga aaaaggtgtc 120
ctctccaaca tctcgtccat caccgacctc ggtggctttg acccagtgtg gcttttcctc 180
tgagtggcca gcccgagcct gagctctgtc aatgacatcc aaggagaaaa tgaggttaat 240
gagagacatt aattaaacac tccctcaccc caccgcacca aaccagttgg gttcttctga 300
tattctggaa tactctgggc tatgttttat gtttatttct tttttaatcg gttgtatttt 360
ggtctttttt tttcttcttc tttttctttt gctcccaaa 399

<210> SEQ ID NO 63
<211> LENGTH: 399
<212> TYPE: DNA
<213> ORGANISM: mouse
<220> FEATURE:
<221> NAME/KEY: unsure
<222> LOCATION: (192)...(192)
<221> NAME/KEY: unsure
<222> LOCATION: (311)...(311)

<400> SEQUENCE: 63
caaagcccac tgtaggctcc gctgaggtag cgattgctgg atttctggtc atctgcatca 60
tagtggtctt aaccatcctg ggctactgtt tcttcaagaa ccaaagaaag gaattccaca 120
gtcccctgca ccacccacct cccacaccag ccagctccac tgtttccacc acagaggaca 180
cagagcacct gntctataat cacacaaccc agcctctctg agcctgggac tcttgccagt 240
cttaccaggt cctgcttgcc aagacagaag ctagaacctg gaaaaacttg gggaccagac 300
tcttcctacc nctttcctgg gcatacttac gctgtctcag aagacagatc tctgggcctc 360
tcgcaggagt ctcagctgca ctcaggccag ttcctgggg 399

<210> SEQ ID NO 64
<211> LENGTH: 2481
<212> TYPE: DNA
<213> ORGANISM: Rat

<400> SEQUENCE: 64
gaactgtatc tggatgggaa ccagtttaca ctggtcccga aggaactctc caactacaaa 60
catttaacac ttatagactt aagtaacaac agaataagca ccctttccaa ccaaagcttc 120

-continued

```
agcaacatga cccaacttct caccttaatt ctcagttaca accgtctgag atgtatccct    180
ccacggacct ttgatggatt gaaatctctt cgtttactgt ctctacatgg aaatgacatt    240
tctgtcgtgc ctgaaggtgc ctttggtgac ctttcagcct tgtcacactt agcaattgga    300
gccaaccctc tttactgtga ttgtaacatg cagtggttat ccgactgggt gaagtcggaa    360
tataaggaac ctggaattgc ccgctgtgcc ggtcccggag aaatggcaga taaattgtta    420
ctcacaactc cctccaaaaa ttttacatgt caaggtcctg tggatgttac tattcaagcc    480
aagtgtaacc cctgcttgtc aaatccatgt aaaaatgatg gcacctgtaa caatgacccg    540
gtggattttt atcgatgcac ctgcccatat ggtttcaagg gccaggactg tgatgtcccc    600
attcatgcct gtacaagtaa tccatgtaaa catggaggaa cttgccattt aaaaccaagg    660
agagaaacat ggatttggtg tacttgtgct gatgggtttg aaggagaaag ctgtgacatc    720
aatattgatg attgcgaaga taatgattgt gaaaataatt ctacatgcgt tgatggaatt    780
aacaactaca cgtgtctttg cccaccggaa tacacaggcg aactgtgtga ggaaaaactg    840
gacttctgtg cacaagacct gaatccctgc cagcatgact ccaagtgcat cctgacgcca    900
aagggattca agtgtgactg cactccggga tacattggtg agcactgtga catcgacttt    960
gatgactgcc aagataacaa gtgcaaaaac ggtgctcatt gcacagatgc agtgaacgga   1020
tacacatgtg tctgtcctga aggctacagt ggcttgttct gtgagttttc tccacccatg   1080
gtcttccttc gcaccagccc ctgtgataat tttgattgtc agaatggagc ccagtgtatc   1140
atcagggtga atgaaccaat atgccagtgt ttgcctggct acttgggaga gaagtgtgag   1200
aaattggtca gtgtgtcaat tttggtaaac aaagagtcct atcttcagat tccttcagcc   1260
aaggttcgac ctcagacaaa catcacactt cagattgcca cagatgaaga cagcggcatc   1320
ctcttgtaca agggtgacaa ggaccacatt gctgtggaat ctatcgaggg cattcgagcc   1380
agctatgaca ccggctctca cccggcttct gccatttaca gtgtggagac aatcaatgat   1440
ggaaacttcc acattgtaga gctactgacc ctggattcga gtctttccct ctctgtggat   1500
ggaggaagcc ctaaaatcat caccaatttg tcaaaacaat ctactctgaa tttcgactct   1560
ccactttacg taggaggtat gcctgggaaa aataacgtgg cttcgctgcg ccaggcccct   1620
gggcagaacg gcaccagctt ccatggctgt atccggaacc tttacattaa cagtgaactg   1680
caggacttcc ggaaagtgcc tatgcaaacc ggaattctgc ctggctgtga accatgccac   1740
aagaaagtgt gtgcccatgg cacatgccag cccagcagcc aatcaggctt cacctgtgaa   1800
tgtgaggaag ggtggatggg gcccctctgt gaccagagaa ccaatgatcc ctgtctcgga   1860
aacaaatgtg tacatgggac ctgcttgccc atcaacgcct tctcctacag ctgcaagtgc   1920
ctggagggcc acggcggggt cctctgtgat gaagaagaag atctgtttaa ccccctgcca   1980
ggtgatcaag tgcaagcacg ggaagtgcag gctctctggg ctcgggcagc cctattgtgg   2040
atgcagcagt ggattcaccg gggacagctg acacagagaa tttcttgtcg aggggaacgg   2100
ataagggatt attaccaaag cagcagggta cgctgcctgt caaacgacta gaagtatctc   2160
gcttggagtg cagaggcggg tgtgctgggg ggcagtgctg tggacctctg agaagcaaga   2220
ggcggaaata ctctttcgaa tgcacagatg gatcttcatt tgtggacgag gtcgagaagg   2280
tggtgaagtg cggctgcacg agatgtgcct cctaagtgca gctcgagaag cttctgtctt   2340
tggcgaaggt tgtacacttc ttgaccatgt tggactaatt catgcttcat aatggaaata   2400
tttgaaatat attgtaaaat acagaacaga cttatttta ttatgataat aaagaattgt    2460
ctgcatttgg aaaaaaaaaa a                                             2481
```

-continued

<210> SEQ ID NO 65
<211> LENGTH: 3008
<212> TYPE: DNA
<213> ORGANISM: mouse
<220> FEATURE:
<221> NAME/KEY: unsure
<222> LOCATION: (1469)...(1469)
<221> NAME/KEY: unsure
<222> LOCATION: (1567)...(1567)

<400> SEQUENCE: 65

```
tagacgggag cctgtggcta caagccactc agcctgatga cgccggccac tatacctgtg     60
ttcccagcaa tggctttctg catccaccgt cagcttctgc ctatctcact gtgctctacc    120
cagcccaggt gacagtcatg cctcccgaga cacccctgcc cactggcatg cgtggggtga    180
tccggtgtcc ggttcgtgct aatcccccac tactgtttgt cacctggacc aaagacggac    240
aggccttgca gctggacaag ttccctggct ggtccctggg cccagaaggt tccctcatca    300
ttgcccttgg gaatgaggat gccttgggag aatactcctg cacccctac aacagtcttg    360
gtactgctgg accctcccct gtgacccggg tgctgctcaa ggctccccg gcttttatag    420
accagcccaa ggaagaatat ttccaagaag tagggcggga gctactcatc ccgtgctccg    480
cccggggaga ccctcctcct attgtctctt gggccaaggt gggccggggg ctgcagggcc    540
aggcccaggt ggacagcaac aacagcctcg tccttcgacc cctgaccaag gaggcccagg    600
gacgatggga atgcagtgcc agcaatgctg tagcccgtgt gaccacttcc accaatgtat    660
atgtgctagg caccagcccc catgtcgtca ccaatgtgtc tgtggtacct ttacccaagg    720
gtgccaatgt ctcttgggag cctggctttg atggtggcta tctgcagaga ttcagtgtct    780
ggtataccc actagccaag cgtcctgacc gagcccacca tgactgggta tctctggctg    840
tgcctatcgg ggctacacac ctcctagtgc cagggctgca ggctcacgcg cagtatcagt    900
tcagtgtcct tgctcagaat aagctgggca gtgggccctt cagtgagatt gtcctgtcta    960
taccagaagg gcttcctacc acaccggctg cccctgggct gcctgcaacc aggagcagag   1020
tgtgagcctg acttcccacg tggagagaag atcagaggcg gatcctggcg cagacgtttt   1080
cggtggcgtc gggcagccct gcgccgattc atcaggcagg cagctaggat gctcacaagg   1140
accgccacgc ccaagaagca gactccaccc acaacaccag ccaatacagg ctggggcagg   1200
agacctggta gctgtgtgcg ggaggggtac acctccaggc cggaagtgga gatgttggct   1260
acgttgctgg ggtcactgac gtagctatca gcgaaggcca cgaggcgaaa ctcatagaga   1320
acgtccttga tgaggccagg caccagcagc tggatttctg tgcccgccac accttggtcc   1380
aggatctccc agccttggga gccttgccgt ccctccagga tgtagccatc cagcctccca   1440
gggatgagtt ctgggggatc cctctgatna tctctccacg tgggaagtca ggctcacact   1500
ctgctcctgg ttcaggcagc cctgacagcg tgaccaagtt caagctccaa ggctccccag   1560
ttcccancct acgccagagt ctgctctggg gggagcctgc tcgaccgcct agccctcacc   1620
cggattctcc acttggccgg ggacccttac cattagagcc catttgcagg ggcccagatg   1680
ggcgctttgt gatgggaccc actgtggccc cctcacaaga aaagttatgt ctggagcgcc   1740
cagaacctcg gacctcagct aaacgcttgg cccagtcctt tgactgtagc agtagcagcc   1800
ccagtggggt cccacaaccc ctctgcatta cagacatcag ccccgtgggg cagcctcttg   1860
cagccgtgcc tagcccccta ccaggtccag gacccctgct ccagtatctg agcctaccct   1920
tcttccgaga gatgaatgtg gacggggact ggccacctct tgaggagccc acgcctgctt   1980
```

-continued

```
cggcttcaaa attcatggat agtcaagccc tgccccacct atctttcctt ccaccaccag   2040

actcacctcc tgcaaatctc agggcaagtg cttcctggga cactgatggg ggtcggggtc   2100

tcctcagagc cccctttacac agctttggct gattggactc tgagggagcg ggtcttgccg   2160

ggccttcttt ctgctgcccc tcgtggtagc ctcaccagcc agagcatggg aggggcaagc   2220

gcctccttcc tgcgccctcc ctcacagccc cctccgcagg ggaagctacc tcagtccact   2280

ccaggagaca caaagcagct ggggccagtg gcccccgaaa ggtggccccg caagggaaca   2340

tgtggtgaca gtcacaaaaa ggaggaacca cctctgtgga tgagaactat gaatgggatt   2400

cggaattccc aggggacatg gagctgctag agacctggca cccaggcttg gccagttctc   2460

ggacccatcc tgaacttgag ccagagttag gtgtcaagac tccagaggag agctgtctcc   2520

tgaacccaac ccacgctgcc ggccccgagg cccgctgtgc tgcccttcgg gaggaattcc   2580

tagctttccg cagacgcagg gatgctacca gggcccggct accagcctat cagcagtcca   2640

tctcttaccc tgaacaggct actctgctat gagcccgctt agtgtgaaac taagaaaggc   2700

ttatatggat ttgcaaagga gtccaagact ttggctccaa gctggggtac tgcccctacc   2760

tctctgtgtc tcggtggcct ggtggtaggc ttgagtgagc ttggtataga gttggatgta   2820

ctgactcttt aattgagttt gggagctgaa caggaatgtg tgtgtgtgtg tgtgtgtgtg   2880

tgtgtgtgtg tgtgtgcgcg cgcaagcgca agcgcgagtt cgaaagtggt gtttatggtg   2940

tgggtgcagg tttttttttt ttaaaaaaca ggtggataat aaatgtttgg aaccgttaaa   3000

aaaaaaaa                                                            3008
```

```
<210> SEQ ID NO 66
<211> LENGTH: 1888
<212> TYPE: DNA
<213> ORGANISM: mouse
<220> FEATURE:
<221> NAME/KEY: unsure
<222> LOCATION: (1690)...(1690)
<221> NAME/KEY: unsure
<222> LOCATION: (1755)...(1755)
<221> NAME/KEY: unsure
<222> LOCATION: (1864)...(1864)

<400> SEQUENCE: 66

aaagtggagg gcgagggccg gggccggtgg gctctggggc tgctgcgcac cttcgacgcc     60

ggcgaattcg caggctggga gaaggtgggc tcgggcggct tcgggcaggt gtacaaggtg    120

cgccatgtgc actggaagac gtggctcgcg atcaagtgct cgcccagtct gcacgtcgac    180

gacagggaac gaatggagct cctggaggaa gctaagaaga tggagatggc caagttccga    240

tacattctac ctgtgtacgg catatgccag gaacctgtcg gcttggtcat ggagtacatg    300

gagacaggct ccctggagaa gctgctggcc tcagagccat tgccttggga cctgcgcttt    360

cgcatcgtgc acgagacagc cgtgggcatg aacttcctgc attgcatgtc tccgccactg    420

ctgcacctag acctgaagcc agcgaacatc ttgctggatg cccactacca aatgtcaaga    480

tttcttgact ttgggctggc caagtgcaat ggcatgtccc actctcatga cctcagcatg    540

gatggcctgt ttggtacaat cggctacctc cctccagagc gaattcgtga gaagagccgc    600

ttgtttgaca ccaaacatga tgtatacagc ttcgccattg tgatctgggg tgtgcttaca    660

cagaataatc catttgcaga tgaaaagaac atcctacaca tcatgatgaa agtggtaaag    720

ggccaccgcc cagagctgcc acccatctgc agaccccggc cgcgtgcctg tgccagcctg    780

atagggctca tgcaacggtg ctggcatgca gacccacagg tgcggcccac cttccaagaa    840
```

-continued

```
attacctctg aaacagaaga cctttgtgag aagcctgatg aggaggtgaa agacctggct    900
catgagccag gcgagaaaag ctctctagag tccaagagtg aggccaggcc cgagtcctca    960
cgcctcaagc gcgcctctgc tccccccttc gataacgact gcagtctctc cgagttgctg   1020
tcacagttgg actctgggat cttcccaaga ctcttgaaag gccccgaaga gctcagccga   1080
agttcctctg aatgcaagct cccatcgtcc agcagtggca agaggctctc ggggggtgtcc   1140
tcagtggact cagccttttc ctccagagga tcgctgtcac tgtcttttga gcgggaagct   1200
tcaacaggcg acctgggccc cacagacatc cagaagaaga agctagtgga tgccatcata   1260
tcaggggaca ccagcaggct gatgaagatc ctacagcccc aagatgtgga cttggttcta   1320
gacagcagtg ccagcctgct gcacctggct gtggaggccg gacaggagga gtgtgtcaag   1380
tggctgctgc ttaacaatgc caaccccaac ctgaccaaca ggaagggctc tacaccactg   1440
catatggctg tggagcggaa gggacgtgga attgtggagc tactgctagc ccggaagacc   1500
agtgtcaatg ccaaggatga agaccagtgg actgccctgc actttgcagc ccaaaatggg   1560
gatgaaggcc agcacaaggc tgctgctaga gaagaatgct tctgtcaatg aggtggactt   1620
tgagggccga acacccatgc atgtagcctg ccagcatgga caggagaaca ttgtgcgcac   1680
cctgctccgn cgtggtgtgg atgtgggcct gcagggaaag gatgcctggt tgcctctgca   1740
ctatgctgcc tgcanggcca ccttcccatt gttaagctgc tagccaagca gcctggggtg   1800
agtgtgaatg cccagacact aacgggagga caccctgacc tgctgttcaa aggggcattt   1860
accngtggct cgcattctca ttgacctg                                      1888
```

<210> SEQ ID NO 67
<211> LENGTH: 1260
<212> TYPE: DNA
<213> ORGANISM: Rat

<400> SEQUENCE: 67

```
cccccagtcg ctttgggtat cagatggatg aaggcaacca gtgtgtggat gtggacgagt     60
gtgcgacaga ttcacaccag tgcaacccta cccagatctg tatcaacacg gaaggagggt    120
acacctgctc ctgcactgat gggtactggc ttctggaagg gcagtgccta gatattgatg    180
aatgtcgcta tggttactgc cagcagctct gtgcgaatgt tcctggatcc tattcctgta    240
cgtgtaaccc tggcttcacc ctcaacgatg atggaaggtc ttgccaagat gtgaacgagt    300
gtgaaactga gaacccctgt gttcagacct gcgtcaacac ctatggttct ttcatctgcc    360
gctgtgaccc akgatatgaa ctggaggaag atggcattca ctgcartgat atggatgagt    420
gcarcttctc cgagttcctc tgtcaacatg agtgtgtgaa ccagccgggc tcatacttct    480
gctcatgccc tccaggctwc ktcttgttgg aagataaccg aagctgccag gatatcaatg    540
aatgtgagcm ccggaaccac acatgcactc ccctgcagac ttgctacaat ctgcaagggg    600
gcttcaaatg tatcgacccc atcgtctgcg aggagcctta tctgctgatt ggggataacc    660
gctgtatgtg ccctgctgag aatactggct gcagggacca gccattcacc atcttgtttc    720
gggacatgga tgtggtatca ggacgctctg ttcctgctga catcttccag atgcaagcaa    780
cgacccgata ccctggcgcc tattacattt tccagatcaa atctgggaac gagggtcgag    840
agttctacat gcggcaaaca gggcctatca gtgccaccct ggtgatgaca cgccccatca    900
aagggcctcg ggacatccag ctggacttgg agatgatcac cgtcaacact gtcatcaact    960
tcagaggcag ctccgtgatc cgactgcgga tatacgtgtc ccagtatccg ttctgagcct   1020
```

-continued

```
cgggttaagg cctctgacac tgccttttac cacgccgagg gacaggagga gagaagaacc   1080

ccaacgaggg acaggaggag agaagaaacc agcaagaatg agagcgagac agacattgca   1140

cctttcctgc tgaacatctc cctggggcat cagcctagca tcctgacccc tacctgtact   1200

atcgcaaact gtcactctga aggacaccat gccccagttc ctatgatgca gtagtatcca   1260
```

<210> SEQ ID NO 68
<211> LENGTH: 1729
<212> TYPE: DNA
<213> ORGANISM: mouse

<400> SEQUENCE: 68

```
gaattcggca cgagcagaat atggctctgg gggttctgat agcagtctgc ctcttgttca     60

aagcaatgaa ggcagcactg agcgaagaag cagaggtgat ccctcctagc acagcacagc    120

agagcaactg gacatttaac aacaccgaag ctgactacat agaagaacct gtagctctga    180

agttctctca tccttgtctg gaagaccata atagttactg cattaatgga gcatgtgcat    240

tccaccatga gctgaagcaa gccatttgca gatgctttac tggttatacg ggacaacgat    300

gtgagcattt gaccctaact tcgtatgctg tggattctta tgaaaaatac attgcgattg    360

ggattggcgt cggattgcta attagtgctt ttcttgctgt cttctattgc tacataagaa    420

aaaggtgtat aaatctgaaa tcaccctaca tcatctgctc tggagggagc ccattgtgag    480

accttataag acatagtcat caagccattt gtcaaaagcc acagggaatc caatggagat    540

ctttggatga tacaaaatgt gataagctaa cttgaaaata atggtggttt gggtcacaat    600

gcagtaactg accattggtt cttagctttg gtcatcgttg ggtgccatgg aagctatggg    660

aatgagctac agtaacagaa gccaagttca ctacccttct ttgggtttgc tgttgggtgg    720

ttgttgtcac tgcaggaaga tttgttctat acttctgacc atctcagatg tgaattttca    780

ttttaattgt tttctactac acatcaatca agtccaagta atgccatttc cgggttcttc    840

gggcactcaa cattttgggc cacccgcctc gatggaccta atagcaaagt atctgtcctt    900

atggaatttc agggaatttg gtatcaattt ttagatgaaa acagtgaatg tctcagctcc    960

ttgagtgaac caaagatgca ttacacctaa accactaaaa gaaaatggaa tatccaaggc   1020

agcataaatc ctacccagct ggtgacaaca gtttgcaaac ttcattcatg tagtttggaa   1080

gaagcagata aattcctgag gactgaaagt cacctggaca gcagatccag agcaggcaaa   1140

ggtagctggt tcctatatcg accataaagc ctgtgtgggc tcatctgtcc cctgatgttt   1200

ttgcctatca tctcagcctt acattggaag actcacactt ggtatccatc gcttgaactg   1260

aagttcgaca attcacctaa tgactaaaag cttacaattg ttcccaaaat atataggaac   1320

aacagcatgt ggaatgtaac cattttttga cgtgttgata gcatatttgc acatgggtta   1380

aaaaaagaaa cagtcgtaga aatacttatt agggaatcag tatccctcct tggaattgct   1440

tctgctacat gattcaatct tgggcaagtc tcttatattc tttgtggttt ggttccattc   1500

tctacaagac ccatgcagtt ccaaaattga actctaatag aactaaaaaa tacctcctat   1560

aactgcatgg caggcaagat tatcctcaat gcttccatcc tcagccccgt ttctaaccct   1620

caaataccca cgaatattat ccttactata tattgtcatg ttcagtttgt aaaataataa   1680

cttattttga aaagaaataa aaaatgaaat tacaaagcaa aaaaaaaaa               1729
```

<210> SEQ ID NO 69
<211> LENGTH: 355
<212> TYPE: DNA
<213> ORGANISM: Rat

-continued

<220> FEATURE:
<221> NAME/KEY: unsure
<222> LOCATION: (35)...(35)

<400> SEQUENCE: 69
ctcgtgccgc aattcggcac gaggattcgc tatantgcat atgaccgagc ctacaaccgg 60
gccagctgca agttcattgt agaagtacaa gtgagacgct gtcctattct gaaaccacca 120
cagcatggct acctcacctg cagctcagcg ggggacaact atggtgcgat ctgtgaatac 180
cactgcgatg gtggttatga acgccaaggg accccttccc gagtctgtca gtcaagtcga 240
cagtggtctg gatcaccacc tgtctgtact cctatgaaga ttaatgtcaa tgttaactca 300
gctgctggcc tcctggatca gttctatgag aaacagcgac tcctcatagt ctcag 355

<210> SEQ ID NO 70
<211> LENGTH: 1421
<212> TYPE: DNA
<213> ORGANISM: Human

<400> SEQUENCE: 70
gattagcgtg gtcgcggccg aggtgtctgt tcccaggagt ccttcggcgg ctgttgtgtc 60
agtggcctga tcgcgatggg gacaaaggcg caagtcgaga ggaaactgtt gtgtctcttc 120
atattggcga tcctgttgtg ctccctggca ttgggcagtg ttacagtgca ctcttctgaa 180
cctgaagtca gaattcctga gaataatcct gtgaagttgt cctgtgccta ctcgggcttt 240
tcttctcccc gtgtggagtg gaagtttgac caaggagaca ccaccagact cgtttgctat 300
aataacaaga tcacagcttc ctatgaggac cgggtgacct tcttgccaac tggtatcacc 360
ttcaagtccg tgacacggga agacactggg acatacactt gtatggtctc tgaggaaggc 420
ggcaacagct atggggaggt caaggtcaag ctcatcgtgc ttgtgcctcc atccaagcct 480
acagttaaca tcccctcctc tgccaccatt gggaaccggg cagtgctgac atgctcagaa 540
caagatggtt ccccaccttc tgaatacacc tggttcaaag atgggatagt gatgcctacg 600
aatcccaaaa gcacccgtgc cttcagcaac tcttcctatg tcctgaatcc cacaacagga 660
gagctggtct ttgatcccct gtcagcctct gatactggag aatacagctg tgaggcacgg 720
aatgggtatg ggacacccat gacttcaaat gctgtgcgca tggaagctgt ggagcggaat 780
gtgggggtca tcgtggcagc cgtccttgta accmtgattc tcctgggaat cttggttttt 840
ggcatctggt ttgcctatag ccgaggccac tttgacagaa caaagaaagg gacttcgagt 900
aagaaggtga tttacagcca gcctagtgcc cgaagtgaar gagaattcaa acagacctcg 960
tcattcctgg tgtgagcctg gtcggctcac cgcctatcat ctgcatttgc cttactcagg 1020
tgctaccgga ctctggcccc tgatgtctgk agtttmacag gatgccttat ttgtctttta 1080
caccccacag ggcccccctac ttcttcggat gtgtttttaa taatgtcagc tatgtgcccc 1140
atcctccttc atgccctccc tccctttcct accactgmtg agtggcctgg aacttgttta 1200
aagtgtttat tccccatttc tttgagggat caggaaggaa tcctgggtat gccattgact 1260
tcccttctaa gtagacagca aaaatggcgg gggtcgcagg aatmtacact caactgccca 1320
cctggctggc agggatcttt gaataggtat cttgagcttg gttctgggct ctttccttgt 1380
gtacctgccc gggcggccgc tcgaaatcaa gcttatcgat a 1421

<210> SEQ ID NO 71
<211> LENGTH: 378
<212> TYPE: DNA
<213> ORGANISM: Human

-continued

<400> SEQUENCE: 71
tagcgtggtc gcggccgagg tacaaaaaaa ccttacataa attaagaatg aatacattta 60
caggcgtaaa tgcaaaccgc ttccaactca aagcaagtaa cagcccacgg tgttctggcc 120
aaagacatca gctaagaaag gaaactgggt cctacggctt ggactttcca accctgacag 180
acccgcaaga caaaacaact ggttcttgcc agcctctaga gaaatcccag aacactcagc 240
cctgacacgt taataccctg cacagatcag aggctgctgg ccacacagac tcaccaagcc 300
acagacttgt cttccacaag cacgttctta ccttagccac gaagtgaccc aagccacacg 360
tacctgcccg ggcggccg 378

<210> SEQ ID NO 72
<211> LENGTH: 267
<212> TYPE: DNA
<213> ORGANISM: mouse

<400> SEQUENCE: 72
ggggcatggg ccatgctgta tggagtctcg atgctctgtg tgctggacct aggtcagccg 60
agtgtagttg aggagcctgg ctgtggccct ggcaaggttc agaacggaag tggcaacaac 120
actcgctgct gcagcctgta tgctccaggc aaggaggact gtccaaaaga aaggtgcata 180
tgtgtcacac ctgagtacca ctgtggagac cctcagtgca agatctgcaa gcactacccc 240
tgccaaccag gccaaagggt ggaagtc 267

<210> SEQ ID NO 73
<211> LENGTH: 1633
<212> TYPE: DNA
<213> ORGANISM: mouse
<220> FEATURE:
<221> NAME/KEY: unsure
<222> LOCATION: (1608)...(1608)

<400> SEQUENCE: 73
ggcacgagcg ggagcctgct actgccctgc tgggttcctt ggggccgact gtagccttgc 60
ctgtccacag ggtcgcttcg gccccagctg tgcccacgtg tgtacatgcg ggcaaggggc 120
ggcatgtgac ccagtgtcgg ggacttgcat ctgtcctccc gggaagacgg gaggccattg 180
tgagcgcggc tgtccccagg accggtttgg caagggctgt gaacacaagt gtgcctgcag 240
gaatgggggc ctgtgtcatg ctaccaatgg cagctgctcc tgcccccctgg gctgkatggg 300 gccacactgt gagcacgcct gccctgctgg gcgctatggt gctgcctgcc tcctggagtg 360
ttcctgtcag aacaatggca gctgtgagcc cacctccggc gcttgcctct gtggccctgg 420
cttctatggt caagcttgtg aagacacctg ccctgccggc ttccatggat ctggttgcca 480
gagagtttgc gagtgtcaac agggcgctcc ctgtgaccct gtcagtggcc ggtgcctctg 540
ccctgctggc ttccgtggcc agttctgcga gagggggtgc aagccaggct tttttggaga 600
tggctgcctg cagcagtgta actgccccac gggtgtgccc tgtgatccca tcagcggcct 660
ctgcctttgc ccaccagggc gcgcaggaac cacatgtgac ctagattgca gaagargccg 720
ctttgggccg ggctgtgccc tgcgctgtga ttgtgggggt ggggctgact gcgaccccat 780
cagtgggcag tgccactgtg tggacagcta cacgggaccc acttgccggg aagtgcccac 840
acagctgtcc tctatcagac cagcacccca gcactccagc agcaaggcca tgaagcacta 900
actcagagga acgcccacag aggcccacta ctgtgttcca gcccaaggga cccaggcctc 960
tgctggtgac taagatagag gtggcacttt tggatccaca cctcttctgg aaagccatgg 1020

-continued

```
attgctgtgg acagctatgg atagtcatat agccacacac ccgggctcca tggtcatggg   1080
gaagaaggcc tcctttggac acaaggaatc caggaagtcg gctgggcttc gggccactgt   1140
ttacatgggg accctgcagg ctgtgctgtg gaatcctggc cctcttcagc gacctgggat   1200
gggaccaagg tgggaataga caaggcccca cctgcctgcc aggtccttct ggtgctaggc   1260
catggactgc tgcagccagc caactgttta cctggaaatg tagtccagac catatttata   1320
taaggtattt atgggcatct ccacctgccg ttatggtcct gggtcagatg gaagctgcct   1380
gaccccagaa cttaggcagt ggcctgtggg gtctccagca agtgggatca agggttttgt   1440
aaaacccagt gagttaaagg cacagtggwg ccccadbgaa ctsrgtttch gtgcadtatg   1500
tagrctccvg vstcvtdccw agakmaggtr ctttagggtc cwykartgks racctscwgt   1560
acmcctctgt aatgacatgc atgtaatgta atgcttcagt caccttangg ttcttcctga   1620
cttccagctc tag                                                      1633
```

<210> SEQ ID NO 74
<211> LENGTH: 1252
<212> TYPE: DNA
<213> ORGANISM: mouse

<400> SEQUENCE: 74

```
ggaagagccg tgcaataatg ggtctgaaat ccttgcttat aacatcgatc tgggagacag     60
ctgcattact gtgggcaaca ctaccacaca cgtgatgaag aacctccttc cagaaacgac    120
ataccggatc agaattcagg ctatcaatga aattggagtt ggaccattta gtcagttcat    180
taaagcaaaa actcggccat taccgccttc gcctcctagg cttgagtgtg ctgcgtctgg    240
tcctcagagc ctgaagctca agtggggaga cagtaactcc aagacacatg ctgctggtga    300
catggtgtac acactacagc tggaagacag gaacaagagg tttatctcaa tctaccgagg    360
acccagccac acctacaagg tccagagact gacagagttt acctgctact cctksrggat    420
ccaggcaatg agcgaggcag gggaggggcc ttactcagaa acctacacct tcagcacaac    480
caaaagcgtg cctcccaccc tcaaagcacc tcgagtgacg cagttagaag ggaattcctg    540
tgaaatcttc tgggagacgg taccaccgat gagaggcgac cctgtgagct acgttctaca    600
ggtgctggtt ggaagagact ctgagtacaa gcaggtgtac aagggagaag aagccacatt    660
ccaaatctca rgcctycaga gcaacacaga ttacaggttc cgcgtgtgtg cctgccgccg    720
ctgtgtggac acgtytcagg agctcagtgg cgcgttcagc ccctctgcgg ctttcatgtt    780
acaacagcgt gaggttatgc ttacagggga cctgggaggc atggaagaag ccaagatgaa    840
gggcatgatg cccaccgacg aacagtttgc tgcactcatc gtgcttggct tcgcgaccct    900
gtccattttg tttgccttta tattacagta cttcttaatg aagtaaatcc agcaggccag    960
tggtatgctc ggaacgccac acgttttaat acacatttac tcagagcctc cccttttttac   1020
gctgtttcgt tctttgattt atacgcttct cttgttttac acatttagct aggggaaaga   1080
gtttggctgc acctatttga gatgcaaaac taggaagagg ttaaactgga ttttttttta   1140
aacaataata aataaaggaa taaagaagag aaggaagcgg cgggcaagct ccagacaccg   1200
agagccagtg tgcccaacga gcttgccttg tcgggcttcc cgtgtgcttc tg            1252
```

<210> SEQ ID NO 75
<211> LENGTH: 2411
<212> TYPE: DNA
<213> ORGANISM: mouse

-continued

<400> SEQUENCE: 75
tcggcacgag agtgggtaca ccttactaca tgtctccaga gagaatacat gaaaatggat 60
acaacttcaa gtctgacatc tggtctcttg gctgtctgct atatgagatg gctgcactgc 120
agagtccttt ctacggcgac aagatgaact tgtattctct gtgtaagaag atagagcagt 180
gtgactaccc gcctctcccg tcagatcact attcggagga gctacgacag ctagttaata 240
tatgcatcaa cccagatcca gagaagcgac ccgacatcgc ctatgtttat gatgtggcaa 300
agaggatgca tgcatgtacc gcaagcacct aaactgtaca agatcctgaa gacggcaacc 360
aagataactt aaaagtgttt ttgtgcagat catacctccc cgcttatgtc tgggtgttaa 420
gattactgtc tcagagctaa tgcgctttga atccttaacc agttttcata tgagcttcat 480
ttttctacca ggctcaatca ccttcccaat ccacaacttt gggatgctca gatggcacca 540
agaatgcaag cccaacaaga gtttttcgtt tgagaattgt ttcgagtttc tgctgataga 600
ctgtgtttat agatagtcag tgcccgatgg tgaagcacac acacataggc acatgtccag 660
agcgatgcag aacctgagga aggacctggg catttgactt gtttgctttt aagtcactta 720
atggacgttg tagtggacat gattgtgaac ttctgatttt tttcttttaa gtttcaagta 780
catgttttag ttcttagcat tagagatctc aaatataatt cttataagac atgcagacat 840
aaactttttg agaaagattt aaaattttta gtttatacat tcaaaatgca actattaaat 900
gtgaaagcat agaggtcaaa atgtgagttg gacactgaag tctatgtttt aatgcctttg 960
aaagcctttt tttgtgtgtg tttaaatggt ataaatgaac ccattttaaa acgtggttaa 1020
ggacttgttt gcctggcgtg atagtcatgt ttaacatgca caaggctttg tgtttttatt 1080
gtacatttga agaatattct tggaataatc ttgcagtagt tatagttcaa tttctttaca 1140
aatctaaata cacttaactc ataactatac actgtaatgc aagcatatat tgttattcat 1200
atattgaagt tttgatcagt tcctcttcag aatctttttt atccaagtta ctttcttatt 1260
tatattgtgt gtgcatttca tccattaaat gtttcagatt ttctgagaat gagttccctt 1320
tttaaaatat atttggtatg ccaacacttt tttaggattg aaaaaaaatt tttttaaatg 1380
tttgggtcat tctaggtgca tctgttttct cttgttagaa agaaaaggtg tgtgttaaaa 1440
tgtgcctgtg aatgtcgata ttgtttggca gggttataat tttagagtat gctctagagt 1500
atgttgaaca gcgtgaagac tggcccttac tgaagacaga actgttccaa gagcagcatt 1560
cccgttgaga tgctttggag taaagtactg tgtatgacga tgacagacat tttagttaag 1620
ggggtgaaaa aaaaaggagg ggtatttagg aaaccctgag gtggaatttt ggtgaatgtc 1680
ttcatcttaa taccagccaa ttccttcaga gaattgtgga gccaaagaac agagtaatcg 1740
tggctgttgc agaacacggt gtgccatggt agagcattgg gaaggctcat cctgccggtg 1800
ggtcggtcag acagccctgt gttggggagc ttgtactctg gcccacagag ctcggttgat 1860
tttcttacag agtattcttt ctacagttat tttcaagtaa ttgtaaattt tcaaagtaat 1920
atctcatctt ttaattcact atgtatgctg tcgtagacaa aggaaatctg ggtttttttt 1980
tgtttttgtt tttgtttttt tttgtcttga aggctgaact gggtacatcc cagatcttag 2040
tggctcatag gatataccca gaggcatgaa gaaatggctt ccggtgacca tttgtgttgk 2100
gktatatccc attgtaatgt cacaggactg attgagatga aacatcccct tcctacaaga 2160
gttgttttct ttccatattt aaaaacatga ggttctgcct ggcagtgatg gtacacacct 2220
ttaatcccag cacccgggag gcagaggcag gaggatttct gagttcgagg ccagcctggt 2280
ctacaaagtg agttccagga cagccaggac tacacagaga aatcctgtct caaaaaacca 2340

-continued

```
aaactaaatg aaaatacaag gcttctcccc ttgtagtgac tttgctttat gaatttgtct   2400

caaaaaaaaa a                                                        2411


<210> SEQ ID NO 76
<211> LENGTH: 1335
<212> TYPE: DNA
<213> ORGANISM: mouse

<400> SEQUENCE: 76

acccaaacag cccgggacca tgctgtcgct ccgctccttg cttccacacc tgggactgtt     60

cctgtgcctg gctctgcact tatccccctc cctctctgcc agtgataatg ggtcctgcgt    120

ggtccttgat aacatctaca cctccgacat cttggaaatc agcactatgg ctaacgtctc    180

tggtggggat gtaacctata cagtgacggt ccccgtgaac gattcagtca gtgccgtgat    240

cctgaaagca gtgaaggagg acgacagccc agtgggcacc tggagtggaa catatgagaa    300

gtgcaacgac agcagtgtct actataactt gacatcccaa agccagtcgg tcttccagac    360

aaactggaca gttcctactt ccgaggatgt gactaaagtc aacctgcagg tcctcatcgt    420

cgtcaatcgc acagcctcaa agtcatccgt gaaaatggaa caagtacaac cctcagcctc    480

aacccctatt cctgagagtt ctgagaccag ccagaccata aacacgactc caactgtgaa    540

cacagccaag actacagcca aggacacagc caacaccaca gccgtgacca cagccaatac    600

cacagccaat accacagccg tgaccacagc caagaccaca gccaaaagcc tggccatccg    660

cactctcggc agccccctgg caggtgccct ccatatcctg cttgtttttc tcattagtaa    720

actcctctty taaagaaaac tggggaagca gatctccaac ctccaggtca tcctcccgag    780

ctcatttcag gccagtgctt aaacataccc gaatgaaggt tttatgtcct cagtccgcag    840

ctccaccacc ttggaccaca gacctgcaac actagtgcac ttgagggata caaatgcttg    900

cctggatctt tcagggcaca aattccgctt cttgtaaata cttagtccat ccatcctgcg    960

tgtaacctga agttctgact ctcagtttaa cctgttgaca gccaatctga acttgtgttt   1020

cttgccaaag gtattcccat gagcctcctg ggtgtggggg tggggaggga atgatccttc   1080

tttactttca aactgatttc agatttctgg ccaaacctac tcaggttgca aaggacttat   1140

gtgacttatg tgactgtagg aaaaagagaa atgagtgatc atcctgtggc tactagcaga   1200

tttccactgt gcccagacca gtcggtaggt tttgaaggaa gtatatgaaa actgtgcctc   1260

agaagccaat gacaggacac atgacttttt ttttctaagt caaataaaca atatattgaa   1320

caaggaaaaa aaaaa                                                    1335


<210> SEQ ID NO 77
<211> LENGTH: 440
<212> TYPE: DNA
<213> ORGANISM: mouse
<220> FEATURE:
<221> NAME/KEY: unsure
<222> LOCATION: (9)...(9)

<400> SEQUENCE: 77

cactagggnc tccaaagaat tcagcacgag gagaagcctt gcccactcaa atacctgggc     60

catcagctgc accggctcca ctcccatctg ctccaggccc tgaagagaag ccaacacttt    120

tcaggcccct caacctccac atcagaacag gcagagcctg tggtgtcagc tgttgatcca    180

aaggcaaccc ttggtggggt tggggttgta aagtagtgat gctaatttct aagcaacaag    240

ctctgagctg cagcccccag gccctccagg gcagtccagg gcagtgccag ggttcagggt    300
```

-continued agttctaggg gtctagtatc tggatcaaca agtcccagag ttgggcccag tggctgctga 360
cttgttcaat gaccaagaat atacgaccta accttttta tttggttggg caaccacagc 420
tccgagtaag tcatcaaggc 440

<210> SEQ ID NO 78
<211> LENGTH: 204
<212> TYPE: DNA
<213> ORGANISM: mouse

<400> SEQUENCE: 78
ctccataaaa ttcctcaaaa tctgttcccc cagcagattt cctgtgccat cttgggctcc 60
cttcctattc tttcccgtct ttagggcctc ctcacagtgt tgttttctaa caacgcaggc 120
atgagaaggc actcactgtg tgctccctca ggcctggcct ctcctggtga ttgtcttctt 180
cctctgtgtc ctcttcatcc caat 204

<210> SEQ ID NO 79
<211> LENGTH: 300
<212> TYPE: DNA
<213> ORGANISM: mouse
<220> FEATURE:
<221> NAME/KEY: unsure
<222> LOCATION: (259)...(259)
<221> NAME/KEY: unsure
<222> LOCATION: (287)...(287)

<400> SEQUENCE: 79
tatttatgac ttgggttaag ggagtttgct gtgcaatcat gaagaccaga gttcagatcc 60
cagcacccat atagcaagag agcatacaag aagcacctgt gactgcactc tgaagaatcc 120
aacaccttct tctggcctcc atggcacaca gaaccccca acacatgctc atccactctc 180
aaagagacat acataaaaat aaatatttag gtcctgggtc cctcagagac tagtcttcac 240
aggtcctaaa tacaaacgna gcggaccgca aagggtgagg gagtggncct gaagaagcta 300

<210> SEQ ID NO 80
<211> LENGTH: 214
<212> TYPE: DNA
<213> ORGANISM: mouse

<400> SEQUENCE: 80
cccagaccct gtgtcagcta tcccagcaga aaaagaagat gcggaccctc tcagcaagtc 60
aggtgaggaa acccaggaag cagggtcatg accccgcaga ggtcggggct cctggtgcag 120
aggatcagat cttgtgtgac ttctgtcttg ggccagcag agtaagggca gtgaaatcct 180
gtctgacctg catggtgaaa tactgtaagg agca 214

<210> SEQ ID NO 81
<211> LENGTH: 152
<212> TYPE: DNA
<213> ORGANISM: mouse
<220> FEATURE:
<221> NAME/KEY: unsure
<222> LOCATION: (22)...(23)

<400> SEQUENCE: 81
ccccttaact aacccaggac cnnccacgaa gtggaaggct ccaccatcca cagaggggc 60 cagtcatttt taagcacacg gaccttttgt gagacagtcg tgatcttaac tgtggtgtca 120
ctgatggagc tgaacggtat cccctaaaag ta 152

-continued

<210> SEQ ID NO 82
<211> LENGTH: 181
<212> TYPE: DNA
<213> ORGANISM: mouse
<220> FEATURE:
<221> NAME/KEY: unsure
<222> LOCATION: (47)...(47)

<400> SEQUENCE: 82
tctcagtgat gatgagaagc tccggaggag gcaggagaaa gcagggnacc gcccctccct 60
gggtctccac ccacccacgc ccgctaaggt cacctgttct cccatggaga tgatgaagaa 120
gctcatagct ggacaaggcc cggaacctca gcccagtaac cgacctactt cccgcctggg 180
a 181

<210> SEQ ID NO 83
<211> LENGTH: 332
<212> TYPE: DNA
<213> ORGANISM: mouse
<220> FEATURE:
<221> NAME/KEY: unsure
<222> LOCATION: (217)...(217)

<400> SEQUENCE: 83
tatagagatg gtgatgtaat gggccagggt gtaagcttca acctggggga ttttgctggt 60
tttgttgttt ccctgtgtag ccctaacaag cctgtgtaga ccaggctggc tttaactttg 120
cagatgacat tcacgtctac ttctctctgt gttggggtta tgggtctgca cacctgccca 180
ggcctaggct gggggatttt gaagtatctt agattangga gtagacccag agtttgcaag 240
tatctgcttt aaagtgacac ataaacatag cctcctgacc atcttccaca gtgggaccct 300
gatctggcct ctccctggaa gaagagagaa ag 332

<210> SEQ ID NO 84
<211> LENGTH: 213
<212> TYPE: DNA
<213> ORGANISM: mouse

<400> SEQUENCE: 84
gcaggcagat aacaatgatt actggacaga gtgcttcaac gcattggaac aggggaggca 60
atatgtggat aatcccacag gcgggaaagt ggacgaggct ctggtgagaa gtgccaccgt 120
acattgttgg ccgcacagca acgtgctgga cacaagcatg ctctcatccc cagatgtggt 180
gcgcatgctg ctgtccctgc agcccttcct gca 213

<210> SEQ ID NO 85
<211> LENGTH: 273
<212> TYPE: DNA
<213> ORGANISM: mouse
<220> FEATURE:
<221> NAME/KEY: unsure
<222> LOCATION: (123)...(123)
<221> NAME/KEY: unsure
<222> LOCATION: (169)...(169)
<221> NAME/KEY: unsure
<222> LOCATION: (189)...(189)
<221> NAME/KEY: unsure
<222> LOCATION: (257)...(257)

<400> SEQUENCE: 85
ccggctctct ctctcctcct tccccgcctc ttctgcctcc cctgcctgga actctgatga 60
ggagggacca ggtggtcagg caccccagtc tgatcaggac tcctgtggcc tccagagttt 120

-continued

```
cantcccccg tccatcctga agcgggctcc tcgggagcgt ccaggtcang tggcctttaa    180

cggcatcanc gtctactatt tcccacggtg ccaaggattc accagtgtgc ccaagccgtg    240

gtggctgtac cctgggnatg gcttctcggc aca                                 273


<210> SEQ ID NO 86
<211> LENGTH: 218
<212> TYPE: DNA
<213> ORGANISM: mouse

<400> SEQUENCE: 86

ctcagccgcc tgctctgggg gctggagggt ctcccactta actgtgtctg ccgttcaggg     60

ggctcaccca gtgctgcgct acacagaggt tttccctcca gctccagtcc gtcctgccta    120

ctccttctat aaccgcctcc aagagctggc ctcactgttg ccccggccgg ataagccctg    180

cccagcctat gtggagccta tgactgtggt ttgtcacc                           218


<210> SEQ ID NO 87
<211> LENGTH: 335
<212> TYPE: DNA
<213> ORGANISM: mouse

<400> SEQUENCE: 87

gaggtggggt gggtgcatag cctgcctgca attgctgccg ctgggcttaa cgtgttgtga     60

gctggccggt ttcctacaca gcagcacctg ccatggagcc tggccacaag gccactcaga    120

gctgggtgga cagagtgtga ccagaaactc cctgtgggtt ctgataaagg attctcccat    180

aggcaaggtt cagagaacct gggcctcctg ttctcaggga ggcctgtcta tccccagcct    240

ctgagctgtt tcgtcctagt tggtgagtta agtggcatag ccctcttgag gcctctgatg    300

tggaaggggc acagaattgc aattattctt gcatg                               335


<210> SEQ ID NO 88
<211> LENGTH: 410
<212> TYPE: DNA
<213> ORGANISM: mouse

<400> SEQUENCE: 88

aaaccccgcc aggaaacaaa taccggtgta tcggctttac tgaatgcatt tattcccaaa     60

gggaaactga aaagcaacct agggacactg taagcagaaa gctgaggctt ttaaaaaccc    120

accttggcaa tgtaacttgg gaggttccca cacacccagg gctgtgcatc gtgaaattct    180

gtctcctgag acgctgagaa acccttcctt gcagctataa tgggcctggc cgcccagtgt    240

ggagctgtag cttcccacga cgtagccctc aggaacttca ggagggatgc cacagtctat    300

ttctgaaaac aaaaccgtgt caacttcttt actttacaaa tgcaagtttt cagaatccac    360

catctctctg cacccatacc ccatgcctca caccccagac cctgtgttag               410


<210> SEQ ID NO 89
<211> LENGTH: 279
<212> TYPE: DNA
<213> ORGANISM: mouse
<220> FEATURE:
<221> NAME/KEY: unsure
<222> LOCATION: (8)...(8)
<221> NAME/KEY: unsure
<222> LOCATION: (201)...(201)

<400> SEQUENCE: 89

gtgcaganag tggattgtca gtggactgct cagttacaaa tgggacatct aacacacaca     60
```

-continued

```
cacacacaca cacacacaca cacacacaca caccccaagg cttagagacc attgcagaag    120

agaagagttt atgggaaatc ttggagaaaa cattggatgg tttgagagaa tggttaggag    180

atcagactag ctagtccagg nagcagtgaa ggggggcggg gttagaagat gaggtcagaa    240

gacagggtgg agggcattgt ccgacagaac cattgctgt                            279


<210> SEQ ID NO 90
<211> LENGTH: 398
<212> TYPE: DNA
<213> ORGANISM: mouse

<400> SEQUENCE: 90

ccaccaaccc agaaatttga caaaggggtt gaatgttgga ctttgcgtcc ttccccggca     60

gtggatgtac tgttttgagc cctgtgtgga acttctgaac ttcgtgctgt aactttcaga    120

actcttagac atgggtgtgc tcactgaact ctagggtctg tgtgctagat gctgccaacg    180

ctgtattcag gacctgaagt gagtacccgt gtggatccag accaatccag tgtgagacta    240

ctgaagaaca tctgttgcca gaacggccac accaaacaga tggagtgccc cagcacttag    300

cttcttaaat aacatcggaa ccattcagcc agcgagtctg tgtttgcttt ttgttaaatt    360

gtccgccgaa tctaaattcc tccaaaaggc ttgtgacc                             398


<210> SEQ ID NO 91
<211> LENGTH: 279
<212> TYPE: DNA
<213> ORGANISM: mouse

<400> SEQUENCE: 91

gttgttactt cagttgctct cggcgggaat tcttaaactg catcctgagt gagggagctt     60

tggcgagaaa gcaagaccca gtggtagaca gattagcatt actgtacagc ttctttgggt    120

gttcgaggaa gcccggctgg accatagtgg ccacggcggt gaggtaggcg tggacagggc    180

tgaccagtcc aagttaagga cgttcgggtc catgttaacc ctgccttgta cgtccagcat    240

cgtaagaaaa aacacttgag aacccgaaga ggagatgga                            279


<210> SEQ ID NO 92
<211> LENGTH: 401
<212> TYPE: DNA
<213> ORGANISM: mouse

<400> SEQUENCE: 92

aaaaagtttt accaaaacct tttattgact tttataaatt agatagtatt tcaaagttta     60

tgtagaatcg tattctttga aactgtactt agcagagcag aagaggcctg ctgacgctag    120

cacgctctgc aatgaatcat gtggcaccga gtctacgcca aggcccccga gaaactttat    180

tccatagatg ggcagatggt tcccaaagtt acactacaga actacaaatc gactcttaaa    240

attaaaacgg gactttacaa gcattctaga agactcaaac ttgaagcaat tttggaaaa     300

taaatgtaca gagaaaagat cttgaagcta ctgaacagag aaccctcatt aaccgagcaa    360

atacatccta tggagcttcc gaggagtaca cagacagacc g                         401


<210> SEQ ID NO 93
<211> LENGTH: 339
<212> TYPE: DNA
<213> ORGANISM: mouse

<400> SEQUENCE: 93

ccactgacct tcccagaagg tgacagccgg cggcggatgt tgtcaaggag ccgagatagt     60
```

-continued

```
ccagcagtgc ctcggtaccc agaagacggg ctgtctcccc ccaaaagacg gcgacattcg    120

atgagaagtc accacagtga tctcacattt tgcgagatta tcctgatgga gatggagtcc    180

catgatgcag cctggccttt cctagagcct gtgaaccctc gcttggtgag tggataccga    240

cgtgtcatca agaaccctat ggatttttcc accatgcgag aacgcctgct ccgtggaggg    300

tacactagct cagaagagtt tgcagctgat gctctgctg                          339


<210> SEQ ID NO 94
<211> LENGTH: 55
<212> TYPE: DNA
<213> ORGANISM: mouse

<400> SEQUENCE: 94

ggggtgtggg caacttggat aacctcagct gcttccatct ggctgacatc tttgg          55


<210> SEQ ID NO 95
<211> LENGTH: 186
<212> TYPE: DNA
<213> ORGANISM: mouse

<400> SEQUENCE: 95

ggactctggc ttcctggggc tgcggccgac ctcggtggat cccgctctga ggcggcggcg     60

gcggggcccc agaaacaaga agcgcggctg gaggaggctc gccgaggagc cgctggggtt    120

agaggtcgac cagttcctgg aagacgtccg gctacaggag cgcacgaccg gtggcttgtt    180

ggcaga                                                               186


<210> SEQ ID NO 96
<211> LENGTH: 244
<212> TYPE: DNA
<213> ORGANISM: mouse

<400> SEQUENCE: 96

ggtgaccaaa accccttctg cccccttccc agagactctg acttgaccct ctttccaatt     60

ccctctcccc aaggccatgg attatgaagc ccctctgtaa gatggtgagc caggggccct    120

aagagggcat gaggcacacc ctgatcactg tctcaggcct ttgtgggcac tgactcgacc    180

ctggcccacc tcacgccccc aggccagttg gcaactggtg gctcttgagg gctcttacgc    240

cctt                                                                 244


<210> SEQ ID NO 97
<211> LENGTH: 116
<212> TYPE: DNA
<213> ORGANISM: mouse
<220> FEATURE:
<221> NAME/KEY: unsure
<222> LOCATION: (11)...(11)
<221> NAME/KEY: unsure
<222> LOCATION: (13)...(13)
<221> NAME/KEY: unsure
<222> LOCATION: (41)...(41)

<400> SEQUENCE: 97

acccggtctg ngnactgccc gccttctggg gcttccttta naggatacag tcttttaccc     60

atctaggact cctgccaccc tgactgctga cttacagcta tgaggtcccg gcttct        116


<210> SEQ ID NO 98
<211> LENGTH: 307
<212> TYPE: DNA
<213> ORGANISM: mouse
```

-continued

<400> SEQUENCE: 98
ccccgggcca tctgtcgcca taccgggccc gtgcaagctt ttgcaggttt tagaagatgg 60
cgaattcatg acacctgtga tccaggacaa cccctcaggc tggggtccct gtgccgttcc 120
tgagcaattt cgggatatgc cctaccagcc attcagcaaa ggagatcggc tgggaaaggt 180
tgcagactgg acaggggcca cataccagga caagaggtac acaaacaagt attcctctca 240
gttcggtggg gggagtcagt atgcatattt ccatgaggag gatgagacaa gctttccagc 300
tgggtgg 307

<210> SEQ ID NO 99
<211> LENGTH: 360
<212> TYPE: DNA
<213> ORGANISM: mouse
<220> FEATURE:
<221> NAME/KEY: unsure
<222> LOCATION: (305)...(305)

<400> SEQUENCE: 99
ccttggtgca ccagctccag cctcaggact tcctcctcct ggccctgaca gcccagctct 60
tgtcccagca gaatccagtg acaggaagga gtttctgagg caggggagga ggcttctcca 120
tgggaaccag acagccttgc ttcactgtat aagtgccctg atcacacgca gaatgaagtg 180
ccaggttgct cagaagcaca aagggtgtgg ctactggccc taaccatgga ctacgtggtt 240
ctaaccaaag actctagaac tctggggtgg gggagaaaca atgtgttctg tgctccagaa 300
ccttnggctt cctggcccat atggatgggc ttggcaagga acctacctct tctctaaggt 360

<210> SEQ ID NO 100
<211> LENGTH: 257
<212> TYPE: DNA
<213> ORGANISM: mouse

<400> SEQUENCE: 100
tgccgcgctg agaggggggg ccgcaccacc agcgccacca ccaccaccgc cgccgccgcc 60
gggtggggtg ggaggggcgg gagccaccgc taccgccgcc gcctcccggg tgggcgccct 120
tctccttaga cgccggcgac ccaggacgag ggcttcatca ctgtaaatgg ttgcaagccg 180
acaaagctgc acctcctgaa aaagacggac agcccatcgc gtgagctgta gaaatttgtg 240
gacgcatttc tatcggt 257

<210> SEQ ID NO 101
<211> LENGTH: 203
<212> TYPE: DNA
<213> ORGANISM: mouse

<400> SEQUENCE: 101
ccaaagtgcc cattgtgatt caagacgata gccttcccac ggggcccccct ccacagatcc 60 gcatcctcaa gaggcccacc agcaacggtg tggtcagcag ccccaactcc accagcaggc 120
cagcccttcc tgtcaagtcc ctagcacagc gggaggcaga gtatgcagag gctcggagac 180
ggatcctagg cagtgccagc cct 203

<210> SEQ ID NO 102
<211> LENGTH: 300
<212> TYPE: DNA
<213> ORGANISM: mouse

<400> SEQUENCE: 102

-continued

```
agtacagaga cctcggctgc agcttaaacc tcggacagtg gcaacgcccc tcaatcaagt     60

agccaacccc aactcagcca tctttggggg agccaggccc agagaggaag tggttcagaa    120

ggagcaagaa tgagcttagg ttgggaggga atggggcgtg ggggagctgg agcaagacca    180

cggcctggtg gcagccggtc gccctacagg ccccattccc gcctggcact gtcctcctta    240

cagcggaaac acagagcttg tgagtgcatg tcagctgtta acaagtggtt tctagtacat    300


<210> SEQ ID NO 103
<211> LENGTH: 370
<212> TYPE: DNA
<213> ORGANISM: mouse
<220> FEATURE:
<221> NAME/KEY: unsure
<222> LOCATION: (222)...(222)

<400> SEQUENCE: 103

cagcaactgt ttcaggagct gcacggtgta cgcctgctga ctgatgcgct ggaactaaca     60

ctgggcgtgg cccccaaaga aaaccctccg gtgatgcttc cagcccaaga gacggagagg    120

gccatggaga tcctcaaagt gctcttgaat atcacctttg actctgtcaa gagggaagtt    180

gatgaggaag atgctgccct tgaccggtac ctggggactc tnctgcggca ctgcgtgatg    240

gttgaagctg ctggggaccg cacagaggag ttccacggcc acacggtgaa tctcctgggg    300

aacttgcccc tcaagtgttt ggatgtgctt ctggccctgg agctccacga aggatcctta    360

gagtcaatgg                                                           370


<210> SEQ ID NO 104
<211> LENGTH: 423
<212> TYPE: DNA
<213> ORGANISM: mouse

<400> SEQUENCE: 104

tttcccagcc tggtggagca gccgactggc gagtgtgcca actgtcccgt gcttcccagc     60

tcctaccttg cctgtcttct ctctcctggg aagatgttcc tggtggggct gacgggaggc    120

atcgcctcag gcaagagctc cgtcatccag gtattccaac agctgggctg tgctgtaatc    180

gacgtggacg tcattgcgcg gcacgttgtc cagccagggt atcctgccca ccggcgtata    240

gtagaggcct ttggcactga agtcttgctg gagaatggcg acatcgaccg caaggtcctc    300

ggagacctga tcttcaacca gcctgaccgt cggcagctgc tcaactccat tacccaccct    360

gagatccgca aggaaatgat gaaggagacc ttcaagtact tctccgaggt accgatacgt    420

gat                                                                  423


<210> SEQ ID NO 105
<211> LENGTH: 117
<212> TYPE: DNA
<213> ORGANISM: mouse

<400> SEQUENCE: 105

agcttggtgc tgttcatatt taaactgata aagactcttc ataggagctg agggtagcaa     60

gcccgcgtcg gtgactgggg tctcacacag gttcagcact tggagcatag tgaggtg       117


<210> SEQ ID NO 106
<211> LENGTH: 133
<212> TYPE: DNA
<213> ORGANISM: mouse

<400> SEQUENCE: 106
```

```
tttttttttt aaaataccac catttccaat cccaaaagaa catggcactt gtttgtttct     60

tcccctcctc attcattcca gactttcaag tgttttcttc aatactgagg ctttctcctg    120

cagctctggt ctg                                                       133


<210> SEQ ID NO 107
<211> LENGTH: 217
<212> TYPE: DNA
<213> ORGANISM: mouse
<220> FEATURE:
<221> NAME/KEY: unsure
<222> LOCATION: (1)...(1)
<221> NAME/KEY: unsure
<222> LOCATION: (11)...(11)
<221> NAME/KEY: unsure
<222> LOCATION: (18)...(23)
<221> NAME/KEY: unsure
<222> LOCATION: (34)...(34)
<221> NAME/KEY: unsure
<222> LOCATION: (37)...(38)
<221> NAME/KEY: unsure
<222> LOCATION: (40)...(42)
<221> NAME/KEY: unsure
<222> LOCATION: (50)...(52)
<221> NAME/KEY: unsure
<222> LOCATION: (55)...(58)
<221> NAME/KEY: unsure
<222> LOCATION: (152)...(152)
<221> NAME/KEY: unsure
<222> LOCATION: (155)...(155)
<221> NAME/KEY: unsure
<222> LOCATION: (165)...(165)

<400> SEQUENCE: 107

ntttttttttg ngcgcacnnn nnngnnnncg cccnggnngn nnagcctacn nncannnngt     60

tttcttctcc aggctgaaga cctgaacgtc aagttggaag gggagccttc catgcggaaa    120

ccaaagcagc ggccgcggcc ggagcccctc ancanccccca ccaangcggg cactttcatc    180

gcccctcctg tctactccaa catcacccct taccaga                             217


<210> SEQ ID NO 108
<211> LENGTH: 346
<212> TYPE: DNA
<213> ORGANISM: mouse
<220> FEATURE:
<221> NAME/KEY: unsure
<222> LOCATION: (34)...(34)
<221> NAME/KEY: unsure
<222> LOCATION: (97)...(97)
<221> NAME/KEY: unsure
<222> LOCATION: (109)...(109)
<221> NAME/KEY: unsure
<222> LOCATION: (190)...(190)

<400> SEQUENCE: 108

gggcatagaa ggcatctcga aaagaatact tatntgagtt gaaggaagat gaagaggcct     60

gcaggaaggc tcagaagaca ggagtgtttt acctctntca tgacctggnt cctttgctcc    120

aggcgtcagg acatcgatac ctggtgcccc ggcttagccg agcagagttg gaagggctgc    180

tgggtaagtn cggacaggat tcgcaaagaa ttgaagattc ggtgctggtt gggtgctccg    240

agcagcagga accatggttt gcgttggatc taggtctgaa gagtgcctcc tccagccgtg    300

gacaagtatc gctgctccag cagcttgact gctgtaaaga ggatct                  346


<210> SEQ ID NO 109
<211> LENGTH: 242
<212> TYPE: DNA
```

-continued

<213> ORGANISM: mouse

<400> SEQUENCE: 109
ccacattgtc cacaactgga aggcacgatg gttcatcctt cggcagaaca cgctcctgta 60
ttacaagcta gagggtggcc ggcgagtaac cccgcccaag gggaggattg tccttgatgg 120
ctgcaccatc acctgcccct gcctggagta tgaaaaccgg ccgctcctca ttaaactgaa 180
gacccgaact tccactgagt acttcctgga agcctgttct cgagaggaga gagactcctg 240
gg 242

<210> SEQ ID NO 110
<211> LENGTH: 310
<212> TYPE: DNA
<213> ORGANISM: mouse
<220> FEATURE:
<221> NAME/KEY: unsure
<222> LOCATION: (196)...(196)
<221> NAME/KEY: unsure
<222> LOCATION: (269)...(269)

<400> SEQUENCE: 110
cccggccggg aatccaggtg gtagctggtg gagtcgcctc cggagagtga cgcgcagact 60
cggctccccc gcggcccgcc ctcctgccgg cctcgccgcg gtctcccttg ctccctgaga 120
tcgctgagcg ctgagcagcg gcccgggaga ggaggccttg ggcgacgggg cgcggagagg 180
gagggcgggc gggcantggg ggcgccgcgg atctctatat ggcgacgggt ctgtcgggtc 240
tggctgtccg gctgtcgcgc tcggccggnc ggccggttcc tatggggtct tctgcaaagg 300
ggttgacccg 310

<210> SEQ ID NO 111
<211> LENGTH: 228
<212> TYPE: DNA
<213> ORGANISM: mouse

<400> SEQUENCE: 111 ttcttttta acatttggtg gttttttct ttactctttt tttcttttcc ttcttttct 60 gccctcaacc ccccaactcc tttggtatga agtactttta acatttatat ttcattgtta 120
cactttaaat tttgtaagga aaactctgat atttcattcc tcctgaacca ctaatgttag 180
aatttatttc taagaatcag tcaacatgta tactcttaat agtgaatt 228

<210> SEQ ID NO 112
<211> LENGTH: 292
<212> TYPE: DNA
<213> ORGANISM: mouse

<400> SEQUENCE: 112
gtggggtccc agacttgcca accaaagggc cattcctggt atatggttct ggcttcagct 60
ctggtggcat ggactatggt atggttggtg gcaaggaggc tgggaccgag tctcgcttca 120
aacagtggac ctcaatgatg gaagggctgc catctgtggc cacacaagaa gccaccatgc 180
acaaaaacgg cgctatagtg gcccctggta agacccgagg aggttcacca tacaaccagt 240
ttgatataat cccaggtgac acactgggtg gccatacggg tcctgctggt ga 292

<210> SEQ ID NO 113
<211> LENGTH: 255
<212> TYPE: DNA
<213> ORGANISM: mouse
<220> FEATURE:

-continued

<221> NAME/KEY: unsure
<222> LOCATION: (44)...(44)
<221> NAME/KEY: unsure
<222> LOCATION: (97)...(97)

<400> SEQUENCE: 113
ttagatgact taggacttta atgttttcca tgcagtcgat tganaacact gatacatgaa 60
caaccagaaa aagacctcag caatgtatag acctggnata tatagtgttg ccctggttaa 120
actacaagaa cagccacgtg atcacagttt gagggtggaa ggcaggggtg tgactgagtt 180
ttgtttaacg gcctaaccga aaagcaaaga atcaaccatt tcttctactt gtggcaagaa 240
acgagagtca tggtg 255

<210> SEQ ID NO 114
<211> LENGTH: 197
<212> TYPE: DNA
<213> ORGANISM: mouse

<400> SEQUENCE: 114
gacccacatg tgaacagccg cgtgtatgtc acactgctct gtgtgtgatt tcttcacgtg 60
tgcatgtgcg ctcttggtct ttccacttat tgcctcgttc gtaagaaacc aaccataagg 120
tgccaaggag gttttattcc tttttttttt aaagatgaca aatgtacaga tgttagtaca 180
gatgttaatg tacagat 197

<210> SEQ ID NO 115
<211> LENGTH: 205
<212> TYPE: DNA
<213> ORGANISM: mouse

<400> SEQUENCE: 115
aaaacatttc acaaaacagc aaaacaaaat tgatacaatc aaaaaaacaa cactataacc 60
aacataggtg aaaacagcca aacacataat gtacaatctg gtgttccagg acaaacatct 120
gtcatataca tggtatatac atatatactt tttcactcaa tatattatga caatatatat 180
ttaaaatttt gttatagaca aaaaa 205

<210> SEQ ID NO 116
<211> LENGTH: 202
<212> TYPE: DNA
<213> ORGANISM: mouse
<220> FEATURE:
<221> NAME/KEY: unsure
<222> LOCATION: (146)...(146)
<221> NAME/KEY: unsure
<222> LOCATION: (178)...(178)

<400> SEQUENCE: 116
cctccctcat cctctacttc ccttttcctt cctgcttgat tttctcattc caaaccccta 60
tgcacacaca cacacacaca cacacacaca cacgaacaca cgcacacaca cacacacacg 120
cacacacaca ctgtccatcc atagtnactt atttagtttt ccattcctag agagatcnaa 180
tcatccccta gtcagtgcct aa 202

<210> SEQ ID NO 117
<211> LENGTH: 240
<212> TYPE: DNA
<213> ORGANISM: mouse

<400> SEQUENCE: 117
ccgccaggag aggagataca cagccagtga tgtggaccac cggatggctg ttgctgctgc 60

-continued cgcttctgct gtgtgaagga gcgcaagccc tggagtgcta cagctgcgtg cagaaggcgg 120
acgatggatg cgctccgcac aggatgaaga cagtcaaatg tggtcccggg gtggacgtct 180
gtaccgaggc cgtgggagcg gtagagacca tccacgggca attctctgtg gcggtgcggg 240

<210> SEQ ID NO 118
<211> LENGTH: 527
<212> TYPE: DNA
<213> ORGANISM: Human

<400> SEQUENCE: 118
ccgtcagtct agaaggataa gagaaagaaa gttaagcaac tacaggaaat ggctttggga 60
gttccaatat cagtctatct tttattcaac gcaatgacag cactgaccga agaggcagcc 120
gtgactgtaa cacctccaat cacagcccag caaggtaact ggacagttaa caaaacagaa 180
gctcacaaca tagaaggacc catagccttg aagttctcac acctttgcct ggaagatcat 240
aacagttact gcatcaacgg tgcttgtgca ttccaccatg agctagagaa agccatctgc 300
aggtgtttta ctggttatac tggagaaagg tgtgagcact tgactttaac ttcatatgct 360
gtggattctt atgaaaaata cattgcaatt gggattggtg ttggattact attaagtggt 420
tttcttgtta ttttttactg ctatataaga aagaggtgtc taaaattgaa atcgccttac 480
aatgtctgtt ctggagaaag acgaccactg tgaggccttt gtgaaga 527

<210> SEQ ID NO 119
<211> LENGTH: 655
<212> TYPE: DNA
<213> ORGANISM: Rat

<400> SEQUENCE: 119
atggcgcgcc ccgcgccctg gtggtggctg cggccgctgg cggcgctcgc cctggcgctg 60
gcgctggtcc gggtgccctc agcccgggcc gggcagatgc cgcgccccgc agagcgcggg 120
cccccagtac ggctcttcac cgaggaggag ctggcccgct acagcggcga ggaggaggat 180
caacccatct acttggcagt gaagggagtg gtgttcgatg tcacctctgg gaaggagttt 240
tatggacgtg gagcccccta caacgccttg gccgggaagg actcgagcag aggtgtggcc 300
aagatgtcgc tggatcctgc agacctcact catgacattt ctggtctcac tgccaaggag 360
ctggaagccc tcgatgacat cttcagcaag gtgtacaaag ccaaataccc cattgttggc 420
tacacggccc gcaggatcct caacgaggat ggcagcccca acctggactt caagcctgaa 480
gaccagcccc attttgacat aaaggacgag ttctaatgtc tagctgagaa gctggttcta 540
gggagaggtg aggggacagg agttaaatgt cccacggaac aagcagggga agcctctgag 600
tgctctgcat ctgaataaaa ctgatattta actgggaaaa aaaaaaaaaa aaaaa 655

<210> SEQ ID NO 120
<211> LENGTH: 176
<212> TYPE: PRT
<213> ORGANISM: Rat

<400> SEQUENCE: 120

Met Val Pro Cys Phe Leu Leu Ser Leu Leu Leu Leu Val Arg Pro Ala
1 5 10 15

Pro Val Val Ala Tyr Ser Val Ser Leu Pro Ala Ser Phe Leu Glu Glu
20 25 30

Val Ala Gly Ser Gly Glu Ala Glu Gly Ser Ser Ala Ser Ser Pro Ser
35 40 45

-continued

Leu Leu Pro Pro Arg Thr Pro Ala Phe Ser Pro Thr Pro Gly Arg Thr
    50                  55                  60

Gln Pro Thr Ala Pro Val Gly Pro Val Pro Pro Thr Asn Leu Leu Asp
65                  70                  75                  80

Gly Ile Val Asp Phe Phe Arg Gln Tyr Val Met Leu Ile Ala Val Val
                85                  90                  95

Gly Ser Leu Thr Phe Leu Ile Met Phe Ile Val Cys Ala Ala Leu Ile
            100                 105                 110

Thr Arg Gln Lys His Lys Ala Thr Ala Tyr Tyr Pro Ser Ser Phe Pro
        115                 120                 125

Glu Lys Lys Tyr Val Asp Gln Arg Asp Arg Ala Gly Gly Pro His Ala
    130                 135                 140

Phe Ser Glu Val Pro Asp Arg Ala Pro Asp Ser Arg Gln Glu Glu Gly
145                 150                 155                 160

Leu Asp Phe Phe Gln Gln Leu Gln Ala Asp Ile Leu Ala Cys Tyr Ser
                165                 170                 175

<210> SEQ ID NO 121
<211> LENGTH: 116
<212> TYPE: PRT
<213> ORGANISM: Rat

<400> SEQUENCE: 121

Met Glu Leu Leu Tyr Trp Cys Leu Leu Cys Leu Leu Leu Pro Leu Thr
 1               5                  10                  15

Ser Arg Thr Gln Lys Leu Pro Thr Arg Asp Glu Glu Leu Phe Gln Met
            20                  25                  30

Gln Ile Arg Asp Lys Ala Leu Phe His Asp Ser Ser Val Ile Pro Asp
        35                  40                  45

Gly Ala Glu Ile Ser Ser Tyr Leu Phe Arg Asp Thr Pro Arg Arg Tyr
    50                  55                  60

Phe Phe Met Val Glu Glu Asp Asn Thr Pro Leu Ser Val Thr Val Thr
65                  70                  75                  80

Pro Cys Asp Ala Pro Leu Glu Trp Lys Leu Ser Leu Gln Glu Leu Pro
                85                  90                  95

Glu Glu Ser Ser Ala Asp Gly Ser Gly Asp Pro Glu Pro Leu Asp Gln
            100                 105                 110

Gln Lys Gln Gln
        115

<210> SEQ ID NO 122
<211> LENGTH: 64
<212> TYPE: PRT
<213> ORGANISM: Human

<400> SEQUENCE: 122

Met Asn Leu Leu Ile Gly Ser Ile Ile Leu Ser Ser Phe Leu Val Leu
 1               5                  10                  15

Ser Asp Gly Asp Thr Thr Ala Ser Pro Ser Ser Met Ser Ser Ser Ser
            20                  25                  30

Val Leu Asn His Ile Ser Ser Ser Ser Ser Ser Val Trp His Leu Phe
        35                  40                  45

Asp Ile Cys Asp Ser Ser Lys Trp Asn Ala Tyr Cys Gln Val Trp Gly
    50                  55                  60

<210> SEQ ID NO 123

-continued

<211> LENGTH: 68
<212> TYPE: PRT
<213> ORGANISM: Human

<400> SEQUENCE: 123

Met Leu Thr Leu Pro Ile Leu Val Cys Lys Val Gln Asp Ser Asn Arg
1 5 10 15

Arg Lys Met Leu Pro Thr Gln Phe Leu Phe Leu Leu Gly Val Leu Gly
20 25 30

Ile Phe Gly Leu Thr Phe Ala Phe Ile Ile Gly Leu Asp Gly Ser Thr
35 40 45

Gly Pro Thr Arg Phe Phe Leu Phe Gly Ile Leu Phe Ser Ile Cys Phe
50 55 60

Ser Cys Leu Leu
65

<210> SEQ ID NO 124
<211> LENGTH: 110
<212> TYPE: PRT
<213> ORGANISM: mouse

<400> SEQUENCE: 124

Met Ile Ser Pro Ala Trp Ser Leu Phe Leu Ile Gly Thr Lys Ile Gly
1 5 10 15

Leu Phe Phe Gln Val Ala Pro Leu Ser Val Val Ala Lys Ser Cys Pro
20 25 30

Ser Val Cys Arg Cys Asp Ala Gly Phe Ile Tyr Cys Asn Asp Arg Ser
35 40 45

Leu Thr Ser Ile Pro Val Gly Ile Pro Glu Asp Ala Thr Thr Leu Tyr
50 55 60

Leu Gln Asn Asn Gln Ile Asn Asn Val Gly Ile Pro Ser Asp Leu Lys
65 70 75 80

Asn Leu Leu Lys Val Gln Arg Ile Tyr Leu Tyr His Asn Ser Leu Asp
85 90 95

Glu Phe Pro Thr Asn Leu Pro Lys Tyr Val Lys Glu Leu His
100 105 110

<210> SEQ ID NO 125
<211> LENGTH: 330
<212> TYPE: PRT
<213> ORGANISM: mouse

<400> SEQUENCE: 125

Met Gly Ser Pro Arg Leu Ala Ala Leu Leu Leu Ser Leu Pro Leu Leu
1 5 10 15

Leu Ile Gly Leu Ala Val Ser Ala Arg Val Ala Cys Pro Cys Leu Arg
20 25 30

Ser Trp Thr Ser His Cys Leu Leu Ala Tyr Arg Val Asp Lys Arg Phe
35 40 45

Ala Gly Leu Gln Trp Gly Trp Phe Pro Leu Leu Val Arg Lys Ser Lys
50 55 60

Ser Pro Pro Lys Phe Glu Asp Tyr Trp Arg His Arg Thr Pro Ala Ser
65 70 75 80

Phe Gln Arg Lys Leu Leu Gly Ser Pro Ser Leu Ser Glu Glu Ser His
85 90 95

Arg Ile Ser Ile Pro Ser Ser Ala Ile Ser His Arg Gly Gln Arg Thr
100 105 110

-continued

```
Lys Arg Ala Gln Pro Ser Ala Ala Glu Gly Arg Glu His Leu Pro Glu
        115                 120                 125

Ala Gly Ser Gln Lys Cys Gly Gly Pro Glu Phe Ser Phe Asp Leu Leu
    130                 135                 140

Pro Glu Val Gln Ala Val Arg Val Thr Ile Pro Ala Gly Pro Lys Ala
145                 150                 155                 160

Ser Val Arg Leu Cys Tyr Gln Trp Ala Leu Glu Cys Glu Asp Leu Ser
                165                 170                 175

Ser Pro Phe Asp Thr Gln Lys Ile Val Ser Gly Gly His Thr Val Asp
            180                 185                 190

Leu Pro Tyr Glu Phe Leu Leu Pro Cys Met Cys Ile Glu Ala Ser Tyr
        195                 200                 205

Leu Gln Glu Asp Thr Val Arg Arg Lys Lys Cys Pro Phe Gln Ser Trp
    210                 215                 220

Pro Glu Ala Tyr Gly Ser Asp Phe Trp Gln Ser Ile Arg Phe Thr Asp
225                 230                 235                 240

Tyr Ser Gln His Asn Gln Met Val Met Ala Leu Thr Leu Arg Cys Pro
                245                 250                 255

Leu Lys Leu Glu Ala Ser Leu Cys Trp Arg Gln Asp Pro Leu Thr Pro
            260                 265                 270

Cys Glu Thr Leu Pro Asn Ala Thr Ala Gln Glu Ser Glu Gly Trp Tyr
        275                 280                 285

Ile Leu Glu Asn Val Asp Leu His Pro Gln Leu Cys Phe Lys Phe Ser
    290                 295                 300

Phe Glu Asn Ser Ser His Val Glu Cys Pro His Gln Ser Gly Ser Leu
305                 310                 315                 320

Pro Ser Trp Thr Val Ser Met Asp Thr Gln
                325                 330


<210> SEQ ID NO 126
<211> LENGTH: 37
<212> TYPE: PRT
<213> ORGANISM: Rat

<400> SEQUENCE: 126

Met Leu Trp Val Leu Leu Ser Leu Thr Pro Leu Leu Ser Pro Leu Ile
 1               5                  10                  15

Phe Phe Pro Val Lys Thr Val Ala Leu Glu Glu Ile Ser Thr Ile Cys
            20                  25                  30

Arg Ala Asp Val Leu
        35


<210> SEQ ID NO 127
<211> LENGTH: 42
<212> TYPE: PRT
<213> ORGANISM: mouse

<400> SEQUENCE: 127

Met Gly Ser Pro Ile Ser Gly Val Cys Pro Val Leu Pro Gly Gly Leu
 1               5                  10                  15

Phe Val Ala Leu Gly Trp Ile Phe Leu Leu Phe His Arg Asp Ala Phe
            20                  25                  30

Ser Leu His Thr Met Ser Ala Gly Phe Pro
        35                  40


<210> SEQ ID NO 128
<211> LENGTH: 253
```

-continued

<212> TYPE: PRT
<213> ORGANISM: mouse

<400> SEQUENCE: 128

Met Met Tyr Trp Ile Val Phe Ala Ile Phe Met Ala Ala Glu Thr Phe
1 5 10 15

Thr Asp Ile Phe Ile Ser Trp Ser Gly Pro Arg Ile Gly Arg Pro Trp
20 25 30

Gly Trp Glu Gly Pro His His His His His Leu Ala Ser Gly Ser His
35 40 45

Lys Pro Leu Pro Leu Leu Thr His Arg Phe Pro Phe Tyr Tyr Glu Phe
50 55 60

Lys Met Ala Phe Val Leu Trp Leu Leu Ser Pro Tyr Thr Lys Gly Ala
65 70 75 80

Ser Leu Leu Tyr Arg Lys Phe Val His Pro Ser Leu Ser Arg His Glu
85 90 95

Lys Glu Ile Asp Ala Cys Ile Val Gln Ala Lys Glu Arg Ser Tyr Glu
100 105 110

Thr Met Leu Ser Phe Gly Lys Arg Ser Leu Asn Ile Ala Ala Ser Ala
115 120 125

Ala Val Gln Ala Ala Thr Lys Ser Gln Gly Ala Leu Ala Gly Arg Leu
130 135 140

Arg Ser Phe Ser Met Gln Asp Leu Arg Ser Ile Pro Asp Thr Pro Val
145 150 155 160

Pro Thr Tyr Gln Asp Pro Leu Tyr Leu Glu Asp Gln Val Pro Arg Arg
165 170 175

Arg Pro Pro Ile Gly Tyr Arg Pro Gly Gly Leu Gln Gly Ser Asp Thr
180 185 190

Glu Asp Glu Cys Trp Ser Asp Asn Glu Ile Val Pro Gln Pro Pro Val
195 200 205

Arg Pro Arg Glu Lys Pro Leu Gly Arg Ser Gln Ser Leu Arg Val Val
210 215 220

Lys Arg Lys Pro Leu Thr Arg Glu Gly Thr Ser Arg Ser Leu Lys Val
225 230 235 240

Arg Thr Arg Lys Lys Ala Met Pro Ser Asp Met Asp Ser
245 250

<210> SEQ ID NO 129
<211> LENGTH: 40
<212> TYPE: PRT
<213> ORGANISM: mouse

<400> SEQUENCE: 129

Met Lys Ala Met Ala Leu Ser Leu Gly Ala Ser Pro Val Leu Ala Phe
1 5 10 15

Leu Leu Ser Gly Tyr Ser Asp Gly Tyr Gln Val Cys Ser Arg Phe Gly
20 25 30

Ser Lys Val Pro Gln Phe Leu Asn
35 40

<210> SEQ ID NO 130
<211> LENGTH: 87
<212> TYPE: PRT
<213> ORGANISM: mouse

<400> SEQUENCE: 130

Met Ile Ala Val Thr Phe Ala Ile Val Leu Gly Val Ile Ile Tyr Arg

-continued

```
 1               5                   10                  15

Ile Ser Thr Ala Ala Ala Leu Ala Met Asn Ser Ser Pro Ser Val Arg
            20                  25                  30

Ser Asn Ile Arg Val Thr Val Thr Ala Thr Ala Val Ile Ile Asn Leu
        35                  40                  45

Val Val Ile Ile Leu Leu Asp Glu Val Tyr Gly Cys Ile Ala Arg Trp
    50                  55                  60

Leu Thr Lys Ile Gly Glu Cys His Val Gln Asp Ser Ile Gly Ser Met
65                  70                  75                  80

Gly Leu Gly Gln Gly Gln Pro
                85


<210> SEQ ID NO 131
<211> LENGTH: 70
<212> TYPE: PRT
<213> ORGANISM: mouse

<400> SEQUENCE: 131

Met Phe Gly Leu Val His Val Cys Thr Cys Val Cys Val Cys Val Cys
 1               5                   10                  15

Val Cys Val Cys Val Cys Ile Cys Ser Cys Gly Tyr Val His Val Pro
            20                  25                  30

Cys Gly Cys Val Cys Leu Trp Gly Pro Glu Val Arg Tyr Leu Pro Leu
        35                  40                  45

Ser Leu His Pro Gly Gly Phe Cys Phe Val Leu Phe Cys Phe Gly Pro
    50                  55                  60

Gly Leu Ser Leu Ile Ser
65                  70


<210> SEQ ID NO 132
<211> LENGTH: 63
<212> TYPE: PRT
<213> ORGANISM: mouse

<400> SEQUENCE: 132

Met Trp Leu Leu Val Ala Leu Thr Leu Ser Val Tyr Ser Leu Val Ala
 1               5                   10                  15

Phe Val Thr Gly Met Leu Cys Asp Thr Val Val Ile Lys Met Leu Met
            20                  25                  30

Ser Leu His Lys Ser Ser Lys Leu Asn Pro Arg Ala Lys Cys Gly Gly
        35                  40                  45

Val Pro Leu Ile Pro Ala Leu Trp Gly Gln Val Gln Val Val Leu
    50                  55                  60


<210> SEQ ID NO 133
<211> LENGTH: 39
<212> TYPE: PRT
<213> ORGANISM: mouse

<400> SEQUENCE: 133

Met Asp Asn Thr Leu Ser Ile Ile Ile Tyr Leu Leu Phe Ile Phe Ala
 1               5                   10                  15

Ile Ser Val Leu Asp Ser Gln Leu Ser Thr Arg Cys Leu Trp Trp Phe
            20                  25                  30

Ser Lys Asp Leu Glu Val Thr
        35


<210> SEQ ID NO 134
```

-continued

<211> LENGTH: 90
<212> TYPE: PRT
<213> ORGANISM: Rat

<400> SEQUENCE: 134

```
Met Pro Thr Met Trp Pro Leu Leu His Val Leu Trp Leu Ala Leu Val
 1               5                  10                  15

Cys Gly Ser Val His Thr Thr Leu Ser Lys Ser Asp Ala Lys Lys Ala
            20                  25                  30

Ala Ser Lys Thr Leu Leu Glu Lys Thr Gln Phe Ser Asp Lys Pro Val
        35                  40                  45

Gln Asp Arg Gly Leu Val Val Thr Asp Ile Lys Ala Glu Asp Val Val
    50                  55                  60

Leu Glu His Arg Ser Tyr Cys Ser Ala Arg Ala Arg Glu Arg Asn Phe
65                  70                  75                  80

Ala Gly Glu Val Leu Gly Ile Cys His Ser
                85                  90
```

<210> SEQ ID NO 135
<211> LENGTH: 193
<212> TYPE: PRT
<213> ORGANISM: Rat

<400> SEQUENCE: 135

```
Met Thr Ser Gly Pro Gly Gly Pro Ala Ala Ala Thr Gly Gly Gly Lys
 1               5                  10                  15

Asp Thr His Gln Trp Tyr Val Cys Asn Arg Glu Lys Leu Cys Glu Ser
            20                  25                  30

Leu Gln Ser Val Phe Val Gln Ser Tyr Leu Asp Gln Gly Thr Gln Ile
        35                  40                  45

Phe Leu Asn Asn Ser Ile Glu Lys Ser Gly Trp Leu Phe Ile Gln Leu
    50                  55                  60

Tyr His Ser Phe Val Ser Ser Val Phe Thr Leu Phe Met Ser Arg Thr
65                  70                  75                  80

Ser Ile Asn Gly Leu Leu Gly Arg Gly Ser Met Phe Val Phe Ser Pro
                85                  90                  95

Asp Gln Phe Gln Arg Leu Leu Lys Ile Asn Pro Asp Trp Lys Thr His
            100                 105                 110

Arg Leu Leu Asp Leu Gly Ala Gly Asp Gly Glu Val Thr Lys Ile Met
        115                 120                 125

Ser Pro His Phe Glu Glu Ile Tyr Ala Thr Glu Leu Ser Glu Thr Met
    130                 135                 140

Ile Trp Gln Leu Gln Lys Lys Lys Tyr Arg Val Leu Gly Ile Asn Glu
145                 150                 155                 160

Trp Gln Asn Thr Gly Phe Gln Tyr Asp Val Ile Ser Cys Leu Asn Leu
                165                 170                 175

Leu Asp Arg Cys Asp Gln Pro Leu Thr Leu Leu Lys Asp Ile Arg Met
            180                 185                 190

Ser
```

<210> SEQ ID NO 136
<211> LENGTH: 106
<212> TYPE: PRT
<213> ORGANISM: Rat

<400> SEQUENCE: 136

```
Met Ala Ala Pro Met Asp Arg Thr His Gly Gly Arg Ala Ala Arg Ala
```

-continued

```
 1               5                  10                  15

Leu Arg Arg Ala Leu Ala Leu Ala Ser Leu Ala Gly Leu Leu Leu Ser
            20                  25                  30

Gly Leu Ala Gly Ala Leu Pro Thr Leu Gly Pro Gly Trp Arg Arg Gln
        35                  40                  45

Asn Pro Glu Pro Pro Ala Ser Arg Thr Arg Ser Leu Leu Leu Asp Ala
    50                  55                  60

Ala Ser Gly Gln Leu Arg Leu Glu Tyr Gly Phe His Pro Asp Ala Val
65                  70                  75                  80

Ala Trp Ala Asn Leu Thr Asn Ala Ile Arg Glu Thr Gly Trp Ala Tyr
                85                  90                  95

Leu Asp Leu Gly Thr Asn Gly Ser Tyr Lys
            100                 105


<210> SEQ ID NO 137
<211> LENGTH: 286
<212> TYPE: PRT
<213> ORGANISM: Rat

<400> SEQUENCE: 137

Met Ala Ala Ala Met Pro Leu Gly Leu Ser Leu Leu Leu Leu Val Leu
 1               5                  10                  15

Val Gly Gln Gly Cys Cys Gly Arg Val Glu Gly Pro Arg Asp Ser Leu
            20                  25                  30

Arg Glu Glu Leu Val Ile Thr Pro Leu Pro Ser Gly Asp Val Ala Ala
        35                  40                  45

Thr Phe Gln Phe Arg Thr Arg Trp Asp Ser Asp Leu Gln Arg Glu Gly
    50                  55                  60

Val Ser His Tyr Arg Leu Phe Pro Lys Ala Leu Gly Gln Leu Ile Ser
65                  70                  75                  80

Lys Tyr Ser Leu Arg Glu Leu His Leu Ser Phe Thr Gln Gly Phe Trp
                85                  90                  95

Arg Thr Arg Tyr Trp Gly Pro Pro Phe Leu Gln Ala Pro Ser Gly Ala
            100                 105                 110

Glu Leu Trp Val Trp Phe Gln Asp Thr Val Thr Asp Val Asp Lys Ser
        115                 120                 125

Trp Lys Glu Leu Ser Asn Val Leu Ser Gly Ile Phe Cys Ala Ser Leu
    130                 135                 140

Asn Phe Ile Asp Ser Thr Asn Thr Val Thr Pro Thr Ala Ser Phe Lys
145                 150                 155                 160

Pro Leu Gly Leu Ala Asn Asp Thr Asp His Tyr Phe Leu Arg Tyr Ala
                165                 170                 175

Val Leu Pro Arg Glu Val Val Cys Thr Glu Asn Leu Thr Pro Trp Lys
            180                 185                 190

Lys Leu Leu Pro Cys Ser Ser Lys Ala Gly Leu Ser Val Leu Leu Lys
        195                 200                 205

Ala Asp Arg Leu Phe His Thr Ser Tyr His Ser Gln Ala Val His Ile
    210                 215                 220

Arg Pro Ile Cys Arg Asn Ala His Cys Thr Ser Ile Ser Trp Glu Leu
225                 230                 235                 240

Arg Gln Thr Leu Ser Val Val Phe Asp Ala Phe Ile Thr Gly Gln Gly
                245                 250                 255

Lys Lys Glu Ala Cys Pro Leu Ala Ser Gln Ser Leu Val Tyr Val Asp
            260                 265                 270
```

-continued

Ile Thr Gly Tyr Ser Gln Asp Asn Glu Thr Leu Glu Val Ser
275 280 285

<210> SEQ ID NO 138
<211> LENGTH: 198
<212> TYPE: PRT
<213> ORGANISM: Rat

<400> SEQUENCE: 138

Met Thr Val Phe Arg Lys Val Thr Thr Met Ile Ser Trp Met Leu Leu
1 5 10 15

Ala Cys Ala Leu Pro Cys Ala Ala Asp Pro Met Leu Gly Ala Phe Ala
20 25 30

Arg Arg Asp Phe Gln Lys Gly Gly Pro Gln Leu Val Cys Ser Leu Pro
35 40 45

Gly Pro Gln Gly Pro Pro Gly Pro Pro Gly Ala Pro Gly Ser Ser Gly
50 55 60

Met Val Gly Arg Met Gly Phe Pro Gly Lys Asp Gly Gln Asp Gly Gln
65 70 75 80

Asp Gly Asp Arg Gly Asp Ser Gly Glu Glu Gly Pro Pro Gly Arg Thr
85 90 95

Gly Asn Arg Gly Lys Gln Gly Pro Lys Gly Lys Ala Gly Ala Ile Gly
100 105 110

Arg Ala Gly Pro Arg Gly Pro Lys Gly Val Ser Gly Thr Pro Gly Lys
115 120 125

His Gly Ile Pro Gly Lys Lys Gly Pro Lys Gly Lys Lys Gly Glu Pro
130 135 140

Gly Leu Pro Gly Pro Cys Ser Cys Gly Ser Ser Arg Ala Lys Ser Ala
145 150 155 160

Phe Ser Val Ala Val Thr Lys Ser Tyr Pro Arg Glu Arg Leu Pro Ile
165 170 175

Lys Phe Asp Lys Ile Leu Met Asn Glu Gly Gly His Tyr Asn Ala Ser
180 185 190

Ser Gly Lys Phe Val Cys
195

<210> SEQ ID NO 139
<211> LENGTH: 233
<212> TYPE: PRT
<213> ORGANISM: Rat

<400> SEQUENCE: 139

Met Ala Ser Ala Leu Glu Glu Leu Gln Lys Asp Leu Glu Glu Val Lys
1 5 10 15

Val Leu Leu Glu Lys Ser Thr Arg Lys Arg Leu Arg Asp Thr Leu Thr
20 25 30

Asn Glu Lys Ser Lys Ile Glu Thr Glu Leu Arg Asn Lys Met Gln Gln
35 40 45

Lys Ser Gln Lys Lys Pro Glu Phe Asp Asn Glu Lys Pro Ala Ala Val
50 55 60

Val Ala Pro Leu Thr Thr Gly Tyr Thr Val Lys Ile Ser Asn Tyr Gly
65 70 75 80

Trp Asp Gln Ser Asp Lys Phe Val Lys Ile Tyr Ile Thr Leu Thr Gly
85 90 95

Val His Gln Val Pro Ala Glu Asn Val Gln Val His Phe Thr Glu Arg
100 105 110

-continued

```
Ser Phe Asp Leu Leu Val Lys Asn Leu Asn Gly Lys Asn Tyr Ser Met
        115                 120                 125

Ile Val Asn Asn Leu Leu Lys Pro Ile Ser Val Glu Ser Ser Ser Lys
    130                 135                 140

Lys Val Lys Thr Asp Thr Val Ile Ile Leu Cys Arg Lys Lys Ala Glu
145                 150                 155                 160

Asn Thr Arg Trp Asp Tyr Leu Thr Gln Val Glu Lys Glu Cys Lys Glu
                165                 170                 175

Lys Glu Lys Pro Ser Tyr Asp Thr Glu Ala Asp Pro Ser Glu Gly Leu
            180                 185                 190

Met Asn Val Leu Lys Lys Ile Tyr Glu Asp Gly Asp Asp Asp Met Lys
        195                 200                 205

Arg Thr Ile Asn Lys Ala Trp Val Glu Ser Arg Glu Lys Gln Ala Arg
    210                 215                 220

Glu Asp Thr Glu Phe Leu Gln Pro Gly
225                 230


<210> SEQ ID NO 140
<211> LENGTH: 38
<212> TYPE: PRT
<213> ORGANISM: Human

<400> SEQUENCE: 140

Met Gly Leu Ala Leu Cys Leu Ala Ser Ala Gly Ile Ser Gly Ser Arg
 1               5                  10                  15

Ser Ala Phe Leu Gly Val Pro Arg Pro Arg Pro Thr Leu Ile Lys Leu
            20                  25                  30

Ile Asp Thr Val Asp Leu
        35


<210> SEQ ID NO 141
<211> LENGTH: 322
<212> TYPE: PRT
<213> ORGANISM: mouse

<400> SEQUENCE: 141

Met Asp Ala Arg Trp Trp Ala Val Val Val Leu Ala Thr Leu Pro Ser
 1               5                  10                  15

Leu Gly Ala Gly Gly Glu Ser Pro Glu Ala Pro Pro Gln Ser Trp Thr
            20                  25                  30

Gln Leu Trp Leu Phe Arg Phe Leu Leu Asn Val Ala Gly Tyr Ala Ser
        35                  40                  45

Phe Met Val Pro Gly Tyr Leu Leu Val Gln Tyr Leu Arg Arg Lys Asn
    50                  55                  60

Tyr Leu Glu Thr Gly Arg Gly Leu Cys Phe Pro Leu Val Lys Ala Cys
65                  70                  75                  80

Val Phe Gly Asn Glu Pro Lys Ala Pro Asp Glu Val Leu Leu Ala Pro
                85                  90                  95

Arg Thr Glu Thr Ala Glu Ser Thr Pro Ser Trp Gln Val Leu Lys Leu
            100                 105                 110

Val Phe Cys Ala Ser Gly Leu Gln Val Ser Tyr Leu Thr Trp Gly Ile
        115                 120                 125

Leu Gln Glu Arg Val Met Thr Gly Ser Tyr Gly Ala Thr Ala Thr Ser
    130                 135                 140

Pro Gly Glu His Phe Thr Asp Ser Gln Phe Leu Val Leu Met Asn Arg
145                 150                 155                 160
```

-continued

Val Leu Ala Leu Val Val Ala Gly Leu Tyr Cys Val Leu Arg Lys Gln
165 170 175

Pro Arg His Gly Ala Pro Met Tyr Arg Tyr Ser Phe Ala Ser Leu Ser
180 185 190

Asn Val Leu Ser Ser Trp Cys Gln Tyr Glu Ala Leu Lys Phe Val Ser
195 200 205

Phe Pro Thr Gln Val Leu Ala Lys Ala Ser Lys Val Ile Pro Val Met
210 215 220

Met Met Gly Lys Leu Val Ser Arg Arg Ser Tyr Glu His Trp Glu Tyr
225 230 235 240

Leu Thr Ala Gly Leu Ile Ser Ile Gly Val Ser Met Phe Leu Leu Ser
245 250 255

Ser Gly Pro Glu Pro Arg Ser Ser Pro Ala Thr Thr Leu Ser Gly Leu
260 265 270

Val Leu Leu Ala Gly Tyr Ile Ala Phe Asp Ser Phe Thr Ser Asn Trp
275 280 285

Gln Asp Ala Leu Phe Ala Tyr Lys Met Ser Ser Val Gln Met Met Phe
290 295 300

Gly Val Asn Leu Phe Ser Cys Leu Phe Thr Val Gly Ser Leu Leu Glu
305 310 315 320

Gln Gly

<210> SEQ ID NO 142
<211> LENGTH: 312
<212> TYPE: PRT
<213> ORGANISM: mouse

<400> SEQUENCE: 142

Met Leu Cys Leu Cys Leu Tyr Val Pro Ile Ala Gly Ala Ala Gln Thr
1 5 10 15

Glu Phe Gln Tyr Phe Glu Ser Lys Gly Leu Pro Ala Glu Leu Lys Ser
20 25 30

Ile Phe Lys Leu Ser Val Phe Ile Pro Ser Gln Glu Phe Ser Thr Tyr
35 40 45

Arg Gln Trp Lys Gln Lys Ile Val Gln Ala Gly Asp Lys Asp Leu Asp
50 55 60

Gly Gln Leu Asp Phe Glu Glu Phe Val His Tyr Leu Gln Asp His Glu
65 70 75 80

Lys Lys Leu Arg Leu Val Phe Lys Ser Leu Asp Lys Lys Asn Asp Gly
85 90 95

Arg Ile Asp Ala Gln Glu Ile Met Gln Ser Leu Arg Asp Leu Gly Val
100 105 110

Lys Ile Ser Glu Gln Gln Ala Glu Lys Ile Leu Lys Ser Met Asp Lys
115 120 125

Asn Gly Thr Met Thr Ile Asp Trp Asn Glu Trp Arg Asp Tyr His Leu
130 135 140

Leu His Pro Val Glu Asn Ile Pro Glu Ile Ile Leu Tyr Trp Lys His
145 150 155 160

Ser Thr Ile Phe Asp Val Gly Glu Asn Leu Thr Val Pro Asp Glu Phe
165 170 175

Thr Val Glu Glu Arg Gln Thr Gly Met Trp Trp Arg His Leu Val Ala
180 185 190

Gly Gly Gly Ala Gly Ala Val Ser Arg Thr Cys Thr Ala Pro Leu Asp
195 200 205

-continued

```
Arg Leu Lys Val Leu Met Gln Val His Ala Ser Arg Ser Asn Asn Met
    210                 215                 220

Cys Ile Val Gly Gly Phe Thr Gln Met Ile Arg Glu Gly Gly Ala Lys
225                 230                 235                 240

Ser Leu Trp Arg Gly Asn Gly Ile Asn Val Leu Lys Ile Ala Pro Glu
                245                 250                 255

Ser Ala Ile Lys Phe Met Ala Tyr Glu Gln Met Lys Arg Leu Val Gly
            260                 265                 270

Ser Asp Gln Glu Thr Leu Arg Ile His Glu Arg Leu Val Ala Gly Ser
        275                 280                 285

Leu Ala Gly Ala Ile Ala Gln Ser Ser Ile Tyr Pro Met Glu Val Leu
    290                 295                 300

Lys Thr Arg Met Ala Leu Arg Lys
305                 310


<210> SEQ ID NO 143
<211> LENGTH: 163
<212> TYPE: PRT
<213> ORGANISM: Rat

<400> SEQUENCE: 143

Met Pro Leu Val Thr Thr Leu Phe Tyr Ala Cys Phe Tyr His Tyr Thr
 1               5                  10                  15

Glu Ser Glu Gly Thr Phe Ser Ser Pro Val Asn Leu Lys Lys Thr Phe
            20                  25                  30

Lys Ile Pro Asp Arg Gln Tyr Val Leu Thr Ala Leu Ala Ala Arg Ala
        35                  40                  45

Lys Leu Arg Ala Trp Asn Asp Val Asp Ala Leu Phe Thr Thr Lys Asn
    50                  55                  60

Trp Leu Gly Tyr Thr Lys Lys Arg Ala Pro Ile Gly Phe His Arg Val
65                  70                  75                  80

Val Glu Ile Leu His Lys Asn Ser Ala Pro Val Gln Ile Leu Gln Glu
                85                  90                  95

Tyr Val Asn Leu Val Glu Asp Val Asp Thr Lys Leu Asn Leu Ala Thr
            100                 105                 110

Lys Phe Lys Cys His Asp Val Val Ile Asp Thr Cys Arg Asp Leu Lys
        115                 120                 125

Asp Arg Gln Gln Leu Leu Ala Tyr Arg Ser Lys Val Asp Lys Gly Ser
    130                 135                 140

Ala Glu Glu Glu Lys Ile Asp Val Ile Leu Ser Ser Ser Gln Ile Arg
145                 150                 155                 160

Trp Lys Asn


<210> SEQ ID NO 144
<211> LENGTH: 330
<212> TYPE: PRT
<213> ORGANISM: Rat

<400> SEQUENCE: 144

Met Ala Gly Trp Ala Gly Ala Glu Leu Ser Val Leu Asn Pro Leu Arg
 1               5                  10                  15

Ala Leu Trp Leu Leu Leu Ala Ala Ala Phe Leu Leu Ala Leu Leu Leu
            20                  25                  30

Gln Leu Ala Pro Ala Arg Leu Leu Pro Ser Cys Ala Leu Phe Gln Asp
        35                  40                  45

Leu Ile Arg Tyr Gly Lys Thr Lys Gln Ser Gly Ser Arg Arg Pro Ala
```

-continued

```
    50                  55                  60

Val Cys Arg Ala Phe Asp Val Pro Lys Arg Tyr Phe Ser His Phe Tyr
65                  70                  75                  80

Val Val Ser Val Leu Trp Asn Gly Ser Leu Leu Trp Phe Leu Ser Gln
                85                  90                  95

Ser Leu Phe Leu Gly Ala Pro Phe Pro Ser Trp Leu Trp Ala Leu Leu
            100                 105                 110

Arg Thr Leu Gly Val Thr Gln Phe Gln Ala Leu Gly Met Glu Ser Lys
        115                 120                 125

Ala Ser Arg Ile Gln Ala Gly Glu Leu Ala Leu Ser Thr Phe Leu Val
    130                 135                 140

Leu Val Phe Leu Trp Val His Ser Leu Arg Arg Leu Phe Glu Cys Phe
145                 150                 155                 160

Tyr Val Ser Val Phe Ser Asn Thr Ala Ile His Val Val Gln Tyr Cys
                165                 170                 175

Phe Gly Leu Val Tyr Tyr Val Leu Val Gly Leu Thr Val Leu Ser Gln
            180                 185                 190

Val Pro Met Asn Asp Lys Asn Val Tyr Ala Leu Gly Lys Asn Leu Leu
        195                 200                 205

Leu Gln Ala Arg Trp Phe His Ile Leu Gly Met Met Met Phe Phe Trp
    210                 215                 220

Ser Ser Ala His Gln Tyr Lys Cys His Val Ile Leu Ser Asn Leu Arg
225                 230                 235                 240

Arg Asn Lys Lys Gly Val Val Ile His Cys Gln His Arg Ile Pro Phe
                245                 250                 255

Gly Asp Trp Phe Glu Tyr Val Ser Ser Ala Asn Tyr Leu Ala Glu Leu
            260                 265                 270

Met Ile Tyr Ile Ser Met Ala Val Thr Phe Gly Leu His Asn Val Thr
        275                 280                 285

Trp Trp Leu Val Val Thr Tyr Val Phe Phe Ser Gln Ala Leu Ser Ala
    290                 295                 300

Phe Phe Asn His Arg Phe Tyr Lys Ser Thr Phe Val Ser Tyr Pro Lys
305                 310                 315                 320

His Arg Lys Ala Phe Leu Pro Phe Leu Phe
                325                 330


<210> SEQ ID NO 145
<211> LENGTH: 301
<212> TYPE: PRT
<213> ORGANISM: Rat

<400> SEQUENCE: 145

Met Leu Val Ala Phe Leu Gly Ala Ser Ala Val Thr Ala Ser Thr Gly
 1               5                  10                  15

Leu Leu Trp Lys Lys Ala His Ala Glu Ser Pro Pro Ser Val Asn Ser
            20                  25                  30

Lys Lys Thr Asp Ala Gly Asp Lys Gly Lys Ser Lys Asp Thr Arg Glu
        35                  40                  45

Val Ser Ser His Glu Gly Ser Ala Ala Asp Thr Ala Ala Glu Pro Tyr
    50                  55                  60

Pro Glu Glu Lys Lys Lys Lys Arg Ser Gly Phe Arg Asp Arg Lys Val
65                  70                  75                  80

Met Glu Tyr Glu Asn Arg Ile Arg Ala Tyr Ser Thr Pro Asp Lys Ile
                85                  90                  95
```

-continued

```
Phe Arg Tyr Phe Ala Thr Leu Lys Val Ile Asn Glu Pro Gly Glu Thr
            100                 105                 110

Glu Val Phe Met Thr Pro Gln Asp Phe Val Arg Ser Ile Thr Pro Asn
        115                 120                 125

Glu Lys Gln Pro Glu His Leu Gly Leu Asp Gln Tyr Ile Ile Lys Arg
    130                 135                 140

Phe Asp Gly Lys Lys Ile Ala Gln Glu Arg Glu Lys Phe Ala Asp Glu
145                 150                 155                 160

Gly Ser Ile Phe Tyr Thr Leu Gly Glu Cys Gly Leu Ile Ser Phe Ser
                165                 170                 175

Asp Tyr Ile Phe Leu Thr Thr Val Leu Ser Thr Pro Gln Arg Asn Phe
            180                 185                 190

Glu Ile Ala Phe Lys Met Phe Asp Leu Asn Gly Asp Gly Glu Val Asp
        195                 200                 205

Met Glu Glu Phe Glu Gln Val Gln Ser Ile Ile Arg Ser Gln Thr Ser
    210                 215                 220

Met Gly Met Arg His Arg Asp Arg Pro Thr Thr Gly Asn Thr Leu Lys
225                 230                 235                 240

Ser Gly Leu Cys Ser Ala Leu Thr Thr Tyr Phe Phe Gly Ala Asp Leu
                245                 250                 255

Lys Gly Lys Leu Thr Ile Lys Asn Phe Leu Glu Phe Gln Arg Lys Leu
            260                 265                 270

Gln Arg Cys Leu Leu Gly Leu Pro Val Trp Glu Gly Ser Pro His Leu
        275                 280                 285

Pro Thr Gly His Trp Leu Arg Glu Leu Trp Ser Leu Leu
    290                 295                 300


<210> SEQ ID NO 146
<211> LENGTH: 61
<212> TYPE: PRT
<213> ORGANISM: Rat

<400> SEQUENCE: 146

Met Glu Asn Ile Tyr Tyr Thr Asn Leu Ile Thr Ile Leu Gly Asn Lys
 1               5                  10                  15

His Ala Asn Gln Met Glu Leu Asn Leu Gln Ala Leu Ile Leu Ser Pro
            20                  25                  30

Trp Phe Ala Val Cys Ala Pro Pro Gly Phe Ala Arg Asp Gln Ala Val
        35                  40                  45

Arg Gly Leu Ala Leu Ala Gly Arg Arg Ile Thr Val Val
    50                  55                  60


<210> SEQ ID NO 147
<211> LENGTH: 105
<212> TYPE: PRT
<213> ORGANISM: Rat

<400> SEQUENCE: 147

Met Leu Arg Arg Gln Leu Val Trp Trp His Leu Leu Ala Leu Leu Phe
 1               5                  10                  15

Leu Pro Phe Cys Leu Cys Gln Asp Glu Tyr Met Glu Ser Pro Gln Ala
            20                  25                  30

Gly Gly Leu Pro Pro Asp Cys Ser Lys Cys Cys His Gly Asp Tyr Gly
        35                  40                  45

Phe Arg Gly Tyr Gln Gly Pro Pro Gly Pro Pro Gly Pro Pro Gly Ile
    50                  55                  60
```

-continued

Pro Gly Asn His Gly Asn Asn Gly Asn Asn Gly Ala Thr Gly His Glu
65 70 75 80

Gly Ala Lys Gly Glu Lys Gly Asp Lys Gly Asp Leu Gly Pro Arg Gly
85 90 95

Glu Arg Gly Gln His Gly Pro Lys Gly
100 105

<210> SEQ ID NO 148
<211> LENGTH: 210
<212> TYPE: PRT
<213> ORGANISM: Rat

<400> SEQUENCE: 148

Met Leu Gly Ala Thr Ser Leu Ser Trp Pro Trp Val Leu Trp Ala Val
1 5 10 15

Ala Gln Arg Asp Ser Val Asp Ala Ile Gly Met Phe Leu Gly Gly Leu
20 25 30

Val Ala Thr Ile Phe Leu Asp Ile Ile Tyr Ile Ser Ile Phe Tyr Ser
35 40 45

Ser Val Ala Val Gly Asp Thr Gly Arg Phe Ser Ala Gly Met Ala Ile
50 55 60

Phe Ser Leu Leu Leu Gln Ala Leu Leu Leu Leu Pro Arg Leu Pro His
65 70 75 80

Ala Pro Gly Ser Glu Gly Val Ser Ser Arg Ser Ala Arg Ile Ser Ser
85 90 95

Asp Leu Leu Arg Asn Ile Val Pro Thr Arg Gln Leu Thr Arg Gln Thr
100 105 110

His Leu Gln Thr Pro Leu Gln Ala Trp Arg Thr Arg Ala Lys Leu Pro
115 120 125

Pro Gly Gly Thr Glu Ala Val Pro Gly Arg Pro Gly Ala Gln Gln Asp
130 135 140

Ala Cys His Leu Leu Tyr Trp Thr Tyr Asn Gly Val Ser Ser Ile Pro
145 150 155 160

Cys His Arg Gly Gly Leu Ser His Val Pro Ser Glu Val Pro Ala Glu
165 170 175

Lys Ser Pro Val Leu Ile Leu His Ala Ala Pro Pro Phe Lys Thr Pro
180 185 190

Val Asn Pro Trp Ala Arg Thr Val Val Gly Phe Phe Pro Ser Ser Pro
195 200 205

Ser Leu
210

<210> SEQ ID NO 149
<211> LENGTH: 301
<212> TYPE: PRT
<213> ORGANISM: Rat

<400> SEQUENCE: 149

Met Leu Val Ala Phe Leu Gly Ala Ser Ala Val Thr Ala Ser Thr Gly
1 5 10 15

Leu Leu Trp Lys Lys Ala His Ala Glu Ser Pro Pro Ser Val Asn Ser
20 25 30

Lys Lys Thr Asp Ala Gly Asp Lys Gly Lys Ser Lys Asp Thr Arg Glu
35 40 45

Val Ser Ser His Glu Gly Ser Ala Ala Asp Thr Ala Ala Glu Pro Tyr
50 55 60

-continued

```
Pro Glu Glu Lys Lys Lys Lys Arg Ser Gly Phe Arg Asp Arg Lys Val
65                  70                  75                  80

Met Glu Tyr Glu Asn Arg Ile Arg Ala Tyr Ser Thr Pro Asp Lys Ile
                85                  90                  95

Phe Arg Tyr Phe Ala Thr Leu Lys Val Ile Asn Glu Pro Gly Glu Thr
            100                 105                 110

Glu Val Phe Met Thr Pro Gln Asp Phe Val Arg Ser Ile Thr Pro Asn
        115                 120                 125

Glu Lys Gln Pro Glu His Leu Gly Leu Asp Gln Tyr Ile Ile Lys Arg
    130                 135                 140

Phe Asp Gly Lys Lys Ile Ala Gln Glu Arg Glu Lys Phe Ala Asp Glu
145                 150                 155                 160

Gly Ser Ile Phe Tyr Thr Leu Gly Glu Cys Gly Leu Ile Ser Phe Ser
                165                 170                 175

Asp Tyr Ile Phe Leu Thr Thr Val Leu Ser Thr Pro Gln Arg Asn Phe
            180                 185                 190

Glu Ile Ala Phe Lys Met Phe Asp Leu Asn Gly Asp Gly Glu Val Asp
        195                 200                 205

Met Glu Glu Phe Glu Gln Val Gln Ser Ile Ile Arg Ser Gln Thr Ser
    210                 215                 220

Met Gly Met Arg His Arg Asp Arg Pro Thr Thr Gly Asn Thr Leu Lys
225                 230                 235                 240

Ser Gly Leu Cys Ser Ala Leu Thr Thr Tyr Phe Phe Gly Ala Asp Leu
                245                 250                 255

Lys Gly Lys Leu Thr Ile Lys Asn Phe Leu Glu Phe Gln Arg Lys Leu
            260                 265                 270

Gln Arg Cys Leu Leu Gly Leu Pro Val Trp Glu Gly Ser Pro His Leu
        275                 280                 285

Pro Thr Gly His Trp Leu Arg Glu Leu Trp Ser Leu Leu
    290                 295                 300


<210> SEQ ID NO 150
<211> LENGTH: 80
<212> TYPE: PRT
<213> ORGANISM: Human

<400> SEQUENCE: 150

Met Lys Leu Ser Gly Met Phe Leu Leu Leu Ser Leu Ala Leu Phe Cys
 1               5                  10                  15

Phe Leu Thr Gly Val Phe Ser Gln Gly Gly Gln Val Asp Cys Gly Glu
            20                  25                  30

Phe Gln Asp Thr Lys Val Tyr Cys Thr Arg Glu Ser Asn Pro His Cys
        35                  40                  45

Gly Ser Asp Gly Gln Thr Tyr Gly Asn Lys Cys Ala Phe Cys Lys Ala
    50                  55                  60

Ile Val Lys Ser Gly Gly Lys Ile Ser Leu Lys His Pro Gly Lys Cys
65                  70                  75                  80


<210> SEQ ID NO 151
<211> LENGTH: 27
<212> TYPE: PRT
<213> ORGANISM: mouse

<400> SEQUENCE: 151

Met Leu Lys Ala Ser Leu His Ile Leu Phe Leu Gly Ile Leu Asn Val
 1               5                  10                  15
```

-continued

```
Pro Ile Val Asp Thr Ser Thr Lys Thr Gly Val
            20                  25


<210> SEQ ID NO 152
<211> LENGTH: 86
<212> TYPE: PRT
<213> ORGANISM: mouse

<400> SEQUENCE: 152

Met Leu Gln Gly Pro Ala Pro Ser Cys Phe Trp Val Phe Ser Gly Ile
 1               5                  10                  15

Cys Val Phe Trp Asp Phe Ile Phe Ile Ile Phe Phe Asn Val Leu Ser
            20                  25                  30

Leu Gly Asn Arg Glu Ile Ser Ala Lys Asp Phe Ala Asp Gln Pro Ala
        35                  40                  45

Gly Ala Gln Gly Met Trp Gly Ile Trp Gly His Thr Ile Thr Cys Gly
    50                  55                  60

Leu Ala Pro Gly Ala Lys Pro Cys Ser Leu Lys Arg Glu Gly Pro Asp
65                  70                  75                  80

Leu Leu Ser Phe Pro Pro
                85


<210> SEQ ID NO 153
<211> LENGTH: 72
<212> TYPE: PRT
<213> ORGANISM: mouse

<400> SEQUENCE: 153

Met Ser Ala Ile Phe Asn Phe Gln Ser Leu Leu Thr Val Ile Leu Leu
 1               5                  10                  15

Leu Ile Cys Thr Cys Ala Tyr Ile Arg Ser Leu Ala Pro Ser Ile Leu
            20                  25                  30

Asp Arg Asn Lys Thr Gly Leu Leu Gly Ile Phe Trp Lys Cys Ala Arg
        35                  40                  45

Ile Gly Glu Arg Lys Ser Pro Tyr Val Ala Ile Cys Cys Ile Val Met
    50                  55                  60

Ala Phe Ser Ile Leu Phe Ile Gln
65                  70


<210> SEQ ID NO 154
<211> LENGTH: 169
<212> TYPE: PRT
<213> ORGANISM: mouse

<400> SEQUENCE: 154

Met Ser Gly Leu Arg Thr Leu Leu Gly Leu Gly Leu Leu Val Ala Gly
 1               5                  10                  15

Ser Arg Leu Pro Arg Val Ile Ser Gln Gln Ser Val Cys Arg Ala Arg
            20                  25                  30

Pro Ile Trp Trp Gly Thr Gln Arg Arg Gly Ser Glu Thr Met Ala Gly
        35                  40                  45

Ala Ala Val Lys Tyr Leu Ser Gln Glu Glu Ala Gln Ala Val Asp Gln
    50                  55                  60

Glu Leu Phe Asn Glu Tyr Gln Phe Ser Val Asp Gln Leu Met Glu Leu
65                  70                  75                  80

Ala Gly Leu Ser Cys Ala Thr Ala Ile Ala Lys Ala Tyr Pro Pro Thr
                85                  90                  95

Ser Met Ser Lys Ser Pro Pro Thr Val Leu Val Ile Cys Gly Pro Gly
```

-continued

```
            100                 105                 110

Asn Asn Gly Gly Asp Gly Leu Val Cys Ala Arg His Leu Lys Leu Phe
        115                 120                 125

Gly Tyr Gln Pro Thr Ile Tyr Tyr Pro Lys Arg Pro Asn Lys Pro Leu
    130                 135                 140

Phe Thr Gly Leu Val Thr Gln Cys Gln Lys Met Asp Ile Pro Phe Leu
145                 150                 155                 160

Gly Glu Met Pro Pro Glu Asp Gly Met
                165


<210> SEQ ID NO 155
<211> LENGTH: 61
<212> TYPE: PRT
<213> ORGANISM: mouse

<400> SEQUENCE: 155

Met Glu Lys Gln Met Asp Ala Ser Val Ser Val Ile Phe Gly Ser Ile
 1               5                  10                  15

Val Ile Ser Ala Phe Leu Tyr Leu Ser Leu Ala Gly Pro Trp Ala Val
            20                  25                  30

Thr Val Thr Gln Met Arg Thr Ile Ile Ile Thr Met Asp Gln Leu Arg
        35                  40                  45

Asp Ala Leu Ile Leu Asp Gln Leu Lys Val Ala Val Ser
    50                  55                  60


<210> SEQ ID NO 156
<211> LENGTH: 131
<212> TYPE: PRT
<213> ORGANISM: mouse

<400> SEQUENCE: 156

Met Ala Pro Ser Leu Trp Lys Gly Leu Val Gly Val Gly Leu Phe Ala
 1               5                  10                  15

Leu Ala His Ala Ala Phe Ser Ala Ala Gln His Arg Ser Tyr Met Arg
            20                  25                  30

Leu Thr Glu Lys Glu Asp Glu Ser Leu Pro Ile Asp Ile Val Leu Gln
        35                  40                  45

Thr Leu Leu Ala Phe Ala Val Thr Cys Tyr Gly Ile Val His Ile Ala
    50                  55                  60

Gly Glu Phe Lys Asp Met Asp Ala Thr Ser Glu Leu Lys Asn Lys Thr
65                  70                  75                  80

Phe Asp Thr Leu Arg Asn His Pro Ser Phe Tyr Val Phe Asn His Arg
                85                  90                  95

Gly Arg Val Leu Phe Arg Pro Ser Asp Ala Thr Asn Ser Ser Asn Leu
            100                 105                 110

Asp Ala Leu Ser Ser Asn Thr Ser Leu Lys Leu Arg Lys Phe Asp Ser
        115                 120                 125

Leu Arg Arg
    130


<210> SEQ ID NO 157
<211> LENGTH: 133
<212> TYPE: PRT
<213> ORGANISM: mouse

<400> SEQUENCE: 157

Met Arg Leu Leu Ala Ala Ala Leu Leu Leu Leu Leu Leu Ala Leu Cys
 1               5                  10                  15
```

-continued

Ala Ser Arg Val Asp Gly Ser Lys Cys Lys Cys Ser Arg Lys Gly Pro
20 25 30

Lys Ile Arg Tyr Ser Asp Val Lys Lys Leu Glu Met Lys Pro Lys Tyr
35 40 45

Pro His Cys Glu Glu Lys Met Val Ile Val Thr Thr Lys Glu His Val
50 55 60

Gln Gly Thr Gly Ala Arg Ser Thr Ala Cys Thr Leu Ser Cys Arg Ala
65 70 75 80

Pro Asn Ala Ser Ser Ser Gly Thr Met Pro Gly Thr Arg Ser Ala Gly
85 90 95

Ser Thr Lys Asn Arg Val Asp Asp His Gly Lys Lys Asn Ser Arg Pro
100 105 110

Val Glu Arg Leu Gln Gln Arg Thr Leu Gln Ile Lys Ile Lys Ala Leu
115 120 125

Ser Phe Ser Gln Ala
130

<210> SEQ ID NO 158
<211> LENGTH: 78
<212> TYPE: PRT
<213> ORGANISM: mouse

<400> SEQUENCE: 158

Gly Thr Arg Lys Pro Leu Pro Met Glu Ala His Ser Arg Arg Glu Lys
1 5 10 15

Ala Ser Gly Leu Arg Leu Ala Trp His Tyr Glu Cys Ser Gly Val Ser
20 25 30

Val Trp Trp Met Cys Val Leu Gly Trp Leu Ser Phe Leu Val Phe Leu
35 40 45

Leu Phe Ser Leu Val Cys Ser Phe Pro Ser Pro Ile Asn His Ser His
50 55 60

Met Leu Pro Cys Leu Phe Leu Arg Gly Gly Gly Ser Asn Val
65 70 75

<210> SEQ ID NO 159
<211> LENGTH: 206
<212> TYPE: PRT
<213> ORGANISM: mouse

<400> SEQUENCE: 159

Met Leu Pro Pro Ala Ile His Leu Ser Leu Ile Pro Leu Leu Cys Ile
1 5 10 15

Leu Met Arg Asn Cys Leu Ala Phe Lys Asn Asp Ala Thr Glu Ile Leu
20 25 30

Tyr Ser His Val Val Lys Pro Val Pro Ala His Pro Ser Ser Asn Ser
35 40 45

Thr Leu Asn Gln Ala Arg Asn Gly Gly Arg His Phe Ser Ser Thr Gly
50 55 60

Leu Asp Arg Asn Ser Arg Val Gln Val Gly Cys Arg Glu Leu Arg Ser
65 70 75 80

Thr Lys Tyr Ile Ser Asp Gly Gln Cys Thr Ser Ile Ser Pro Leu Lys
85 90 95

Glu Leu Val Cys Ala Gly Glu Cys Leu Pro Leu Pro Val Leu Pro Asn
100 105 110

Trp Ile Gly Gly Gly Tyr Gly Thr Lys Tyr Trp Ser Arg Arg Ser Ser
115 120 125

-continued

```
Gln Glu Trp Arg Cys Val Asn Asp Lys Thr Arg Thr Gln Arg Ile Gln
    130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Ser Lys His Ser Leu Ser
        195                 200                 205


<210> SEQ ID NO 160
<211> LENGTH: 169
<212> TYPE: PRT
<213> ORGANISM: mouse

<400> SEQUENCE: 160

Met Ser Gly Leu Arg Thr Leu Leu Gly Leu Gly Leu Leu Val Ala Gly
 1               5                  10                  15

Ser Arg Leu Pro Arg Val Ile Ser Gln Gln Ser Val Cys Arg Ala Arg
            20                  25                  30

Pro Ile Trp Trp Gly Thr Gln Arg Arg Gly Ser Glu Thr Met Ala Gly
        35                  40                  45

Ala Ala Val Lys Tyr Leu Ser Gln Glu Glu Ala Gln Ala Val Asp Gln
    50                  55                  60

Glu Leu Phe Asn Glu Tyr Gln Phe Ser Val Asp Gln Leu Met Glu Leu
65                  70                  75                  80

Ala Gly Leu Ser Cys Ala Thr Ala Ile Ala Lys Ala Tyr Pro Pro Thr
                85                  90                  95

Ser Met Ser Lys Ser Pro Pro Thr Val Leu Val Ile Cys Gly Pro Gly
            100                 105                 110

Asn Asn Gly Gly Asp Gly Leu Val Cys Ala Arg His Leu Lys Leu Phe
        115                 120                 125

Gly Tyr Gln Pro Thr Ile Tyr Tyr Pro Lys Arg Pro Asn Lys Pro Leu
    130                 135                 140

Phe Thr Gly Leu Val Thr Gln Cys Gln Lys Met Asp Ile Pro Phe Leu
145                 150                 155                 160

Gly Glu Met Pro Pro Glu Asp Gly Met
                165


<210> SEQ ID NO 161
<211> LENGTH: 114
<212> TYPE: PRT
<213> ORGANISM: mouse

<400> SEQUENCE: 161

Met Ser Val Thr Ile Gly Arg Leu Ala Leu Phe Leu Ile Gly Ile Leu
 1               5                  10                  15

Leu Cys Pro Val Ala Pro Ser Leu Thr Arg Ser Trp Pro Gly Pro Asp
            20                  25                  30

Thr Cys Ser Leu Phe Leu Gln His Ser Leu Ser Leu Ser Leu Arg Leu
        35                  40                  45

Gly Gln Ser Leu Glu Gly Gly Leu Ser Val Cys Phe His Val Cys Ile
    50                  55                  60

His Ala Cys Glu Cys Val Ala Cys Cys Arg Val Leu Trp Asp Pro Lys
65                  70                  75                  80
```

-continued

```
Pro Arg Gly Ser Ser Leu Cys Arg Trp Val Leu Gly Ser Ile Thr Cys
                85                  90                  95

Leu Phe Met Tyr Glu Val Gly Gly Trp Thr Gln Gly Gly Leu Ile Val
            100                 105                 110

Ser Leu


<210> SEQ ID NO 162
<211> LENGTH: 46
<212> TYPE: PRT
<213> ORGANISM: mouse

<400> SEQUENCE: 162

Met His Tyr Pro Cys Leu Ala Cys Leu Phe Val Asn Val His Trp Cys
 1               5                  10                  15

Phe Ala Trp Met Cys Ile Leu Val Lys Met Ser Glu Leu Leu Glu Leu
            20                  25                  30

Glu Leu Glu Thr Met Val Ser Cys Leu Val Asp Val Gly Asn
        35                  40                  45


<210> SEQ ID NO 163
<211> LENGTH: 122
<212> TYPE: PRT
<213> ORGANISM: mouse

<400> SEQUENCE: 163

Met Phe Thr Phe Val Val Leu Val Ile Thr Ile Val Ile Cys Leu Cys
 1               5                  10                  15

His Val Cys Phe Gly His Phe Lys Tyr Leu Ser Ala His Asn Tyr Lys
            20                  25                  30

Ile Glu His Thr Glu Thr Asp Ala Val Ser Ser Arg Ser Asn Gly Arg
        35                  40                  45

Pro Pro Thr Ala Gly Ala Val Pro Lys Ser Ala Lys Tyr Ile Ala Gln
    50                  55                  60

Val Leu Gln Asp Ser Glu Gly Asp Gly Asp Gly Asp Gly Ala Pro Gly
65                  70                  75                  80

Ser Ser Gly Asp Glu Pro Pro Ser Ser Ser Ser Gln Asp Glu Glu Leu
                85                  90                  95

Leu Met Pro Pro Asp Gly Leu Thr Asp Thr Asp Phe Gln Ser Cys Glu
            100                 105                 110

Asp Ser Leu Ile Glu Asn Glu Ile His Gln
        115                 120


<210> SEQ ID NO 164
<211> LENGTH: 60
<212> TYPE: PRT
<213> ORGANISM: Rat

<400> SEQUENCE: 164

Met Ser Phe Val Lys Ile Glu Ala Thr Pro Thr Gln Thr Lys Trp Pro
 1               5                  10                  15

Phe Ser Val Val Pro Gln Ser Leu Leu Val Thr Val Tyr Ile Cys Tyr
            20                  25                  30

Ile Phe Leu Val Ile Phe Phe Phe Phe Phe Glu Ala Cys Gln Glu Val
        35                  40                  45

Leu Cys Ser Phe Phe Asp Phe Ser Arg Arg Arg Gly
    50                  55                  60
```

-continued

<210> SEQ ID NO 165
<211> LENGTH: 57
<212> TYPE: PRT
<213> ORGANISM: mouse

<400> SEQUENCE: 165

Met Gly Ser Pro Ile Ser Gly Val Cys Pro Val Leu Pro Gly Gly Leu
1 5 10 15

Phe Val Ala Leu Gly Trp Ile Phe Leu Leu Phe His Arg Asp Ala Phe
20 25 30

Ser Leu His Thr Met Ser Ala Gly Phe Pro Lys Ser Pro Ala Asn Pro
35 40 45

His His Pro Pro Leu Arg Leu Ser Pro
50 55

<210> SEQ ID NO 166
<211> LENGTH: 75
<212> TYPE: PRT
<213> ORGANISM: mouse

<400> SEQUENCE: 166

Lys Thr Arg Arg Thr Leu Thr Gly Gln Leu Gly Leu Phe Ser Val Asp
1 5 10 15

Phe Met Val Cys Ile Phe Leu Phe Leu Phe Phe Cys Phe Leu Phe Pro
20 25 30

Phe Pro Leu Phe Leu Val Arg Lys His Ile Leu Leu Ser His Cys Lys
35 40 45

Gln Trp Glu Gly Ser Thr Met Thr His Thr His Thr His Thr His Ile
50 55 60

His Ile His Thr Pro Pro Arg Gln Cys Gln Ser
65 70 75

<210> SEQ ID NO 167
<211> LENGTH: 52
<212> TYPE: PRT
<213> ORGANISM: mouse

<400> SEQUENCE: 167

Val Arg Ser Leu Glu Gln Leu Gly Leu Phe Ser Val Asp Phe Met Val
1 5 10 15

Cys Ile Phe Leu Phe Leu Phe Phe Cys Phe Leu Phe Pro Phe Pro Leu
20 25 30

Phe Leu Val Arg Lys His Ile Leu Leu Ser His Cys Lys Gln Trp Glu
35 40 45

Gly Ser Thr Met
50

<210> SEQ ID NO 168
<211> LENGTH: 119
<212> TYPE: PRT
<213> ORGANISM: Rat

<400> SEQUENCE: 168

Met Leu Gly Ala Thr Ser Leu Ser Trp Pro Trp Val Leu Trp Ala Val
1 5 10 15

Ala Gln Arg Asp Ser Val Asp Ala Ile Gly Met Phe Leu Gly Gly Leu
20 25 30

Val Ala Thr Ile Phe Leu Asp Ile Ile Tyr Ile Ser Ile Phe Tyr Ser
35 40 45

-continued

```
Ser Val Ala Val Gly Asp Thr Gly Arg Phe Ser Ala Gly Met Ala Ile
    50                  55                  60

Phe Ser Leu Leu Leu Gln Ala Leu Leu Leu Leu Pro Arg Leu Pro His
65                  70                  75                  80

Ala Pro Gly Ser Glu Gly Val Ser Ser Arg Ser Ala Arg Ile Ser Ser
                85                  90                  95

Asp Leu Leu Arg Asn Ile Val Pro Thr Arg Gln Leu Thr Arg Gln Thr
            100                 105                 110

His Leu Gln Thr Pro Leu Gln
        115


<210> SEQ ID NO 169
<211> LENGTH: 104
<212> TYPE: PRT
<213> ORGANISM: Rat
<220> FEATURE:
<221> NAME/KEY: UNSURE
<222> LOCATION: (46)...(46)
<221> NAME/KEY: UNSURE
<222> LOCATION: (48)...(48)
<221> NAME/KEY: UNSURE
<222> LOCATION: (85)...(85)

<400> SEQUENCE: 169

Leu Val Pro Lys Ser Ala Arg Ala Ser Leu Leu Cys Cys Gly Pro Lys
 1               5                  10                  15

Leu Ala Ala Cys Gly Ile Val Leu Ser Ala Trp Gly Val Ile Met Leu
            20                  25                  30

Ile Met Leu Gly Ile Phe Phe Asn Val His Ser Ala Val Xaa Ile Xaa
        35                  40                  45

Asp Val Pro Phe Thr Glu Lys Asp Phe Glu Asn Gly Pro Gln Asn Ile
    50                  55                  60

Tyr Asn Leu Tyr Glu Gln Val Ser Tyr Asn Cys Phe Ile Ala Ala Gly
65                  70                  75                  80

Leu Tyr Leu Leu Xaa Gly Gly Phe Ser Phe Cys Gln Val Arg Leu Asn
                85                  90                  95

Lys Arg Lys Glu Tyr Met Val Arg
            100


<210> SEQ ID NO 170
<211> LENGTH: 123
<212> TYPE: PRT
<213> ORGANISM: Rat
<220> FEATURE:
<221> NAME/KEY: UNSURE
<222> LOCATION: (27)...(27)
<221> NAME/KEY: UNSURE
<222> LOCATION: (104)...(104)
<221> NAME/KEY: UNSURE
<222> LOCATION: (118)...(118)

<400> SEQUENCE: 170

Met Arg Pro Gly Ala Asp Trp Ala Ala Val Cys Ala Leu Trp Pro Ser
 1               5                  10                  15

Trp Arg Pro Ser Cys Ser Leu Pro Ser Ser Xaa Arg Ile Gln Pro Asp
            20                  25                  30

Glu Leu Trp Leu Tyr Arg Asn Pro Tyr Val Lys Ala Glu Tyr Phe Pro
        35                  40                  45

Thr Gly Pro Met Phe Val Ile Ala Phe Leu Thr Pro Leu Ser Leu Ile
    50                  55                  60

Phe Phe Ala Lys Phe Leu Arg Lys Ala Asp Ala Asp Arg Gln Arg Ala
```

-continued

```
65                  70                  75                  80

Ser Leu Pro Arg Cys Gln Pro Cys Pro Ser Ala Lys Trp Cys Leu Tyr
                85                  90                  95

Gln His His Lys Thr Asp Ser Xaa Gln Gly His Ala Gln Ile Ala Ser
            100                 105                 110

Thr Glu Cys Ser Pro Xaa Gly Ile Ala His Ser
        115                 120


<210> SEQ ID NO 171
<211> LENGTH: 75
<212> TYPE: PRT
<213> ORGANISM: Rat

<400> SEQUENCE: 171

Ser Ala Gly Val Met Thr Ala Ala Val Phe Phe Gly Cys Ala Phe Ile
 1               5                  10                  15

Ala Phe Gly Pro Ala Leu Ser Leu Tyr Val Phe Thr Ile Ala Thr Asp
            20                  25                  30

Pro Leu Arg Val Ile Phe Leu Ile Ala Gly Ala Phe Phe Trp Leu Val
        35                  40                  45

Ser Leu Leu Leu Ser Ser Val Phe Trp Phe Leu Val Arg Val Ile Thr
    50                  55                  60

Asp Asn Arg Asp Gly Pro Val Gln Asn Tyr Leu
65                  70                  75


<210> SEQ ID NO 172
<211> LENGTH: 79
<212> TYPE: PRT
<213> ORGANISM: Human

<400> SEQUENCE: 172

Lys Thr Ser Tyr His Tyr His Thr Asn Val Glu Glu Leu Thr Ile Pro
 1               5                  10                  15

Glu Thr Arg Asn Asn Leu Tyr Ile Ser Ile Ser Trp Leu Trp Cys Leu
            20                  25                  30

Val Leu Val Leu Leu Ser Thr Met Ile Leu Asn Lys His Gly Trp Met
        35                  40                  45

Lys Ala Asn Ala Tyr Ser Leu Val Pro Ser Ile Ile Tyr Ser Pro Ser
    50                  55                  60

Tyr Leu Lys Leu Leu Leu Arg Leu Tyr Lys Leu Gln Ile Cys Cys
65                  70                  75


<210> SEQ ID NO 173
<211> LENGTH: 134
<212> TYPE: PRT
<213> ORGANISM: Human
<220> FEATURE:
<221> NAME/KEY: UNSURE
<222> LOCATION: (10)...(10)
<221> NAME/KEY: UNSURE
<222> LOCATION: (13)...(13)
<221> NAME/KEY: UNSURE
<222> LOCATION: (127)...(127)

<400> SEQUENCE: 173

Leu Arg Gly Arg Gly Arg Gly Val Cys Xaa Gln Glu Xaa Phe Gly Gly
 1               5                  10                  15

Cys Cys Val Ser Gly Leu Ile Ala Met Gly Thr Lys Ala Gln Val Glu
            20                  25                  30

Arg Lys Leu Leu Cys Leu Phe Ile Leu Ala Ile Leu Leu Cys Ser Leu
```

-continued

```
        35                  40                  45

Ala Leu Gly Ser Val Thr Val His Ser Ser Glu Pro Glu Val Arg Ile
    50                  55                  60

Pro Glu Asn Asn Pro Val Lys Leu Ser Cys Ala Tyr Ser Gly Phe Ser
65                  70                  75                  80

Ser Pro Arg Val Glu Trp Lys Phe Asp Gln Gly Asp Thr Thr Arg Leu
                85                  90                  95

Val Cys Tyr Asn Asn Lys Ile Thr Ala Ser Tyr Glu Asp Arg Val Thr
            100                 105                 110

Phe Leu Pro Thr Gly Ile Thr Phe Lys Ser Val Thr Arg Glu Xaa Thr
        115                 120                 125

Gly Thr Tyr Thr Cys Met
    130


<210> SEQ ID NO 174
<211> LENGTH: 137
<212> TYPE: PRT
<213> ORGANISM: Human

<400> SEQUENCE: 174

Ala Trp Ser Arg Pro Arg Tyr Asp Ser Val Leu Ala Leu Ser Ala Ala
 1               5                  10                  15

Leu Gln Ala Thr Arg Ala Leu Met Val Val Ser Leu Val Leu Gly Phe
            20                  25                  30

Leu Ala Met Phe Val Ala Thr Met Gly Met Lys Cys Thr Arg Cys Gly
        35                  40                  45

Gly Asp Asp Lys Val Lys Lys Ala Arg Ile Ala Met Gly Gly Gly Ile
    50                  55                  60

Ile Phe Ile Val Ala Gly Leu Ala Ala Leu Val Ala Cys Ser Trp Tyr
65                  70                  75                  80

Gly His Gln Ile Val Thr Asp Phe Tyr Asn Pro Leu Ile Pro Thr Asn
                85                  90                  95

Ile Lys Tyr Glu Phe Gly Pro Ala Ile Phe Ile Gly Trp Ala Gly Ser
            100                 105                 110

Ala Leu Val Ile Leu Gly Gly Ala Leu Ser Pro Val Pro Val Leu Gly
        115                 120                 125

Ile Arg Ala Gly Leu Gly Thr Cys Pro
    130                 135


<210> SEQ ID NO 175
<211> LENGTH: 43
<212> TYPE: PRT
<213> ORGANISM: Human

<400> SEQUENCE: 175

Met Lys Leu Ser Gly Met Phe Leu Leu Leu Ser Leu Ala Leu Phe Cys
 1               5                  10                  15

Phe Leu Thr Gly Val Phe Ser Gln Gly Gly Gln Val Asp Cys Gly Glu
            20                  25                  30

Ser Arg Thr Pro Arg Pro Thr Ala Leu Gly Asn
        35                  40


<210> SEQ ID NO 176
<211> LENGTH: 63
<212> TYPE: PRT
<213> ORGANISM: Rat

<400> SEQUENCE: 176
```

-continued

```
Pro Asn Thr Arg Pro Arg Arg His Thr Ala Cys Arg Val Ser Ile Ser
 1               5                  10                  15

Val Leu Tyr Met Leu His Thr Glu Leu Lys Lys Cys Trp Phe Phe Leu
            20                  25                  30

Phe Cys Phe Ser Leu Phe Leu Trp Phe Cys Phe Trp Phe Cys Phe Leu
        35                  40                  45

Leu Pro Arg Phe Asp Tyr Leu Pro Met Pro Ser Thr Gly Pro Arg
    50                  55                  60


<210> SEQ ID NO 177
<211> LENGTH: 52
<212> TYPE: PRT
<213> ORGANISM: mouse

<400> SEQUENCE: 177

Met Leu Gln Gly Pro Ala Pro Ser Cys Phe Trp Val Phe Ser Gly Ile
 1               5                  10                  15

Cys Val Phe Trp Asp Phe Ile Phe Ile Ile Phe Phe Asn Val Leu Ser
            20                  25                  30

Leu Gly Asn Arg Glu Ile Ser Ala Lys Asp Phe Ala Asp Gln Pro Ala
        35                  40                  45

Gly Ala Gln Gly
    50


<210> SEQ ID NO 178
<211> LENGTH: 62
<212> TYPE: PRT
<213> ORGANISM: mouse

<400> SEQUENCE: 178

Val Ser Pro Arg Pro Thr Tyr Pro Ser Thr Ala Ser Ser Met Ala Ala
 1               5                  10                  15

Phe Leu Val Thr Gly Phe Phe Phe Ser Leu Phe Val Val Leu Gly Met
            20                  25                  30

Glu Pro Arg Ala Leu Phe Arg Pro Asp Lys Ala Leu Pro Leu Ser Cys
        35                  40                  45

Ala Lys Pro Thr Ser Leu Cys Val Gln Ser Ser Phe Leu Gly
    50                  55                  60


<210> SEQ ID NO 179
<211> LENGTH: 123
<212> TYPE: PRT
<213> ORGANISM: mouse

<400> SEQUENCE: 179

Ala Ser Arg Thr Ala Val Met Ser Leu Cys Arg Cys Gln Gln Gly Ser
 1               5                  10                  15

Arg Ser Arg Met Asp Leu Asp Val Val Asn Met Phe Val Ile Ala Gly
            20                  25                  30

Gly Thr Leu Ala Ile Pro Ile Leu Ala Phe Val Ala Ser Phe Leu Leu
        35                  40                  45

Trp Pro Ser Ala Leu Ile Arg Ile Tyr Tyr Trp Tyr Trp Arg Arg Thr
    50                  55                  60

Leu Gly Met Gln Val Arg Tyr Ala His His Glu Asp Tyr Gln Phe Cys
65                  70                  75                  80

Tyr Ser Phe Arg Gly Arg Pro Gly His Lys Pro Ser Ile Leu Met Leu
                85                  90                  95
```

-continued

```
His Gly Phe Ser Ala His Lys Gly His Val Ala Gln Arg Gly Gln Val
            100                 105                 110

Pro Ser Arg Lys Asn Leu His Phe Gly Cys Val
        115                 120


<210> SEQ ID NO 180
<211> LENGTH: 120
<212> TYPE: PRT
<213> ORGANISM: mouse
<220> FEATURE:
<221> NAME/KEY: UNSURE
<222> LOCATION: (5)...(5)

<400> SEQUENCE: 180

Ala Arg Arg Arg Xaa Arg Trp Arg Arg Gly Cys Cys Trp Leu Ile Gly
 1               5                  10                  15

Thr Gly Leu Arg Ala Ala Thr Trp Thr Val Leu Cys Ser Pro Asn Ser
            20                  25                  30

Ser Leu Val Val Ala Arg His Thr Lys Ser Phe Pro Pro Lys Lys Pro
        35                  40                  45

Leu Gln Ala Leu Thr Met Ser Ile Met Asp His Ser Pro Thr Thr Gly
    50                  55                  60

Val Val Thr Val Ile Val Ile Leu Ile Ala Ile Ala Ala Leu Gly Gly
65                  70                  75                  80

Leu Ile Leu Gly Cys Trp Cys Tyr Leu Arg Leu Gln Arg Ile Ser Gln
                85                  90                  95

Ser Glu Asp Glu Glu Ser Ile Val Gly Asp Gly Glu Thr Lys Glu Pro
            100                 105                 110

Phe Tyr Trp Cys Ser Thr Leu Leu
        115                 120


<210> SEQ ID NO 181
<211> LENGTH: 60
<212> TYPE: PRT
<213> ORGANISM: mouse

<400> SEQUENCE: 181

Lys Gly Pro Glu Val Ser Cys Cys Ile Lys Tyr Phe Ile Phe Gly Phe
 1               5                  10                  15

Asn Val Ile Phe Trp Phe Leu Gly Ile Thr Phe Leu Gly Ile Gly Leu
            20                  25                  30

Trp Ala Trp Asn Glu Lys Gly Val Leu Ser Asn Ile Ser Ser Ile Thr
        35                  40                  45

Asp Leu Gly Gly Phe Asp Pro Val Trp Leu Phe Leu
    50                  55                  60


<210> SEQ ID NO 182
<211> LENGTH: 72
<212> TYPE: PRT
<213> ORGANISM: mouse
<220> FEATURE:
<221> NAME/KEY: UNSURE
<222> LOCATION: (64)...(64)

<400> SEQUENCE: 182

Lys Pro Thr Val Gly Ser Ala Glu Val Ala Ile Ala Gly Phe Leu Val
 1               5                  10                  15

Ile Cys Ile Ile Val Val Leu Thr Ile Leu Gly Tyr Cys Phe Phe Lys
            20                  25                  30

Asn Gln Arg Lys Glu Phe His Ser Pro Leu His His Pro Pro Pro Thr
```

-continued

```
        35                  40                  45

Pro Ala Ser Ser Thr Val Ser Thr Thr Glu Asp Thr Glu His Leu Xaa
    50                  55                  60

Tyr Asn His Thr Thr Gln Pro Leu
65                  70


<210> SEQ ID NO 183
<211> LENGTH: 771
<212> TYPE: PRT
<213> ORGANISM: Rat
<220> FEATURE:
<221> NAME/KEY: UNSURE
<222> LOCATION: (717)...(717)

<400> SEQUENCE: 183

Glu Leu Tyr Leu Asp Gly Asn Gln Phe Thr Leu Val Pro Lys Glu Leu
 1               5                  10                  15

Ser Asn Tyr Lys His Leu Thr Leu Ile Asp Leu Ser Asn Asn Arg Ile
            20                  25                  30

Ser Thr Leu Ser Asn Gln Ser Phe Ser Asn Met Thr Gln Leu Leu Thr
        35                  40                  45

Leu Ile Leu Ser Tyr Asn Arg Leu Arg Cys Ile Pro Pro Arg Thr Phe
    50                  55                  60

Asp Gly Leu Lys Ser Leu Arg Leu Leu Ser Leu His Gly Asn Asp Ile
65                  70                  75                  80

Ser Val Val Pro Glu Gly Ala Phe Gly Asp Leu Ser Ala Leu Ser His
                85                  90                  95

Leu Ala Ile Gly Ala Asn Pro Leu Tyr Cys Asp Cys Asn Met Gln Trp
            100                 105                 110

Leu Ser Asp Trp Val Lys Ser Glu Tyr Lys Glu Pro Gly Ile Ala Arg
        115                 120                 125

Cys Ala Gly Pro Gly Glu Met Ala Asp Lys Leu Leu Leu Thr Thr Pro
    130                 135                 140

Ser Lys Asn Phe Thr Cys Gln Gly Pro Val Asp Val Thr Ile Gln Ala
145                 150                 155                 160

Lys Cys Asn Pro Cys Leu Ser Asn Pro Cys Lys Asn Asp Gly Thr Cys
                165                 170                 175

Asn Asn Asp Pro Val Asp Phe Tyr Arg Cys Thr Cys Pro Tyr Gly Phe
            180                 185                 190

Lys Gly Gln Asp Cys Asp Val Pro Ile His Ala Cys Thr Ser Asn Pro
        195                 200                 205

Cys Lys His Gly Gly Thr Cys His Leu Lys Pro Arg Arg Glu Thr Trp
    210                 215                 220

Ile Trp Cys Thr Cys Ala Asp Gly Phe Glu Gly Glu Ser Cys Asp Ile
225                 230                 235                 240

Asn Ile Asp Asp Cys Glu Asp Asn Asp Cys Glu Asn Asn Ser Thr Cys
                245                 250                 255

Val Asp Gly Ile Asn Asn Tyr Thr Cys Leu Cys Pro Pro Glu Tyr Thr
            260                 265                 270

Gly Glu Leu Cys Glu Glu Lys Leu Asp Phe Cys Ala Gln Asp Leu Asn
        275                 280                 285

Pro Cys Gln His Asp Ser Lys Cys Ile Leu Thr Pro Lys Gly Phe Lys
    290                 295                 300

Cys Asp Cys Thr Pro Gly Tyr Ile Gly Glu His Cys Asp Ile Asp Phe
305                 310                 315                 320
```

-continued

```
Asp Asp Cys Gln Asp Asn Lys Cys Lys Asn Gly Ala His Cys Thr Asp
                325                 330                 335

Ala Val Asn Gly Tyr Thr Cys Val Cys Pro Glu Gly Tyr Ser Gly Leu
            340                 345                 350

Phe Cys Glu Phe Ser Pro Pro Met Val Phe Leu Arg Thr Ser Pro Cys
        355                 360                 365

Asp Asn Phe Asp Cys Gln Asn Gly Ala Gln Cys Ile Ile Arg Val Asn
    370                 375                 380

Glu Pro Ile Cys Gln Cys Leu Pro Gly Tyr Leu Gly Glu Lys Cys Glu
385                 390                 395                 400

Lys Leu Val Ser Val Ser Ile Leu Val Asn Lys Glu Ser Tyr Leu Gln
                405                 410                 415

Ile Pro Ser Ala Lys Val Arg Pro Gln Thr Asn Ile Thr Leu Gln Ile
            420                 425                 430

Ala Thr Asp Glu Asp Ser Gly Ile Leu Leu Tyr Lys Gly Asp Lys Asp
        435                 440                 445

His Ile Ala Val Glu Ser Ile Glu Gly Ile Arg Ala Ser Tyr Asp Thr
    450                 455                 460

Gly Ser His Pro Ala Ser Ala Ile Tyr Ser Val Glu Thr Ile Asn Asp
465                 470                 475                 480

Gly Asn Phe His Ile Val Glu Leu Leu Thr Leu Asp Ser Ser Leu Ser
                485                 490                 495

Leu Ser Val Asp Gly Gly Ser Pro Lys Ile Ile Thr Asn Leu Ser Lys
            500                 505                 510

Gln Ser Thr Leu Asn Phe Asp Ser Pro Leu Tyr Val Gly Gly Met Pro
        515                 520                 525

Gly Lys Asn Asn Val Ala Ser Leu Arg Gln Ala Pro Gly Gln Asn Gly
    530                 535                 540

Thr Ser Phe His Gly Cys Ile Arg Asn Leu Tyr Ile Asn Ser Glu Leu
545                 550                 555                 560

Gln Asp Phe Arg Lys Val Pro Met Gln Thr Gly Ile Leu Pro Gly Cys
                565                 570                 575

Glu Pro Cys His Lys Lys Val Cys Ala His Gly Thr Cys Gln Pro Ser
            580                 585                 590

Ser Gln Ser Gly Phe Thr Cys Glu Cys Glu Glu Gly Trp Met Gly Pro
        595                 600                 605

Leu Cys Asp Gln Arg Thr Asn Asp Pro Cys Leu Gly Asn Lys Cys Val
    610                 615                 620

His Gly Thr Cys Leu Pro Ile Asn Ala Phe Ser Tyr Ser Cys Lys Cys
625                 630                 635                 640

Leu Glu Gly His Gly Gly Val Leu Cys Asp Glu Glu Glu Asp Leu Phe
                645                 650                 655

Asn Pro Leu Pro Gly Asp Gln Val Gln Ala Arg Glu Val Gln Ala Leu
            660                 665                 670

Trp Ala Arg Ala Ala Leu Leu Trp Met Gln Gln Trp Ile His Arg Gly
        675                 680                 685

Gln Leu Thr Gln Arg Ile Ser Cys Arg Gly Glu Arg Ile Arg Asp Tyr
    690                 695                 700

Tyr Gln Ser Ser Arg Val Arg Cys Leu Ser Asn Asp Xaa Glu Val Ser
705                 710                 715                 720

Arg Leu Glu Cys Arg Gly Gly Cys Ala Gly Gly Gln Cys Cys Gly Pro
                725                 730                 735

Leu Arg Ser Lys Arg Arg Lys Tyr Ser Phe Glu Cys Thr Asp Gly Ser
```

-continued

```
            740                 745                 750

Ser Phe Val Asp Glu Val Glu Lys Val Val Lys Cys Gly Cys Thr Arg
        755                 760                 765

Cys Ala Ser
    770


<210> SEQ ID NO 184
<211> LENGTH: 340
<212> TYPE: PRT
<213> ORGANISM: mouse

<400> SEQUENCE: 184

Asp Gly Ser Leu Trp Leu Gln Ala Thr Gln Pro Asp Asp Ala Gly His
 1               5                  10                  15

Tyr Thr Cys Val Pro Ser Asn Gly Phe Leu His Pro Pro Ser Ala Ser
            20                  25                  30

Ala Tyr Leu Thr Val Leu Tyr Pro Ala Gln Val Thr Val Met Pro Pro
        35                  40                  45

Glu Thr Pro Leu Pro Thr Gly Met Arg Gly Val Ile Arg Cys Pro Val
    50                  55                  60

Arg Ala Asn Pro Pro Leu Leu Phe Val Thr Trp Thr Lys Asp Gly Gln
65                  70                  75                  80

Ala Leu Gln Leu Asp Lys Phe Pro Gly Trp Ser Leu Gly Pro Glu Gly
                85                  90                  95

Ser Leu Ile Ile Ala Leu Gly Asn Glu Asp Ala Leu Gly Glu Tyr Ser
            100                 105                 110

Cys Thr Pro Tyr Asn Ser Leu Gly Thr Ala Gly Pro Ser Pro Val Thr
        115                 120                 125

Arg Val Leu Leu Lys Ala Pro Pro Ala Phe Ile Asp Gln Pro Lys Glu
    130                 135                 140

Glu Tyr Phe Gln Glu Val Gly Arg Glu Leu Leu Ile Pro Cys Ser Ala
145                 150                 155                 160

Arg Gly Asp Pro Pro Pro Ile Val Ser Trp Ala Lys Val Gly Arg Gly
                165                 170                 175

Leu Gln Gly Gln Ala Gln Val Asp Ser Asn Asn Ser Leu Val Leu Arg
            180                 185                 190

Pro Leu Thr Lys Glu Ala Gln Gly Arg Trp Glu Cys Ser Ala Ser Asn
        195                 200                 205

Ala Val Ala Arg Val Thr Thr Ser Thr Asn Val Tyr Val Leu Gly Thr
    210                 215                 220

Ser Pro His Val Val Thr Asn Val Ser Val Val Pro Leu Pro Lys Gly
225                 230                 235                 240

Ala Asn Val Ser Trp Glu Pro Gly Phe Asp Gly Gly Tyr Leu Gln Arg
                245                 250                 255

Phe Ser Val Trp Tyr Thr Pro Leu Ala Lys Arg Pro Asp Arg Ala His
            260                 265                 270

His Asp Trp Val Ser Leu Ala Val Pro Ile Gly Ala Thr His Leu Leu
        275                 280                 285

Val Pro Gly Leu Gln Ala His Ala Gln Tyr Gln Phe Ser Val Leu Ala
    290                 295                 300

Gln Asn Lys Leu Gly Ser Gly Pro Phe Ser Glu Ile Val Leu Ser Ile
305                 310                 315                 320

Pro Glu Gly Leu Pro Thr Thr Pro Ala Ala Pro Gly Leu Pro Ala Thr
                325                 330                 335
```

-continued

```
Arg Ser Arg Val
            340


<210> SEQ ID NO 185
<211> LENGTH: 536
<212> TYPE: PRT
<213> ORGANISM: mouse

<400> SEQUENCE: 185

Lys Val Glu Gly Glu Gly Arg Gly Arg Trp Ala Leu Gly Leu Leu Arg
 1               5                  10                  15

Thr Phe Asp Ala Gly Glu Phe Ala Gly Trp Glu Lys Val Gly Ser Gly
            20                  25                  30

Gly Phe Gly Gln Val Tyr Lys Val Arg His Val His Trp Lys Thr Trp
        35                  40                  45

Leu Ala Ile Lys Cys Ser Pro Ser Leu His Val Asp Asp Arg Glu Arg
    50                  55                  60

Met Glu Leu Leu Glu Glu Ala Lys Lys Met Glu Met Ala Lys Phe Arg
65                  70                  75                  80

Tyr Ile Leu Pro Val Tyr Gly Ile Cys Gln Glu Pro Val Gly Leu Val
                85                  90                  95

Met Glu Tyr Met Glu Thr Gly Ser Leu Glu Lys Leu Leu Ala Ser Glu
            100                 105                 110

Pro Leu Pro Trp Asp Leu Arg Phe Arg Ile Val His Glu Thr Ala Val
        115                 120                 125

Gly Met Asn Phe Leu His Cys Met Ser Pro Pro Leu Leu His Leu Asp
    130                 135                 140

Leu Lys Pro Ala Asn Ile Leu Leu Asp Ala His Tyr Gln Met Ser Arg
145                 150                 155                 160

Phe Leu Asp Phe Gly Leu Ala Lys Cys Asn Gly Met Ser His Ser His
                165                 170                 175

Asp Leu Ser Met Asp Gly Leu Phe Gly Thr Ile Gly Tyr Leu Pro Pro
            180                 185                 190

Glu Arg Ile Arg Glu Lys Ser Arg Leu Phe Asp Thr Lys His Asp Val
        195                 200                 205

Tyr Ser Phe Ala Ile Val Ile Trp Gly Val Leu Thr Gln Asn Asn Pro
    210                 215                 220

Phe Ala Asp Glu Lys Asn Ile Leu His Ile Met Met Lys Val Val Lys
225                 230                 235                 240

Gly His Arg Pro Glu Leu Pro Pro Ile Cys Arg Pro Arg Pro Arg Ala
                245                 250                 255

Cys Ala Ser Leu Ile Gly Leu Met Gln Arg Cys Trp His Ala Asp Pro
            260                 265                 270

Gln Val Arg Pro Thr Phe Gln Glu Ile Thr Ser Glu Thr Glu Asp Leu
        275                 280                 285

Cys Glu Lys Pro Asp Glu Glu Val Lys Asp Leu Ala His Glu Pro Gly
    290                 295                 300

Glu Lys Ser Ser Leu Glu Ser Lys Ser Glu Ala Arg Pro Glu Ser Ser
305                 310                 315                 320

Arg Leu Lys Arg Ala Ser Ala Pro Pro Phe Asp Asn Asp Cys Ser Leu
                325                 330                 335

Ser Glu Leu Leu Ser Gln Leu Asp Ser Gly Ile Phe Pro Arg Leu Leu
            340                 345                 350

Lys Gly Pro Glu Glu Leu Ser Arg Ser Ser Ser Glu Cys Lys Leu Pro
        355                 360                 365
```

-continued

```
Ser Ser Ser Ser Gly Lys Arg Leu Ser Gly Val Ser Ser Val Asp Ser
    370                 375                 380

Ala Phe Ser Ser Arg Gly Ser Leu Ser Leu Ser Phe Glu Arg Glu Ala
385                 390                 395                 400

Ser Thr Gly Asp Leu Gly Pro Thr Asp Ile Gln Lys Lys Lys Leu Val
                405                 410                 415

Asp Ala Ile Ile Ser Gly Asp Thr Ser Arg Leu Met Lys Ile Leu Gln
            420                 425                 430

Pro Gln Asp Val Asp Leu Val Leu Asp Ser Ser Ala Ser Leu Leu His
        435                 440                 445

Leu Ala Val Glu Ala Gly Gln Glu Glu Cys Val Lys Trp Leu Leu Leu
    450                 455                 460

Asn Asn Ala Asn Pro Asn Leu Thr Asn Arg Lys Gly Ser Thr Pro Leu
465                 470                 475                 480

His Met Ala Val Glu Arg Lys Gly Arg Gly Ile Val Glu Leu Leu Leu
                485                 490                 495

Ala Arg Lys Thr Ser Val Asn Ala Lys Asp Glu Asp Gln Trp Thr Ala
            500                 505                 510

Leu His Phe Ala Ala Gln Asn Gly Asp Glu Gly Gln His Lys Ala Ala
        515                 520                 525

Ala Arg Glu Glu Cys Phe Cys Gln
    530                 535


<210> SEQ ID NO 186
<211> LENGTH: 337
<212> TYPE: PRT
<213> ORGANISM: Rat
<220> FEATURE:
<221> NAME/KEY: UNSURE
<222> LOCATION: (14)...(124)
<221> NAME/KEY: UNSURE
<222> LOCATION: (135)...(135)
<221> NAME/KEY: UNSURE
<222> LOCATION: (141)...(141)
<221> NAME/KEY: UNSURE
<222> LOCATION: (166)...(166)
<221> NAME/KEY: UNSURE
<222> LOCATION: (167)...(167)
<221> NAME/KEY: UNSURE
<222> LOCATION: (183)...(183)

<400> SEQUENCE: 186

Pro Ser Arg Phe Gly Tyr Gln Met Asp Glu Gly Asn Gln Cys Val Asp
 1               5                  10                  15

Val Asp Glu Cys Ala Thr Asp Ser His Gln Cys Asn Pro Thr Gln Ile
            20                  25                  30

Cys Ile Asn Thr Glu Gly Gly Tyr Thr Cys Ser Cys Thr Asp Gly Tyr
        35                  40                  45

Trp Leu Leu Glu Gly Gln Cys Leu Asp Ile Asp Glu Cys Arg Tyr Gly
    50                  55                  60

Tyr Cys Gln Gln Leu Cys Ala Asn Val Pro Gly Ser Tyr Ser Cys Thr
65                  70                  75                  80

Cys Asn Pro Gly Phe Thr Leu Asn Asp Asp Gly Arg Ser Cys Gln Asp
                85                  90                  95

Val Asn Glu Cys Glu Thr Glu Asn Pro Cys Val Gln Thr Cys Val Asn
            100                 105                 110

Thr Tyr Gly Ser Phe Ile Cys Arg Cys Asp Pro Xaa Tyr Glu Leu Glu
        115                 120                 125
```

-continued

```
Glu Asp Gly Ile His Cys Xaa Asp Met Asp Glu Cys Xaa Phe Ser Glu
    130                 135                 140

Phe Leu Cys Gln His Glu Cys Val Asn Gln Pro Gly Ser Tyr Phe Cys
145                 150                 155                 160

Ser Cys Pro Pro Gly Xaa Xaa Leu Leu Glu Asp Asn Arg Ser Cys Gln
                165                 170                 175

Asp Ile Asn Glu Cys Glu Xaa Arg Asn His Thr Cys Thr Pro Leu Gln
            180                 185                 190

Thr Cys Tyr Asn Leu Gln Gly Gly Phe Lys Cys Ile Asp Pro Ile Val
        195                 200                 205

Cys Glu Glu Pro Tyr Leu Leu Ile Gly Asp Asn Arg Cys Met Cys Pro
    210                 215                 220

Ala Glu Asn Thr Gly Cys Arg Asp Gln Pro Phe Thr Ile Leu Phe Arg
225                 230                 235                 240

Asp Met Asp Val Val Ser Gly Arg Ser Val Pro Ala Asp Ile Phe Gln
                245                 250                 255

Met Gln Ala Thr Thr Arg Tyr Pro Gly Ala Tyr Tyr Ile Phe Gln Ile
            260                 265                 270

Lys Ser Gly Asn Glu Gly Arg Glu Phe Tyr Met Arg Gln Thr Gly Pro
        275                 280                 285

Ile Ser Ala Thr Leu Val Met Thr Arg Pro Ile Lys Gly Pro Arg Asp
    290                 295                 300

Ile Gln Leu Asp Leu Glu Met Ile Thr Val Asn Thr Val Ile Asn Phe
305                 310                 315                 320

Arg Gly Ser Ser Val Ile Arg Leu Arg Ile Tyr Val Ser Gln Tyr Pro
                325                 330                 335

Phe


<210> SEQ ID NO 187
<211> LENGTH: 152
<212> TYPE: PRT
<213> ORGANISM: mouse

<400> SEQUENCE: 187

Met Ala Leu Gly Val Leu Ile Ala Val Cys Leu Leu Phe Lys Ala Met
 1               5                  10                  15

Lys Ala Ala Leu Ser Glu Glu Ala Glu Val Ile Pro Pro Ser Thr Ala
            20                  25                  30

Gln Gln Ser Asn Trp Thr Phe Asn Asn Thr Glu Ala Asp Tyr Ile Glu
        35                  40                  45

Glu Pro Val Ala Leu Lys Phe Ser His Pro Cys Leu Glu Asp His Asn
    50                  55                  60

Ser Tyr Cys Ile Asn Gly Ala Cys Ala Phe His His Glu Leu Lys Gln
65                  70                  75                  80

Ala Ile Cys Arg Cys Phe Thr Gly Tyr Thr Gly Gln Arg Cys Glu His
                85                  90                  95

Leu Thr Leu Thr Ser Tyr Ala Val Asp Ser Tyr Glu Lys Tyr Ile Ala
            100                 105                 110

Ile Gly Ile Gly Val Gly Leu Leu Ile Ser Ala Phe Leu Ala Val Phe
        115                 120                 125

Tyr Cys Tyr Ile Arg Lys Arg Cys Ile Asn Leu Lys Ser Pro Tyr Ile
    130                 135                 140

Ile Cys Ser Gly Gly Ser Pro Leu
145                 150
```

-continued

<210> SEQ ID NO 188
<211> LENGTH: 118
<212> TYPE: PRT
<213> ORGANISM: Rat
<220> FEATURE:
<221> NAME/KEY: UNSURE
<222> LOCATION: (12)...(12)

<400> SEQUENCE: 188

```
Leu Val Pro Gln Phe Gly Thr Arg Ile Arg Tyr Xaa Ala Tyr Asp Arg
 1               5                  10                  15

Ala Tyr Asn Arg Ala Ser Cys Lys Phe Ile Val Glu Val Gln Val Arg
            20                  25                  30

Arg Cys Pro Ile Leu Lys Pro Pro Gln His Gly Tyr Leu Thr Cys Ser
        35                  40                  45

Ser Ala Gly Asp Asn Tyr Gly Ala Ile Cys Glu Tyr His Cys Asp Gly
    50                  55                  60

Gly Tyr Glu Arg Gln Gly Thr Pro Ser Arg Val Cys Gln Ser Ser Arg
65                  70                  75                  80

Gln Trp Ser Gly Ser Pro Pro Val Cys Thr Pro Met Lys Ile Asn Val
                85                  90                  95

Asn Val Asn Ser Ala Ala Gly Leu Leu Asp Gln Phe Tyr Glu Lys Gln
            100                 105                 110

Arg Leu Leu Ile Val Ser
        115
```

<210> SEQ ID NO 189
<211> LENGTH: 299
<212> TYPE: PRT
<213> ORGANISM: Human
<220> FEATURE:
<221> NAME/KEY: UNSURE
<222> LOCATION: (247)...(247)
<221> NAME/KEY: UNSURE
<222> LOCATION: (289)...(289)

<400> SEQUENCE: 189

```
Met Gly Thr Lys Ala Gln Val Glu Arg Lys Leu Leu Cys Leu Phe Ile
 1               5                  10                  15

Leu Ala Ile Leu Leu Cys Ser Leu Ala Leu Gly Ser Val Thr Val His
            20                  25                  30

Ser Ser Glu Pro Glu Val Arg Ile Pro Glu Asn Asn Pro Val Lys Leu
        35                  40                  45

Ser Cys Ala Tyr Ser Gly Phe Ser Ser Pro Arg Val Glu Trp Lys Phe
    50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
```

-continued

```
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
        195                 200                 205

Glu Tyr Ser Cys Glu Ala Arg Asn Gly Tyr Gly Thr Pro Met Thr Ser
    210                 215                 220

Asn Ala Val Arg Met Glu Ala Val Glu Arg Asn Val Gly Val Ile Val
225                 230                 235                 240

Ala Ala Val Leu Val Thr Xaa Ile Leu Leu Gly Ile Leu Val Phe Gly
                245                 250                 255

Ile Trp Phe Ala Tyr Ser Arg Gly His Phe Asp Arg Thr Lys Lys Gly
            260                 265                 270

Thr Ser Ser Lys Lys Val Ile Tyr Ser Gln Pro Ser Ala Arg Ser Glu
        275                 280                 285

Xaa Glu Phe Lys Gln Thr Ser Ser Phe Leu Val
    290                 295


<210> SEQ ID NO 190
<211> LENGTH: 91
<212> TYPE: PRT
<213> ORGANISM: Human

<400> SEQUENCE: 190

Gln Pro Thr Val Phe Trp Pro Lys Thr Ser Ala Lys Lys Gly Asn Trp
 1               5                  10                  15

Val Leu Arg Leu Gly Leu Ser Asn Pro Asp Arg Pro Ala Arg Gln Asn
            20                  25                  30

Asn Trp Phe Leu Pro Ala Ser Arg Glu Ile Pro Glu His Ser Ala Leu
        35                  40                  45

Thr Arg Tyr Pro Ala Gln Ile Arg Gly Cys Trp Pro His Arg Leu Thr
    50                  55                  60

Lys Pro Gln Thr Cys Leu Pro Gln Ala Arg Ser Tyr Leu Ser His Glu
65                  70                  75                  80

Val Thr Gln Ala Thr Arg Thr Cys Pro Gly Gly
                85                  90


<210> SEQ ID NO 191
<211> LENGTH: 89
<212> TYPE: PRT
<213> ORGANISM: mouse

<400> SEQUENCE: 191

Gly Ala Trp Ala Met Leu Tyr Gly Val Ser Met Leu Cys Val Leu Asp
 1               5                  10                  15

Leu Gly Gln Pro Ser Val Val Glu Glu Pro Gly Cys Gly Pro Gly Lys
            20                  25                  30

Val Gln Asn Gly Ser Gly Asn Asn Thr Arg Cys Cys Ser Leu Tyr Ala
        35                  40                  45

Pro Gly Lys Glu Asp Cys Pro Lys Glu Arg Cys Ile Cys Val Thr Pro
    50                  55                  60

Glu Tyr His Cys Gly Asp Pro Gln Cys Lys Ile Cys Lys His Tyr Pro
65                  70                  75                  80

Cys Gln Pro Gly Gln Arg Val Glu Val
                85
```

-continued

<210> SEQ ID NO 192
<211> LENGTH: 299
<212> TYPE: PRT
<213> ORGANISM: mouse
<220> FEATURE:
<221> NAME/KEY: UNSURE
<222> LOCATION: (98)...(98)
<221> NAME/KEY: UNSURE
<222> LOCATION: (239)...(239)

<400> SEQUENCE: 192

```
Ala Arg Ala Gly Ala Cys Tyr Cys Pro Ala Gly Phe Leu Gly Ala Asp
 1               5                  10                  15

Cys Ser Leu Ala Cys Pro Gln Gly Arg Phe Gly Pro Ser Cys Ala His
            20                  25                  30

Val Cys Thr Cys Gly Gln Gly Ala Ala Cys Asp Pro Val Ser Gly Thr
        35                  40                  45

Cys Ile Cys Pro Pro Gly Lys Thr Gly Gly His Cys Glu Arg Gly Cys
    50                  55                  60

Pro Gln Asp Arg Phe Gly Lys Gly Cys Glu His Lys Cys Ala Cys Arg
65                  70                  75                  80

Asn Gly Gly Leu Cys His Ala Thr Asn Gly Ser Cys Ser Cys Pro Leu
                85                  90                  95

Gly Xaa Met Gly Pro His Cys Glu His Ala Cys Pro Ala Gly Arg Tyr
            100                 105                 110

Gly Ala Ala Cys Leu Leu Glu Cys Ser Cys Gln Asn Asn Gly Ser Cys
        115                 120                 125

Glu Pro Thr Ser Gly Ala Cys Leu Cys Gly Pro Gly Phe Tyr Gly Gln
    130                 135                 140

Ala Cys Glu Asp Thr Cys Pro Ala Gly Phe His Gly Ser Gly Cys Gln
145                 150                 155                 160

Arg Val Cys Glu Cys Gln Gln Gly Ala Pro Cys Asp Pro Val Ser Gly
                165                 170                 175

Arg Cys Leu Cys Pro Ala Gly Phe Arg Gly Gln Phe Cys Glu Arg Gly
            180                 185                 190

Cys Lys Pro Gly Phe Phe Gly Asp Gly Cys Leu Gln Gln Cys Asn Cys
        195                 200                 205

Pro Thr Gly Val Pro Cys Asp Pro Ile Ser Gly Leu Cys Leu Cys Pro
    210                 215                 220

Pro Gly Arg Ala Gly Thr Thr Cys Asp Leu Asp Cys Arg Arg Xaa Arg
225                 230                 235                 240

Phe Gly Pro Gly Cys Ala Leu Arg Cys Asp Cys Gly Gly Gly Ala Asp
                245                 250                 255

Cys Asp Pro Ile Ser Gly Gln Cys His Cys Val Asp Ser Tyr Thr Gly
            260                 265                 270

Pro Thr Cys Arg Glu Val Pro Thr Gln Leu Ser Ser Ile Arg Pro Ala
        275                 280                 285

Pro Gln His Ser Ser Ser Lys Ala Met Lys His
    290                 295
```

<210> SEQ ID NO 193
<211> LENGTH: 314
<212> TYPE: PRT
<213> ORGANISM: mouse
<220> FEATURE:
<221> NAME/KEY: UNSURE
<222> LOCATION: (138)...(138)
<221> NAME/KEY: UNSURE
<222> LOCATION: (139)...(139)

-continued

<221> NAME/KEY: UNSURE
<222> LOCATION: (224)...(224)
<221> NAME/KEY: UNSURE
<222> LOCATION: (245)...(245)

<400> SEQUENCE: 193

```
Glu Glu Pro Cys Asn Asn Gly Ser Glu Ile Leu Ala Tyr Asn Ile Asp
 1               5                  10                  15

Leu Gly Asp Ser Cys Ile Thr Val Gly Asn Thr Thr Thr His Val Met
            20                  25                  30

Lys Asn Leu Leu Pro Glu Thr Thr Tyr Arg Ile Arg Ile Gln Ala Ile
        35                  40                  45

Asn Glu Ile Gly Val Gly Pro Phe Ser Gln Phe Ile Lys Ala Lys Thr
    50                  55                  60

Arg Pro Leu Pro Pro Ser Pro Pro Arg Leu Glu Cys Ala Ala Ser Gly
65                  70                  75                  80

Pro Gln Ser Leu Lys Leu Lys Trp Gly Asp Ser Asn Ser Lys Thr His
                85                  90                  95

Ala Ala Gly Asp Met Val Tyr Thr Leu Gln Leu Glu Asp Arg Asn Lys
            100                 105                 110

Arg Phe Ile Ser Ile Tyr Arg Gly Pro Ser His Thr Tyr Lys Val Gln
        115                 120                 125

Arg Leu Thr Glu Phe Thr Cys Tyr Ser Xaa Xaa Ile Gln Ala Met Ser
    130                 135                 140

Glu Ala Gly Glu Gly Pro Tyr Ser Glu Thr Tyr Thr Phe Ser Thr Thr
145                 150                 155                 160

Lys Ser Val Pro Pro Thr Leu Lys Ala Pro Arg Val Thr Gln Leu Glu
                165                 170                 175

Gly Asn Ser Cys Glu Ile Phe Trp Glu Thr Val Pro Pro Met Arg Gly
            180                 185                 190

Asp Pro Val Ser Tyr Val Leu Gln Val Leu Val Gly Arg Asp Ser Glu
        195                 200                 205

Tyr Lys Gln Val Tyr Lys Gly Glu Glu Ala Thr Phe Gln Ile Ser Xaa
    210                 215                 220

Leu Gln Ser Asn Thr Asp Tyr Arg Phe Arg Val Cys Ala Cys Arg Arg
225                 230                 235                 240

Cys Val Asp Thr Xaa Gln Glu Leu Ser Gly Ala Phe Ser Pro Ser Ala
                245                 250                 255

Ala Phe Met Leu Gln Gln Arg Glu Val Met Leu Thr Gly Asp Leu Gly
            260                 265                 270

Gly Met Glu Glu Ala Lys Met Lys Gly Met Met Pro Thr Asp Glu Gln
        275                 280                 285

Phe Ala Ala Leu Ile Val Leu Gly Phe Ala Thr Leu Ser Ile Leu Phe
    290                 295                 300

Ala Phe Ile Leu Gln Tyr Phe Leu Met Lys
305                 310
```

<210> SEQ ID NO 194
<211> LENGTH: 109
<212> TYPE: PRT
<213> ORGANISM: mouse

<400> SEQUENCE: 194

```
Gly Thr Arg Val Gly Thr Pro Tyr Tyr Met Ser Pro Glu Arg Ile His
 1               5                  10                  15

Glu Asn Gly Tyr Asn Phe Lys Ser Asp Ile Trp Ser Leu Gly Cys Leu
```

-continued

```
            20                  25                  30

Leu Tyr Glu Met Ala Ala Leu Gln Ser Pro Phe Tyr Gly Asp Lys Met
        35                  40                  45

Asn Leu Tyr Ser Leu Cys Lys Lys Ile Glu Gln Cys Asp Tyr Pro Pro
    50                  55                  60

Leu Pro Ser Asp His Tyr Ser Glu Glu Leu Arg Gln Leu Val Asn Ile
65                  70                  75                  80

Cys Ile Asn Pro Asp Pro Glu Lys Arg Pro Asp Ile Ala Tyr Val Tyr
                85                  90                  95

Asp Val Ala Lys Arg Met His Ala Cys Thr Ala Ser Thr
            100                 105


<210> SEQ ID NO 195
<211> LENGTH: 237
<212> TYPE: PRT
<213> ORGANISM: mouse

<400> SEQUENCE: 195

Met Leu Ser Leu Arg Ser Leu Leu Pro His Leu Gly Leu Phe Leu Cys
 1               5                  10                  15

Leu Ala Leu His Leu Ser Pro Ser Leu Ser Ala Ser Asp Asn Gly Ser
            20                  25                  30

Cys Val Val Leu Asp Asn Ile Tyr Thr Ser Asp Ile Leu Glu Ile Ser
        35                  40                  45

Thr Met Ala Asn Val Ser Gly Gly Asp Val Thr Tyr Thr Val Thr Val
    50                  55                  60

Pro Val Asn Asp Ser Val Ser Ala Val Ile Leu Lys Ala Val Lys Glu
65                  70                  75                  80

Asp Asp Ser Pro Val Gly Thr Trp Ser Gly Thr Tyr Glu Lys Cys Asn
                85                  90                  95

Asp Ser Ser Val Tyr Tyr Asn Leu Thr Ser Gln Ser Gln Ser Val Phe
            100                 105                 110

Gln Thr Asn Trp Thr Val Pro Thr Ser Glu Asp Val Thr Lys Val Asn
        115                 120                 125

Leu Gln Val Leu Ile Val Val Asn Arg Thr Ala Ser Lys Ser Ser Val
    130                 135                 140

Lys Met Glu Gln Val Gln Pro Ser Ala Ser Thr Pro Ile Pro Glu Ser
145                 150                 155                 160

Ser Glu Thr Ser Gln Thr Ile Asn Thr Thr Pro Thr Val Asn Thr Ala
                165                 170                 175

Lys Thr Thr Ala Lys Asp Thr Ala Asn Thr Thr Ala Val Thr Thr Ala
            180                 185                 190

Asn Thr Thr Ala Asn Thr Thr Ala Val Thr Thr Ala Lys Thr Thr Ala
        195                 200                 205

Lys Ser Leu Ala Ile Arg Thr Leu Gly Ser Pro Leu Ala Gly Ala Leu
    210                 215                 220

His Ile Leu Leu Val Phe Leu Ile Ser Lys Leu Leu Phe
225                 230                 235


<210> SEQ ID NO 196
<211> LENGTH: 154
<212> TYPE: PRT
<213> ORGANISM: Human

<400> SEQUENCE: 196

Met Ala Leu Gly Val Pro Ile Ser Val Tyr Leu Leu Phe Asn Ala Met
```

-continued

```
 1               5                  10                  15

Thr Ala Leu Thr Glu Glu Ala Ala Val Thr Val Thr Pro Pro Ile Thr
            20                  25                  30

Ala Gln Gln Gly Asn Trp Thr Val Asn Lys Thr Glu Ala His Asn Ile
        35                  40                  45

Glu Gly Pro Ile Ala Leu Lys Phe Ser His Leu Cys Leu Glu Asp His
    50                  55                  60

Asn Ser Tyr Cys Ile Asn Gly Ala Cys Ala Phe His His Glu Leu Glu
65                  70                  75                  80

Lys Ala Ile Cys Arg Cys Phe Thr Gly Tyr Thr Gly Glu Arg Cys Glu
                85                  90                  95

His Leu Thr Leu Thr Ser Tyr Ala Val Asp Ser Tyr Glu Lys Tyr Ile
            100                 105                 110

Ala Ile Gly Ile Gly Val Gly Leu Leu Leu Ser Gly Phe Leu Val Ile
        115                 120                 125

Phe Tyr Cys Tyr Ile Arg Lys Arg Cys Leu Lys Leu Lys Ser Pro Tyr
    130                 135                 140

Asn Val Cys Ser Gly Glu Arg Arg Pro Leu
145                 150
```

<210> SEQ ID NO 197
<211> LENGTH: 171
<212> TYPE: PRT
<213> ORGANISM: Rat

<400> SEQUENCE: 197

```
Met Ala Arg Pro Ala Pro Trp Trp Trp Leu Arg Pro Leu Ala Ala Leu
 1               5                  10                  15

Ala Leu Ala Leu Ala Leu Val Arg Val Pro Ser Ala Arg Ala Gly Gln
            20                  25                  30

Met Pro Arg Pro Ala Glu Arg Gly Pro Pro Val Arg Leu Phe Thr Glu
        35                  40                  45

Glu Glu Leu Ala Arg Tyr Ser Gly Glu Glu Glu Asp Gln Pro Ile Tyr
    50                  55                  60

Leu Ala Val Lys Gly Val Val Phe Asp Val Thr Ser Gly Lys Glu Phe
65                  70                  75                  80

Tyr Gly Arg Gly Ala Pro Tyr Asn Ala Leu Ala Gly Lys Asp Ser Ser
                85                  90                  95

Arg Gly Val Ala Lys Met Ser Leu Asp Pro Ala Asp Leu Thr His Asp
            100                 105                 110

Ile Ser Gly Leu Thr Ala Lys Glu Leu Glu Ala Leu Asp Asp Ile Phe
        115                 120                 125

Ser Lys Val Tyr Lys Ala Lys Tyr Pro Ile Val Gly Tyr Thr Ala Arg
    130                 135                 140

Arg Ile Leu Asn Glu Asp Gly Ser Pro Asn Leu Asp Phe Lys Pro Glu
145                 150                 155                 160

Asp Gln Pro His Phe Asp Ile Lys Asp Glu Phe
                165                 170
```

<210> SEQ ID NO 198
<211> LENGTH: 1399
<212> TYPE: DNA
<213> ORGANISM: Mouse

<400> SEQUENCE: 198

```
ggcaaagact tcggcacgag asaacagcaa agcagagctg gctgcagcca ttcactggcc     60
```

-continued tcgggcgggc gtgccacaga ggcagttgaa gtgaaagtga aagagaaacg ataagagaac 120
ggagaccaca ggtgctaagt gagggtgctc acagaacccc ctcttcagcc agagatcact 180
agcaggggaa ctgtggagaa ggcagccagc aaggaagagc ctgagagtag cctccatggg 240
cttggagccc agctggtatc tgctgctctg tttggctgtc tctggggcag cagggactga 300
ccctcccaca gcgcccacca cagcagaaag acagcggcag cccacggaca tcatcttaga 360
ctgcttcttg gtgacagaag acaggcaccg cggggctttt gccagcagtg gggacaggga 420
gagggccttg cttgtgctga agcaggtacc agtgctggat gatggctccc tggaaggcat 480
cacagatttc caggggagca ctgagaccaa acaggattca cctgttatct ttgaggcctc 540
agtggacttg gtacagattc cccaggcaga ggcgttgctc catgctgact gcagcgggaa 600
ggcagtgacc tgcgagatct ccaagtattt cctccaggcc agacaagagg ccacttttga 660
gaaagcacat tggttcatca gcaacatgca ggtttctaga ggtggcccca gtgtctccat 720
ggtgatgaag actctaagag atgctgaagt tggagctgtc cggcacccta cactgaacct 780
acctctgagt gcccagggca cagtgaagac tcaagtggag ttccaggtga catcagagac 840
ccaaaccctg aaccacctgc tggggtcctc tgtctccctg cactgcagtt tctccatggc 900
accagacctg gacctcactg gcgtggagtg gcggctgcag cataaaggca gcggccagct 960
ggtgtacagc tggaagacag ggcaggggca ggccaagcgc aagggcgcta cactggagcc 1020
tgaggagcta ctcagggctg gaaacgcctc tctcacctta cccaacctca ctctaaagga 1080
tgaggggacc tacatctgcc agatctccac ctctctgtat caagctcaac agatcatgcc 1140
acttaacatc ctggctcccc ccaaagtaca actgcacttg gcaaacaagg atcctctgcc 1200
ttccctcgtc tgcagcattg ccggctacta tcctctggat gtgggagtga cgtggattcg 1260
agaggagctg ggtggaattc cagcccaagt ctctggtgcc tccttctcca gcctcaggca 1320
gagcacgatg ggaacctaca gcatttcttc cacggtgatg gctgacccag gccccacagg 1380
tgccacttat acctgccaa 1399

<210> SEQ ID NO 199
<211> LENGTH: 469
<212> TYPE: DNA
<213> ORGANISM: Rat

<400> SEQUENCE: 199
ggggcgctgg ccagtcatgg cggagccttg ggctgggcag tttctgcaag ctttgcccgc 60
cacggtgctc ggagcgctgg gcaccctggg cagcgagttt ctgcgggagt gggagacaca 120
agatatgcga gtgactctct tcaagcttct cctgctttgg ttggtgttaa gtctcctggg 180
catccagctg gcgtgggggt tctacgggaa cacagtgacc gggttgtatc accgtccagg 240
gaaatggcag caaatgaagc tctcaaaact cacagagaat aaaggaaggc agcaggagaa 300
gggtctccag agatatcgct gggtctgctg gctcctgtgc tgtaccttgc tgctatccag 360
accccttagg caactgcaga gggcttgggt tgggggactg gagtaccatg atgctcccag 420
ggtgagcctc cactgccctc agccttgcct ccaacagcgt caggtactg 469

<210> SEQ ID NO 200
<211> LENGTH: 529
<212> TYPE: DNA
<213> ORGANISM: Rat

<400> SEQUENCE: 200

-continued aaagcttcca tcctcaacat gccactagtg acgacactct tctacgcctg cttctatcac 60
tacacggagt ccgaggggac cttcagcagt ccagtcaacc tgaagaaaac attcaagatc 120
ccagacagac agtatgtgct gacagccttg gctgcgcggg ccaagcttag agcctggaat 180
gatgtcgacg ccttgttcac cacaaagaac tggttgggtt acaccaagaa gagagcaccc 240
attggcttcc atcgagttgt ggaaattttg cacaagaaca gtgcccctgt ccagatattg 300
caggaatatg tcaatctggt ggaagatgtg gacacaaagt tgaacttagc cactaagttc 360
aagtgccatg atgttgtcat tgatacttgc cgagacctga aggatcgtca acagttgctt 420
gcatacagga gcaaagtaga taaaggatct gctgaggaag agaaaatcga tgtcatcctc 480
agcagctcgc aaattcgatg gaagaactaa ggttcttttg ctacccaga 529

<210> SEQ ID NO 201
<211> LENGTH: 1230
<212> TYPE: DNA
<213> ORGANISM: Rat

<400> SEQUENCE: 201
aagaattcgg cacgaggcca tggctggttg ggcgggggcc gagctctcgg tcctgaaccc 60
gctgcgtgcg ctgtggctgt tgctggccgc cgccttcctg ctcgcactgc tgctgcagct 120
ggcgcccgcc aggctgctac cgagctgcgc gctcttccag gacctcatcc gctacgggaa 180
gaccaagcag tccggctcgc ggcgccccgc cgtctgcagg gccttcgacg tccccaagag 240
gtacttttct cacttctacg tcgtctcagt gttatggaat ggctccctgc tctggttcct 300
gtctcagtct ctgttcctgg gagcgccgtt tccaagctgg ctttgggctt tgctcagaac 360
tcttggggtc acgcagttcc aagccctggg gatggagtcc aaggcttctc ggatacaagc 420
aggcgagctg gctctgtcta ccttcttagt gttggtgttc ctctgggtcc atagtcttcg 480
gagactcttc gagtgcttct acgtcagcgt cttctctaac acggccattc acgtcgtgca 540
gtactgtttc gggctggtct actatgtcct tgttggcctg accgtactga gccaagtgcc 600
catgaatgac aagaacgtgt acgctctggg gaagaatcta ctgctacaag ctcggtggtt 660
ccacatcttg ggaatgatga tgttcttctg gtcctctgcc catcagtata agtgccacgt 720
cattctcagc aatctcagga gaaataagaa aggtgtggtc atccactgcc agcacagaat 780
cccctttgga gactggttcg agtatgtgtc ttctgctaac tacctagcag agctgatgat 840
ctacatctcc atggctgtca ccttcgggct ccacaacgta acctggtggc tggtggtgac 900
ctatgtcttc ttcagccaag ccttgtctgc gttcttcaac cacaggttct acaaaagcac 960
atttgtgtcc tacccaaagc ataggaaagc tttcctcccg ttcttgtttt gaacaggctt 1020
tatggtgaag agcgcagccc aggtgacagg ttcccttcct cgagacgctg agacaggctg 1080
aagtacactt tctgcagctg gcgcccgcca ggctgctacc gagctgcgcg ctcttccagg 1140
acctcatccg ctacgggaag accaagcagt ccggctcgcg gcgccccgcc gtctgcagcc 1200
cgggggatcc actagttcta gagcgccgcc 1230

<210> SEQ ID NO 202
<211> LENGTH: 778
<212> TYPE: DNA
<213> ORGANISM: Rat

<400> SEQUENCE: 202
ctgcaggtcg acactagtgg atccaaagat tcggcacgag ataaggcaca tttgcttcat 60
aaaataaaaa aaaaggaaat ttacttagcc gcatgtcagt cacccaaatt ttgagtgtac 120

-continued

```
aaatgaaatg gaaaacattt attacacaaa tttaattaca attctaggga ataaacatgc    180
aaatcagatg gagctcaatc tgcaggcgct gatcctctcc ccctggtttg cagtctgtgc    240
acctcctgga ttcgcccgcg accaggcagt cagaggcctg gctcttgcag gcaggaggat    300
cactgttgta aagaacagcg tcacatttag cgcatctggc gtagtagcag tttttaacac    360
tttgcgcagg tgcctccctt cccccacccg cgctttgtta ggtctacctc tctaaatctc    420
tgccttcctc gcacagtaag tgacctctcc atgacaaagg gcccccagac agcagttata    480
aatcaatgtg ttttgggttt gtttgtttgt ttgttttgtt ttaaagaaaa acccggccat    540
gcttggtggc acttgccttt aatagtagcg cttggtagac agaggcaagc ggttctctgt    600
aagttcaagg ccagcctggt ctacacagtg agaccgggtc tcaaaaacaa aacaacaaaa    660
aacaactcct attgaatcca ctacaggaag ggggggcgcg gatcactgtc tgcaaactaa    720
agtgacttga gctcctgtca cagcctttcc agcaagggca agcttcttta ttagttat      778
```

<210> SEQ ID NO 203
<211> LENGTH: 1123
<212> TYPE: DNA
<213> ORGANISM: Rat

<400> SEQUENCE: 203

```
gggccccccc tcgagtcgac gktatcgata agcttgatat cgaattcctg caggtcgaca     60
ctagtggatc caaagaattc ggcacgagcc tgaggcgact acggtgcggg tgccgggtgc    120
cgggtgccta cagcccccat cagcttcccc ggggagattc tgccgatttg tcacgagcca    180
tgctcaggag gcagctcgtc tggtggcacc tgctggcttt gcttttcctc ccattttgcc    240
tgtgtcaaga tgaatacatg gagtctccac aagctggagg actgccccca gactgcagca    300
agtgttgcca tggagattat ggattccgtg gttaccaagg gcccccctgga cccccaggtc    360
ctcctggcat tccaggaaac catggaaaca atggaaataa cggagccact ggccacgaag    420
gggccaaggg tgagaaagga gacaaaggcg acctggggcc tcgaggggaa cgggggcagc    480
atggccccaa aggatagaag ggatacccag gggtgccacc agagctgcag attgcgttca    540
tggcttctct agcgactcac ttcagcaatc agaacagtgg cattatcttc agcagtgttg    600
agaccaacat tggaaacttc ttcgatgtca tgactggtag atttggggcc cccgtatcag    660
gcgtgtattt cttcaccttc agcatgatga agcatgagga cgtggaggaa gtgtatgtgt    720
accttatgca caatggtaac acggtgttca gcatgtacag ctatgaaaca aagggaaaat    780
cagatacatc cagcaaccat gcagtgctga agttggccaa aggagatgaa gtctggctaa    840
gaatgggcaa cggtgccctc catggggacc accagcgctt ctctaccttc gcaggctttc    900
tgctttttga aactaagtga tgaggaagtc aggatagctc catgctaagg gcgatttgta    960
ggtgagctag ggttgttagg atctgagggg tgttggagtt gggcttctct atggagtatt   1020
taactgttac attggtcaca ctgctactca ttctaatggc ataccaatta tgttggatac   1080
tttaggggct aggaagaata gaccacaagg taatattccc aga                     1123
```

<210> SEQ ID NO 204
<211> LENGTH: 434
<212> TYPE: DNA
<213> ORGANISM: Mouse

<400> SEQUENCE: 204

```
accaccaagc agatggaatg ctggcacacc catgcacctg catggcgtca caggtggaag     60
```

-continued attgttaaaa aattgacatc agaaatattt acagaaatag atacctgttt gaataaagtt 120
agagatgaaa tttttgctaa acttcaaccg aagcttagat gcacattagg tgacatggaa 180
agtcctgtgt ttgcacttcc tgtactgtta aagcttgaac cccatgttga aagcctcttt 240
acatattctt tttcttggaa ttttgaatgt tcccattgtg gacaccagta ccaaaacagg 300
tgtgtgaaga gtctggtcac ctttaccaat attgttcctg agtggcatcc actcaatgct 360
gcccattttg gtccatgtaa cagctgcaac agtaaatcac aaataagaaa aatggtgttg 420
gaaagagcgt cgcc 434

<210> SEQ ID NO 205
<211> LENGTH: 783
<212> TYPE: DNA
<213> ORGANISM: Mouse

<400> SEQUENCE: 205
aattcggcac gaggctagtc gaatgtccgg gctgcggacg ctgctggggc tggggctgct 60
ggttgcgggc tcgcgcctgc cacgggtcat cagccagcag agtgtgtgtc gtgcaaggcc 120
catctggtgg ggaacacagc gccggggctc ggagaccatg gcgggcgctg cggtgaagta 180
cttaagtcag gaggaggctc aggccgtgga ccaagagctt tttaacgagt atcagttcag 240
cgtggatcaa ctcatggagc tggccgggtt gagctgtgcc acggctattg ccaaggctta 300 tcccccccacg tctatgtcca agagtccccc gactgtcttg gtcatctgtg gccccggaaa 360
taacggaggg gatgggctgg tctgtgcgcg acacctcaaa ctttttggtt accagccaac 420
tatctattac cccaaaagac ctaacaagcc cctcttcact gggctagtga ctcagtgtca 480
gaaaatggac attcctttcc ttggtgaaat gcccccagag gatgggatgt agagaaggga 540
aaccctagcg gaatccaacc agacttactc atctcactga cggcacccaa gaagtctgca 600
actcacttta ctggccgata tcattacctt gggggtcgct ttgtaccacc tgctctagag 660
aagaagtacc agctgaacct gccatcttac cctgacacag agtgtgtcta ccgtctacag 720
taagggaggt gggtaggcag gattctcaat aaagacttgg tactttctgt cttgaaaaaa 780
aaa 783

<210> SEQ ID NO 206
<211> LENGTH: 480
<212> TYPE: DNA
<213> ORGANISM: Mouse

<400> SEQUENCE: 206
aaatgaaaac tcttggarct cgcgcgcctg caggtcgaca ctagtggatc caaagaattc 60
ggcacgagtt aaggttttca gactttattt catggtattt gacattgaca catactgagt 120
tagtaacaag ataccatgca gctccctcta gcctcggatc accgaagcag gaagaaggtc 180
agactgcccc catcccagat ttgcttagtt tgtctcccaa tgtgctggac tttaaagaca 240
gggaatggag aagcagatgg atgcttcagt ttcagtcatt tttggctcta tagtgatctc 300
tgccttcctg tacctgtcct tggctggacc ctgggcagta actgtcactc agatgaggac 360
gatcatcatt acaatggacc aactgaggga tgccctcata ttagaccaat taaaagttgc 420
tgtgagttaa accaggaatg accgcacttc cacatcagaa atcaaacaaa atcaatggtt 480

<210> SEQ ID NO 207
<211> LENGTH: 501
<212> TYPE: DNA
<213> ORGANISM: Mouse

-continued

<400> SEQUENCE: 207
ctgcaggtcg acactagtgg atccaaagaa ttcggcacga gaatcatggc gccgtcgctg 60
tggaaggggc ttgtaggtgt cgggcttttt gccctagccc acgctgcctt ttcagctgcg 120
cagcatcgtt cttatatgcg actaacagaa aaggaagatg aatcattacc aatagatata 180
gttcttcaga cacttctggc ctttgcagtt acctgttatg gcatagttca tatcgcaggg 240
gagttcaaag acatggatgc cacttcagaa ttaaagaata agacatttga taccttaagg 300
aatcacccat ctttttatgt gtttaaccat cgtggtcgag tgctgttccg gccttcagat 360
gcaacaaatt cttcaaacct agatgcattg tcctctaata catcgttgaa gttacgaaag 420
tttgactcac tgcgccgtta agctttttac aaattaaata acaggacaga cacagaattg 480
agtattggag tttggggtgt a 501

<210> SEQ ID NO 208
<211> LENGTH: 480
<212> TYPE: DNA
<213> ORGANISM: Mouse

<400> SEQUENCE: 208
ggcacgagga agcctcttcc catggaagca cactctagga gagagaaggc ctctgggctc 60
cgcctggcct ggcattatga atgcagtggg gtcagtgtgt ggtggatgtg tgtactgggt 120
tggctttcct ttttagtttt tttacttttt agtttagttt gttcttttcc ttccccaata 180
aatcattctc acatgcttcc atgtttgttt ctgagaggtg ggggctcaaa tgtatagaaa 240
gtaggcccca gtccataagg aggtgtgaac acaccccctt actgcttatc acccatttga 300
caggaacgcc caggaggga gggggagggg aagaggtgag ttctgcacag tcggacattt 360
ctgttgcttt tgcatgttta atatagacgt tcctgtcgat ccttgggaga tcatggcctt 420
cagatatgca cacgaccttt gaattgtgcc tactaattat agcaggggac ttgggtaccc 480

<210> SEQ ID NO 209
<211> LENGTH: 962
<212> TYPE: DNA
<213> ORGANISM: Mouse

<400> SEQUENCE: 209
ggcacgagat tagcggctcc tcagcccagc aaatcctcca ctcatcatgc ttcctcctgc 60
cattcatctc tctctcattc ccctgctctg catcctgatg agaaactgtt tggcttttaa 120
aaatgatgcc acagaaatcc tttattcaca tgtggttaaa cctgtcccgg cacaccccag 180
cagcaacagc accctgaatc aagccaggaa tggaggcagg catttcagta gcactggact 240
ggatcgaaac agtcgagttc aagtgggctg cagggaactg cggtccacca aatacatttc 300
ggacggccag tgcaccagca tcagccctct gaaggagctg gtgtgcgcgg gcgagtgctt 360
gcccctgccg gtgcttccca actggatcgg aggaggctac ggaacaaagt actggagccg 420
gaggagctct caggagtggc ggtgtgtcaa cgacaagacg cgcacccaga ggatccagct 480
gcagtgtcag gacggcagca cgcgcaccta caaaatcacc gtggtcacgg cgtgcaagtg 540
caagaggtac acccgtcagc acaacgagtc cagccacaac tttgaaagcg tgtcgccagc 600
caagcccgcc cagcaccaca gagagcggaa gagagccagc aaatccagca agcacagtct 660
gagctagacc tggactgact aggaagcatc tgctacccag atttgattgc ttggaagact 720
ctctctcgag cctgccattg ctctttcctc acttgaaagt atatgctttc tgctttgatc 780

-continued

```
aagcccagca ggctgtcctt ctctgggact agcttttcct ttgcaagtgt ctcaagatgt    840

aatgagtggt ttgcagtgaa agccaggcat cctgtagttt ccatcccctc ccccatccca    900

gtcatttctt taaaagcacc tgatgctgca ttctgttaca gtttaaaaaa aaaaaaaaaa    960

aa                                                                   962
```

<210> SEQ ID NO 210
<211> LENGTH: 778
<212> TYPE: DNA
<213> ORGANISM: Mouse

<400> SEQUENCE: 210

```
ggcacgaggc tagtcgaatg tccgggctgc ggacgctgct ggggctgggg ctgctggttg     60

cgggctcgcg cctgccacgg gtcatcagcc agcagagtgt gtgtcgtgca aggcccatct    120

ggtggggaac acagcgccgg ggctcggaga ccatggcggg cgctgcggtg aagtacttaa    180

gtcaggagga ggctcaggcc gtggaccaag agctttttaa cgagtatcag ttcagcgtgg    240

atcaactcat ggagctggcc gggttgagct gtgccacggc tattgccaag gcttatcccc    300

ccacgtctat gtccaagagt cccccgactg tcttggtcat ctgtggcccc ggaaataacg    360

gaggggatgg gctggtctgt gcgcgacacc tcaaactttt tggttaccag ccaactatct    420

attaccccaa aagacctaac aagcccctct tcactgggct agtgactcag tgtcagaaaa    480

tggacattcc tttccttggt gaaatgcccc cagaggatgg gatgtagaga agggaaaccc    540

tagcggaatc caaccagact tactcatctc actgacggca cccaagaagt ctgcaactca    600

ctttactggc cgatatcatt accttggggg tcgctttgta ccacctgctc tagagaagaa    660

gtaccagctg aacctgccat cttaccctga cacagagtgt gtctaccgtc tacagtaagg    720

gaggtgggta ggcaggattc tcaataaaga cttggtactt tctgtcttga aaaaaaaa      778
```

<210> SEQ ID NO 211
<211> LENGTH: 1152
<212> TYPE: DNA
<213> ORGANISM: Mouse

<400> SEQUENCE: 211

```
ggcacgagct tctcagggcc tgccacccaa ataagtctgg ccctagcctc aactctctct     60

caggctgggc cacaggaagc tgctgactgg ccacttgaca ccctccccct aaagctaatg    120

tctgtgacta tagggaggtt agcacttttt ctaattggaa ttcttctctg tcctgtggcc    180

ccatccctca cccgctcttg gcctggacca gatacatgca gcctctttct ccagcacagc    240

ctttccctga gcctgaggtt agggcagagt ttagagggtg ggctaagtgt atgttttcat    300

gtatgcattc atgcctgtga gtgtgtggct tgctgtcgtg tcctctggga tcccaagcca    360

cgcgggtctt ccctctgtag atgggtcctg ggttctatca cctgcttatt tatgtacgag    420

gttgggggt ggacccaggg tgggttgatt gtctctttgt aaggaagtat gtgtcggggg    480

tgacacgagg ctaagcccga gaaaccccgg gagacagcac tgcataagaa actggtttcc    540

magactgcag agggagctgc acttttgttt tgaccaaaaa caaaaaacaa aacaaaacaa    600

aaacaaaaca aaaataactc tgaagggcgg gaggataccc aagcctgatg cctgagagga    660

gtccctagac ttcagcaact ccgctgcgtg gcctgagccc agcgggaggg atggggagag    720

aattttttgg agtccgtgcc tgtggtgggc agtcctgagc cttcagctga agcagtgctt    780

tttggctgcc ctcacctcgc actacttgac cttgaggctc tgagtatctc ctgtgcacag    840

gagaagctcc tgcaccagaa agcaccaaar sccmtggcac cccatcttac tccactctcc    900
```

-continued

```
ccagggactc ccaggtggga actgctgtgg cagtgagctc agcccggaca gacactgcca    960

accctgtctc ctggcattgg gctccggctc tacctcccca agcagggcga ggccccgcct   1020

tctcagccta gcaccacctg tccccgagtc ttctcagctt gcccatcatt ctcggcgccc   1080

acacaggtga cagtcccaag tagataacct ccatgggaca agttgggtgt tgccttaccc   1140

gcctgcccag cc                                                        1152
```

```
<210> SEQ ID NO 212
<211> LENGTH: 446
<212> TYPE: DNA
<213> ORGANISM: Mouse

<400> SEQUENCE: 212

ggcacgagct tgagtctgga gtgctgcaaa taatagtatg cactatccct gcctggcatg     60

tttgtttgtt aatgtgcact ggtgttttgc ctggatgtgt atacttgtga agatgtcaga    120

actcctggag ctggagttag agacaatggt gagctgcctt gtggatgttg ggaattgaac    180

ccaggtcctc tggagaaata accagtgctc ttaaccacta agccatctca acagccccaa    240

attatttttt taataagttg cctcggtcat gttgtcttaa tcagagcgat agaaaagtaa    300

ctaatataga ttatttatga attcaggtgg cttaatggta tatgcatgaa ttagtagtaa    360

aacaagaact agggccagca agtggcttaa gggtgcctgc taaccatctc agccacctga    420

gttcagtctc caggaaccac acagtg                                         446
```

```
<210> SEQ ID NO 213
<211> LENGTH: 2728
<212> TYPE: DNA
<213> ORGANISM: Mouse

<400> SEQUENCE: 213

ggggagggag ggccctgttt tggcggagca gggcgcgcgg ctgggcccct gaagtggagc     60

gagagggagg cgcttcgccg ggtgccactg ccggggaggc tcgtcgggac ccagcgccgg    120

tcgcggctcc ctcaggatcg atgcaccgcg gttaacccgt gaggaggcgg cggccgggga    180

agatggtgtt gccgacagtg ttaattctgc tcctctcctg ggcggcgggg ctgggaggtg    240

agacacgacc ccgggcggcg acggagcggc ggtcggtcgg gccgagcgca cgtcgcggag    300

ccgggccgcg cgtgtcaggt ctcctcggct tctgtcagct ctctcagctc gcctcagccg    360

accccgagcg acgctccccg cgcgctattg tccctcgcgc gccccgaccg cgctcccgcc    420

ggcggccctg cctgcccggc ttctcgcgcc gctttccccg ggagcggcgg agcccaggcc    480

agccgccctc gcgcactccg cagccacctc agccctgccg gggtccgagc cccgggaccg    540

cgcagactcg cagcaacttg cgaggttggc agcgcggcgg gagcattgtt ctgcaagcga    600

gcgagcggac ccgggccggg tgtcggacgc cggtgtgcgt gtcccacccg agtgccttcc    660

ctccgcctcg tgctcttttc ggagtgtttg tagccagcgc gccggaggtt gtgtgtgtgt    720

gtgtgtctgt cgttctgtct gtctgtcttc tgtctccccg gggcaagact ttagttgact    780

gaggagaagg gcaagccgtt ttaggatgct cttcgatcca tctgtctttt tgagttgagt    840

ccacagagaa gcaagaccga cccttcctgg gcgaaccaac ttgcagagtt ttcttaaact    900

ctcaggtgga gcagacgtac tgcttagtca gaggattgtc agggctgtgc tccctccccc    960

tgcaaattgg agttcactgt tgcttcaagt ttcctgatgc ttcgggtttg agacagcggt   1020

atttcattcc caggctttcc taggacaggt tgcatgatta ttttgttcct atgagaaagt   1080
```

-continued

```
gctttaccat aggtaagcta atttgccgcc caagtgtctg gagagaggtt agcttaaaag   1140
cattgaattg gaaacaaccc ccagaacttc caggggtgct tcggatggtt gtcagcagcc   1200
taatttgata ctttagaaaa tatcctagtg ttttctgtag tgtattgtct gtgttcatcc   1260
ctttgtctca ttgacttaaa ctgcaggacc cagcctattt ttgtctggca ttctgcttac   1320
tctgaagttg gttttgtgta ctcagtttct gttgttgtgt gtactattca tttattaagt   1380
acacatttta gatgacagcc actaatagat gcttattttt gttttgtttt tgttttttgt   1440
tttttttaag aaccagattg cagaccgttt gtaaagagcc tctttattta acatttgtat   1500
ttctgtaaca cggcttatag tcctggctgg ctgttttcac tttttgtgat tatggtcagg   1560
aattagacac tgttctctat gaggtaataa aatctaagtt aaatgtgata cactttgata   1620
acgtagtgat acaaaatgcc ttttattaag gaaaactaaa accaatgtgg cctgttgttt   1680
ggggaaaaaa gtaaattaac agcataagca ttgtgggtga agagttttat tcagatcttt   1740
ggagtttctt tctgcactaa gtaatgattc aaaggccagg ttttgttgtg cttctgctaa   1800
aaacttaaaa aaaaaaataa aagttttcac ttaagtatta tgtcaaattt gtaatacttg   1860
agtatgtagg tatatttata atttggggct gtggaatgta gcccagtggc aattgcctag   1920
caaggccatg caaggctttg gattcaacat ctctgtttaa ggcccaaaac tcctcctatg   1980
tttatttgta actcattata ctatatgctg ggtttttttt ttttatctga actgaatcgc   2040
atatagctaa gtttatatat ttttgtgatg ttttgtaggc tagtgtgcat tcaaacttag   2100
tagatattgg ctgtagtgca ttggaaagtt gaaatgtttg taaggttagg gtagttgtag   2160
aaatacagaa ctttaaggta taagccatgt tcaggtgaaa ctaaactctg ttggttgctt   2220
tcatcttgcc tgtttgtgtt aatcactgtt gtgtgtgaat gtttttctta ctgcacataa   2280
tgtgaggggt gggaagctgg aaggaggcaa taaagtgctt aaatactaaa acaacttttc   2340
tagttttccc ttctatgttg gtggatgtcc tgcccagtgt tgtatttgta gaaagatacc   2400
atgatagttt ttgagtttat gaagtgtctg tatggaagta ttcatatatc tgtacaaaat   2460
gcttctaaaa agttatttgt tgcctagcaa aatggctcag taggtgggag cacttgcttt   2520
gaaagcctga ctatctgatt tctagtcccc atccctttag ttgaaggaga gaaccaactc   2580
ctgaaaatta tcttttgacc ttcacatgca caccatggtt cctcgtgccc ttactcacac   2640
atgtacacta cacacaatta taagataata aagttatttg gagacgtgtt aggaacttat   2700
tggcactatc ctgattagcc acaatttt                                       2728
```

<210> SEQ ID NO 214
<211> LENGTH: 2046
<212> TYPE: DNA
<213> ORGANISM: Rat

<400> SEQUENCE: 214

```
cggtatcgat aagcttgata tcgaattcct gcaggtcgac actagtggat ccaaagaatt     60
cggcacgaga aaataaccaa ccaaacaaac tttcctcttc ccgctagaaa aaacaaattc    120
tttaaggatg gagctgctct actggtgttt gctgtgcctc ctgttaccac tcacctccag    180
gacccagaag ctgcccacca gagatgagga actttttcag atgcagatcc gggataaggc    240
attgtttcac gattcatccg tgattccaga tggagctgaa atcagcagtt acctatttag    300
agatacacct agaaggtatt tcttcatggt tgaggaagat aacaccccac tgtcagtcac    360
agtgacacct tgtgatgcgc ctttggaatg gaagcttagc ctccaggagc tgcctgagga    420
gtccagtgca gatgggtcag gtgacccaga accacttgac cagcagaagc agcagatgac    480
```

-continued

```
tgatgtggag ggcacagaac tgttctccta caagggcaat gatgtagagt attttctgtc    540

ttcaagttcc ccatctggtt tgtatcagtt ggagcttctt tcaacagaga aagacacaca    600

tttcaaagta tatgccacca ccactccaga atctgatcaa ccataccctg acttaccata    660

tgaccccaga gttgatgtga cctctattgg acgtaccaca gtcactttgg cctggaagca    720

aagccccaca gcttctatgc tgaaacaacc catagagtac tgtgtggtca tcaacaagga    780

gcacaatttc aaaagccttt gtgcagcaga aacaaaaatg agtgcagatg atgccttcat    840

ggtggcgccc aaacctggcc tagactttag ccccttttgac tttgcccatt tcggatttcc    900

aacagataat ttgggtaagg atcgcagctt cctggcaaag ccttctccca aagtggggcg    960

ccatgtctac tggaggccta aggttgacat aaaaaaaatc tgcataggaa gtaaaaatat   1020

tttcacagtc tccgacctga agcccaatac ccagtactac tttgatgtct tcatggtcaa   1080

taccaacact aacatgaaca cagcttttgt gggtgccttt gccaggacca aggaggaggc   1140

aaaacagaag acagtggagc tcaaagatgg gagggtcaca gatgtggtcg ttaaaaggaa   1200

agggaaaaag tttctacggt ttgctccagt ctcctctcac caaaaagtca ccctctttat   1260

tcactcttgt atggacactg ttcaagtcca agtgagaaga gatgggaagc tgcttctgtc   1320

acagaatgtg gaaggcattc ggcagttcca gttaagagga aaacccaaag gaaagtacct   1380

cattcgactg aaaggcaaca agaaaggagc atcaatgttg aaaatactag ccaccaccag   1440

gcccagtaag cacgcattcc cctctcttcc tgatgacaca agaatcaaag cctttgacaa   1500

gctacgcact tgctcttcag tcacggtggc ttggcttggc acccaagaga ggagaaagtt   1560

ttgtatctac agaaaggaag tgggtggaaa ctacagtgaa gagcagaaga gaagagagag   1620

aaaccagtgc ctaggaccag acaccagaaa gaagtcagag aaggttcttt gcaagtactt   1680

ccacagccaa aacctgcaga aagcagtgac gacagagaca atcagagatc tgcaacctgg   1740

caagtcttac ctactggacg tttatgttgt aggacatggg ggacactctg tgaagtatca   1800

gagtaaactt gtgaaaacaa ggaaggtctg ttagttacct taagtgaaga tcagtagaac   1860

tcccggagag atatggaatc acactgcctg ttactgacta ctctcatgac aaacagaagt   1920

tgtacttgaa agaaaggata acaacatgtg tacattgatg cctgtgtaat gtaacgtgga   1980

gacttgtatt cacgcacacc tgtggtactt agggtccatc tgtctaatgc tggctaatgt   2040

caaagg                                                              2046
```

<210> SEQ ID NO 215
<211> LENGTH: 493
<212> TYPE: DNA
<213> ORGANISM: Mouse

<400> SEQUENCE: 215

```
cccacccagc agaagatcct ctaccaatga atgctgactg agcctgccca actttttgtg     60

cacaagaaga accagccacc ttcacacagc agcctccggc ttcactttag gaccctagca    120

ggagcactgg ccctttcttc aacacagatg agttggggac tacagattct cccctgcctg    180

agcctaatcc ttcttctttg gaaccaagtg ccagggcttg agggtcaaga gttccgattt    240

gggtcttgcc aagtgacagg ggtggttctc ccagaactgt gggaggcctt ctggactgtg    300

aagaacactg tgcaaactca ggatgacatc acaagcatcc ggctgttgaa gccgcaggtt    360

ctgcggaatg tctcggtaat cagatgggaa ggggatagct agctctctaa gaggggctga    420

tgggagtcgt tcccttctgc tctgatccct atacaggaca aggctgagca tgaggcaaag    480
```

-continued tggtctctgt ctg 493

<210> SEQ ID NO 216
<211> LENGTH: 511
<212> TYPE: DNA
<213> ORGANISM: Mouse

<400> SEQUENCE: 216
gggcatagtg ctggagtaga tgagaattct atgtcatgtt cccaaggcaa ccaggagaag 60
attgtcttcc aggtagcttg gagaagggtc tcagagtgat gcatttcctc caatgcccac 120
tccaacaggg ctatttccct ggccaagcat attcaaacca ccacagtgac taaaggccaa 180
gtggatggat gtctggtctg ggttgccact ggagaccttg tggatatatg aggctgtgct 240
gccttggctg ctgatggggc aggggcatgc ctgggtctgt ggtcctattg cactctgggt 300
ctttgttaat gtcccaggct tatgttacca ccaaaagcca ttcagatgcc cctggtctgg 360
attgctgccc gaagcactgt gctagccctg cctcttgctg accaccacac tcagaagagc 420
tgtccctacc tcttgcctgg gcagcacaat agagctgacc ctgatgaagt ggaagcactg 480
gtgaactggc tccctccttc atctactgta g 511

<210> SEQ ID NO 217
<211> LENGTH: 1107
<212> TYPE: DNA
<213> ORGANISM: Rat

<400> SEQUENCE: 217
cggcatctca agctgctgca agcaggactg agcactacca gagcagcaac ctcggatggc 60
cctggacgtg gcacgcgcgg ggcacagagg caagaagact tgatgaagcc tctcttccca 120
acccatatcc agaaagaacg atttagatga cagtttttag aaaggtgacc accatgatct 180
cctggatgct cttggcctgt gcccttccgt gtgctgctga cccaatgctt ggtgcctttg 240
ctcgcaggga cttccagaag ggtggtcctc aactggtgtg cagtctgcct ggtccccaag 300
gcccacctgg ccctccagga gcaccaggat cctcaggaat ggtgggaaga atgggttttc 360
ctggtaagga tggccaagac ggccaggacg gagaccgagg ggacagtgga gaagaaggtc 420
cacctggcag gacaggcaac cgaggaaaac aaggaccaaa gggcaaagct ggggccattg 480
ggagagcggg tcctcgagga cccaaggggg tcagtggtac ccccgggaaa catggtatac 540
cgggcaagaa gggacctaag ggcaagaaag gggaacctgg gctcccaggc ccctgtagct 600
gcggcagtag ccgagccaag tcggcctttt cggtggcggt aaccaagagt tacccacgtg 660
agcgactgcc catcaagttt gacaagattc tgatgaatga gggaggccac tacaatgcat 720
ccagtggcaa gttcgtctgc agcgtgccag ggatctatta ctttacctat gacattacgc 780
tggccaacaa acacctggcc atcggcctag tgcacaatgg ccagtaccgc attcggactt 840
ttgacgccaa caccggcaac cacgacgtgg cctcgggctc caccatccta gctctcaagg 900
agggtgatga agtctggtta cagattttct actcggagca gaatggactc ttctacgacc 960
cttattggac cgacagcctg ttcaccggct tcctcatcta cgctgatcaa ggagacccca 1020
atgaggtata gacaagctgg ggttgagccg tccaggcagg gactaagatt ccgcaagggt 1080
gctgatagaa gaggatctct gaactga 1107

<210> SEQ ID NO 218
<211> LENGTH: 1001
<212> TYPE: DNA
<213> ORGANISM: Rat

-continued

<400> SEQUENCE: 218

```
ggagcaagaa gcaacccgaa gctaggagtc tgtcagcgag ggcaggggct gcctggttgg     60
ggtaggagtg ggagcagggc cagcaggagg gtctgaggaa gccattcaaa gcgagcagct    120
gggagagctg gggagccggg aagggcctac agactacaag agaggatcct ggcgtctggg    180
cctcctgggt catcaccatg aggccacttc ttgccctgct gcttctgggt ctggcatcag    240
gctctcctcc tctggacgac aacaagatcc ccagcctgtg tcccgggcag cccggcctcc    300
caggcacacc aggccaccac ggcagccaag gcctgcctgg ccgtgacggc cgtgatggcc    360
gcgacggtgc acccggagct ccgggagaga aaggcgaggg cgggagaccg ggactacctg    420
ggccacgtgg ggagcccggg ccgcgtggag aggcaggacc tgtgggggct atcgggcctg    480
cgggggagtg ctcggtgccc ccacgatcag ccttcagtgc caagcgatca gagagccggg    540
tacctccgcc agccgacaca cccctaccct tcgaccgtgt gctgctcaat gagcagggac    600
attacgatgc cactaccggc aagttcacct gccaagtgcc tggtgtctac tactttgctg    660
tccatgccac tgtctaccgg gccagcctac agtttgatct tgtcaaaaat ggccaatcca    720
tagcttcttt cttccagttt tttggggggt ggccaaagcc agcctcgctc tcaggggggtg   780
cgatggtgag gctagaacct gaggaccagg tatgggttca ggtgggtgtg ggtgattaca    840
ttggcatcta tgccagcatc aaaacagaca gtaccttctc tggatttctc gtctattctg    900
actggcacag ctccccagtc ttcgcttaaa atacagtgaa cccggagctg gcacttgctc    960
ctagtggagg gtgtgacatt ggtccagcgc gcataccagg a                       1001
```

<210> SEQ ID NO 219
<211> LENGTH: 2206
<212> TYPE: DNA
<213> ORGANISM: Rat

<400> SEQUENCE: 219

```
gtttcgtctt aacgccctct ctgcgttggc agaactggcc gtgggctccc gctggtacca     60
tggaacatct cagcccacac agactaagcg gagactgatg ttggtggcgt tcctcggagc    120
atccgcggtg actgcaagta ccggtctcct gtggaagaag gctcacgcag aatctccacc    180
gagcgtcaac agcaagaaga ctgacgctgg agataagggg aagagcaagg acacccggga    240
agtgtccagc catgaaggaa gcgctgcaga cactgcggcc gagccttacc cagaggagaa    300
gaagaagaag cgttctggat tcagagacag aaaagtaatg gagtatgaga ataggatccg    360
agcctactcc acaccagaca aatcttccg gtattttgcc accttgaaag taatcaacga     420
acctggtgaa actgaagtgt tcatgacccc acaggacttt gtgcgctcca taacacccaa    480
tgagaagcag ccagaacact tgggcctgga tcagtacata ataaagcgct tcgatggaaa    540
gaaaattgcc caggaacgag aaaagtttgc tgacgaaggc agcatcttct ataccccttgg   600
agagtgtgga ctcatctcct tctctgacta catcttcctc acaacggtgc tctccactcc    660
tcagagaaat ttcgaaattg ccttcaagat gtttgacttg aatggagatg gagaagtaga    720
catggaggag tttgagcagg ttcaaagcat cattcgctcc cagaccagca tgggcatgcg    780
tcacagagat cgtccaacta ctgggaacac cctcaagtct ggcttatgtt cggccctcac    840
gacctacttt tttggagctg atctcaaagg gaaactgacc attaaaaact tcctggaatt    900
tcagcgtaaa ctgcagcatg acgttctaaa gctggagttt gaacgccatg acccggtaga    960
cgggagaatc tctgagaggc agttcggtgg catgctgctg gcctacagtg gagtgcagtc   1020
```

-continued

```
caagaagctg accgccatgc agaggcagct gaagaagcac ttcaaggatg ggaagggcct   1080

gactttccag gaggtggaga acttcttcac tttcctgaag aacattaatg acgtggacac   1140

tgcgttaagc ttttaccaca tggctggagc atccctcgat aaagtgacca tgcagcaagt   1200

ggccaggaca gtggcgaaag tcgagctgtc ggaccacgtg tgtgacgtgg tgtttgcact   1260

ctttgactgc gacggcaatg gggagctgag caataaggag tttgtctcca tcatgaagca   1320

gcggctgatg agaggcctgg agaagcccaa ggacatgggc tttacccgtc tcatgcaggc   1380

catgtggaaa tgtgcccaag aaaccgcctg ggactttgct ctacccaaat agtaccccac   1440

ctcctgcacc ttagcacccc gcaatcctgg agtggccttc atgctgctga tgcttctggg   1500

agtagtgccc acatccccat ctttctggaa gtgacctctg gcctcagctg gctgacctct   1560

ccatcctccc ctgacccagt cagtgttccg ctaggctctg aatctgcagt cagatcaaag   1620

gtctaagaca ggaacaagtc ttcaaagcag agaccatagc tcccttaacc agtgccccgt   1680

gggtaaatgc ggggagccct cccacactgg cagccccagg aggcatctct gcagtctctc   1740

actgtggatt taagtaacac aaacgtccct gccatcttcc tcccactgtt ttaaagctgc   1800

aagtttggaa atactctggc aggcaaaggg aagtctgtga tgaacggtaa tgcagatgac   1860

cctggtaccc tgatctggca gggcacctgg tcaggggaag ggtctgcgtc agacaccagc   1920

ggcaccagga aggctctttg ccaccagcac agctcccgat tcaaagtcgc tgctttgagc   1980

ggctctccag aacctcctgc tcttttttttt ttcctcccgg ctccctgcga tgcctcctct   2040

gggactctgc ttcactagag ccagggctga gcccctgttc cttgtgtctt gtcccctctc   2100

tatagacctg cagagcgcag ctcagagcct atctgccctc tgtctaatac actcgtaaat   2160

atcactttaa ttatagcact ttgcaggaaa taccccaaaa aaaaaa                  2206
```

<210> SEQ ID NO 220
<211> LENGTH: 376
<212> TYPE: DNA
<213> ORGANISM: Human

<400> SEQUENCE: 220

```
atcggcatca ccttctacaa caagtggctg acaaagagct tccatttccc cctcttcatg     60

acgatgctgc acctggccgt gatcttcctc ttctccgccc tgtccagggc gctggttcag    120

tgctccagcc acagggcccg tgtggtgctg agctgggccg actacctcag aagagtggct    180

cccacagctc tggcgacggc gcttgacgtg ggcttgtcca actggagctt cctgtatgtc    240

accgtctcgc tgtgagtact ggccatgccc tgctgcctcc cttcaggctg aagctgtctg    300

tctgtccagc ggggtgtctg cacacccggc tgctaggcca gccactccac cactctggga    360

ccagcccttg ctctct                                                     376
```

<210> SEQ ID NO 221
<211> LENGTH: 433
<212> TYPE: DNA
<213> ORGANISM: Human

<400> SEQUENCE: 221

```
agcttcttct cagagcaaac agtaagcaac agaaaatata catttgatga aacattcttt     60

gcattagaga aacatgaaaa taaatataat tcaaggaagt ataatgattc tctaatatgt    120

ctttctcaga cctgtactag tttaccggtt caagaagctc tcatcacatt tttcacttgt    180

attttacata ttgctattcg ggtaattcaa ataaaatgca ggtcttgtaa aagaataaaa    240

acattgacaa gtatgcatgt gccagggacc aaattagagg gttctttggt gcagttagtc    300
```

-continued caaattctca gatttgaagg ataatatgta ccaataaaaa aaaaatctgc tgctagacat 360
ttacagcagt gctctgtctt gcttcacatt agaaatcgaa aacagctgtt ctcaacaagc 420
caattttatt ttt 433

<210> SEQ ID NO 222
<211> LENGTH: 530
<212> TYPE: DNA
<213> ORGANISM: Human

<400> SEQUENCE: 222
gtttcaagcc tgtaatcata gcgttgggaa tgctaaggca gaatcccata gttgagggca 60
gcctgagtta gatagagaaa cactgccaaa ctcaaaaata ttcagtctga ggatgactta 120
atattgactt tgtaagaagt atactcttgg aaataggtgc taagcaaata gtgtttggga 180
cctctaagct tatgtgaccg gagttttact cttttgtcct taattttctc attttctttt 240
gactggtgaa aagttgcagt gtaagttaga atttggctcg aagcctgctt ccttagttga 300
atgccctgtg ttttgttttt tttttttttt ttgagcactt caaaaagtat gatatatagt 360
tccttaatgt taggactcta tataccttca gaggcatgtg tgttgggatt gaaattcaaa 420
ttctgatcat gtgaaaatgg cactagttgt tagaggaagt ctctccttca atctcagcat 480
ttacttacat actaactgaa gagaaaatca cgtctcctag ttctttgtaa 530

<210> SEQ ID NO 223
<211> LENGTH: 550
<212> TYPE: DNA
<213> ORGANISM: Mouse

<400> SEQUENCE: 223
aagctgctgg ttttaaatat ttactttccc aggaggtggg tttcttcagg tgtttgttta 60
aagagggctg tcacaggtga atggtttggg gaacccttct tggcagagtt ttagctgcct 120
tactgaacat tgtcccaaca gaaagttcct atcgttctcc ttccttcttg gcaggcttca 180
ggttttgctg cagcccctgg agccaacatt ttggttgtgg gaggctgacc tcttgcctgc 240
ctccttgtgt ggacagagtg gtgaagacgt attcctcacc tccttgcctt tcagtaaatg 300
gccacgatgt gactatttgt tgaggtttcc agcctcttcc aagaccttgc caggctgagt 360
ggggcctgag agcttgcagg cacttaaagc ttcctggcaa aggggccggc cacaggcaga 420
gggaaaggaa caggtcagag gcgttgctct ggcagaggcg gctcgggctg cccatcgtgt 480
ttctgcgggg ttgaggtggg ctcccttctt tgtagatgcc tttcctctcg taataacaac 540
tccttgcccc 550

<210> SEQ ID NO 224
<211> LENGTH: 470
<212> TYPE: DNA
<213> ORGANISM: Mouse

<400> SEQUENCE: 224
aggcctgttc accaccactc ctgttctccg ctaagctttt ctttggcttt tggtggtttg 60
ttttttgtta ctgttattca acagttcagc ctaattatac catggcagag aacgagcctt 120
ttatgtttgg gctgtgccac tgaactgttt actgtagcgt gtgggtgaag gtggaactaa 180
tgggctcagt ccttacctcc tgcttctgtg taggaggctc agccgaggct tggaactggc 240
taccttcagc cagcagtctt ttcccctgct gtatagcaac ccttctaccc ttgcttttct 300

-continued

```
tgcttcctca tcttcactca accttaagca gagttcaaag actcaacttc aacattggtc    360

atctgggtgt gtatttatat gtgaataatg atatcagatc cagagtaaca cctttgctgt    420

cttcttagga tgggtgagtg cacggggctc gggctctttg ctgaatactt               470


<210> SEQ ID NO 225
<211> LENGTH: 1752
<212> TYPE: DNA
<213> ORGANISM: Rat

<400> SEQUENCE: 225

ggcacgagct gacatgaagc cccctagacc cagagattgg ttcctgctgt gacatgccta     60

ccatgtggcc acttcttcat gtcctctggc ttgctctggt ctgtggctct gttcacacca    120

ccctgtcaaa gtcagatgcc aaaaaagctg cctcaaagac gctgctggaa aagactcagt    180

tttcggataa acctgtccaa gaccggggtc tggtggtgac ggacatcaaa gctgaggatg    240

tggttcttga acatcgtagc tactgctcag caagggctcg ggagagaaac tttgctggag    300

aggtcctagg ctatgtcact ccatggaaca gccatggcta tgatgttgcc aaggtctttg    360

ggagcaagtt cacacagatc tcaccagtct ggttgcagct gaagagacgt ggtcgggaga    420

tgtttgaaat cacaggcctc catgatgtgg accaagggtg gatgcgagct gtcaagaagc    480

atgccaaagg cgtgcgcata gtgcctcggc ttctgtttga agactggact tacgatgatt    540

tccgaagcgt cctagacagt gaggatgaga tagaagagct cagcaagact gtggtacagg    600

tggcaaagaa ccagcatttt gacggctttg tggtggaggt ctggagccag ttgctgagcc    660

agaaacatgt aggcctcatt cacatgctta ctcacttggc tgaggcgctg caccaggcca    720

ggctgctggt cattctggtc atcccacctg ctgtcacccc tgggactgac cagctgggca    780

tgtttacaca caaggagttt gagcagctgg cccccatact agatggcttc agcctcatga    840

catacgacta ctccacatca cagcagcctg gccctaatgc tccattgtca tggatccgag    900

cctgtgttca ggtcctagac cccaagtcac agtggcgtag caagatcctc ctgggattga    960

acttctatgg catggattat gcagcctcca aggatgcccg tgagcctgtc attggagcca   1020

gggcagtttt gaaggtggct ctgccattgg ctgtctcatc ccagcagatc tggacattgg   1080

gaagaggagg gtccaccagt gccctactcc tggcaggctt ggggctggcc tcagagccct   1140

gtacaaagag cgaggaggtt ccaaagaaga gcctcttaga tacagtttgg cactggcagg   1200

gagagccagg agcactgtgt agaggtcgtc ttcacacctg gatcctagtg agcgcggtcc   1260

cgcaggcctg cacatgcctg tttcagtgat ggcctcacga ggcagcaccg gctctagctg   1320

cactgctttc tttgattagc tttggccatg ggagacacag gtagcagcat agcgggtcag   1380

gaacctcttg agcagatcca accaaaggct ttttgtcact tgccagctct gcatggtcag   1440

cctgtgacac cgtctcactc aaggccttct ggagttggcc ctcagctcag atgtcatgtg   1500

agggataccc taaggagatg atggggctcc ctcttgcctg agcttgcagg attggatctt   1560

gggcagatca gggcagtgga aacgtcagac cttctacccg tacatacaga cgctgaagga   1620

ccacaggccc cgtgtggtat gggacagcca ggctgcggaa cacttctttg agtacaagaa   1680

gaatcgcggc gggaggcacg ttgtcttcta cccaacgctg aagtctctgc aggtgcggct   1740

ggagctagcc ag                                                       1752


<210> SEQ ID NO 226
<211> LENGTH: 2165
<212> TYPE: DNA
<213> ORGANISM: Mouse
```

-continued

<400> SEQUENCE: 226

```
ggcacgagcc tgctgccctc ttgcagacag gaaagacatg gtctctgcgc ccggatccta     60
cagaagctca tggggagccc cagactggca gccttgctcc tgtctctccc gctactgctc    120
atcggcctcg ctgtgtctgc tcgggttgcc tgcccctgcc tgcggagttg gaccagccac    180
tgtctcctgg cctaccgtgt ggataaacgt tttgctggcc ttcagtgggg ctggttccct    240
ctcttggtga ggaaatctaa aagtcctcct aaatttgaag actattggag gcacaggaca    300
ccagcatcct tccagaggaa gctgctaggc agcccttccc tgtctgagga aagccatcga    360
atttccatcc cctcctcagc catctcccac agaggccaac gcaccaaaag ggcccagcct    420
tcagctgcag aaggaagaga acatctccct gaagcagggt cacaaaagtg tggaggacct    480
gaattctcct ttgatttgct gcccgaggtg caggctgttc gggtgactat tcctgcaggc    540
cccaaggcca gtgtgcgcct ttgttatcag tgggcactgg aatgtgaaga cttgagtagc    600
ccttttgata cccagaaaat tgtgtctgga ggccacactg tagacctgcc ttatgaattc    660
cttctgccct gcatgtgcat agaggcctcc tacctgcaag aggacactgt gaggcgcaaa    720
aagtgtccct tccagagctg gcctgaagct tatggctcag acttctggca gtcaatacgc    780
ttcactgact acagccagca caatcagatg gtcatggctc tgacactccg ctgcccactg    840
aaactggagg cctccctctg ctggaggcag gacccactca caccctgcga aacccttccc    900
aacgccacag cacaggagtc agaaggatgg tatatcctgg agaatgtgga cttgcacccc    960
cagctctgct ttaagttctc atttgaaaac agcagccacg ttgaatgtcc ccaccagagt   1020
ggctctctcc catcctggac tgtgagcatg gatacccagg cccagcagct gacgcttcac   1080
ttttcttcga ggacatatgc caccttcagt gctgcctgga gtgacccagg tttggggccg   1140
gataccccca tgcctcctgt gtacagcatc agccagaccc agggctcagt cccagtgacg   1200
ctagacctca tcatcccctt cctgaggcag gagaattgca tcctggtgtg gaggtcagat   1260
gtccattttg cctggaagca cgtcttgtgt cctgatgacg cccettaccc tactcagctg   1320
ttgctccggt ccctaggctc cggtcgaaca aggccagttt tactcctaca tgcagcggac   1380
tcagaggcac agcgacgcct ggtgggagct ttggccgaac tgctgcggac ggcgctggga   1440
ggtggacgcg acgtgatcgt ggatctctgg gaagggacgc acgtagcacg cattggacca   1500
ctgccgtggc tttgggcagc gcgggagcgc gtggcgcggg agcagggcac agtgctgctc   1560
ctgtggaact gtgcgggtcc cagcaccgcc tgcagcggtg acccgcaggc tgcgtccctt   1620
cgcaccttgt tgtgcgctgc tccacgtccg ctgctgctcg cctacttcag tcgcctctgc   1680
gccaaaggtg acatcccccg gccgctgcgc gctctgccac gctaccgcct gcttcgtgac   1740
ctgccgcgcc tgctgagagc actggatgct cagcctgcca ccctagcctc cagctggagt   1800
caccttgggg ctaagcggtg cttgaaaaac cgtctggagc agtgtcacct gctggaactt   1860
gaggctgcca aagatgacta ccaaggctca accaatagtc cctgtggttt cagctgtctg   1920
tagcctcagc ctgtgtagca acagcaggaa ctccagaatg aggcctcaca catgtactct   1980
ttgggggtgc ttcttgtccc ccaaaccgta agactcacct taagtcccac acttgaccaa   2040
cctccctcac atttgctccc tcttagagtt cctgagagga acttgggctt tcctgatagg   2100
tcctcagccc tttctgagaa ggagggacga tttttccatt tcttttcaaa actgaaaaaa   2160
aaaaa                                                               2165
```

<210> SEQ ID NO 227

-continued

<211> LENGTH: 1348
<212> TYPE: DNA
<213> ORGANISM: Mouse
<220> FEATURE:
<221> NAME/KEY: unsure
<222> LOCATION: (644)...(644)

<400> SEQUENCE: 227
caaagaattc ggcacgagac cggcctcact atgtctgcca ttttcaattt tcagagtctg 60
ttgactgtaa tcttgctgct tatatgtaca tgtgcttata tccgatccct ggcacccagc 120
atcctggaca gaaataaaac tggactattg ggaatatttt ggaagtgtgc ccgaattggg 180
gaacgcaaga gtccttatgt cgccatatgc tgtatagtga tggccttcag catcctcttc 240
atacagtagc tttggaaact accagcatgt gcttgctatc agactgtaaa caaggacttg 300
cctccagaaa ataatgggaa gaatggttaa gccatttgtc tctgaacatg gaatgagata 360
aacttcaaga tgctgttctc tatttttatg ctattggacc aatgagctga atgaataatt 420
aagatgtaac agttcaatac acaggaatgt gattgtatcc atcaacctca gttctctcac 480
tccagtatta cattctgcaa atgtcattct gttgtgtcag gactgctttt cataaggttc 540
ttcgggcacg aagtagaaac ccagtggcaa attccaaggc tcctttgact agggcttcaa 600
aataatgtct tcacagaatg gtacctctag cgactgtcct attnttattg agaaaaaaac 660
ttgttctatt tttgttgttg ttactgttct tatggattgc attcatattt aaaccctttg 720
gattgctaac cagagtacct ctattcttgg caaattccgc agtttattac aggtgtttaa 780
agtattttaa acaaaactct gaatttcttt agttagccta agagttggct tctagtcaca 840
aagatacagc tgccacactg tgacgaagag caccttagaa agaaaagcag caagtgagcg 900
gtgagcaagt aagcaccgtg cagtcttcgt gcaagtaagc accgtgcagt cttcgttctc 960
tgtagtcttg tcttccaaat agaacgtcca tcgtagttac ccaaaggtgg tatttgtggt 1020
gttcttaatg cagtgcttta agtctagtgt atgttctgtc agcttgaact ggaatctctc 1080
ttgtaacttt gtaggttata aacatatctc atatctgctt tagtctgggt actatgctct 1140
aagtacattt cagctttgac acagaatgtg aatagacgaa tatcaaagga tacttacaag 1200
tttgtatcca acatttcttc aggttcagct gaaaatcagt tactgtttca aaacaaagag 1260
gaattaaatc ctagctgaaa actatacata gcatttatta attaattact gggtttaact 1320
gctcttttta aaagtttgaa aaaaaaaa 1348

<210> SEQ ID NO 228
<211> LENGTH: 2296
<212> TYPE: DNA
<213> ORGANISM: Mouse
<220> FEATURE:
<221> NAME/KEY: unsure
<222> LOCATION: (2255)...(2255)

<400> SEQUENCE: 228
ctggagctcg cgcgcctgca ggtcgacact agtggatcca aagcttaaaa gagactccac 60
ccactccagt agaccgggga ctaaaacaga aattctgaga aagcagcaag aagcagaaga 120
aatagctatt tcacagcagt aacagaagct acctgctata ataaagacct caacactgct 180
gaccatgatc agcccagcct ggagcctctt cctcatcggg actaaaattg ggctgttctt 240
ccaagtggca cctctgtcag ttgtggctaa atcctgtcca tctgtatgtc gctgtgacgc 300
aggcttcatt tactgtaacg atcgctctct gacatccatt ccagtgggaa ttccggagga 360
tgctacaaca ctctaccttc agaacaacca aataaacaat gttgggattc cttccgattt 420

-continued

```
gaagaacttg ctgaaagtac aaagaatata cctataccac aacagtttag atgaattccc    480
taccaacctt ccaaagtatg tcaaagagtt acatttgcaa gagaataaca taaggactat    540
cacctatgat tcactttcga aaattccgta tctggaagag ttacacttgg atgataactc    600
agtctcggct gttagcatcg aagagggagc atttcgagac agtaactatc tgcggctgct    660
ttttctgtcc cgtaaccacc ttagcacaat cccgggggc ttgcccagga ctattgagga    720
attacgcctg gatgacaatc gcatatcaac gatctcttcc ccatcacttc atggtctcac    780
aagcctgaaa cgcctggttt tagatggaaa cttgttgaac aaccatggtt tgggtgacaa    840
agttttcttc aacttagtaa acttaacaga gctgtccctg gtgaggaatt ccttgacagc    900
agcgccagtg aaccttcccg gcacaagcct gaggaagctt taccttcaag acaaccatat    960
caaccgggta cccccaaatg ctttttctta tttaaggcag ctgtatcgac tcgatatgtc   1020
taataataac ctaagcaatt tacctcaggg tatctttgat gatttggaca atataaccca   1080
actgattctt cgcaacaatc cttggtattg tggatgcaag atgaaatggg tacgagactg   1140
gttacagtcg ctaccggtga aggtcaatgt gcgtgggctc atgtgccaag ccccagaaaa   1200
ggtccgtgga atggctatca aggacctcag tgcagaactg tttgattgta aagacagtgg   1260
gattgtgagc accattcaga taaccactgc aatacccaac acagcatatc ctgctcaagg   1320
acagtggcca gctcctgtga ccaaacaacc agatattaaa aaccccaagc tcattaagga   1380
tcagcgaact acaggcagcc cctcacggaa aacaatttta attactgtga aatctgtcac   1440
ccctgacaca atccacatat cctggagact tgctctgcct atgactgctc tgcgactcag   1500
ctggcttaaa ctgggccata gcccagcctt tggatctata acagaaacaa tcgtaacagg   1560
agaacgcagt gaatacttgg tcaccgccct agaacctgaa tcaccctata gagtatgcat   1620
ggttcccatg gaaaccagta acctttacct gtttgatgaa acacctgttt gtattgagac   1680
ccaaactgcc cctcttcgaa tgtacaaccc cacaaccacc ctcaatcgag agcaagagaa   1740
agaaccttac aaaaatccaa atttaccttt ggctgccatc attggtgggg ctgtggccct   1800
ggtaagcatc gccctccttg ctttggtgtg ttggtatgtg cataggaacg ggtcactgtt   1860
ttcacggaac tgtgcgtaca gcaaagggcg gaggagaaag gatgactatg cagaagccgg   1920
tactaagaaa gacaactcca tcctggaaat cagggaaact tctttccaga tgctaccgat   1980
aagcaatgaa cccatctcca aggaggagtt tgtaatacac accatatttc ctccgaatgg   2040
gatgaatctg tacaagaaca acctcagtga gagcagtagt aaccggagct acagagacag   2100
tggcatccca gactcggacc actcacactc atgatgcaag gaggtcccac accagactgt   2160
tccgggtttt tttttaaaaa acctaagaaa ggtgatggta ggaactctgt tctactgcaa   2220
aacactggaa aagagactga gagaagcaat gtacntgtac atttgccata taatttatat   2280
ttaagaactt tttatt                                                   2296
```

<210> SEQ ID NO 229
<211> LENGTH: 1704
<212> TYPE: DNA
<213> ORGANISM: Rat
<220> FEATURE:
<221> NAME/KEY: unsure
<222> LOCATION: (1252)...(1252)
<221> NAME/KEY: unsure
<222> LOCATION: (1441)...(1441)

<400> SEQUENCE: 229

```
ccaaagaatt cggcacgagg cggctcggga tggcggcccc catggaccgg acccatggtg     60
```

-continued gccgggcagc ccgggcgctg cggcgggctc tggcgctggc ctcgctggcc gggctattgc 120
tgagcggcct ggcgggtgct ctccccaccc tcgggcccgg ctggcggcgc caaaaccccg 180
agccgccggc ctcccgcacc cgctcgctgc tgctggacgc cgcttcgggc cagctgcgcc 240
tggagtacgg cttccacccc gatgcggtgg cctgggctaa cctcaccaac gccatccgcg 300
agactgggtg ggcctatctg gacctgggca caaatggcag ctacaagtgg atcccccggg 360
ctgcaggcct atgcagctgg tgtggtggag gcctctgtgt ccgaggagct catctacatg 420
cactggatga acacggtggt caattactgc ggccccttcg agtacgaagt cggctactgt 480
gagaagctca agagcttcct ggaggccaac ctggagtgga tgcagaggga aatggagctt 540
agcccggact cgccatactg gcaccaggtg cggctgaccc tcgggctgca gctgaagagg 600
cctggaggac agctatgaag gccgtttaac cttcccaact gggaggttca acatcaaacc 660
cttggggttc ctcctgctgc aggaatctct ggagatctgg aagacctaga gacagccctg 720
aataagacca acgaccaagc gcttccgtgg gctccggttc gtgctctgcc ctcatcaagc 780
tgctgcccgg cagccatgat ctcctggtgg ctcacaacac ttggaactcc taccagaaca 840
tgttacgcat catcatggag tcccccgggc tgcagttccg ggaggggccg caagaaggag 900
taccccctga ttgccggcaa caacttgatt ttttcgtctt acccgggcac catcttctcc 960
ggtgatgact tctacatcct gggcagtggg ctggtcaccc tggagaccac caatcggcaa 1020
caaagaaccc aagcgctgtg gaagtacgtg caaccccagg gctgtgtgct ggagtggatt 1080
cgaaacattg tggccaaccc gcctggcctt ggatggggcc acctgggcag atgtcttcag 1140
gcggttcaat agtggcacgt ataataacca gtggatgatt gtggactaca aggcattcat 1200
ccccaatggg cccagccctg gaagccgggt gctcaccatc ctagaacaga tnccgggcat 1260
ggtggtggtg gcatcccccg ggctgcagga attcgatatc aagcttatcg atacacgtcg 1320
aaccctcgag ccaagatctt ccagagggac cagtcactag tagaggacgt agacaccatg 1380
gtccggctca tgaggtacaa tgacttcctt catgaccctc tgtcgttgtg tgaggcctgc 1440
agcccgaagc ccaacgcaga gaacgccatc tctgccccgc tctgatctca accctgctaa 1500
ntggctccta cccatttcag gccctgcgtc agcgcgccca tggcggcatt gatgtgaagg 1560
tgaccagcgt tgcactggct aagtacatga gcatgctggc agccagtggc cccacgtggg 1620
accagttgcc accgttccag tggagtaaat caccattcca caacatgctg cacatgggcc 1680
aagcctgatc tttggatgtt ctca 1704

<210> SEQ ID NO 230
<211> LENGTH: 2004
<212> TYPE: DNA
<213> ORGANISM: Rat

<400> SEQUENCE: 230
ctcgaggtcg acggtatcga taagcttgat taattaaccc tcactaaagg gaacaaaagc 60
tggagctcgc gsgctgcagg tcgacactag tggatccaaa gaattcggca cgaggcggaa 120
gcagccgcag gtatggcggc tgccatgccg ctgggtttat cgttgctgtt gctggtgcta 180
gtggggcagg gctgctgtgg ccgcgtggag ggcccacgcg acagcctgcg agaggaactc 240
gttatcactc cgctgccttc cggcgacgtg gccgccacat tccagttccg cacgcgttgg 300
gattccgatc tgcagcggga aggagtgtcc cattacaggc tcttccctaa agccctggga 360
cagttgatct ccaagtactc tctgcgggag ctacacctgt cattcacgca aggcttttgg 420

-continued

```
aggacccgat actgggggcc acccttcctg caggctccat caggtgcaga gctctgggtc    480

tggttccaag acactgtcac agatgtggat aagtcttgga aggagctcag taatgtcctc    540

tcagggatct tctgcgcgtc cctcaacttc atcgactcca ccaataccgt cactcccaca    600

gcctccttca aacctctggg gctggccaat gacactgacc actacttcct gcgctatgct    660

gtgctgcccc gggaggtcgt ctgcaccgag aatctcacgc cgtggaagaa gctcctgccc    720

tgtagctcca aggcagggct gtccgtgcta ctgaaagcag atcgattgtt ccacaccagt    780

taccactccc aggcagtgca tatccggcca atctgcagaa atgctcactg caccagtatc    840

tcctgggagc tgaggcagac cctttcagtt gtctttgatg ccttcatcac cggacagggg    900

aagaaagact ggtctctctt ccgcatgttc tcccggactc tcacagaggc ctgtccattg    960

gcatctcaga gcctagttta tgtggacatc acaggctaca gccaggacaa cgaaacactg   1020

gaggtgagcc ctcccccaac ttccacatac caggatgtca ttttgggcac caggaagacc   1080

tatgccgtct atgacttgtt tgacacagcc atgatcaata actcccgaaa cctcaacatc   1140

cagctcaaat ggaagagacc cccagataat gaagccctgc ccgtgccctt cctgcatgca   1200

cagcggtacg tgagtggtta tgggctacag aagggcgagc tgagcaccct gttgtacaac   1260

tctcatcctt accgggcctt ccctgtgctg ctactggatg ctgtgccctg gtacctgcgg   1320

ctgtatgtgc acaccctcac catcacctcc aagggcaagg ataataaacc aagttatatc   1380

cactaccagc ctgcccagga ccggcagcag ccccacctcc tggagatgct cattcagctg   1440

ccggccaact ccgtcaccaa ggtctccatc cagtttgaac gagccctgct caagtggaca   1500

gaatacacgc cagaccccaa ccatggcttc tatgtcagcc catctgtcct cagtgccctt   1560

gtgcccagca tggtggcagc caaaccagtg gactgggaag agagccctct cttcaacacc   1620

ttgttcccgg tgtctgatgg ctccagctac tttgtccgac tctacacaga gcccttgcta   1680

gtgaacctgc ccacccccga cttcagcatg ccctacaatg tgatctgcct tacatgcact   1740

gtggtggccg tgtgctatgg ctccttctac aatctcctca cccgaacctt ccacattgaa   1800

gagcccaaat ccggcggcct ggccaagcgg ctggctaacc tcatccggcg tgctcgtggt   1860

gttcccccctc tctaagattc cctttcttca gcaactacag cttcatactc acctgcccca   1920

ggggagcagt ggcagggctt tttctgccat gccctctttc cccagagtta gcttctgaag   1980

ctaactcccc ctggatctgg tctg                                          2004
```

<210> SEQ ID NO 231
<211> LENGTH: 1397
<212> TYPE: DNA
<213> ORGANISM: Rat

<400> SEQUENCE: 231

```
cgggcccccc ctcgaggtcg acggtatcga taagcttgat taattaaccc tcactaaagg     60

gaacaaaagc tggagctcgc gcgcctgcag gtcgacacta gtggatccaa agaattcggc    120

acgagcggca cgagcggccc cgaagggggc tgcacgggcg acttggcggc gatggctcga    180

gctccggcgg cgacgacggt ggccggaggc ggcggctcct cctccttctc ctcctgggct    240

tgggcccggc ggtgatccga gctggcggcc gcggcccccc gatgagactg ttggcgggct    300

ggctgtgcct gagcctggcg tccgtgtggc tggcgcggag gatgtggacg ctgcggagcc    360

cgctctcccg ctctctgtac gtgaacatga ctagcggccc tggcgggcca gcggcggcca    420

cgggcggcgg gaaggacacg caccagtggt atgtgtgcaa cagagagaaa ttatgcgaat    480

cacttcagtc tgtctttgtt cagagttatc ttgaccaagg aacacagatc ttcttaaaca    540
```

-continued

```
acagcattga gaaatctggc tggctattta tccaactcta tcattctttt gtatcatctg    600

tttttagcct gtttatgtct agaacatcta ttaacgggtt gctaggaaga ggctccatgt    660

ttgtgttctc accagatcag tttcagagac tgcttaaaat taatccggac tggaaaaccc    720

atagacttct tgatttaggt gctggagatg gagaagtcac gaaaatcatg agccctcatt    780

ttgaagaaat ttatgccact gaactttctg aaacaatgat ctggcagctc cagaagaaga    840

aatacagagt gcttggtata aatgaatggc agaatacagg gttccagtat gatgtcatca    900

gctgcttaaa tctgctggat cgctgtgatc agcctctgac attgttaaaa gatatcagaa    960

gtgtcttgga gcccacccaa ggcagggtca tcctggcctt ggttttgccc tttcatccct   1020

atgtggaaaa cgtaggtggc aagtgggaga aaccatcaga aattctggaa atcaagggac   1080

agaattggga agagcaagtg aatagcctgc ctgaggtgtt caggaaagct ggctttgtca   1140

tcgaagcttt cactagactg ccatacctgt gtgaaggtga catgtacaat gactactatg   1200

ttctggacga cgctgtcttt gttctcagac cagtgtaaac atgtggaggc ccaagtcttc   1260

agagtcaccc ctggaatctg ccctccagaa gaggaggtgc atccagtgat gtgagggggga   1320

cctctgggga ctgtcattct cagtatcatg taggaattta aaaagccaaa atactaattc   1380

tttctttgta gtgtgta                                                 1397
```

<210> SEQ ID NO 232
<211> LENGTH: 861
<212> TYPE: DNA
<213> ORGANISM: Rat

<400> SEQUENCE: 232

```
gaattcggca cgagaggaga gaaagagaag tgtgcacaaa gaaacttgta ttattattaa     60

ttagcaccta gcttgtttgt gtctgataca ccaccaagta gtaattgttg aaaaaacgaa    120

gaagaaaaaa aaaaaacaaa aaaaccaaac agtgggtact caaataagat aggagaaaaa    180

tgagagaaca gacccagttc tcgacccttg cttctcaagg tcctcccacc aggctgccaa    240

agcaagatgg tgttgctctg atccagtcag tattcttttg actttttttt ttaatctcca    300

ggttttggtt caggctccca tattcatacc ctggctcatt tagctttccc tcatgttgtg    360

ggttcttctg tccctcaccc ccttactctc cccactgata ttcttcccag tcaagactgt    420

ggctctggaa gaaatatcca ccatttgcag agctgatgtt ctgtagatcg taatgttgaa    480

gcgctgggtg tcctggttgg cagaatcact cctgtattac tctggtacat aggtgtctcc    540

tgatagactc cctggcctta gtcatggggt gttttctaga ggcagactaa gacaggagtc    600

aaaaaagatt tagaggaagg agctgaggaa agaaagacag ttgtgggagg aaaatcaagt    660

tctactcagg atcccgagtg tttctgtaga tgtagattgg aatgtgtcca taacagagag    720

gccagtgaga gacatcccca aggacctgcc aggctttcct tcgctccagg aagacgcacc    780

atcactcaaa aggggtttcc tagaaagaaa gacaagtgac ttaaaaaatc tgccagtggg    840

ttcttgaagt catcgaacct a                                             861
```

<210> SEQ ID NO 233
<211> LENGTH: 445
<212> TYPE: DNA
<213> ORGANISM: Mouse

<400> SEQUENCE: 233

```
ggaagtagaa gggcccggcg ttttcatggc ggcgtcctgg gggcaggtgc ttgctctggt     60
```

-continued gctggtggcc gcactgtggg gtggcacgca gccgctgctg aagcgagcct cctccggcct 120
ggagcaagtg cgtgagcgga cgtgggcctg gcagctgttg caggagataa aggctctctt 180
cgggaatact gaggtgcgtc tagctctcac ggacgagccc ctgaaaattt caccataggt 240
cggccgtatt cccagcccat ctcttactca ctagaagttc ctggaagagt catttatcct 300
cttacctgat gccctttctc ctcaatcaga gtggatccct tctctactac ttgactttgg 360
catcaacaga tctgacgtta gctgtgccca tctgcaactc tctggccatc gtctttacac 420
tgattgttgg gaaggtcctt ggaga 445

<210> SEQ ID NO 234
<211> LENGTH: 565
<212> TYPE: DNA
<213> ORGANISM: Human

<400> SEQUENCE: 234
cagcatcctc aatcaatcca acagcatatt cggttgcatc ttctacacac tacagctatt 60
gttaggttgc ctgcggacac gctgggcctc tgtcctgatg ctgctgagct ccctggtgtc 120
tctcgctggt tctgtctacc tggcctggat cctgttcttc gtgctctatg atttctgcat 180
tgtttgtatc accacctatg ctatcaacgt gagcctgatg tggctcagtt tccggaaggt 240
ccaagaaccc cagggcaagg ctaagaggca ctgagccctc aacccaagcc aggctgacct 300
ctgctttgct ttggcatgtg agccttgcct aagggggcat atctgggtcc ctagaaggcc 360
ctagatgtgg ggcttctaga ttacccccctc ctcctgccat acccgcacat gacaatggac 420
caaatgtgcc acacgctcgc tctttttac acccagtgcc tctgactctg tccccatggg 480
ctggtctcca aagctctttc cattgcccag ggagggaagg ttctgagcaa taaagtttct 540
tagatcaatc aaaaaaaaaa aaaaa 565

<210> SEQ ID NO 235
<211> LENGTH: 476
<212> TYPE: DNA
<213> ORGANISM: Human

<400> SEQUENCE: 235
ggtggctttc attggtgctg tccccggcat aggtccatct ctgcagaagc catttcagga 60
gtacctggag gctcaacggc agaagcttca ccacaaaagc gaaatgggca caccacaggg 120
agaaaactgg ttgtcctgga tgtttgaaaa gttggtcgtt gtcatggtgt gttacttcat 180
cctatctatc attaactcca tggcacaaag ttatgccaaa cgaatccagc agcggttgaa 240
ctcagaggag aaaactaaat aagtagagaa agttttaaac tgcagaaatt ggagtggatg 300
ggttctgcct taaattggga ggactccaag ccgggaagga aaattccctt ttccaacctg 360
tatcaatttt tacaactttt ttcctgaaag cagtttagtc catactttgc actgacatac 420
tttttccttc tgtgctaagg taaggtatcc accctcgatg caatccacct tgtttt 476

<210> SEQ ID NO 236
<211> LENGTH: 607
<212> TYPE: DNA
<213> ORGANISM: Human

<400> SEQUENCE: 236
tatgtccact aacaatatgt cggacccacg gaggccgaac aaagtgctga ggtacaagcc 60
cccgccgagc gaatgtaacc cggccttgga cgacccgacg cggactacat gaacctgctg 120
ggcatgatct tcagcatgtg cggcctcatg cttaagctga agtggtgtgc ttgggtcgct 180

-continued

```
gtctactgct ccttcatcag ctttgccaac tctcggagct cggaggacac gaagcaaatg    240
atgagtagct tcatgctgtc catctctgcc gtggtgatgt cctatctgca gaatcctcag    300
cccatgacgc cccatggtg ataccagcct agaagggtca cattttggac cctgtctatc    360
cactaggcct gggctttggc tgctaaacct gctgccttca gctgccatcc tggacttccc    420
tgaatgaggc cgtctcggtg cccccagctg gatagaggga acctggccct ttcctaggga    480
acaccctagg cttacccctc ctgcctccct tcccctgcct gctgctgggg gagatgctgt    540
ccatgtttct aggggtattc atttgctttc tcgttgaaac ctgttgttaa taaagttttt    600
cactctg                                                              607
```

<210> SEQ ID NO 237
<211> LENGTH: 513
<212> TYPE: DNA
<213> ORGANISM: Mouse

<400> SEQUENCE: 237

```
ttctccatta cctctatgcc taatattcat cagccttcat tactctctag catattcacc     60
ttgattcaac agattcaaac ttcctacagc cttctactga tgtcttacaa gctcttgcct    120
ctgtgccttt ctcatgctat tctttttgct tagattgctc tttggtccca gctcatgttc    180
atcactccct tcaaagcctt tcttccttta tatcttctga ctgagctctc cctgattgac    240
atcacctcat gcgatgacct ccctcattct gtgctgcctc agcacttatc ttttgagttt    300
gtactgtggt ccatgtactt actaatatgt tgctttgtaa ttattttcta gcactctgtg    360
ttacagtttc atatttgtat ttatttccaa aattaaattg taagctcctt gagggcagga    420
ataataactt ttacatttgt atctctgcac ccccgagtgc ctagtatagt gctgagcaca    480
tagtaggcgt ttaataaatg cttgttgaag tat                                 513
```

<210> SEQ ID NO 238
<211> LENGTH: 944
<212> TYPE: DNA
<213> ORGANISM: Rat

<400> SEQUENCE: 238

```
ggcacgaggg gccgccgagt cccgccgggt cggtgtagct cgctgccgac gctgcgacgc     60
tcgtgggtgc cgtgttcggc ttttcctgtc tacttcagtg caccgctgca gctccggcct    120
cgggtctgac gcgccacagc atggcttccg ctttggagga gttgcagaaa gacctagaag    180
aggtcaaagt gctgctggaa aagtccacta ggaaaagact acgtgatact cttacaaatg    240
aaaaatccaa gattgagacg gaactaagga acaagatgca gcagaagtca cagaagaaac    300
cagaatttga taatgaaaag ccagctgctg tggttgctcc tcttacaaca gggtacactg    360
tgaaaatcag taattatgga tgggatcagt cagataagtt tgtgaaaatc tacattactt    420
taactggagt tcatcaggtt cctgctgaga atgtgcaagt acacttcaca gagaggtcat    480
ttgatctttt ggtaaaaaac ctcaatggca agaattactc catgattgtg aacaatcttt    540
tgaaacctat ctctgtggaa agcagttcaa aaaaagtcaa gactgataca gttattatcc    600
tatgtagaaa gaaagcagaa aacacacgat gggactactt aactcaggtg gaaaaagaat    660
gcaaagagaa agaaaagcct tcctacgaca ctgaggcaga tcctagtgag ggattaatga    720
atgttctaaa gaaaatttat gaagatggag atgatgacat gaagcgaacc attaataaag    780
cgtgggtgga atcccgagag aagcaagcca gggaagacac agaattctga ggctttaaaa    840
```

-continued

```
gtcctgtggg aaccgtcatg tggagtgctc gtgtttccag tagggactgt tggtgaactg    900

cacacatgtg ttcatgtggg tatgtagttt tggacagatg acta                     944


<210> SEQ ID NO 239
<211> LENGTH: 386
<212> TYPE: DNA
<213> ORGANISM: Rat

<400> SEQUENCE: 239

ctcgtgccga attcggcacg agtggcgaga tggggaatgc ggccctggga gcggagctgg     60

gcgtgcgggt cctgctcttt gtggccttcc tggcgaccga gctgctccct cccttccagc    120

ggcggattca gcccgaggag ctgtggcttt accggaaccc gtacgtggag gcggaatact    180

tccccaccgg ccccatgttt gtcattgcct ttctcacccc actgtccctg atcttcttcg    240

ccaagtttct gaggaaagct gacgccaccg acagcaagca agcctgcctc gctgccagcc    300

ttgccctagc tctgaatggt gtctttacca acatcataaa actgatagtg ggcaggccac    360

gcccagattt cttctaccga tgcttc                                         386


<210> SEQ ID NO 240
<211> LENGTH: 228
<212> TYPE: DNA
<213> ORGANISM: Rat

<400> SEQUENCE: 240

ttccgcgggc gtcatgacgg ctgcggtgtt ctttggttgc gccttcatcg ccttcgggcc     60

cgcgctctcc ctttacgtct tcaccatcgc cactgatcct ttgcgagtca tcttcctcat    120

cgccggtgcc ttcttctggt tggtgtctct gctgctttcg tctgttttct ggttcctagt    180

gagagtcatc actgacaaca gagatggacc agtacagaat tacctgct                 228


<210> SEQ ID NO 241
<211> LENGTH: 452
<212> TYPE: DNA
<213> ORGANISM: Human

<400> SEQUENCE: 241

ttcgagcggc cgcccgggca ggttgaaact ttagaaagaa gagccgggag gatgtattgg     60

ttgttaggaa aatgtaggct accagtagaa aatgacattc tctattaata agatctgagg    120

tgcgacacac ataattgtcc caatttttaa gattgatggg gagcatgaag cattttttta    180

atgtgttggc aggccccatt aaatgcataa actgcatagg actcatgtgg tctgaatgta    240

ttttagggct ttctgggaat tgtcttgaca gagaacctca gctggacaaa gcagccttga    300

tctgagtgag ctaactgaca caatgaaact gtcaggcatg tttctgctcc tctctctggc    360

tcttttctgc tttttaacag gtgtcttcag tcagggagga caggttgact gtggtgagtc    420

caggacacca aggcctactg cactcgggaa cc                                  452


<210> SEQ ID NO 242
<211> LENGTH: 1311
<212> TYPE: DNA
<213> ORGANISM: Mouse

<400> SEQUENCE: 242

ctgcaacaag gctgttggtt cctctccaat gggctccagt gaagggctcc tgggcctggg     60

ccctgggccc aatggtcaca gtcacctgct gaagaccccca ctgggtggcc agaaacgcag    120

tttttcccac ctgctgccct cacctgagcc cagcccagag ggcagctacg tgggccagca    180
```

-continued

```
ctcccagggc ctcggcggcc actacgcgga ctcctacctg aagcggaaga ggattttcta    240

aggggtcgac accagagatg ctccaagggc ctgcaccaag ttgcttttgg gtttttctg     300

gtatttgtgt tttctgggat tttattttta ttattttttt taatgtcctt tctttgggta    360

atagagaaat ctctgcaaaa gactttgctg accaaccagc tggagctcaa ggaatgtggg    420

gtatctgggg ccacaccatt acctgtgggc ttgctcctgg agccaaaccc tgcagcctta    480

agagagaggg gcctgacctg ctctctttcc ctccctagct ccaggcctcc tctcctgcct    540

cgtcactcct gtgttctggc ctcttgagtg cctttggagg tgtctctgac ctgtgaggat    600

cagagacagt ccccgttttt aaacttcgac aattgacttt tatttccttt tctaattttt    660

attatttttt aaaacaacca ggatgattat cacatctact cccccatccg tccagaaaag    720

ccccaaattg attccttcag ggtctggcct gcccaggctc tattccacat gtgcaggttc    780

caacagctta accctattct cttcccagtc atctgctgca ggtatagctg tctcatgccc    840

ctgcctgcct attctggcca gtaccctaag ccccaagatc tccagcccct gccccagtat    900

ccttgccttc tgatgcctta aagttgggcc acaggtcctg ctgggtcaga gcctcacaga    960

tgcggagctc caaaagctcc gctcaggacc aaagagctct ggcctagggt tcatcctttc   1020

tccaggtgtc tgccctgtgg acagaaggct aaagccttga tcttggcaaa ccaccccttt   1080

tgcccaaagc ctggatgcag agaccagtat tttctgctgg cttcaacagt ctcccctgct   1140

gtctgtgaaa ggtgaccatt gtacccaggc cactgggcct ctaccatgtt ctttcaaacc   1200

caggtcatta ccatccccag gctggatcac tggagcaggc ctcctctctg tccatgtgag   1260

ggggacctag ggctctgcc  cttagccagc tgagccacca ccagcctccc t            1311
```

<210> SEQ ID NO 243
<211> LENGTH: 399
<212> TYPE: DNA
<213> ORGANISM: Mouse

<400> SEQUENCE: 243

```
aagggtcctg aagtcagttg ttgcatcaaa tacttcattt ttggcttcaa tgtcatattt     60

tggtttttgg gaataacgtt tcttggaatc ggactgtggg cgtggaatga aaaaggtgtc    120

ctctccaaca tctcgtccat caccgacctc ggtggctttg acccagtgtg gcttttcctc    180

tgagtggcca gcccgagcct gagctctgtc aatgacatcc aaggagaaaa tgaggttaat    240

gagagacatt aattaaacac tccctcaccc caccgcacca aaccagttgg gttcttctga    300

tattctggaa tactctgggc tatgttttat gtttatttct tttttaatcg gttgtatttt    360

ggtctttttt tttcttcttc tttttctttt gctcccaaa                           399
```

<210> SEQ ID NO 244
<211> LENGTH: 1421
<212> TYPE: DNA
<213> ORGANISM: Mouse
<220> FEATURE:
<221> NAME/KEY: unsure
<222> LOCATION: (1370)...(1370)
<221> NAME/KEY: unsure
<222> LOCATION: (1395)...(1395)

<400> SEQUENCE: 244

```
gccgaggcgg gcaggcacca gccagagcag ctggcggcag acagtcggac cgagacagtt     60

ggaccgagac agtcgaacgg tctaacaggg cctggcttgc ctacctggca gctgcacccg    120

gtccttttcc cagagctggt tctgtgggtc aacatggtcc cctgcttcct cctgtctctg    180
```

-continued

```
ctgctacttg tgaggcctgc gcctgtggtg gcctactctg tgtccctccc ggcctccttc    240

ctggaggaag tggcgggcag tggggaagct gagggttctt cagcctcttc cccaagcctg    300

ctgccgcccc ggactccagc cttcagtccc acaccaggga ggacccagcc cacagctccg    360

gtcggccctg tgccacccac caacctcctg gatgggatcg tggacttctt ccgccagtat    420

gtgatgctca ttgcggtggt gggctcgctg acctttctca tcagttcata gtctgcgcgg    480

cactcatcac gcgccagaag cacaaggcca cagcctacta cccgtcctct ttccccgaaa    540

agaagtatgt ggaccagaga gaccgggctg gggggcccca tgccttcagc gaggtccctg    600

acagggcacc tgacagccgg caggaagagg gcctggactc ctcccagcag ctccaggctg    660

acattctggc tgctactcag aacctccggt ctccagctag agccctgcca ggcagtgggg    720

agggaacaaa acaggtgaag ggtgggtcgg aggaggagga ggagaaggaa gaggaggtgt    780

tcagtggcca ggaggagccc cgggaagccc cagtatgtgg ggtcactgaa gagaagccgg    840

aggtccctga cgagacagcc tcagcagagg ctgaaggggt tcccgcagcc agcgagggcc    900

aaggggaacc agaagggtct ttctccttag cccaggaacc ccagggagca gctggtcctt    960

ccgaaaggtc ctgtgcctgc aacagaatct cccctaatgt gtaacaggcc ccagaactgt   1020

gaggcctgac tcttgggtcc tcgaaggtca cctccttggt caagaaaggc attcagcttt   1080

gactgcttct tgacaccctg ccttggccat tgtgggtgcc aatcctgacc ctgaatgggc   1140

aaagctgctg gcctctggtg taccccagga aacaccaccc caagttccag cgcccttaat   1200

gactctcaca tcctgggggc ttcaccccga agcaccactt ttctggaagg ggaaggtcag   1260

acacatccca gtttggagcc gcaatgaggc agtcctcaga acagaagggg aacaggccag   1320

aggctgactg tgacatacac agtaaacacc cctgcttgca ccttggctgn ggagacaaga   1380

ggggctgttg atcanatggc ctgcggtgtc ctatctgccg t                       1421
```

<210> SEQ ID NO 245
<211> LENGTH: 461
<212> TYPE: DNA
<213> ORGANISM: Mouse

<400> SEQUENCE: 245

```
cgcctgcagg tcgacactag tggatccaaa gttctttttc ttttcttttt cttttttttg     60

tgtgtgtgtg ttttggtttg ttgttgtttt ggttttcctg gaactcactc tgtagaccag    120

gctagcccca aactcagaaa tctgcctccc gagtgctggg actaagggtg tgcaccacca    180

ctgccctggt gcagatgact cctttaagga gctagagtaa cccttgttcg cctcggtgag    240

agtctgagaa tcaggcgctt tggctacaca gctcaattta cacagccaag cctttagctt    300

ctatgtgtgc tgggcatgga cagagcctcc tcatcgccag tgatgatggc cgggtttcca    360

ggcagccgtg gtcctgtctg aatattgtct ctaactgcca cagtttcaga gaaaggggaa    420

caagttctcc tttgcttctt gccctcccag atagaccctt g                        461
```

<210> SEQ ID NO 246
<211> LENGTH: 1280
<212> TYPE: DNA
<213> ORGANISM: Mouse

<400> SEQUENCE: 246

```
ttggactcgc gcgcctgcag gtcgacacta gtggatccaa agaattcggc acgagagaac     60

attcgagaat atgttcggtg gatgatgtat tggattgtct ttgcgatctt catggcagca    120
```

-continued

```
gaaaccttca cagacatctt catttcctgg tccggcccaa ggattggcag gccatggggt    180
tgggaagggc ctcaccacca ccaccacctg gcctctggct cacacaaacc cctccccttg    240
cttacacaca ggttcccgtt ttattacgag ttcaagatgg cttttgtgct gtggctgctc    300
tcaccttaca ccaagggggc cagcctgctt taccgaaagt ttgtccaccc atccctatcc    360
cgccatgaga aggagatcga cgcatgtatc gtgcaggcaa aggagcgcag ctatgaaacc    420
atgctcagtt ttgggaagcg gagcctcaac atcgctgcct cagctgctgt gcaggctgct    480
accaagagtc aaggcgctct agctggaagg ctacggagtt tctctatgca agacctgcgc    540
tctatccctg acacccctgt ccccacctac caagatcccc tctacctgga agaccaggta    600
ccccgacgta gaccccctat tggataccgg ccaggcggcc tgcagggcag tgacacagag    660
gatgagtgtt ggtcagacaa tgagattgtc ccccagccac ctgttgggcc ccgagagaag    720
cctctaggcc gcagccagag ccttcgggtg gtcaagagga agccattgac tcgagagggc    780
acctcacgct ccctgaaggt ccgaaccccg aaaaaggcca tgccctcaga catggacagc    840
tagagtctgc agattgaggc caccttacct ctggagccag caggggacct ttcgctgcta    900
caccagctac cggggttctg ctccgtctgg cttgtgccta aatggcacat ggcgtggtac    960
cctgcacagg gagacattca ctgtaccaaa gcagcccagg cctggggcct atttattgcc   1020
ttcctctgcc ttttgctttc tcagacatgg gaccagagcc ccaccagtcc ctaccgacga   1080
aaccaaaagt ccaaccagct gtgttcattc cttcttgtcc ttcaaaatac ttgacagcct   1140
tttccaaggc ctggtgtgtg tgtgtgtgtg tgtgtgtgtg tgtgtgtgtg tgtgtttacg   1200
tacactagct gcatgtttcg tgttggtgag tgaggtcagg cttatgaata tttttatata   1260
aataaatacc aaacagtgaa                                               1280
```

<210> SEQ ID NO 247
<211> LENGTH: 833
<212> TYPE: DNA
<213> ORGANISM: Rat

<400> SEQUENCE: 247

```
gtgccctccg ccgggtcggg atggagctgc ctgccgtgaa cttgaaggtt attctcctgg     60
ttcactggct gttgacaacc tggggctgct tggcgttctc aggctcctat gcttggggca    120
acttcactat cctggccctg ggtgtgtggg ctgtggccca gcgggactct gttgatgcca    180
ttggcatgtt tcttggtggc ttggttgcca ccatcttcct ggacattatc tacattagca    240
tcttctactc aagcgttgcc gttggggaca ctggccgctt cagtgccggc atggccatct    300
tcagcttgct gctgaagccc ttctcctgct gcctcgtcta ccacatgcac cgggagcgag    360
gggtgagct cccgctccgc tcggatttct tcggaccttc tcaggaacat agtgcctacc     420
agacaattga ctcgtcagac tcacctgcag accccttgc aagcctggag aacaagggcc     480
aagctgcccc ccgggggtac tgaagctgtc cctggccgtc ctggggccca gcaggatgct    540
tgtcaccttc tttactggac ctacaatggg gtatcctcca ttccctgcca cagaggtggc    600
ctgagtcatg tgccctcgga ggtcccagct gagaagagcc cagtcctaat tctccatgct    660
gcccctccat tcaagacacc tgttaacccc tgggctagaa ctgtggttgg tttcttcccc    720
tcctccccat cactataaca cacaaccgcc gagctgtgca gagtgttcag ggccatccag    780
gccttatggg ccaatgatca ctgcctctca ggctacccca aggtgaccca gcc           833
```

<210> SEQ ID NO 248
<211> LENGTH: 1308

-continued

<212> TYPE: DNA
<213> ORGANISM: Rat

<400> SEQUENCE: 248
gccgaggcgg gcaggcacca gccagagcag ctggcggcag acagtcggac cgagacagtt 60
ggaccgagac agtcgaacgg tctaacaggg cctggcttgc ctacctggca gctgcacccg 120
gtccttttcc cagagctggt tctgtgggtc aacatggtcc cctgcttcct cctgtctctg 180
ctgctacttg tgaggcctgc gcctgtggtg gcctactctg tgtccctccc ggcctccttc 240
ctggaggaag tggcgggcag tggggaagct gagggttctt cagcctcttc cccaagcctg 300
ctgccgcccc ggactccagc cttcagtccc acaccaggga ggacccagcc cacagctccg 360
gtcggccctg tgccacccac caaccttctg gatgggatcg tggacttctt ccgccagtat 420
gtgatgctca ttgcggtggt gggctcgctg acctttctca tcatgttcat agtctgcgcg 480
gcactcatca cgcgccagaa gcacaaggcc acagcctact acccgtcctc tttccccgaa 540
aagaagtatg tggaccagag agaccgggct gggggccccc atgccttcag cgaggtccct 600
gacagggcac ctgacagccg gcaggaagag ggcctggact cctcccagca gctccaggct 660
gacattctgg ctgctactca gaacctccgg tctccagcta gagccctgcc aggcagtggg 720
gagggaacaa aacaggtgaa gggtgggtcg gaggaggagg aggagaagga agaggaggtg 780
ttcagtggcc aggaggagcc ccgggaagcc ccagtatgtg gggtcactga agagaagccg 840
gaggtccctg acgagacagc ctcagcagag gctgaagggg ttcccgcagc cagcgagggc 900
caaggggaac cagaagggtc tttctcctta gcccaggaac cccagggagc agctggtcct 960
tccgaaaggt cctgtgcctg caacagaatc tcccctaatg tgtaacaggc cccagaactg 1020
tgaggcctga ctcttgggtc ctcgaaggtc acctccttgg tcaagaaagg cattcagctt 1080
tgactgcttc ttgacaccct gccttggcca ttgtgggtgc caatcctgac cctgaatggg 1140
caaagctgct ggcctctggt gtaccccagg aaacaccacc ccaagttcca gcgcccttaa 1200
tgactctcac catcctgggg gcttcacccc gaagcaccac ttctctggaa ggggaaggtc 1260
agacacatcc cagttggagc cgcaatgagg cagtcctcag aacagaag 1308

<210> SEQ ID NO 249
<211> LENGTH: 1212
<212> TYPE: DNA
<213> ORGANISM: Human

<400> SEQUENCE: 249
tagcgtggtc gcggccgagg tactacagac tttgtgataa ggctgaagct tggggcatcg 60
tcctagaaac ggtggccaca gctggggttg tgacctcggt ggccttcatg ctcactctcc 120
cgatcctcgt ctgcaaggtg caggactcca acaggcgaaa aatgctgcct actcagtttc 180
tcttcctcct gggtgtgttg ggcatctttg gcctcacctt cgccttcatc atcggactgg 240
acgggagcac agggcccaca cgcttcttcc tctttgggat cctcttttcc atctgcttct 300
cctgcctgct ggctcatgct gtcagtctga ccaagctcgt ccgggggagg aagcccctt 360 ccctgttggt gattctgggt ctggccgtgg gcttcagcct agtccaggat gttatcgcta 420
ttgaatatat tgtcctgacc atgaatagga ccaacgtcaa tgtcttttct gagctttccg 480
ctcctcgtcg caatgaagac tttgtcctcc tgctcaccta cgtcctcttc ttgatggcgc 540
tgaccttcct catgtcctcc ttcaccttct gtggttcctt cacgggctgg aagagacatg 600
gggcccacat ctacctcacg atgctcctct ccattgccat ctgggtggcc tggatcaccc 660

-continued

```
tgctcatgct tcctgacttt gaccgcaggt gggatgacac catcctcagc tccgccttgg    720

ctgccaatgg ctgggtgttc ctgttggctt atgttagtcc cgagttttgg ctgctcacaa    780

agcaacgaaa ccccatggat tatcctgttg aggatgcttt ctgtaaacct caactcgtga    840

agaagagcta tggtgtggag aacagagcct actctcaaga ggaaatcact caaggttttg    900

aagagacagg ggacacgctc tatgcccccct attccacaca ttttcagctg cagaaccagc    960

ctccccaaaa ggaattctcc atcccacggg cccacgcttg gccgagccct tacaaagact   1020

atgaagtaaa gaaagagggc agctaactct gtcctgaaga gtgggacaaa tgcagccggg   1080

cggcagatct agcgggagct caaagggatg tgggcgaaat cttgagtctt ctgagaaaac   1140

tgtacctgcc cgggcggccg ctcgaaatca agcttatcga taccgtcgac ctcgaggggg   1200

ggcccggtac ac                                                        1212
```

<210> SEQ ID NO 250
<211> LENGTH: 453
<212> TYPE: DNA
<213> ORGANISM: Human

<400> SEQUENCE: 250

```
aagaattcca aatgcttact tttctggtgc agaaagattg ttgggaacag acaggaacca     60

atgtgggaat tcaacttcaa gttcaaaaaa cagtccccta ggttaaagag caagtgtaca    120

ggaggattgc agcctcccgt tcagtacgaa gatgttcata ccaatccaga ccaggactgc    180

tgcctactgc aggtcaccac cctcaatttc atctttattc cgattgtcat gggaatgata    240

tttactctgt ttactatcaa tgtgagcacg gacatgcggc atcatcgagt gagactggtg    300

ttccaagatt cccctgtcca tggtggtcgg aaactgcgca gtgaacaggg tgtgcaagtc    360

atcctggacc agtgcacagc gttcggctct ttgactggtg gcatcctcag tacccattct    420

ccctgagagc gtagttactg cttcccatcc ctt                                 453
```

<210> SEQ ID NO 251
<211> LENGTH: 242
<212> TYPE: DNA
<213> ORGANISM: Human

<400> SEQUENCE: 251

```
gagagagaga actagtctcg agttttttgt atttttattt ttgttcatct gctgctgttt     60

acattctggg gggttagggg gagtccccct ccctcccttt cccccccaag cacagagggg    120

agaggggcca gggaagtgga tgtctcctcc cctcccaccc caccctgttg tagcccctcc    180

tacccctcc ccatccaggg gctgtgtatt attgtgagcg aataaacaga gagacgctaa    240

ca                                                                   242
```

<210> SEQ ID NO 252
<211> LENGTH: 358
<212> TYPE: DNA
<213> ORGANISM: Human

<400> SEQUENCE: 252

```
gatggcccca gtcccaagtt ggccctgtgg ctgccctcac cagctcccac agcagcccca     60

acagccctgg gggaggctgg tcttgccgag cacagccaga gggatgaccg gtggctgctg    120

gtggcactcc tggtgccaac gtgtgtcttt ttggtggtcc tgcttgcact gggcatcgtg    180

tactgcaccc gctgtggccc ccatgcaccc aacaagcgca tcactgactg ctatcgctgg    240

gtcatccatg ctgggagcaa gagcccaaca gaacccatgc cccccagggg cagcctcaca    300
```

-continued

```
ggggtgcaga cctgcagaac cagcgtgtga tggggtgcag acccccctca tggagtat      358


<210> SEQ ID NO 253
<211> LENGTH: 568
<212> TYPE: DNA
<213> ORGANISM: Human

<400> SEQUENCE: 253

catctgtcat ggcggctggg ctgtttggtt tgagcgctcg ccgtcttttg gcggcagcgg     60

cgacgcgagg gctcccggcc gcccgcgtcc gctgggaatc tagcttctcc aggactgtgg    120

tcgccccgtc cgctgtggcg ggaaagcggc ccccagaacc gaccacaccg tggcaagagg    180

acccagaacc cgaggacgaa aacttgtatg agaagaaccc agactcccat ggttatgaca    240

aggaccccgt tttggacgtc tggaacatgc gacttgtctt cttctttggc gtctccatca    300

tcctggtcct tggcagcacc tttgtggcct atctgcctga ctacaggatg aaagagtggt    360

cccgccgcga agctgagagg cttgtgaaat accgagaggc caatggcctt cccatcatgg    420

aatccaactg cttcgacccc agcaagatcc agctgccaga ggatgagtga ccagttgcta    480

agtggggctc aagaagcacc gccttcccca ccccctgcct gccattctga cctcttctca    540

gagcacctaa ttaaaggggc tgaaagtc                                       568


<210> SEQ ID NO 254
<211> LENGTH: 1421
<212> TYPE: DNA
<213> ORGANISM: Human

<400> SEQUENCE: 254

gattagcgtg gtcgcggccg aggtgtctgt tcccaggagt ccttcggcgg ctgttgtgtc     60

agtggcctga tcgcgatggg gacaaaggcg caagtcgaga ggaaactgtt gtgtctcttc    120

atattggcga tcctgttgtg ctccctggca ttgggcagtg ttacagtgca ctcttctgaa    180

cctgaagtca gaattcctga gaataatcct gtgaagttgt cctgtgccta ctcgggcttt    240

tcttctcccc gtgtggagtg gaagtttgac caaggagaca ccaccagact cgtttgctat    300

aataacaaga tcacagcttc ctatgaggac cgggtgacct tcttgccaac tggtatcacc    360

ttcaagtccg tgacacggga agacactggg acatacactt gtatggtctc tgaggaaggc    420

ggcaacagct atggggaggt caaggtcaag ctcatcgtgc ttgtgcctcc atccaagcct    480

acagttaaca tcccctcctc tgccaccatt gggaaccggg cagtgctgac atgctcagaa    540

caagatggtt ccccaccttc tgaatacacc tggttcaaag atgggatagt gatgcctacg    600

aatcccaaaa gcacccgtgc cttcagcaac tcttcctatg tcctgaatcc cacaacagga    660

gagctggtct ttgatcccct gtcagcctct gatactggag aatacagctg tgaggcacgg    720

aatgggtatg ggacacccat gacttcaaat gctgtgcgca tggaagctgt ggagcggaat    780

gtgggggtca tcgtggcagc cgtccttgta accctgattc tcctgggaat cttggttttt    840

ggcatctggt ttgcctatag ccgaggccac tttgacagaa caaagaaagg gacttcgagt    900

aagaaggtga tttacagcca gcctagtgcc cgaagtgaaa gagaattcaa acagacctcg    960

tcattcctgg tgtgagcctg gtcggctcac cgcctatcat ctgcatttgc cttactcagg   1020

tgctaccgga ctctggcccc tgatgtctgt agtttcacag gatgccttat ttgtctttta   1080

caccccacag ggccccctac ttcttcggat gtgtttttaa taatgtcagc tatgtgcccc   1140

atcctccttc atgccctccc tccctttcct accactggtg agtggcctgg aacttgttta   1200
```

-continued

```
aagtgtttat tccccatttc tttgagggat caggaaggaa tcctgggtat gccattgact   1260

tcccttctaa gtagacagca aaaatggcgg gggtcgcagg aatctacact caactgccca   1320

cctggctggc agggatcttt gaataggtat cttgagcttg gttctgggct ctttccttgt   1380

gtacctgccc gggcggccgc tcgaaatcaa gcttatcgat a                        1421
```

<210> SEQ ID NO 255
<211> LENGTH: 1464
<212> TYPE: DNA
<213> ORGANISM: Mouse

<400> SEQUENCE: 255

```
ggcacgagcg ggagcctgct actgccctgc tgggttcctt ggggccgact gtagccttgc     60

ctgtccacag ggtcgcttcg gccccagctg tgcccacgtg tgtacatgcg ggcaaggggc    120

ggcatgtgac ccagtgtcgg ggacttgcat ctgtcctccc gggaagacgg gaggccattg    180

tgagcgcggc tgtccccagg accggtttgg caagggctgt gaacacaagt gtgcctgcag    240

gaatgggggc ctgtgtcatg ctaccaatgg cagctgctcc tgccccctgg gctggatggg    300

gccacactgt gagcacgcct gccctgctgg gcgctatggt gctgcctgcc tcctggagtg    360

ttcctgtcag aacaatggca gctgtgagcc cacctccggc gcttgcctct gtggccctgg    420

cttctatggt caagcttgtg aagacacctg ccctgccggc ttccatggat ctggttgcca    480

gagagtttgc gagtgtcaac agggcgctcc ctgtgaccct gtcagtggcc ggtgcctctg    540

ccctgctggc ttccgtggcc agttctgcga gagggggtgc aagccaggct tttttggaga    600

tggctgcctg cagcagtgta actgccccac gggtgtgccc tgtgatccca tcagcggcct    660

ctgcctttgc ccaccagggc gcgcaggaac cacatgtgac ctagattgca gaagaggccg    720

ctttgggccg ggctgtgccc tgcgctgtga ttgtgggggt ggggctgact gcgaccccat    780

cagtgggcag tgccactgtg tggacagcta cacgggaccc acttgccggg aagtgcccac    840

acagctgtcc tctatcagac cagcacccca gcactccagc agcaaggcca tgaagcacta    900

actcagagga acgcccacag aggcccacta ctgtgttcca gcccaaggga cccaggcctc    960

tgctggtgac taagatagag gtggcacttt tggatccaca cctcttctgg aaagccatgg   1020

attgctgtgg acagctatgg atagtcatat agccacacac ccgggctcca tggtcatggg   1080

gaagaaggcc tcctttggac acaaggaatc caggaagtcg gctgggcttc gggccactgt   1140

ttacatgggg accctgcagg ctgtgctgtg gaatcctggc cctcttcagc gacctgggat   1200

gggaccaagg tgggaataga caaggcccca cctgcctgcc aggtccttct ggtgctaggc   1260

catggactgc tgcagccagc caactgttta cctggaaatg tagtccagac catatttata   1320

taaggtattt atgggcatct ccacctgccg ttatggtcct gggtcagatg gaagctgcct   1380

gaccccagaa cttaggcagt ggcctgtggg gtctccagca agtgggatca agggttttgt   1440

aaaacccagt gagttaaagg caca                                           1464
```

<210> SEQ ID NO 256
<211> LENGTH: 2411
<212> TYPE: DNA
<213> ORGANISM: Mouse

<400> SEQUENCE: 256

```
tcggcacgag agtgggtaca ccttactaca tgtctccaga gagaatacat gaaaatggat     60

acaacttcaa gtctgacatc tggtctcttg gctgtctgct atatgagatg gctgcactgc    120

agagtccttt ctacggcgac aagatgaact tgtattctct gtgtaagaag atagagcagt    180
```

-continued

```
gtgactaccc gcctctcccg tcagatcact attcggagga gctacgacag ctagttaata    240
tatgcatcaa cccagatcca gagaagcgac ccgacatcgc ctatgtttat gatgtggcaa    300
agaggatgca tgcatgtacc gcaagcacct aaactgtaca agatcctgaa gacggcaacc    360
aagataactt aaaagtgttt ttgtgcagat catacctccc cgcttatgtc tgggtgttaa    420
gattactgtc tcagagctaa tgcgctttga atccttaacc agttttcata tgagcttcat    480
ttttctacca ggctcaatca ccttcccaat ccacaacttt gggatgctca gatggcacca    540
agaatgcaag cccaacaaga gtttttcgtt tgagaattgt ttcgagtttc tgctgataga    600
ctgtgtttat agatagtcag tgcccgatgg tgaagcacac acacataggc acatgtccag    660
agcgatgcag aacctgagga aggacctggg catttgactt gtttgctttt aagtcactta    720
atggacgttg tagtggacat gattgtgaac ttctgatttt tttcttttaa gtttcaagta    780
catgttttag ttcttagcat tagagatctc aaatataatt cttataagac atgcagacat    840
aaactttttg agaaagattt aaaattttta gtttatacat tcaaaatgca actattaaat    900
gtgaaagcat agaggtcaaa atgtgagttg gacactgaag tctatgtttt aatgcctttg    960
aaagcctttt tttgtgtgtg tttaaatggt ataaatgaac ccattttaaa acgtggttaa   1020
ggacttgttt gcctggcgtg atagtcatgt ttaacatgca caaggctttg tgtttttatt   1080
gtacatttga agaatattct tggaataatc ttgcagtagt tatagttcaa tttctttaca   1140
aatctaaata cacttaactc ataactatac actgtaatgc aagcatatat tgttattcat   1200
atattgaagt tttgatcagt tcctcttcag aatctttttt atccaagtta ctttcttatt   1260
tatattgtgt gtgcatttca tccattaaat gtttcagatt ttctgagaat gagttccctt   1320
tttaaaatat atttggtatg ccaacacttt tttaggattg aaaaaaaatt tttttaaatg   1380
tttgggtcat tctaggtgca tctgttttct cttgttagaa agaaaaggtg tgtgttaaaa   1440
tgtgcctgtg aatgtcgata ttgtttggca gggttataat tttagagtat gctctagagt   1500
atgttgaaca gcgtgaagac tggcccttac tgaagacaga actgttccaa gagcagcatt   1560
cccgttgaga tgctttggag taaagtactg tgtatgacga tgacagacat tttagttaag   1620
ggggtgaaaa aaaaaggagg ggtatttagg aaaccctgag gtggaatttt ggtgaatgtc   1680
ttcatcttaa taccagccaa ttccttcaga gaattgtgga gccaaagaac agagtaatcg   1740
tggctgttgc agaacacggt gtgccatggt agagcattgg gaaggctcat cctgccggtg   1800
ggtcggtcag acagccctgt gttggggagc ttgtactctg gcccacagag ctcggttgat   1860
tttcttacag agtattcttt ctacagttat tttcaagtaa ttgtaaattt tcaaagtaat   1920
atctcatctt ttaattcact atgtatgctg tcgtagacaa aggaaatctg ggtttttttt   1980
tgtttttgtt tttgtttttt tttgtcttga aggctgaact gggtacatcc cagatcttag   2040
tggctcatag gatataccca gaggcatgaa gaaatggctt ccggtgacca tttgtgttgk   2100
gktatatccc attgtaatgt cacaggactg attgagatga aacatcccct tcctacaaga   2160
gttgttttct ttccatattt aaaaacatga ggttctgcct ggcagtgatg gtacacacct   2220
ttaatcccag cacccgggag gcagaggcag gaggatttct gagttcgagg ccagcctggt   2280
ctacaaagtg agttccagga cagccaggac tacacagaga aatcctgtct caaaaaacca   2340
aaactaaatg aaaatacaag gcttctcccc ttgtagtgac tttgctttat gaatttgtct   2400
caaaaaaaaa a                                                        2411
```

<210> SEQ ID NO 257

-continued

<211> LENGTH: 3516
<212> TYPE: DNA
<213> ORGANISM: Mouse

<400> SEQUENCE: 257
aaagtggagg gcgagggccg gggccggtgg gctctggggc tgctgcgcac cttcgacgcc 60
ggcgaattcg caggctggga gaaggtgggc tcgggcggct tcgggcaggt gtacaaggtg 120
cgccatgtgc actggaagac gtggctcgcg atcaagtgct cgcccagtct gcacgtcgac 180
gacagggaac gaatggagct cctggaggaa gctaagaaga tggagatggc caagttccga 240
tacattctac ctgtgtacgg catatgccag gaacctgtcg gcttggtcat ggagtacatg 300
gagacaggct ccctggagaa gctgctggcc tcagagccat tgccttggga cctgcgcttt 360
cgcatcgtgc acgagacagc cgtgggcatg aacttcctgc attgcatgtc tccgccactg 420
ctgcacctag acctgaagcc agcgaacatc ctgctggatg cccactacca tgtcaagatt 480
tctgactttg ggctggccaa gtgcaatggc atgtcccact ctcatgacct cagcatggat 540
ggcctgtttg gtacaatcgc ttacctccct ccagagcgaa ttcgtgagaa gagccgcttg 600
tttgacacca aacatgatgt atacagcttc gccattgtga tctggggtgt gcttacacag 660
aagaagccat ttgcagatga aaagaacatc ctacacatca tgatgaaagt ggtaaagggc 720
caccgcccag agctgccacc catctgcaga ccccggccgc gtgcctgtgc cagcctgata 780
gggctcatgc aacggtgctg gcatgcagac ccacaggtgc ggcccacctt ccaagaaatt 840
acctctgaaa cagaagacct ttgtgagaag cctgatgagg aggtgaaaga cctggctcat 900
gagccaggcg agaaaagctc tctagagtcc aagagtgagg ccaggcccga gtcctcacgc 960
ctcaagcgcg cctctgctcc cccttcgat aacgactgca gtctctccga gttgctgtca 1020
cagttggact ctgggatctc ccagactctt gaaggccccg aagagctcag ccgaagttcc 1080
tctgaatgca agctcccatc gtccagcagt ggcaagaggc tctcgggggt gtcctcagtg 1140
gactcagcct tttcctccag aggatcgctg tcactgtctt ttgagcggga agcttcaaca 1200
ggcgacctgg gccccacaga catccagaag aagaagctag tggatgccat catatcaggg 1260
gacaccagca ggctgatgaa gatcctacag ccccaagatg tggacttggt tctagacagc 1320
agtgccagcc tgctgcacct ggctgtggag gccggacagg aggagtgtgt caagtggctg 1380
ctgcttaaca atgccaaccc caacctgacc aacaggaagg gctctacacc actgcatatg 1440
gctgtggagc ggaagggacg tggaattgtg gagctactgc tagcccggaa gaccagtgtc 1500
aatgccaagg atgaagacca gtggactgcc ctgcactttg cagcccagaa tggggatgag 1560
gccagcacaa ggctgctgct agagaagaat gcttctgtca atgaggtgga ctttgagggc 1620
cgaacaccca tgcatgtagc ctgccagcat ggacaggaga acattgtgcg caccctgctc 1680
cgccgtggtg tggatgtggg cctgcaggga aaggatgcct ggttgcctct gcactatgct 1740
gcctggcagg gccaccttcc cattgttaag ctgctagcca agcagcctgg ggtgagtgtg 1800
aatgcccaga cactagacgg gaggacaccc ctgcacctgg ctgctcagag ggggcattac 1860
cgtgtggctc gcattctcat tgacctgtgc tctgatgtta acatctgcag cctacaggca 1920
cagacacctc tgcatgttgc tgcagagact ggacacacta gtactgccag gctactcttg 1980
catcgtggtg ctggcaagga ggctttgacc tcagagggct atactgcctt gcacctggca 2040
gcccagaatg gacacctggc tactgtcaag ctgctcatag aggagaaggc tgatgtgatg 2100
gctcggggtc ccctgaatca gacagcactg cacctggctg ctgcccgtgg acactcagag 2160
gtggtagaag agctggtcag tgctgacctc attgacctgt ctgatgagca gggcctcagc 2220

-continued

```
gcactgcacc tggctgctca gggcaggcat tcacagactg tggagacact gctcaaacat   2280
ggagcacaca tcaacttgca gagtctcaag ttccaaggag gccagagctc tgctgccacg   2340
ttgctccgac gcagcaagac ctagcttgcc accacaaaac cagggctccg tgtaggcttc   2400
tggaccatcc ttgtttcctc atggggacag aatggtcctg ggacactgct caccctgttg   2460
gtggcctgcc catacactga ccaagcagag gctaatggac aaggcaggag tagctgtctt   2520
ggggcacagt agccaaagtg tctgatgtca gatgggacta ggttggtgtc atgtcactgt   2580
ggtattgatt ggctgctgat gcaggccttt tatgacaaag cctatacaag aatgtctcct   2640
ctgtccatag agcaagccat ttctgcttgc ttggagcatg acatcttcag tagagatgtg   2700
ggaagggcag tgtcctttgt cttctcattg tgatgggcag agtagctgtc tctgaaggca   2760
tagtgggttc ttaatatatg agtgacatgg tagctttgct tgagacctgt gaggatctgg   2820
ctgctggagt ctagaaaggg agtgattata aagccacagg gttggtccta acactggaca   2880
gccttgccaa catgaaactg ctgtttcatt tggtattttg gttttggttt ttagttttga   2940
tgtctaggtc accatgcctc gttcccccga tttccctgct gagttctcag ctaaaatgtc   3000
agagccatat atataaaagt taccggaaat ttttttgtaa atgggtttta tactaaaagt   3060
tgtttagtca aacagtttgc tctttcaggc tctcttggtg aagtgatggt ttgggccaag   3120
ggctttgctg acttgccctt tagcaacttc tgctatgttc cagttacagt agatgaatgt   3180
gggcagaggt ggccattgga gattgttgta ctctgaggag tcagattcga tagccttttg   3240
ttgtaccttc cccatttctg ttctgaacac tgtcactgta gagatgacct gtgtgcaaac   3300
atgctatagc atggtatgtg acacagaatg atattaatgt actgtgtact ttgacatgaa   3360
tcatggacag gatactcttt catgacagga agtagtggag ctggctatgt tttaatatgc   3420
ctcaatttgt cttcactgct tccctctctt gtgtaaaaca cggggaccat aggagatctg   3480
ttttatgtca ataaaggact ccgcctaaaa aaaaaa                             3516
```

<210> SEQ ID NO 258
<211> LENGTH: 946
<212> TYPE: DNA
<213> ORGANISM: Mouse

<400> SEQUENCE: 258

```
cctggctgca aatcctgcac tgtgtgtcgt catggcctgt gtcgctccgt ggagaaggac     60
agcgtagtgt gtgagtgcca cccgggatgg accggtccgc tatgtgatca ggaagctcgg    120
gacccctgcc ttggtcacag ctgcaggcac gggacatgca tggcgactgg ggactcctac    180
gtgtgcaagt gtgccgaggg ctacggaggg gctttgtgtg accagaagaa tgactctgcc    240
agtgcctgct cagccttcaa gtgccaccat gggcagtgtc acatctcaga tcgaggggag    300
ccctattgcc tatgccagcc tggcttcagt ggccatcact gtgagcaaga gaatccatgt    360
atgggggaga tagtccgtga agccatccgc cgccagaaag actacgcctc ttgtgccacg    420
gcgtccaagg tgcccatcat ggaatgccgc gggggctgcg ggaccacgtg ctgccagccg    480
attcgaagca agcggcggaa atatgtcttc cagtgcacgg acggctcctc attcgtggaa    540
gaggtggaga gacacttgga atgtggctgc cgcgcgtgtt cctgagcccc ctctgccacc    600
cacccatcct ccgcctttcg gaccccagct cattgggctg ggaacagcca catggaacct    660
ctttgagatt cagaacgaag gagagaaatc tggagagcaa gaggcaaaag agagaatatt    720
aagtatattg taaaataacc aaaaatagaa cttattttta ttatggaaag tgactatttt    780
```

-continued

```
catcttttat tatataaata tatcacaccg tctgagtata tggactatac agtgagttat    840

ttttaccaag ttttgttttg tgttgtgtat ttgttgtgtt tttataaaca gctgtttata    900

aaattttaag acaaagaaaa aacactaata aaaatgtttt aaacac                   946
```

<210> SEQ ID NO 259
<211> LENGTH: 1018
<212> TYPE: DNA
<213> ORGANISM: Human

<400> SEQUENCE: 259

```
gctaccgcta ctgccagcac cgctgcgtga acctgcctgg ctccttccgc tgccagtgcg     60

agccgggctt ccagctgggg cctaacaacc gctcctgtgt tgatgtgaac gagtgtgaca    120

tgggggcccc atgcgagcag cgctgcttca actcctatgg gaccttcctg tgtcgctgcc    180

accagggcta tgagctgcat cgggatggct tctcctgcag tgatattgat gagtgtagct    240

actccagcta cctctgtcag taccgctgcg tcaacgagcc aggccgtttc tcctgccact    300

gcccacaggg ttaccagctg ctggccacac gcctctgcca agacattgat gagtgtgagt    360

ctggtgcgca ccagtgctcc gaggcccaaa cctgtgtcaa cttccatggg ggctaccgct    420

gcgtggacac caaccgctgc gtggagccct acatccaggt ctctgagaac cgctgtctct    480

gcccggcctc caaccctcta tgtcgagagc agccttcatc cattgtgcac cgctacatga    540

ccatcacctc ggagcggagc gtgcccgctg acgtgttcca gatccaggcg acctccgtct    600

accccggtgc ctacaatgcc tttcagatcc gtgctggaaa ctcgcagggg gacttttaca    660

ttaggcaaat caacaacgtc agcgccatgc tggtcctcgc ccggccggtg acgggccccc    720

gggagtacgt gctggacctg gagatggtca ccatgaattc cctcatgagc taccgggcca    780

gctctgtact gaggctcacc gtctttgtag ggcctacac cttctgagga gcaggaggga    840

gccaccctcc ctgcagctac cctagctgag gagcctgttg tgaggggcag aatgagaaag    900

gcccaggggc ccccattgac aggagctggg agctctgcac cacgagcttc agtcaccccg    960

agaggagagg aggtaacgag gagggcggac tccaggcccc ggcccagaga tttggact     1018
```

<210> SEQ ID NO 260
<211> LENGTH: 2800
<212> TYPE: DNA
<213> ORGANISM: Mouse

<400> SEQUENCE: 260

```
ggcacgagga agagccgtgc aataatgggt ctgaaatcct tgcttataac atcgatctgg     60

gagacagctg cattactgtg ggcaacacta ccacacacgt gatgaagaac ctccttccag    120

aaacgacata ccggatcaga attcaggcta tcaatgaaat tggagttgga ccatttagtc    180

agttcattaa agcaaaaact cggccattac cgccttcgcc tcctaggctt gagtgtgctg    240

cgtctggtcc tcagagcctg aagctcaagt ggggagacag taactccaag acacatgctg    300

ctggtgacat ggtgtacaca ctacagctgg aagacaggaa caagaggttt atctcaatct    360

accgaggacc cagccacacc tacaaggtcc agagactgac agagtttacc tgctactcct    420

tcaggatcca ggcaatgagc gaggcagggg aggggcctta ctcagaaacc tacaccttca    480

gcacaaccaa aagcgtgcct cccaccctca aagcacctcg agtgacgcag ttagaaggga    540

attcctgtga aatcttctgg gagacggtac caccgatgag aggcgaccct gtgagctacg    600

ttctacaggt gctggttgga agagactctg agtacaagca ggtgtacaag ggagaagaag    660

ccacattcca aatctcaggc ctccagagca acacagatta caggttccgc gtgtgtgcct    720
```

-continued

```
gccgccgctg tgtggacacg tctcaggagc tcagtggcgc gttcagcccc tctgcggctt    780
tcatgttaca acagcgtgag gttatgctta caggggacct gggaggcatg gaagaggcca    840
agatgaaggg catgatgccc accgacgaac agtttgctgc actcatcgtg cttggcttcg    900
cgaccctgtc cattttgttt gcctttatat tacagtactt cttaatgaag taaatccagc    960
aggccagtgg tatgctcgga acgccacacg ttttaataca catttactca gagcctcccc   1020
tttttacgct gtttcgttct ttgatttata cgcttctctt gttttacaca tttagctagg   1080
ggaaagagtt tggctgcacc tatttgagat gcaaaactag gaagaggtta aactggattt   1140
ttttttaaac aataataaat aaaggaataa agaagagaag gaagcggcgg gcaagctcca   1200
gacaccgaga gccagtgtgc ccaacgagct tgccttgtcg ggcttccccg tgtgcttctg   1260
gtctgttccc actgatgtct ttcgcaagcc tttgatcatc ttgtgtgtta cagttcagta   1320
atttatattc acagtcattt cttgatcatc tatacctgtt aacagaatca cagtgtatgt   1380
agttcagggc tgggattccg gtgttgtcag agtattgcca catgagaata ttcagtgtgc   1440
cttcggagga ggccacctcg accatcctta cgtcactcag ttacgtaact gtgttagctc   1500
atctaagtca aagtgtgtac tttaatctaa aatgttttat tactctgtat cccttatgat   1560
tttaacacta tgagttgcct gtctaagaag tcacataacc aaatgcgcct ataaatgata   1620
gagcattgta gattttcaca tcggtccata gcagtaactt taagagggca ttgtgcaata   1680
gttagttgtt tcttgttcgg ctactttaaa agctgcttta acttgtctgt ctgtctttgt   1740
acataactac ttctaatata atcactagag ttattatatt ctgttatgtt tgaccggaat   1800
tatgtgacga gagctcatgg cagttgtgaa ctgtctcctt acatgttggc ccatcatatt   1860
tgaaagactt gcctttggct attctttggg gtgtcagtga cgtgaatgaa gttgaatacc   1920
atatttcagt gcccatgata ctaatgtagc agtagataga aatcttactg ataaagccca   1980
ccacaaggga accatttaca tttgtcctgt ttctgggggc ttcatctggc cgcatggaga   2040
gagggagtgg aaactggctg tgagcatgag atgtttgggg gccaaagagc ctactagatt   2100
ctctccctgg gtctgtcact aatttgcttt gtgacctctc tgtgcctgtt ttcccatgca   2160
tgagtaatca aatcaaatgg ggattcaata cctgtaagtg ctaagagacc ttggatccac   2220
cggtgctatg taagtgcgga gaatcactct cacggattca cttagagtca tgaggtaatg   2280
agttctaacc caaagtcatt ggatccctca accaagtcca caatgttcaa gtacctcagg   2340
gacacttaag aagttggagg tgcaactgta ttccaaaagg gtgcgacaga cacagccgat   2400
tcccctcttc ctgttttttt gtatattttt gctccttggt tttcttgat catagctact    2460
ttgtgcttgg tctatgttgt ctatgatgca gtaagtaccc tgtactagct tatactattc   2520
ccataccaaa gtcatgggga aaccaacatt attttgtttt gggtttattt atactctatt   2580
ctgcatacag tactttaaat gccaatgaca gtgcaatctt tatttattgt aatgttaaat   2640
gtacttatta ctaatgtgcc ctcctagcat gttatatttt gtgtgtttta tactttttgt   2700
aattttaggt cagtttagtt ccttggcaac atctgtagta ttagccttct gacatctttc   2760
ttgtgttttt aaagataaga gcatctaact cattaaatgc                         2800
```

<210> SEQ ID NO 261
<211> LENGTH: 1335
<212> TYPE: DNA
<213> ORGANISM: Mouse

<400> SEQUENCE: 261

-continued

```
acccaaacag cccgggacca tgctgtcgct ccgctccttg cttccacacc tgggactgtt      60
cctgtgcctg gctctgcact tatccccctc cctctctgcc agtgataatg ggtcctgcgt     120
ggtccttgat aacatctaca cctccgacat cttggaaatc agcactatgg ctaacgtctc     180
tggtggggat gtaacctata cagtgacggt ccccgtgaac gattcagtca gtgccgtgat     240
cctgaaagca gtgaaggagg acgacagccc agtgggcacc tggagtggaa catatgagaa     300
gtgcaacgac agcagtgtct actataactt gacatcccaa agccagtcgg tcttccagac     360
aaactggaca gttcctactt ccgaggatgt gactaaagtc aacctgcagg tcctcatcgt     420
cgtcaatcgc acagcctcaa agtcatccgt gaaaatggaa caagtacaac cctcagcctc     480
aaccccctatt cctgagagtt ctgagaccag ccagaccata aacacgactc caactgtgaa     540
cacagccaag actacagcca aggacacagc caacaccaca gccgtgacca cagccaatac     600
cacagccaat accacagccg tgaccacagc caagaccaca gccaaaagcc tggccatccg     660
cactctcggc agccccctgg caggtgccct ccatatcctg cttgtttttc tcattagtaa     720
actcctcttc taaagaaaac tggggaagca gatctccaac ctccaggtca tcctcccgag     780
ctcatttcag gccagtgctt aaacataccc gaatgaaggt tttatgtcct cagtccgcag     840
ctccaccacc ttggaccaca gacctgcaac actagtgcac ttgagggata caaatgcttg     900
cctggatctt tcagggcaca aattccgctt cttgtaaata cttagtccat ccatcctgcg     960
tgtaacctga agttctgact ctcagtttaa cctgttgaca gccaatctga acttgtgttt    1020
cttgccaaag gtattcccat gagcctcctg ggtgtggggg tggggaggga atgatccttc    1080
tttactttca aactgatttc agatttctgg ccaaacctac tcaggttgca aaggacttat    1140
gtgacttatg tgactgtagg aaaaagagaa atgagtgatc atcctgtggc tactagcaga    1200
tttccactgt gcccagacca gtcggtaggt tttgaaggaa gtatatgaaa actgtgcctc    1260
agaagccaat gacaggacac atgacttttt ttttctaagt caaataaaca atatattgaa    1320
caaggaaaaa aaaaa                                                      1335
```

<210> SEQ ID NO 262
<211> LENGTH: 1816
<212> TYPE: DNA
<213> ORGANISM: Mouse

<400> SEQUENCE: 262

```
ggcacgagga cttctgctag tacttgctcc tggcggtggc tgagcaaccg gtctcaccag      60
catgctctgc ctgtgcctgt atgtgcccat cgccggggcg gctcagactg agttccagta     120
ctttgagtcc aaggggcttc ctgccgagct gaaatccatc ttcaaactca gtgtctttat     180
cccctctcaa gagttctcca cataccgcca atggaagcag aaaattgtgc aagcaggtga     240
caaggacctt gatgggcaac tggactttga agagtttgta cattacctcc aagatcatga     300
gaaaaaactg aggctggtgt tcaagagtct ggacaaaaag aatgatggtc gaatcgatgc     360
tcaggagatc atgcagtccc tgcgggacct gggtgtcaag atctcggaac agcaggcgga     420
gaagattctt aagagcatgg ataagaatgg cacgatgacc atcgactgga acgagtggag     480
ggactaccac ctcctgcacc ctgtggagaa catcccggag atcatcctgt actggaagca     540
ctcgacgatc ttcgatgtcg gtgagaatct gacagtccca gatgagttca cagtggagga     600
gaggcagacg ggatgtggt ggaggcacct ggtggcagga ggtggggcag gggcagtttc     660
cagaacctgc actgcccccc tggacagact gaaggtgctc atgcaggtcc atgcctcccg     720
cagcaacaac atgtgcatcg taggtggatt cacacagatg attcgagaag gggagccaa     780
```

-continued gtcactctgg cggggcaacg gcatcaatgt cctcaaaatt gcccctgagt cggccatcaa 840
attcatggca tatgagcaga tgaaacggct tgtcggtagt gatcaggaga cgctgaggat 900
ccacgaaagg cttgtggcag gctccttggc cggagccatt gcccagagta gcatctaccc 960
aatggaggtt ctgaagaccc gaatggccct gcggaaaaca ggacagtact ccggcatgct 1020
ggactgtgcc aggaggatct tggctaaaga gggtgtagct gccttctaca aaggctacat 1080
ccccaacatg ctggggatca tcccctatgc tggcatcgac ctagctgtct atgagacatt 1140
gaaaaatacc tggctccagc gctacgcagt aaacagtgca gaccccggtg tgttcgtgct 1200
cctggcctgt ggtactatct ccagtacttg tggccagctg gccagctacc cactagccct 1260
ggtcaggacc cggatgcagg cacaagcctc cattgagggc gcacctgagg taaccatgag 1320
cagcctcttc aaacagattc tgcggactga gggggccttt gggctctacc gggggctggc 1380
ccccaacttc atgaaggtga tcccggctgt gagcatcagc tacgtggtct acgaaaacct 1440
gaagatcacc ctgggcgtgc agtctcggtg acgggagggt ggtggacttg gtgagcctgg 1500
gctgcggccc agggtatgca gccacctcat tctgtgaatg tgccaacact aagctgactt 1560
acccaagctg tgaaacccag gataccatag gggacgggca gggagctggc aagctctggg 1620
ctggttctgc tgacctggca gaccttcgtg tctcttccaa ggaagacctg tggatgttcc 1680
ttggggttca ggggtcagta agatgtaggc tcctgcacta gagacaggac gttttcctca 1740
gtgcctgcca gatagcgagc ttggatgcca gcttagttct tccatctcgt tcactcagcc 1800
ggacctcagc cacggg 1816

<210> SEQ ID NO 263
<211> LENGTH: 764
<212> TYPE: DNA
<213> ORGANISM: Mouse

<400> SEQUENCE: 263
gcagcaccca gcgccaagcg caccaggcac cgcgacagac ggcaggagca cccatcgacg 60
ggcgtactgg agcgagccga gcagagcaga gagaggcgtg cttgaaaccg agaaccaagc 120
cgggcggcat cccccggccg ccgcacgcac aggccggcgc cctccttgcc tccctgctcc 180
ccaccgcgcc cctccggcca gcatgaggct cctggcggcc gcgctgctcc tgctgctcct 240
ggcgctgtgc gcctcgcgcg tggacgggtc caagtgtaag tgttcccgga aggggcccaa 300
gatccgctac agcgacgtga agaagctgga aatgaagcca aagtacccac actgcgagga 360
gaagatggtt atcgtcacca ccaagagcat gtccaggtac cggggccagg agcactgcct 420
gcaccctaag ctgcagagca ccaaacgctt catcaagtgg tacaatgcct ggaacgagaa 480
gcgcagggtc tacgaagaat agggtggacg atcatggaaa gaaaaactcc aggccagttg 540
agagacttca gcagaggact ttgcagatta aaataaaagc cctttctttc tcacaagcat 600
aagacaaatt atatattgct atgaagctct tcttaccagg gtcagttttt acattttata 660
gctgtgtgtg aaaggcttcc agatgtgaga tccagctcgc ctgcgcacca gacttcatta 720
caagtggctt tttgctgggc ggttggcggg gggcgggggg acct 764

<210> SEQ ID NO 264
<211> LENGTH: 1697
<212> TYPE: DNA
<213> ORGANISM: Mouse

<400> SEQUENCE: 264

-continued

```
gcgcggcccg ggggactcac attccccggt ccccccctccg ccccacgcgg ctgggccatg     60
gacgccagat ggtgggcagt agtggtactc gccacactcc cttccttggg agcaggtgga    120
gagtcacccg aagcccctcc gcagtcctgg acacagctgt ggctcttccg cttcttgttg    180
aatgtagcgg gctatgccag ctttatggta cctggctacc tcctggtgca gtacttaaga    240
cggaagaact acctggagac aggcaggggt ctctgcttcc ccctggtgaa agcctgtgtg    300
tttggcaatg agcccaaggc tcctgatgag gttctcctgg ctccgcggac agagacagcg    360
gaatccaccc cgtcttggca ggtcctgaag ctggtcttct gtgcctcggg tctccaggtg    420
tcctatctga cttggggcat actgcaggaa agagtgatga ctggcagcta cggggccaca    480
gccacatcac caggagagca tttcacagac tcccagtttc tggtgctgat gaaccgtgtg    540
ctggcgctgg ttgtggcagg cctctactgt gtcctgcgca agcagccccg tcatggtgca    600
cccatgtacc ggtactcctt tgccagtctg tcaaatgtgc ttagcagctg gtgccagtat    660
gaagcactta agttcgtcag cttccctacc caggtgctgg cgaaggcctc caaggtgatc    720
cctgtcatga tgatgggaaa gctggtgtcc cggcgcagct atgaacactg ggaatacctg    780
actgccggcc tcatctccat tggagtgagc atgtttcttc tatccagtgg accagagcct    840
agaagctctc cagccaccac actctctggc ttggtcctac tggcaggcta tattgctttc    900
gacagcttca cctcaaattg gcaggatgcc ctgtttgcct ataagatgtc atcggtgcag    960
atgatgtttg ggtcaattt attctcctgt cttttcacag taggctcact actggaacag   1020
ggggccctac tggagggggc acgcttcatg ggcggcaca gtgagtttgc gctccatgct   1080
ctcctcctct ccatctgctc cgcctttggg cagctcttca tcttctacac cattggacaa   1140
tttggagctg ctgtcttcac tatcatcatg actctacgcc aggctattgc catcctcctc   1200
tcctgcctcc tctatggcca tactgtcact gtggtggggg gactgggagt agctgtggtc   1260
ttcactgccc tcctactcag agtctatgcc cggggccgga agcagcgggg aaagaaggct   1320
gtgcccactg agcccccagt acagaaggtg tgagcagtgc agtaaagacc ctcatcttct   1380
gaggcactgg ctcagtatca gcatacagca gaggattgga gccctggagg cagcctcttt   1440
tgccttaaaa gcccccactt catggaaatg acagctgtgg gtgtttggtt agaggtgacc   1500
cagagctcct cccccaatct ctgaaatctt gctggtggcc aagcaaacca gcaccagggc   1560
tttgctcata gcacgcaccc ttgaggctac caggcaccag ctgggaagag aatttacagg   1620
tcctgcagtt cccctagggg ccagtgagaa tggtgctgtg ccagaaggga caaaggcccc   1680
cagcccagtt ggggccc                                                 1697
```

```
<210> SEQ ID NO 265
<211> LENGTH: 159
<212> TYPE: DNA
<213> ORGANISM: Mouse
<220> FEATURE:
<221> NAME/KEY: unsure
<222> LOCATION: (94)...(94)
<221> NAME/KEY: unsure
<222> LOCATION: (97)...(97)
<221> NAME/KEY: unsure
<222> LOCATION: (107)...(107)

<400> SEQUENCE: 265

gttttcttct ccaggctgaa gacctgaacg tcaagttgga aggggagcct tccatgcgga     60
aaccaaagca gcggccgcgg ccggagcccc tcancanccc caccaangcg ggcactttca    120
tcgcccctcc tgtctactcc aacatcaccc cttaccaga                          159
```

-continued

<210> SEQ ID NO 266
<211> LENGTH: 292
<212> TYPE: DNA
<213> ORGANISM: Mouse

<400> SEQUENCE: 266
gtggggtccc agacttgcca accaaagggc cattcctggt atatggttct ggcttcagct 60
ctggtggcat ggactatggt atggttggtg gcaaggaggc tgggaccgag tctcgcttca 120
aacagtggac ctcaatgatg gaagggctgc catctgtggc cacacaagaa gccaccatgc 180
acaaaaacgg cgctatagtg gcccctggta agacccgagg aggttcacca tacaaccagt 240
ttgatataat cccaggtgac acactgggtg gccatacggg tcctgctggt ga 292

<210> SEQ ID NO 267
<211> LENGTH: 339
<212> TYPE: DNA
<213> ORGANISM: Mouse

<400> SEQUENCE: 267
ccactgacct tcccagaagg tgacagccgg cggcggatgt tgtcaaggag ccgagatagt 60
ccagcagtgc ctcggtaccc agaagacggg ctgtctcccc ccaaaagacg gcgacattcg 120
atgagaagtc accacagtga tctcacattt tgcgagatta tcctgatgga gatggagtcc 180
catgatgcag cctggccttt cctagagcct gtgaaccctc gcttggtgag tggataccga 240
cgtgtcatca agaaccctat ggatttttcc accatgcgag aacgcctgct ccgtggaggg 300
tacactagct cagaagagtt tgcagctgat gctctgctg 339

<210> SEQ ID NO 268
<211> LENGTH: 153
<212> TYPE: DNA
<213> ORGANISM: Mouse

<400> SEQUENCE: 268
ctgaagttct ctcatccttg tctggaagac cataatagtt actgcattaa tggagcatgt 60
gcattccacc atgagctgaa gcaagccatt tgcagatgct ttactggtta tacgggacaa 120
cgatgtgagc atttgaccct aacttcgtat gct 153

<210> SEQ ID NO 269
<211> LENGTH: 153
<212> TYPE: DNA
<213> ORGANISM: Mouse

<400> SEQUENCE: 269
ttgaagttct cacacctttg cctggaagat cataacagtt actgcatcaa cggtgcttgt 60
gcattccacc atgagctaga gaaagccatc tgcaggtgtt ttactggtta tactggagaa 120
aggtgtgagc acttgacttt aacttcatat gct 153

<210> SEQ ID NO 270
<211> LENGTH: 288
<212> TYPE: DNA
<213> ORGANISM: Mouse

<400> SEQUENCE: 270
gcggccgcgc tgctcctgct gctgctggcg ctgtacaccg cgcgtgtgga cgggtccaaa 60
tgcaagtgct cccggaaggg acccaagatc cgctacagcg acgtgaagaa gctggaaatg 120
aagccaaagt acccgcactg cgaggagaag atggttatca tcaccaccaa gagcgtgtcc 180

-continued aggtaccgag gtcaggagca ctgcctgcac cccaagctgc agagcaccaa gcgcttcatc 240
aagtggtaca acgcctggaa cgagaagcgc agggtctacg aagaatag 288

<210> SEQ ID NO 271
<211> LENGTH: 234
<212> TYPE: DNA
<213> ORGANISM: Mouse

<400> SEQUENCE: 271
tccaagtgta agtgttcccg gaaggggccc aagatccgct acagcgacgt gaagaagctg 60
gaaatgaagc caaagtaccc acactgcgag gagaagatgg ttatcgtcac caccaagagc 120
atgtccaggt accggggcca ggagcactgc ctgcacccta agctgcagag caccaaacgc 180
ttcatcaagt ggtacaatgc ctggaacgag aagcgcaggg tctacgaaga atag 234

<210> SEQ ID NO 272
<211> LENGTH: 234
<212> TYPE: DNA
<213> ORGANISM: Mouse

<400> SEQUENCE: 272
tccaaatgca agtgctcccg gaagggaccc aagatccgct acagcgacgt gaagaagctg 60
gaaatgaagc caaagtaccc gcactgcgag gagaagatgg ttatcatcac caccaagagc 120
gtgtccaggt accgaggtca ggagcactgc ctgcacccca agctgcagag caccaagcgc 180
ttcatcaagt ggtacaacgc ctggaacgag aagcgcaggg tctacgaaga atag 234

<210> SEQ ID NO 273
<211> LENGTH: 645
<212> TYPE: DNA
<213> ORGANISM: Mouse

<400> SEQUENCE: 273
atgctgtcgc tccgctcctt gcttccacac ctgggactgt tcctgtgcct ggctctgcac 60
ttatccccct ccctctctgc cagtgataat gggtcctgcg tggtccttga taacatctac 120
acctccgaca tcttggaaat cagcactatg gctaacgtct ctggtgggga tgtaacctat 180
acagtgacgg tccccgtgaa cgattcagtc agtgccgtga tcctgaaagc agtgaaggag 240
gacgacagcc cagtgggcac ctggagtgga acatatgaga agtgcaacga cagcagtgtc 300
tactataact tgacatccca aagccagtcg gtcttccaga caaactggac agttcctact 360
tccgaggatg tgactaaagt caacctgcag gtcctcatcg tcgtcaatcg cacagcctca 420
aagtcatccg tgaaaatgga acaagtacaa ccctcagcct caacccctat tcctgagagt 480
tctgagacca gccagaccat aaacacgact ccaactgtga acacagccaa gactacagcc 540
aaggacacag ccaacaccac agccgtgacc acagccaata ccacagccaa taccacagcc 600
gtgaccacag ccaagaccac agccaaaagc ctggccatcc gcact 645

<210> SEQ ID NO 274
<211> LENGTH: 63
<212> TYPE: DNA
<213> ORGANISM: Mouse

<400> SEQUENCE: 274
gggtacagtg atggttacca agtgtgtagt aggttcggaa gcaaagtgcc tcagtttctg 60
aac 63

-continued

<210> SEQ ID NO 275
<211> LENGTH: 388
<212> TYPE: PRT
<213> ORGANISM: Rat

<400> SEQUENCE: 275

```
Met Gly Leu Glu Pro Ser Trp Tyr Leu Leu Leu Cys Leu Ala Val Ser
 1               5                  10                  15

Gly Ala Ala Gly Thr Asp Pro Pro Thr Ala Pro Thr Thr Ala Glu Arg
            20                  25                  30

Gln Arg Gln Pro Thr Asp Ile Ile Leu Asp Cys Phe Leu Val Thr Glu
        35                  40                  45

Asp Arg His Arg Gly Ala Phe Ala Ser Ser Gly Asp Arg Glu Arg Ala
    50                  55                  60

Leu Leu Val Leu Lys Gln Val Pro Val Leu Asp Asp Gly Ser Leu Glu
65                  70                  75                  80

Gly Ile Thr Asp Phe Gln Gly Ser Thr Glu Thr Lys Gln Asp Ser Pro
                85                  90                  95

Val Ile Phe Glu Ala Ser Val Asp Leu Val Gln Ile Pro Gln Ala Glu
            100                 105                 110

Ala Leu Leu His Ala Asp Cys Ser Gly Lys Ala Val Thr Cys Glu Ile
        115                 120                 125

Ser Lys Tyr Phe Leu Gln Ala Arg Gln Glu Ala Thr Phe Glu Lys Ala
    130                 135                 140

His Trp Phe Ile Ser Asn Met Gln Val Ser Arg Gly Gly Pro Ser Val
145                 150                 155                 160

Ser Met Val Met Lys Thr Leu Arg Asp Ala Glu Val Gly Ala Val Arg
                165                 170                 175

His Pro Thr Leu Asn Leu Pro Leu Ser Ala Gln Gly Thr Val Lys Thr
            180                 185                 190

Gln Val Glu Phe Gln Val Thr Ser Glu Thr Gln Thr Leu Asn His Leu
        195                 200                 205

Leu Gly Ser Ser Val Ser Leu His Cys Ser Phe Ser Met Ala Pro Asp
    210                 215                 220

Leu Asp Leu Thr Gly Val Glu Trp Arg Leu Gln His Lys Gly Ser Gly
225                 230                 235                 240

Gln Leu Val Tyr Ser Trp Lys Thr Gly Gln Gly Gln Ala Lys Arg Lys
                245                 250                 255

Gly Ala Thr Leu Glu Pro Glu Glu Leu Leu Arg Ala Gly Asn Ala Ser
            260                 265                 270

Leu Thr Leu Pro Asn Leu Thr Leu Lys Asp Glu Gly Thr Tyr Ile Cys
        275                 280                 285

Gln Ile Ser Thr Ser Leu Tyr Gln Ala Gln Gln Ile Met Pro Leu Asn
    290                 295                 300

Ile Leu Ala Pro Pro Lys Val Gln Leu His Leu Ala Asn Lys Asp Pro
305                 310                 315                 320

Leu Pro Ser Leu Val Cys Ser Ile Ala Gly Tyr Tyr Pro Leu Asp Val
                325                 330                 335

Gly Val Thr Trp Ile Arg Glu Glu Leu Gly Gly Ile Pro Ala Gln Val
            340                 345                 350

Ser Gly Ala Ser Phe Ser Ser Leu Arg Gln Ser Thr Met Gly Thr Tyr
        355                 360                 365

Ser Ile Ser Ser Thr Val Met Ala Asp Pro Gly Pro Thr Gly Ala Thr
    370                 375                 380
```

-continued

```
Tyr Thr Cys Gln
385


<210> SEQ ID NO 276
<211> LENGTH: 151
<212> TYPE: PRT
<213> ORGANISM: Rat

<400> SEQUENCE: 276

Met Ala Glu Pro Trp Ala Gly Gln Phe Leu Gln Ala Leu Pro Ala Thr
 1               5                  10                  15

Val Leu Gly Ala Leu Gly Thr Leu Gly Ser Glu Phe Leu Arg Glu Trp
            20                  25                  30

Glu Thr Gln Asp Met Arg Val Thr Leu Phe Lys Leu Leu Leu Leu Trp
        35                  40                  45

Leu Val Leu Ser Leu Leu Gly Ile Gln Leu Ala Trp Gly Phe Tyr Gly
    50                  55                  60

Asn Thr Val Thr Gly Leu Tyr His Arg Pro Gly Lys Trp Gln Gln Met
65                  70                  75                  80

Lys Leu Ser Lys Leu Thr Glu Asn Lys Gly Arg Gln Gln Glu Lys Gly
                85                  90                  95

Leu Gln Arg Tyr Arg Trp Val Cys Trp Leu Leu Cys Cys Thr Leu Leu
            100                 105                 110

Leu Ser Arg Pro Leu Arg Gln Leu Gln Arg Ala Trp Val Gly Gly Leu
        115                 120                 125

Glu Tyr His Asp Ala Pro Arg Val Ser Leu His Cys Pro Gln Pro Cys
    130                 135                 140

Leu Gln Gln Arg Gln Val Leu
145                 150


<210> SEQ ID NO 277
<211> LENGTH: 163
<212> TYPE: PRT
<213> ORGANISM: Rat

<400> SEQUENCE: 277

Met Pro Leu Val Thr Thr Leu Phe Tyr Ala Cys Phe Tyr His Tyr Thr
 1               5                  10                  15

Glu Ser Glu Gly Thr Phe Ser Ser Pro Val Asn Leu Lys Lys Thr Phe
            20                  25                  30

Lys Ile Pro Asp Arg Gln Tyr Val Leu Thr Ala Leu Ala Ala Arg Ala
        35                  40                  45

Lys Leu Arg Ala Trp Asn Asp Val Asp Ala Leu Phe Thr Thr Lys Asn
    50                  55                  60

Trp Leu Gly Tyr Thr Lys Lys Arg Ala Pro Ile Gly Phe His Arg Val
65                  70                  75                  80

Val Glu Ile Leu His Lys Asn Ser Ala Pro Val Gln Ile Leu Gln Glu
                85                  90                  95

Tyr Val Asn Leu Val Glu Asp Val Asp Thr Lys Leu Asn Leu Ala Thr
            100                 105                 110

Lys Phe Lys Cys His Asp Val Val Ile Asp Thr Cys Arg Asp Leu Lys
        115                 120                 125

Asp Arg Gln Gln Leu Leu Ala Tyr Arg Ser Lys Val Asp Lys Gly Ser
    130                 135                 140

Ala Glu Glu Glu Lys Ile Asp Val Ile Leu Ser Ser Ser Gln Ile Arg
145                 150                 155                 160
```

-continued

```
Trp Lys Asn


<210> SEQ ID NO 278
<211> LENGTH: 330
<212> TYPE: PRT
<213> ORGANISM: Rat

<400> SEQUENCE: 278

Met Ala Gly Trp Ala Gly Ala Glu Leu Ser Val Leu Asn Pro Leu Arg
 1               5                  10                  15

Ala Leu Trp Leu Leu Leu Ala Ala Ala Phe Leu Leu Ala Leu Leu Leu
            20                  25                  30

Gln Leu Ala Pro Ala Arg Leu Leu Pro Ser Cys Ala Leu Phe Gln Asp
        35                  40                  45

Leu Ile Arg Tyr Gly Lys Thr Lys Gln Ser Gly Ser Arg Arg Pro Ala
    50                  55                  60

Val Cys Arg Ala Phe Asp Val Pro Lys Arg Tyr Phe Ser His Phe Tyr
65                  70                  75                  80

Val Val Ser Val Leu Trp Asn Gly Ser Leu Leu Trp Phe Leu Ser Gln
                85                  90                  95

Ser Leu Phe Leu Gly Ala Pro Phe Pro Ser Trp Leu Trp Ala Leu Leu
            100                 105                 110

Arg Thr Leu Gly Val Thr Gln Phe Gln Ala Leu Gly Met Glu Ser Lys
        115                 120                 125

Ala Ser Arg Ile Gln Ala Gly Glu Leu Ala Leu Ser Thr Phe Leu Val
    130                 135                 140

Leu Val Phe Leu Trp Val His Ser Leu Arg Arg Leu Phe Glu Cys Phe
145                 150                 155                 160

Tyr Val Ser Val Phe Ser Asn Thr Ala Ile His Val Val Gln Tyr Cys
                165                 170                 175

Phe Gly Leu Val Tyr Tyr Val Leu Val Gly Leu Thr Val Leu Ser Gln
            180                 185                 190

Val Pro Met Asn Asp Lys Asn Val Tyr Ala Leu Gly Lys Asn Leu Leu
        195                 200                 205

Leu Gln Ala Arg Trp Phe His Ile Leu Gly Met Met Met Phe Phe Trp
    210                 215                 220

Ser Ser Ala His Gln Tyr Lys Cys His Val Ile Leu Ser Asn Leu Arg
225                 230                 235                 240

Arg Asn Lys Lys Gly Val Val Ile His Cys Gln His Arg Ile Pro Phe
                245                 250                 255

Gly Asp Trp Phe Glu Tyr Val Ser Ser Ala Asn Tyr Leu Ala Glu Leu
            260                 265                 270

Met Ile Tyr Ile Ser Met Ala Val Thr Phe Gly Leu His Asn Val Thr
        275                 280                 285

Trp Trp Leu Val Val Thr Tyr Val Phe Phe Ser Gln Ala Leu Ser Ala
    290                 295                 300

Phe Phe Asn His Arg Phe Tyr Lys Ser Thr Phe Val Ser Tyr Pro Lys
305                 310                 315                 320

His Arg Lys Ala Phe Leu Pro Phe Leu Phe
                325                 330


<210> SEQ ID NO 279
<211> LENGTH: 61
<212> TYPE: PRT
<213> ORGANISM: Rat
```

-continued

<400> SEQUENCE: 279

```
Met Glu Asn Ile Tyr Tyr Thr Asn Leu Ile Thr Ile Leu Gly Asn Lys
 1               5                  10                  15

His Ala Asn Gln Met Glu Leu Asn Leu Gln Ala Leu Ile Leu Ser Pro
            20                  25                  30

Trp Phe Ala Val Cys Ala Pro Pro Gly Phe Ala Arg Asp Gln Ala Val
        35                  40                  45

Arg Gly Leu Ala Leu Ala Gly Arg Arg Ile Thr Val Val
    50                  55                  60
```

<210> SEQ ID NO 280
<211> LENGTH: 105
<212> TYPE: PRT
<213> ORGANISM: Rat

<400> SEQUENCE: 280

```
Met Leu Arg Arg Gln Leu Val Trp Trp His Leu Leu Ala Leu Leu Phe
 1               5                  10                  15

Leu Pro Phe Cys Leu Cys Gln Asp Glu Tyr Met Glu Ser Pro Gln Ala
            20                  25                  30

Gly Gly Leu Pro Pro Asp Cys Ser Lys Cys Cys His Gly Asp Tyr Gly
        35                  40                  45

Phe Arg Gly Tyr Gln Gly Pro Pro Gly Pro Pro Gly Pro Pro Gly Ile
    50                  55                  60

Pro Gly Asn His Gly Asn Asn Gly Asn Asn Gly Ala Thr Gly His Glu
65                  70                  75                  80

Gly Ala Lys Gly Glu Lys Gly Asp Lys Gly Asp Leu Gly Pro Arg Gly
                85                  90                  95

Glu Arg Gly Gln His Gly Pro Lys Gly
            100                 105
```

<210> SEQ ID NO 281
<211> LENGTH: 27
<212> TYPE: PRT
<213> ORGANISM: Mouse

<400> SEQUENCE: 281

```
Met Leu Lys Ala Ser Leu His Ile Leu Phe Leu Gly Ile Leu Asn Val
 1               5                  10                  15

Pro Ile Val Asp Thr Ser Thr Lys Thr Gly Val
            20                  25
```

<210> SEQ ID NO 282
<211> LENGTH: 169
<212> TYPE: PRT
<213> ORGANISM: Mouse

<400> SEQUENCE: 282

```
Met Ser Gly Leu Arg Thr Leu Leu Gly Leu Gly Leu Leu Val Ala Gly
 1               5                  10                  15

Ser Arg Leu Pro Arg Val Ile Ser Gln Gln Ser Val Cys Arg Ala Arg
            20                  25                  30

Pro Ile Trp Trp Gly Thr Gln Arg Arg Gly Ser Glu Thr Met Ala Gly
        35                  40                  45

Ala Ala Val Lys Tyr Leu Ser Gln Glu Glu Ala Gln Ala Val Asp Gln
    50                  55                  60

Glu Leu Phe Asn Glu Tyr Gln Phe Ser Val Asp Gln Leu Met Glu Leu
```

-continued

```
65                  70                  75                  80

Ala Gly Leu Ser Cys Ala Thr Ala Ile Ala Lys Ala Tyr Pro Pro Thr
                85                  90                  95

Ser Met Ser Lys Ser Pro Pro Thr Val Leu Val Ile Cys Gly Pro Gly
            100                 105                 110

Asn Asn Gly Gly Asp Gly Leu Val Cys Ala Arg His Leu Lys Leu Phe
        115                 120                 125

Gly Tyr Gln Pro Thr Ile Tyr Tyr Pro Lys Arg Pro Asn Lys Pro Leu
    130                 135                 140

Phe Thr Gly Leu Val Thr Gln Cys Gln Lys Met Asp Ile Pro Phe Leu
145                 150                 155                 160

Gly Glu Met Pro Pro Glu Asp Gly Met
                165


<210> SEQ ID NO 283
<211> LENGTH: 61
<212> TYPE: PRT
<213> ORGANISM: Mouse

<400> SEQUENCE: 283

Met Glu Lys Gln Met Asp Ala Ser Val Ser Val Ile Phe Gly Ser Ile
 1               5                  10                  15

Val Ile Ser Ala Phe Leu Tyr Leu Ser Leu Ala Gly Pro Trp Ala Val
            20                  25                  30

Thr Val Thr Gln Met Arg Thr Ile Ile Ile Thr Met Asp Gln Leu Arg
        35                  40                  45

Asp Ala Leu Ile Leu Asp Gln Leu Lys Val Ala Val Ser
    50                  55                  60


<210> SEQ ID NO 284
<211> LENGTH: 131
<212> TYPE: PRT
<213> ORGANISM: Mouse

<400> SEQUENCE: 284

Met Ala Pro Ser Leu Trp Lys Gly Leu Val Gly Val Gly Leu Phe Ala
 1               5                  10                  15

Leu Ala His Ala Ala Phe Ser Ala Ala Gln His Arg Ser Tyr Met Arg
            20                  25                  30

Leu Thr Glu Lys Glu Asp Glu Ser Leu Pro Ile Asp Ile Val Leu Gln
        35                  40                  45

Thr Leu Leu Ala Phe Ala Val Thr Cys Tyr Gly Ile Val His Ile Ala
    50                  55                  60

Gly Glu Phe Lys Asp Met Asp Ala Thr Ser Glu Leu Lys Asn Lys Thr
65                  70                  75                  80

Phe Asp Thr Leu Arg Asn His Pro Ser Phe Tyr Val Phe Asn His Arg
                85                  90                  95

Gly Arg Val Leu Phe Arg Pro Ser Asp Ala Thr Asn Ser Ser Asn Leu
            100                 105                 110

Asp Ala Leu Ser Ser Asn Thr Ser Leu Lys Leu Arg Lys Phe Asp Ser
        115                 120                 125

Leu Arg Arg
    130


<210> SEQ ID NO 285
<211> LENGTH: 78
<212> TYPE: PRT
```

-continued

<213> ORGANISM: Mouse

<400> SEQUENCE: 285

Gly Thr Arg Lys Pro Leu Pro Met Glu Ala His Ser Arg Arg Glu Lys
1 5 10 15

Ala Ser Gly Leu Arg Leu Ala Trp His Tyr Glu Cys Ser Gly Val Ser
20 25 30

Val Trp Trp Met Cys Val Leu Gly Trp Leu Ser Phe Leu Val Phe Leu
35 40 45

Leu Phe Ser Leu Val Cys Ser Phe Pro Ser Pro Ile Asn His Ser His
50 55 60

Met Leu Pro Cys Leu Phe Leu Arg Gly Gly Gly Ser Asn Val
65 70 75

<210> SEQ ID NO 286
<211> LENGTH: 206
<212> TYPE: PRT
<213> ORGANISM: Mouse

<400> SEQUENCE: 286

Met Leu Pro Pro Ala Ile His Leu Ser Leu Ile Pro Leu Leu Cys Ile
1 5 10 15

Leu Met Arg Asn Cys Leu Ala Phe Lys Asn Asp Ala Thr Glu Ile Leu
20 25 30

Tyr Ser His Val Val Lys Pro Val Pro Ala His Pro Ser Ser Asn Ser
35 40 45

Thr Leu Asn Gln Ala Arg Asn Gly Gly Arg His Phe Ser Ser Thr Gly
50 55 60

Leu Asp Arg Asn Ser Arg Val Gln Val Gly Cys Arg Glu Leu Arg Ser
65 70 75 80

Thr Lys Tyr Ile Ser Asp Gly Gln Cys Thr Ser Ile Ser Pro Leu Lys
85 90 95

Glu Leu Val Cys Ala Gly Glu Cys Leu Pro Leu Pro Val Leu Pro Asn
100 105 110

Trp Ile Gly Gly Gly Tyr Gly Thr Lys Tyr Trp Ser Arg Arg Ser Ser
115 120 125

Gln Glu Trp Arg Cys Val Asn Asp Lys Thr Arg Thr Gln Arg Ile Gln
130 135 140

Leu Gln Cys Gln Asp Gly Ser Thr Arg Thr Tyr Lys Ile Thr Val Val
145 150 155 160

Thr Ala Cys Lys Cys Lys Arg Tyr Thr Arg Gln His Asn Glu Ser Ser
165 170 175

His Asn Phe Glu Ser Val Ser Pro Ala Lys Pro Ala Gln His His Arg
180 185 190

Glu Arg Lys Arg Ala Ser Lys Ser Ser Lys His Ser Leu Ser
195 200 205

<210> SEQ ID NO 287
<211> LENGTH: 169
<212> TYPE: PRT
<213> ORGANISM: Mouse

<400> SEQUENCE: 287

Met Ser Gly Leu Arg Thr Leu Leu Gly Leu Gly Leu Leu Val Ala Gly
1 5 10 15

Ser Arg Leu Pro Arg Val Ile Ser Gln Gln Ser Val Cys Arg Ala Arg
20 25 30

-continued

Pro Ile Trp Trp Gly Thr Gln Arg Arg Gly Ser Glu Thr Met Ala Gly
35 40 45

Ala Ala Val Lys Tyr Leu Ser Gln Glu Glu Ala Gln Ala Val Asp Gln
50 55 60

Glu Leu Phe Asn Glu Tyr Gln Phe Ser Val Asp Gln Leu Met Glu Leu
65 70 75 80

Ala Gly Leu Ser Cys Ala Thr Ala Ile Ala Lys Ala Tyr Pro Pro Thr
85 90 95

Ser Met Ser Lys Ser Pro Pro Thr Val Leu Val Ile Cys Gly Pro Gly
100 105 110

Asn Asn Gly Gly Asp Gly Leu Val Cys Ala Arg His Leu Lys Leu Phe
115 120 125

Gly Tyr Gln Pro Thr Ile Tyr Tyr Pro Lys Arg Pro Asn Lys Pro Leu
130 135 140

Phe Thr Gly Leu Val Thr Gln Cys Gln Lys Met Asp Ile Pro Phe Leu
145 150 155 160

Gly Glu Met Pro Pro Glu Asp Gly Met
165

<210> SEQ ID NO 288
<211> LENGTH: 114
<212> TYPE: PRT
<213> ORGANISM: Mouse

<400> SEQUENCE: 288

Met Ser Val Thr Ile Gly Arg Leu Ala Leu Phe Leu Ile Gly Ile Leu
1 5 10 15

Leu Cys Pro Val Ala Pro Ser Leu Thr Arg Ser Trp Pro Gly Pro Asp
20 25 30

Thr Cys Ser Leu Phe Leu Gln His Ser Leu Ser Leu Ser Leu Arg Leu
35 40 45

Gly Gln Ser Leu Glu Gly Gly Leu Ser Val Cys Phe His Val Cys Ile
50 55 60

His Ala Cys Glu Cys Val Ala Cys Cys Arg Val Leu Trp Asp Pro Lys
65 70 75 80

Pro Arg Gly Ser Ser Leu Cys Arg Trp Val Leu Gly Ser Ile Thr Cys
85 90 95

Leu Phe Met Tyr Glu Val Gly Gly Trp Thr Gln Gly Gly Leu Ile Val
100 105 110

Ser Leu

<210> SEQ ID NO 289
<211> LENGTH: 46
<212> TYPE: PRT
<213> ORGANISM: Mouse

<400> SEQUENCE: 289

Met His Tyr Pro Cys Leu Ala Cys Leu Phe Val Asn Val His Trp Cys
1 5 10 15

Phe Ala Trp Met Cys Ile Leu Val Lys Met Ser Glu Leu Leu Glu Leu
20 25 30

Glu Leu Glu Thr Met Val Ser Cys Leu Val Asp Val Gly Asn
35 40 45

<210> SEQ ID NO 290
<211> LENGTH: 199

-continued

<212> TYPE: PRT
<213> ORGANISM: Mouse

<400> SEQUENCE: 290

Met Val Leu Pro Thr Val Leu Ile Leu Leu Leu Ser Trp Ala Ala Gly
1 5 10 15

Leu Gly Gly Glu Thr Arg Pro Arg Ala Ala Thr Glu Arg Arg Ser Val
20 25 30

Gly Pro Ser Ala Arg Arg Gly Ala Gly Pro Arg Val Ser Gly Leu Leu
35 40 45

Gly Phe Cys Gln Leu Ser Gln Leu Ala Ser Ala Asp Pro Glu Arg Arg
50 55 60

Ser Pro Arg Ala Ile Val Pro Arg Ala Pro Arg Pro Arg Ser Arg Arg
65 70 75 80

Arg Pro Cys Leu Pro Gly Phe Ser Arg Arg Phe Pro Arg Glu Arg Arg
85 90 95

Ser Pro Gly Gln Pro Pro Ser Arg Thr Pro Gln Pro Pro Gln Pro Cys
100 105 110

Arg Gly Pro Ser Pro Gly Thr Ala Gln Thr Arg Ser Asn Leu Arg Gly
115 120 125

Trp Gln Arg Gly Gly Ser Ile Val Leu Gln Ala Ser Glu Arg Thr Arg
130 135 140

Ala Gly Cys Arg Thr Pro Val Cys Val Ser His Pro Ser Ala Phe Pro
145 150 155 160

Pro Pro Arg Ala Leu Phe Gly Val Phe Val Ala Ser Ala Pro Glu Val
165 170 175

Val Cys Val Cys Val Ser Val Val Leu Ser Val Cys Leu Leu Ser Pro
180 185 190

Arg Gly Lys Thr Leu Val Asp
195

<210> SEQ ID NO 291
<211> LENGTH: 568
<212> TYPE: PRT
<213> ORGANISM: Rat

<400> SEQUENCE: 291

Met Glu Leu Leu Tyr Trp Cys Leu Leu Cys Leu Leu Leu Pro Leu Thr
1 5 10 15

Ser Arg Thr Gln Lys Leu Pro Thr Arg Asp Glu Glu Leu Phe Gln Met
20 25 30

Gln Ile Arg Asp Lys Ala Leu Phe His Asp Ser Ser Val Ile Pro Asp
35 40 45

Gly Ala Glu Ile Ser Ser Tyr Leu Phe Arg Asp Thr Pro Arg Arg Tyr
50 55 60

Phe Phe Met Val Glu Glu Asp Asn Thr Pro Leu Ser Val Thr Val Thr
65 70 75 80

Pro Cys Asp Ala Pro Leu Glu Trp Lys Leu Ser Leu Gln Glu Leu Pro
85 90 95

Glu Glu Ser Ser Ala Asp Gly Ser Gly Asp Pro Glu Pro Leu Asp Gln
100 105 110

Gln Lys Gln Gln Met Thr Asp Val Glu Gly Thr Glu Leu Phe Ser Tyr
115 120 125

Lys Gly Asn Asp Val Glu Tyr Phe Leu Ser Ser Ser Ser Pro Ser Gly
130 135 140

-continued

```
Leu Tyr Gln Leu Glu Leu Leu Ser Thr Glu Lys Asp Thr His Phe Lys
145                 150                 155                 160

Val Tyr Ala Thr Thr Thr Pro Glu Ser Asp Gln Pro Tyr Pro Asp Leu
                165                 170                 175

Pro Tyr Asp Pro Arg Val Asp Val Thr Ser Ile Gly Arg Thr Thr Val
            180                 185                 190

Thr Leu Ala Trp Lys Gln Ser Pro Thr Ala Ser Met Leu Lys Gln Pro
        195                 200                 205

Ile Glu Tyr Cys Val Val Ile Asn Lys Glu His Asn Phe Lys Ser Leu
    210                 215                 220

Cys Ala Ala Glu Thr Lys Met Ser Ala Asp Asp Ala Phe Met Val Ala
225                 230                 235                 240

Pro Lys Pro Gly Leu Asp Phe Ser Pro Phe Asp Phe Ala His Phe Gly
                245                 250                 255

Phe Pro Thr Asp Asn Leu Gly Lys Asp Arg Ser Phe Leu Ala Lys Pro
            260                 265                 270

Ser Pro Lys Val Gly Arg His Val Tyr Trp Arg Pro Lys Val Asp Ile
        275                 280                 285

Lys Lys Ile Cys Ile Gly Ser Lys Asn Ile Phe Thr Val Ser Asp Leu
    290                 295                 300

Lys Pro Asn Thr Gln Tyr Tyr Phe Asp Val Phe Met Val Asn Thr Asn
305                 310                 315                 320

Thr Asn Met Asn Thr Ala Phe Val Gly Ala Phe Ala Arg Thr Lys Glu
                325                 330                 335

Glu Ala Lys Gln Lys Thr Val Glu Leu Lys Asp Gly Arg Val Thr Asp
            340                 345                 350

Val Val Val Lys Arg Lys Gly Lys Lys Phe Leu Arg Phe Ala Pro Val
        355                 360                 365

Ser Ser His Gln Lys Val Thr Leu Phe Ile His Ser Cys Met Asp Thr
    370                 375                 380

Val Gln Val Gln Val Arg Arg Asp Gly Lys Leu Leu Leu Ser Gln Asn
385                 390                 395                 400

Val Glu Gly Ile Arg Gln Phe Gln Leu Arg Gly Lys Pro Lys Gly Lys
                405                 410                 415

Tyr Leu Ile Arg Leu Lys Gly Asn Lys Lys Gly Ala Ser Met Leu Lys
            420                 425                 430

Ile Leu Ala Thr Thr Arg Pro Ser Lys His Ala Phe Pro Ser Leu Pro
        435                 440                 445

Asp Asp Thr Arg Ile Lys Ala Phe Asp Lys Leu Arg Thr Cys Ser Ser
    450                 455                 460

Val Thr Val Ala Trp Leu Gly Thr Gln Glu Arg Arg Lys Phe Cys Ile
465                 470                 475                 480

Tyr Arg Lys Glu Val Gly Gly Asn Tyr Ser Glu Glu Gln Lys Arg Arg
                485                 490                 495

Glu Arg Asn Gln Cys Leu Gly Pro Asp Thr Arg Lys Lys Ser Glu Lys
            500                 505                 510

Val Leu Cys Lys Tyr Phe His Ser Gln Asn Leu Gln Lys Ala Val Thr
        515                 520                 525

Thr Glu Thr Ile Arg Asp Leu Gln Pro Gly Lys Ser Tyr Leu Leu Asp
    530                 535                 540

Val Tyr Val Val Gly His Gly Gly His Ser Val Lys Tyr Gln Ser Lys
545                 550                 555                 560

Leu Val Lys Thr Arg Lys Val Cys
```

-continued

565

<210> SEQ ID NO 292
<211> LENGTH: 123
<212> TYPE: PRT
<213> ORGANISM: Mouse

<400> SEQUENCE: 292

Met Leu Thr Glu Pro Ala Gln Leu Phe Val His Lys Lys Asn Gln Pro
1 5 10 15

Pro Ser His Ser Ser Leu Arg Leu His Phe Arg Thr Leu Ala Gly Ala
20 25 30

Leu Ala Leu Ser Ser Thr Gln Met Ser Trp Gly Leu Gln Ile Leu Pro
35 40 45

Cys Leu Ser Leu Ile Leu Leu Leu Trp Asn Gln Val Pro Gly Leu Glu
50 55 60

Gly Gln Glu Phe Arg Phe Gly Ser Cys Gln Val Thr Gly Val Val Leu
65 70 75 80

Pro Glu Leu Trp Glu Ala Phe Trp Thr Val Lys Asn Thr Val Gln Thr
85 90 95

Gln Asp Asp Ile Thr Ser Ile Arg Leu Leu Lys Pro Gln Val Leu Arg
100 105 110

Asn Val Ser Val Ile Arg Trp Glu Gly Asp Ser
115 120

<210> SEQ ID NO 293
<211> LENGTH: 66
<212> TYPE: PRT
<213> ORGANISM: Mouse

<400> SEQUENCE: 293

Met Asp Val Trp Ser Gly Leu Pro Leu Glu Thr Leu Trp Ile Tyr Glu
1 5 10 15

Ala Val Leu Pro Trp Leu Leu Met Gly Gln Gly His Ala Trp Val Cys
20 25 30

Gly Pro Ile Ala Leu Trp Val Phe Val Asn Val Pro Gly Leu Cys Tyr
35 40 45

His Gln Lys Pro Phe Arg Cys Pro Trp Ser Gly Leu Leu Pro Glu Ala
50 55 60

Leu Cys
65

<210> SEQ ID NO 294
<211> LENGTH: 294
<212> TYPE: PRT
<213> ORGANISM: Rat

<400> SEQUENCE: 294

Met Thr Val Phe Arg Lys Val Thr Thr Met Ile Ser Trp Met Leu Leu
1 5 10 15

Ala Cys Ala Leu Pro Cys Ala Ala Asp Pro Met Leu Gly Ala Phe Ala
20 25 30

Arg Arg Asp Phe Gln Lys Gly Gly Pro Gln Leu Val Cys Ser Leu Pro
35 40 45

Gly Pro Gln Gly Pro Pro Gly Pro Pro Gly Ala Pro Gly Ser Ser Gly
50 55 60

Met Val Gly Arg Met Gly Phe Pro Gly Lys Asp Gly Gln Asp Gly Gln
65 70 75 80

-continued

```
Asp Gly Asp Arg Gly Asp Ser Gly Glu Glu Gly Pro Pro Gly Arg Thr
                85                  90                  95

Gly Asn Arg Gly Lys Gln Gly Pro Lys Gly Lys Ala Gly Ala Ile Gly
            100                 105                 110

Arg Ala Gly Pro Arg Gly Pro Lys Gly Val Ser Gly Thr Pro Gly Lys
        115                 120                 125

His Gly Ile Pro Gly Lys Lys Gly Pro Lys Gly Lys Lys Gly Glu Pro
    130                 135                 140

Gly Leu Pro Gly Pro Cys Ser Cys Gly Ser Ser Arg Ala Lys Ser Ala
145                 150                 155                 160

Phe Ser Val Ala Val Thr Lys Ser Tyr Pro Arg Glu Arg Leu Pro Ile
                165                 170                 175

Lys Phe Asp Lys Ile Leu Met Asn Glu Gly Gly His Tyr Asn Ala Ser
            180                 185                 190

Ser Gly Lys Phe Val Cys Ser Val Pro Gly Ile Tyr Tyr Phe Thr Tyr
        195                 200                 205

Asp Ile Thr Leu Ala Asn Lys His Leu Ala Ile Gly Leu Val His Asn
    210                 215                 220

Gly Gln Tyr Arg Ile Arg Thr Phe Asp Ala Asn Thr Gly Asn His Asp
225                 230                 235                 240

Val Ala Ser Gly Ser Thr Ile Leu Ala Leu Lys Glu Gly Asp Glu Val
                245                 250                 255

Trp Leu Gln Ile Phe Tyr Ser Glu Gln Asn Gly Leu Phe Tyr Asp Pro
            260                 265                 270

Tyr Trp Thr Asp Ser Leu Phe Thr Gly Phe Leu Ile Tyr Ala Asp Gln
        275                 280                 285

Gly Asp Pro Asn Glu Val
    290


<210> SEQ ID NO 295
<211> LENGTH: 243
<212> TYPE: PRT
<213> ORGANISM: Rat

<400> SEQUENCE: 295

Met Arg Pro Leu Leu Ala Leu Leu Leu Leu Gly Leu Ala Ser Gly Ser
 1               5                  10                  15

Pro Pro Leu Asp Asp Asn Lys Ile Pro Ser Leu Cys Pro Gly Gln Pro
            20                  25                  30

Gly Leu Pro Gly Thr Pro Gly His His Gly Ser Gln Gly Leu Pro Gly
        35                  40                  45

Arg Asp Gly Arg Asp Gly Arg Asp Gly Ala Pro Gly Ala Pro Gly Glu
    50                  55                  60

Lys Gly Glu Gly Gly Arg Pro Gly Leu Pro Gly Pro Arg Gly Glu Pro
65                  70                  75                  80

Gly Pro Arg Gly Glu Ala Gly Pro Val Gly Ala Ile Gly Pro Ala Gly
                85                  90                  95

Glu Cys Ser Val Pro Pro Arg Ser Ala Phe Ser Ala Lys Arg Ser Glu
            100                 105                 110

Ser Arg Val Pro Pro Pro Ala Asp Thr Pro Leu Pro Phe Asp Arg Val
        115                 120                 125

Leu Leu Asn Glu Gln Gly His Tyr Asp Ala Thr Thr Gly Lys Phe Thr
    130                 135                 140

Cys Gln Val Pro Gly Val Tyr Tyr Phe Ala Val His Ala Thr Val Tyr
```

-continued

```
145                 150                 155                 160

Arg Ala Ser Leu Gln Phe Asp Leu Val Lys Asn Gly Gln Ser Ile Ala
                165                 170                 175

Ser Phe Phe Gln Phe Phe Gly Gly Trp Pro Lys Pro Ala Ser Leu Ser
            180                 185                 190

Gly Gly Ala Met Val Arg Leu Glu Pro Glu Asp Gln Val Trp Val Gln
        195                 200                 205

Val Gly Val Gly Asp Tyr Ile Gly Ile Tyr Ala Ser Ile Lys Thr Asp
    210                 215                 220

Ser Thr Phe Ser Gly Phe Leu Val Tyr Ser Asp Trp His Ser Ser Pro
225                 230                 235                 240

Val Phe Ala


<210> SEQ ID NO 296
<211> LENGTH: 444
<212> TYPE: PRT
<213> ORGANISM: Rat

<400> SEQUENCE: 296

Met Leu Val Ala Phe Leu Gly Ala Ser Ala Val Thr Ala Ser Thr Gly
 1               5                  10                  15

Leu Leu Trp Lys Lys Ala His Ala Glu Ser Pro Pro Ser Val Asn Ser
            20                  25                  30

Lys Lys Thr Asp Ala Gly Asp Lys Gly Lys Ser Lys Asp Thr Arg Glu
        35                  40                  45

Val Ser Ser His Glu Gly Ser Ala Ala Asp Thr Ala Ala Glu Pro Tyr
    50                  55                  60

Pro Glu Glu Lys Lys Lys Lys Arg Ser Gly Phe Arg Asp Arg Lys Val
65                  70                  75                  80

Met Glu Tyr Glu Asn Arg Ile Arg Ala Tyr Ser Thr Pro Asp Lys Ile
                85                  90                  95

Phe Arg Tyr Phe Ala Thr Leu Lys Val Ile Asn Glu Pro Gly Glu Thr
            100                 105                 110

Glu Val Phe Met Thr Pro Gln Asp Phe Val Arg Ser Ile Thr Pro Asn
        115                 120                 125

Glu Lys Gln Pro Glu His Leu Gly Leu Asp Gln Tyr Ile Ile Lys Arg
    130                 135                 140

Phe Asp Gly Lys Lys Ile Ala Gln Glu Arg Glu Lys Phe Ala Asp Glu
145                 150                 155                 160

Gly Ser Ile Phe Tyr Thr Leu Gly Glu Cys Gly Leu Ile Ser Phe Ser
                165                 170                 175

Asp Tyr Ile Phe Leu Thr Thr Val Leu Ser Thr Pro Gln Arg Asn Phe
            180                 185                 190

Glu Ile Ala Phe Lys Met Phe Asp Leu Asn Gly Asp Gly Glu Val Asp
        195                 200                 205

Met Glu Glu Phe Glu Gln Val Gln Ser Ile Ile Arg Ser Gln Thr Ser
    210                 215                 220

Met Gly Met Arg His Arg Asp Arg Pro Thr Thr Gly Asn Thr Leu Lys
225                 230                 235                 240

Ser Gly Leu Cys Ser Ala Leu Thr Thr Tyr Phe Phe Gly Ala Asp Leu
                245                 250                 255

Lys Gly Lys Leu Thr Ile Lys Asn Phe Leu Glu Phe Gln Arg Lys Leu
            260                 265                 270

Gln His Asp Val Leu Lys Leu Glu Phe Glu Arg His Asp Pro Val Asp
```

-continued

```
        275                 280                 285

Gly Arg Ile Ser Glu Arg Gln Phe Gly Gly Met Leu Leu Ala Tyr Ser
    290                 295                 300

Gly Val Gln Ser Lys Lys Leu Thr Ala Met Gln Arg Gln Leu Lys Lys
305                 310                 315                 320

His Phe Lys Asp Gly Lys Gly Leu Thr Phe Gln Glu Val Glu Asn Phe
                325                 330                 335

Phe Thr Phe Leu Lys Asn Ile Asn Asp Val Asp Thr Ala Leu Ser Phe
            340                 345                 350

Tyr His Met Ala Gly Ala Ser Leu Asp Lys Val Thr Met Gln Gln Val
        355                 360                 365

Ala Arg Thr Val Ala Lys Val Glu Leu Ser Asp His Val Cys Asp Val
    370                 375                 380

Val Phe Ala Leu Phe Asp Cys Asp Gly Asn Gly Glu Leu Ser Asn Lys
385                 390                 395                 400

Glu Phe Val Ser Ile Met Lys Gln Arg Leu Met Arg Gly Leu Glu Lys
                405                 410                 415

Pro Lys Asp Met Gly Phe Thr Arg Leu Met Gln Ala Met Trp Lys Cys
            420                 425                 430

Ala Gln Glu Thr Ala Trp Asp Phe Ala Leu Pro Lys
        435                 440


<210> SEQ ID NO 297
<211> LENGTH: 65
<212> TYPE: PRT
<213> ORGANISM: Human

<400> SEQUENCE: 297

Met Thr Met Leu His Leu Ala Val Ile Phe Leu Phe Ser Ala Leu Ser
 1               5                  10                  15

Arg Ala Leu Val Gln Cys Ser Ser His Arg Ala Arg Val Val Leu Ser
            20                  25                  30

Trp Ala Asp Tyr Leu Arg Arg Val Ala Pro Thr Ala Leu Ala Thr Ala
        35                  40                  45

Leu Asp Val Gly Leu Ser Asn Trp Ser Phe Leu Tyr Val Thr Val Ser
    50                  55                  60

Leu
65


<210> SEQ ID NO 298
<211> LENGTH: 52
<212> TYPE: PRT
<213> ORGANISM: Human

<400> SEQUENCE: 298

Met Lys Ile Asn Ile Ile Gln Gly Ser Ile Met Ile Leu Leu Ile Cys
 1               5                  10                  15

Leu Ser Gln Thr Cys Thr Ser Leu Pro Val Gln Glu Ala Leu Ile Thr
            20                  25                  30

Phe Cys His Leu Tyr Phe Thr Tyr Cys Tyr Ser Gly Asn Ser Asn Lys
        35                  40                  45

Met Gln Val Leu
    50


<210> SEQ ID NO 299
<211> LENGTH: 41
<212> TYPE: PRT
```

-continued

<213> ORGANISM: Human

<400> SEQUENCE: 299

Met Pro Cys Val Leu Phe Phe Phe Phe Phe Leu Ser Thr Ser Lys Ser
1 5 10 15

Met Ile Tyr Ser Ser Leu Met Leu Gly Leu Tyr Ile Pro Ser Glu Ala
20 25 30

Cys Val Leu Gly Leu Lys Phe Lys Phe
35 40

<210> SEQ ID NO 300
<211> LENGTH: 80
<212> TYPE: PRT
<213> ORGANISM: Mouse

<400> SEQUENCE: 300

Met Val Trp Gly Thr Leu Leu Gly Arg Val Leu Ala Ala Leu Leu Asn
1 5 10 15

Ile Val Pro Thr Glu Ser Ser Tyr Arg Ser Pro Ser Phe Leu Ala Gly
20 25 30

Phe Arg Phe Cys Cys Ser Pro Trp Ser Gln His Phe Gly Cys Gly Arg
35 40 45

Leu Thr Ser Cys Leu Pro Pro Cys Val Asp Arg Val Val Lys Thr Tyr
50 55 60

Ser Ser Pro Pro Cys Leu Ser Val Asn Gly His Asp Val Thr Ile Cys
65 70 75 80

<210> SEQ ID NO 301
<211> LENGTH: 82
<212> TYPE: PRT
<213> ORGANISM: Mouse

<400> SEQUENCE: 301

Met Gly Ser Val Leu Thr Ser Cys Phe Cys Val Gly Gly Ser Ala Glu
1 5 10 15

Ala Trp Asn Trp Leu Pro Ser Ala Ser Ser Leu Phe Pro Cys Cys Ile
20 25 30

Ala Thr Leu Leu Pro Leu Leu Phe Leu Leu Pro His Leu His Ser Thr
35 40 45

Leu Ser Arg Val Gln Arg Leu Asn Phe Asn Ile Gly His Leu Gly Val
50 55 60

Tyr Leu Tyr Val Asn Asn Asp Ile Arg Ser Arg Val Thr Pro Leu Leu
65 70 75 80

Ser Ser

<210> SEQ ID NO 302
<211> LENGTH: 411
<212> TYPE: PRT
<213> ORGANISM: Rat

<400> SEQUENCE: 302

Met Pro Thr Met Trp Pro Leu Leu His Val Leu Trp Leu Ala Leu Val
1 5 10 15

Cys Gly Ser Val His Thr Thr Leu Ser Lys Ser Asp Ala Lys Lys Ala
20 25 30

Ala Ser Lys Thr Leu Leu Glu Lys Thr Gln Phe Ser Asp Lys Pro Val
35 40 45

Gln Asp Arg Gly Leu Val Val Thr Asp Ile Lys Ala Glu Asp Val Val

-continued

```
    50                  55                  60

Leu Glu His Arg Ser Tyr Cys Ser Ala Arg Ala Arg Glu Arg Asn Phe
65                  70                  75                  80

Ala Gly Glu Val Leu Gly Tyr Val Thr Pro Trp Asn Ser His Gly Tyr
                85                  90                  95

Asp Val Ala Lys Val Phe Gly Ser Lys Phe Thr Gln Ile Ser Pro Val
            100                 105                 110

Trp Leu Gln Leu Lys Arg Arg Gly Arg Glu Met Phe Glu Ile Thr Gly
        115                 120                 125

Leu His Asp Val Asp Gln Gly Trp Met Arg Ala Val Lys Lys His Ala
    130                 135                 140

Lys Gly Val Arg Ile Val Pro Arg Leu Leu Phe Glu Asp Trp Thr Tyr
145                 150                 155                 160

Asp Asp Phe Arg Ser Val Leu Asp Ser Glu Asp Glu Ile Glu Glu Leu
                165                 170                 175

Ser Lys Thr Val Val Gln Val Ala Lys Asn Gln His Phe Asp Gly Phe
            180                 185                 190

Val Val Glu Val Trp Ser Gln Leu Leu Ser Gln Lys His Val Gly Leu
        195                 200                 205

Ile His Met Leu Thr His Leu Ala Glu Ala Leu His Gln Ala Arg Leu
    210                 215                 220

Leu Val Ile Leu Val Ile Pro Pro Ala Val Thr Pro Gly Thr Asp Gln
225                 230                 235                 240

Leu Gly Met Phe Thr His Lys Glu Phe Glu Gln Leu Ala Pro Ile Leu
                245                 250                 255

Asp Gly Phe Ser Leu Met Thr Tyr Asp Tyr Ser Thr Ser Gln Gln Pro
            260                 265                 270

Gly Pro Asn Ala Pro Leu Ser Trp Ile Arg Ala Cys Val Gln Val Leu
        275                 280                 285

Asp Pro Lys Ser Gln Trp Arg Ser Lys Ile Leu Leu Gly Leu Asn Phe
    290                 295                 300

Tyr Gly Met Asp Tyr Ala Ala Ser Lys Asp Ala Arg Glu Pro Val Ile
305                 310                 315                 320

Gly Ala Arg Ala Val Leu Lys Val Ala Leu Pro Leu Ala Val Ser Ser
                325                 330                 335

Gln Gln Ile Trp Thr Leu Gly Arg Gly Gly Ser Thr Ser Ala Leu Leu
            340                 345                 350

Leu Ala Gly Leu Gly Leu Ala Ser Glu Pro Cys Thr Lys Ser Glu Glu
        355                 360                 365

Val Pro Lys Lys Ser Leu Leu Asp Thr Val Trp His Trp Gln Gly Glu
    370                 375                 380

Pro Gly Ala Leu Cys Arg Gly Arg Leu His Thr Trp Ile Leu Val Ser
385                 390                 395                 400

Ala Val Pro Gln Ala Cys Thr Cys Leu Phe Gln
                405                 410


<210> SEQ ID NO 303
<211> LENGTH: 617
<212> TYPE: PRT
<213> ORGANISM: Mouse

<400> SEQUENCE: 303

Met Gly Ser Pro Arg Leu Ala Ala Leu Leu Leu Ser Leu Pro Leu Leu
 1               5                  10                  15
```

-continued

```
Leu Ile Gly Leu Ala Val Ser Ala Arg Val Ala Cys Pro Cys Leu Arg
            20                  25                  30

Ser Trp Thr Ser His Cys Leu Leu Ala Tyr Arg Val Asp Lys Arg Phe
        35                  40                  45

Ala Gly Leu Gln Trp Gly Trp Phe Pro Leu Leu Val Arg Lys Ser Lys
    50                  55                  60

Ser Pro Pro Lys Phe Glu Asp Tyr Trp Arg His Arg Thr Pro Ala Ser
65                  70                  75                  80

Phe Gln Arg Lys Leu Leu Gly Ser Pro Ser Leu Ser Glu Glu Ser His
                85                  90                  95

Arg Ile Ser Ile Pro Ser Ser Ala Ile Ser His Arg Gly Gln Arg Thr
            100                 105                 110

Lys Arg Ala Gln Pro Ser Ala Ala Glu Gly Arg Glu His Leu Pro Glu
        115                 120                 125

Ala Gly Ser Gln Lys Cys Gly Gly Pro Glu Phe Ser Phe Asp Leu Leu
    130                 135                 140

Pro Glu Val Gln Ala Val Arg Val Thr Ile Pro Ala Gly Pro Lys Ala
145                 150                 155                 160

Ser Val Arg Leu Cys Tyr Gln Trp Ala Leu Glu Cys Glu Asp Leu Ser
                165                 170                 175

Ser Pro Phe Asp Thr Gln Lys Ile Val Ser Gly Gly His Thr Val Asp
            180                 185                 190

Leu Pro Tyr Glu Phe Leu Leu Pro Cys Met Cys Ile Glu Ala Ser Tyr
        195                 200                 205

Leu Gln Glu Asp Thr Val Arg Arg Lys Lys Cys Pro Phe Gln Ser Trp
    210                 215                 220

Pro Glu Ala Tyr Gly Ser Asp Phe Trp Gln Ser Ile Arg Phe Thr Asp
225                 230                 235                 240

Tyr Ser Gln His Asn Gln Met Val Met Ala Leu Thr Leu Arg Cys Pro
                245                 250                 255

Leu Lys Leu Glu Ala Ser Leu Cys Trp Arg Gln Asp Pro Leu Thr Pro
            260                 265                 270

Cys Glu Thr Leu Pro Asn Ala Thr Ala Gln Glu Ser Glu Gly Trp Tyr
        275                 280                 285

Ile Leu Glu Asn Val Asp Leu His Pro Gln Leu Cys Phe Lys Phe Ser
    290                 295                 300

Phe Glu Asn Ser Ser His Val Glu Cys Pro His Gln Ser Gly Ser Leu
305                 310                 315                 320

Pro Ser Trp Thr Val Ser Met Asp Thr Gln Ala Gln Gln Leu Thr Leu
                325                 330                 335

His Phe Ser Ser Arg Thr Tyr Ala Thr Phe Ser Ala Ala Trp Ser Asp
            340                 345                 350

Pro Gly Leu Gly Pro Asp Thr Pro Met Pro Pro Val Tyr Ser Ile Ser
        355                 360                 365

Gln Thr Gln Gly Ser Val Pro Val Thr Leu Asp Leu Ile Ile Pro Phe
    370                 375                 380

Leu Arg Gln Glu Asn Cys Ile Leu Val Trp Arg Ser Asp Val His Phe
385                 390                 395                 400

Ala Trp Lys His Val Leu Cys Pro Asp Asp Ala Pro Tyr Pro Thr Gln
                405                 410                 415

Leu Leu Leu Arg Ser Leu Gly Ser Gly Arg Thr Arg Pro Val Leu Leu
            420                 425                 430

Leu His Ala Ala Asp Ser Glu Ala Gln Arg Arg Leu Val Gly Ala Leu
```

-continued

```
        435                 440                 445

Ala Glu Leu Leu Arg Thr Ala Leu Gly Gly Gly Arg Asp Val Ile Val
    450                 455                 460

Asp Leu Trp Glu Gly Thr His Val Ala Arg Ile Gly Pro Leu Pro Trp
465                 470                 475                 480

Leu Trp Ala Ala Arg Glu Arg Val Ala Arg Glu Gln Gly Thr Val Leu
                485                 490                 495

Leu Leu Trp Asn Cys Ala Gly Pro Ser Thr Ala Cys Ser Gly Asp Pro
            500                 505                 510

Gln Ala Ala Ser Leu Arg Thr Leu Leu Cys Ala Ala Pro Arg Pro Leu
        515                 520                 525

Leu Leu Ala Tyr Phe Ser Arg Leu Cys Ala Lys Gly Asp Ile Pro Arg
    530                 535                 540

Pro Leu Arg Ala Leu Pro Arg Tyr Arg Leu Leu Arg Asp Leu Pro Arg
545                 550                 555                 560

Leu Leu Arg Ala Leu Asp Ala Gln Pro Ala Thr Leu Ala Ser Ser Trp
                565                 570                 575

Ser His Leu Gly Ala Lys Arg Cys Leu Lys Asn Arg Leu Glu Gln Cys
            580                 585                 590

His Leu Leu Glu Leu Glu Ala Ala Lys Asp Asp Tyr Gln Gly Ser Thr
        595                 600                 605

Asn Ser Pro Cys Gly Phe Ser Cys Leu
    610                 615


<210> SEQ ID NO 304
<211> LENGTH: 72
<212> TYPE: PRT
<213> ORGANISM: Mouse

<400> SEQUENCE: 304

Met Ser Ala Ile Phe Asn Phe Gln Ser Leu Leu Thr Val Ile Leu Leu
 1               5                  10                  15

Leu Ile Cys Thr Cys Ala Tyr Ile Arg Ser Leu Ala Pro Ser Ile Leu
            20                  25                  30

Asp Arg Asn Lys Thr Gly Leu Leu Gly Ile Phe Trp Lys Cys Ala Arg
        35                  40                  45

Ile Gly Glu Arg Lys Ser Pro Tyr Val Ala Ile Cys Cys Ile Val Met
    50                  55                  60

Ala Phe Ser Ile Leu Phe Ile Gln
65                  70


<210> SEQ ID NO 305
<211> LENGTH: 649
<212> TYPE: PRT
<213> ORGANISM: Mouse

<400> SEQUENCE: 305

Met Ile Ser Pro Ala Trp Ser Leu Phe Leu Ile Gly Thr Lys Ile Gly
 1               5                  10                  15

Leu Phe Phe Gln Val Ala Pro Leu Ser Val Val Ala Lys Ser Cys Pro
            20                  25                  30

Ser Val Cys Arg Cys Asp Ala Gly Phe Ile Tyr Cys Asn Asp Arg Ser
        35                  40                  45

Leu Thr Ser Ile Pro Val Gly Ile Pro Glu Asp Ala Thr Thr Leu Tyr
    50                  55                  60

Leu Gln Asn Asn Gln Ile Asn Asn Val Gly Ile Pro Ser Asp Leu Lys
```

-continued

```
65                  70                  75                  80

Asn Leu Leu Lys Val Gln Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Gly Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu His Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Ser Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Ser Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Ala Tyr Pro Ala Gln Gly Gln Trp Pro Ala Pro
    370                 375                 380

Val Thr Lys Gln Pro Asp Ile Lys Asn Pro Lys Leu Ile Lys Asp Gln
385                 390                 395                 400

Arg Thr Thr Gly Ser Pro Ser Arg Lys Thr Ile Leu Ile Thr Val Lys
                405                 410                 415

Ser Val Thr Pro Asp Thr Ile His Ile Ser Trp Arg Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Glu Ser Pro Tyr Arg Val Cys Met Val
465                 470                 475                 480

Pro Met Glu Thr Ser Asn Leu Tyr Leu Phe Asp Glu Thr Pro Val Cys
                485                 490                 495
```

-continued

Ile Glu Thr Gln Thr Ala Pro Leu Arg Met Tyr Asn Pro Thr Thr Thr
500 505 510

Leu Asn Arg Glu Gln Glu Lys Glu Pro Tyr Lys Asn Pro Asn Leu Pro
515 520 525

Leu Ala Ala Ile Ile Gly Gly Ala Val Ala Leu Val Ser Ile Ala Leu
530 535 540

Leu Ala Leu Val Cys Trp Tyr Val His Arg Asn Gly Ser Leu Phe Ser
545 550 555 560

Arg Asn Cys Ala Tyr Ser Lys Gly Arg Arg Arg Lys Asp Asp Tyr Ala
565 570 575

Glu Ala Gly Thr Lys Lys Asp Asn Ser Ile Leu Glu Ile Arg Glu Thr
580 585 590

Ser Phe Gln Met Leu Pro Ile Ser Asn Glu Pro Ile Ser Lys Glu Glu
595 600 605

Phe Val Ile His Thr Ile Phe Pro Pro Asn Gly Met Asn Leu Tyr Lys
610 615 620

Asn Asn Leu Ser Glu Ser Ser Ser Asn Arg Ser Tyr Arg Asp Ser Gly
625 630 635 640

Ile Pro Asp Ser Asp His Ser His Ser
645

<210> SEQ ID NO 306
<211> LENGTH: 150
<212> TYPE: PRT
<213> ORGANISM: Rat

<400> SEQUENCE: 306

Met Ala Ala Pro Met Asp Arg Thr His Gly Gly Arg Ala Ala Arg Ala
1 5 10 15

Leu Arg Arg Ala Leu Ala Leu Ala Ser Leu Ala Gly Leu Leu Leu Ser
20 25 30

Gly Leu Ala Gly Ala Leu Pro Thr Leu Gly Pro Gly Trp Arg Arg Gln
35 40 45

Asn Pro Glu Pro Pro Ala Ser Arg Thr Arg Ser Leu Leu Leu Asp Ala
50 55 60

Ala Ser Gly Gln Leu Arg Leu Glu Tyr Gly Phe His Pro Asp Ala Val
65 70 75 80

Ala Trp Ala Asn Leu Thr Asn Ala Ile Arg Glu Thr Gly Trp Ala Tyr
85 90 95

Leu Asp Leu Gly Thr Asn Gly Ser Tyr Lys Trp Ile Pro Arg Ala Ala
100 105 110

Gly Leu Cys Ser Trp Cys Gly Gly Gly Leu Cys Val Arg Gly Ala His
115 120 125

Leu His Ala Leu Asp Glu His Gly Gly Gln Leu Leu Arg Pro Leu Arg
130 135 140

Val Arg Ser Arg Leu Leu
145 150

<210> SEQ ID NO 307
<211> LENGTH: 580
<212> TYPE: PRT
<213> ORGANISM: Rat

<400> SEQUENCE: 307

Met Ala Ala Ala Met Pro Leu Gly Leu Ser Leu Leu Leu Leu Val Leu
1 5 10 15

-continued

```
Val Gly Gln Gly Cys Cys Gly Arg Val Glu Gly Pro Arg Asp Ser Leu
            20                  25                  30

Arg Glu Glu Leu Val Ile Thr Pro Leu Pro Ser Gly Asp Val Ala Ala
        35                  40                  45

Thr Phe Gln Phe Arg Thr Arg Trp Asp Ser Asp Leu Gln Arg Glu Gly
    50                  55                  60

Val Ser His Tyr Arg Leu Phe Pro Lys Ala Leu Gly Gln Leu Ile Ser
65                  70                  75                  80

Lys Tyr Ser Leu Arg Glu Leu His Leu Ser Phe Thr Gln Gly Phe Trp
                85                  90                  95

Arg Thr Arg Tyr Trp Gly Pro Pro Phe Leu Gln Ala Pro Ser Gly Ala
            100                 105                 110

Glu Leu Trp Val Trp Phe Gln Asp Thr Val Thr Asp Val Asp Lys Ser
        115                 120                 125

Trp Lys Glu Leu Ser Asn Val Leu Ser Gly Ile Phe Cys Ala Ser Leu
    130                 135                 140

Asn Phe Ile Asp Ser Thr Asn Thr Val Thr Pro Thr Ala Ser Phe Lys
145                 150                 155                 160

Pro Leu Gly Leu Ala Asn Asp Thr Asp His Tyr Phe Leu Arg Tyr Ala
                165                 170                 175

Val Leu Pro Arg Glu Val Val Cys Thr Glu Asn Leu Thr Pro Trp Lys
            180                 185                 190

Lys Leu Leu Pro Cys Ser Ser Lys Ala Gly Leu Ser Val Leu Leu Lys
        195                 200                 205

Ala Asp Arg Leu Phe His Thr Ser Tyr His Ser Gln Ala Val His Ile
    210                 215                 220

Arg Pro Ile Cys Arg Asn Ala His Cys Thr Ser Ile Ser Trp Glu Leu
225                 230                 235                 240

Arg Gln Thr Leu Ser Val Val Phe Asp Ala Phe Ile Thr Gly Gln Gly
                245                 250                 255

Lys Lys Asp Trp Ser Leu Phe Arg Met Phe Ser Arg Thr Leu Thr Glu
            260                 265                 270

Ala Cys Pro Leu Ala Ser Gln Ser Leu Val Tyr Val Asp Ile Thr Gly
        275                 280                 285

Tyr Ser Gln Asp Asn Glu Thr Leu Glu Val Ser Pro Pro Pro Thr Ser
    290                 295                 300

Thr Tyr Gln Asp Val Ile Leu Gly Thr Arg Lys Thr Tyr Ala Val Tyr
305                 310                 315                 320

Asp Leu Phe Asp Thr Ala Met Ile Asn Asn Ser Arg Asn Leu Asn Ile
                325                 330                 335

Gln Leu Lys Trp Lys Arg Pro Pro Asp Asn Glu Ala Leu Pro Val Pro
            340                 345                 350

Phe Leu His Ala Gln Arg Tyr Val Ser Gly Tyr Gly Leu Gln Lys Gly
        355                 360                 365

Glu Leu Ser Thr Leu Leu Tyr Asn Ser His Pro Tyr Arg Ala Phe Pro
    370                 375                 380

Val Leu Leu Leu Asp Ala Val Pro Trp Tyr Leu Arg Leu Tyr Val His
385                 390                 395                 400

Thr Leu Thr Ile Thr Ser Lys Gly Lys Asp Asn Lys Pro Ser Tyr Ile
                405                 410                 415

His Tyr Gln Pro Ala Gln Asp Arg Gln Gln Pro His Leu Leu Glu Met
            420                 425                 430
```

-continued

```
Leu Ile Gln Leu Pro Ala Asn Ser Val Thr Lys Val Ser Ile Gln Phe
        435                 440                 445

Glu Arg Ala Leu Leu Lys Trp Thr Glu Tyr Thr Pro Asp Pro Asn His
    450                 455                 460

Gly Phe Tyr Val Ser Pro Ser Val Leu Ser Ala Leu Val Pro Ser Met
465                 470                 475                 480

Val Ala Ala Lys Pro Val Asp Trp Glu Glu Ser Pro Leu Phe Asn Thr
                485                 490                 495

Leu Phe Pro Val Ser Asp Gly Ser Ser Tyr Phe Val Arg Leu Tyr Thr
            500                 505                 510

Glu Pro Leu Leu Val Asn Leu Pro Thr Pro Asp Phe Ser Met Pro Tyr
        515                 520                 525

Asn Val Ile Cys Leu Thr Cys Thr Val Val Ala Val Cys Tyr Gly Ser
    530                 535                 540

Phe Tyr Asn Leu Leu Thr Arg Thr Phe His Ile Glu Glu Pro Lys Ser
545                 550                 555                 560

Gly Gly Leu Ala Lys Arg Leu Ala Asn Leu Ile Arg Arg Ala Arg Gly
                565                 570                 575

Val Pro Pro Leu
            580


<210> SEQ ID NO 308
<211> LENGTH: 283
<212> TYPE: PRT
<213> ORGANISM: Rat

<400> SEQUENCE: 308

Met Thr Ser Gly Pro Gly Gly Pro Ala Ala Ala Thr Gly Gly Gly Lys
 1               5                  10                  15

Asp Thr His Gln Trp Tyr Val Cys Asn Arg Glu Lys Leu Cys Glu Ser
            20                  25                  30

Leu Gln Ser Val Phe Val Gln Ser Tyr Leu Asp Gln Gly Thr Gln Ile
        35                  40                  45

Phe Leu Asn Asn Ser Ile Glu Lys Ser Gly Trp Leu Phe Ile Gln Leu
    50                  55                  60

Tyr His Ser Phe Val Ser Ser Val Phe Ser Leu Phe Met Ser Arg Thr
65                  70                  75                  80

Ser Ile Asn Gly Leu Leu Gly Arg Gly Ser Met Phe Val Phe Ser Pro
                85                  90                  95

Asp Gln Phe Gln Arg Leu Leu Lys Ile Asn Pro Asp Trp Lys Thr His
            100                 105                 110

Arg Leu Leu Asp Leu Gly Ala Gly Asp Gly Glu Val Thr Lys Ile Met
        115                 120                 125

Ser Pro His Phe Glu Glu Ile Tyr Ala Thr Glu Leu Ser Glu Thr Met
    130                 135                 140

Ile Trp Gln Leu Gln Lys Lys Lys Tyr Arg Val Leu Gly Ile Asn Glu
145                 150                 155                 160

Trp Gln Asn Thr Gly Phe Gln Tyr Asp Val Ile Ser Cys Leu Asn Leu
                165                 170                 175

Leu Asp Arg Cys Asp Gln Pro Leu Thr Leu Leu Lys Asp Ile Arg Ser
            180                 185                 190

Val Leu Glu Pro Thr Gln Gly Arg Val Ile Leu Ala Leu Val Leu Pro
        195                 200                 205

Phe His Pro Tyr Val Glu Asn Val Gly Gly Lys Trp Glu Lys Pro Ser
    210                 215                 220
```

-continued

```
Glu Ile Leu Glu Ile Lys Gly Gln Asn Trp Glu Glu Gln Val Asn Ser
225                 230                 235                 240

Leu Pro Glu Val Phe Arg Lys Ala Gly Phe Val Ile Glu Ala Phe Thr
                245                 250                 255

Arg Leu Pro Tyr Leu Cys Glu Gly Asp Met Tyr Asn Asp Tyr Tyr Val
            260                 265                 270

Leu Asp Asp Ala Val Phe Val Leu Arg Pro Val
        275                 280


<210> SEQ ID NO 309
<211> LENGTH: 37
<212> TYPE: PRT
<213> ORGANISM: Rat

<400> SEQUENCE: 309

Met Leu Trp Val Leu Leu Ser Leu Thr Pro Leu Leu Ser Pro Leu Ile
 1               5                  10                  15

Phe Phe Pro Val Lys Thr Val Ala Leu Glu Glu Ile Ser Thr Ile Cys
            20                  25                  30

Arg Ala Asp Val Leu
        35


<210> SEQ ID NO 310
<211> LENGTH: 70
<212> TYPE: PRT
<213> ORGANISM: Mouse

<400> SEQUENCE: 310

Met Ala Ala Ser Trp Gly Gln Val Leu Ala Leu Val Leu Val Ala Ala
 1               5                  10                  15

Leu Trp Gly Gly Thr Gln Pro Leu Leu Lys Arg Ala Ser Ser Gly Leu
            20                  25                  30

Glu Gln Val Arg Glu Arg Thr Trp Ala Trp Gln Leu Leu Gln Glu Ile
        35                  40                  45

Lys Ala Leu Phe Gly Asn Thr Glu Val Arg Leu Ala Leu Thr Asp Glu
    50                  55                  60

Pro Leu Lys Ile Ser Pro
65                  70


<210> SEQ ID NO 311
<211> LENGTH: 58
<212> TYPE: PRT
<213> ORGANISM: Human

<400> SEQUENCE: 311

Met Leu Leu Ser Ser Leu Val Ser Leu Ala Gly Ser Val Tyr Leu Ala
 1               5                  10                  15

Trp Ile Leu Phe Phe Val Leu Tyr Asp Phe Cys Ile Val Cys Ile Thr
            20                  25                  30

Thr Tyr Ala Ile Asn Val Ser Leu Met Trp Leu Ser Phe Arg Lys Val
        35                  40                  45

Gln Glu Pro Gln Gly Lys Ala Lys Arg His
    50                  55


<210> SEQ ID NO 312
<211> LENGTH: 52
<212> TYPE: PRT
<213> ORGANISM: Human
```

-continued

<400> SEQUENCE: 312

Met Gly Thr Pro Gln Gly Glu Asn Trp Leu Ser Trp Met Phe Glu Lys
1 5 10 15

Leu Val Val Val Met Val Cys Tyr Phe Ile Leu Ser Ile Ile Asn Ser
20 25 30

Met Ala Gln Ser Tyr Ala Lys Arg Ile Gln Gln Arg Leu Asn Ser Glu
35 40 45

Glu Lys Thr Lys
50

<210> SEQ ID NO 313
<211> LENGTH: 70
<212> TYPE: PRT
<213> ORGANISM: Human

<400> SEQUENCE: 313

Met Asn Leu Leu Gly Met Ile Phe Ser Met Cys Gly Leu Met Leu Lys
1 5 10 15

Leu Lys Trp Cys Ala Trp Val Ala Val Tyr Cys Ser Phe Ile Ser Phe
20 25 30

Ala Asn Ser Arg Ser Ser Glu Asp Thr Lys Gln Met Met Ser Ser Phe
35 40 45

Met Leu Ser Ile Ser Ala Val Val Met Ser Tyr Leu Gln Asn Pro Gln
50 55 60

Pro Met Thr Pro Pro Trp
65 70

<210> SEQ ID NO 314
<211> LENGTH: 58
<212> TYPE: PRT
<213> ORGANISM: Mouse

<400> SEQUENCE: 314

Met Phe Ile Thr Pro Phe Lys Ala Phe Leu Pro Leu Tyr Leu Leu Thr
1 5 10 15

Glu Leu Ser Leu Ile Asp Ile Thr Ser Cys Asp Asp Leu Pro His Ser
20 25 30

Val Leu Pro Gln His Leu Ser Phe Glu Phe Val Leu Trp Ser Met Tyr
35 40 45

Leu Leu Ile Cys Cys Phe Val Ile Ile Phe
50 55

<210> SEQ ID NO 315
<211> LENGTH: 229
<212> TYPE: PRT
<213> ORGANISM: Rat

<400> SEQUENCE: 315

Met Ala Ser Ala Leu Glu Glu Leu Gln Lys Asp Leu Glu Glu Val Lys
1 5 10 15

Val Leu Leu Glu Lys Ser Thr Arg Lys Arg Leu Arg Asp Thr Leu Thr
20 25 30

Asn Glu Lys Ser Lys Ile Glu Thr Glu Leu Arg Asn Lys Met Gln Gln
35 40 45

Lys Ser Gln Lys Lys Pro Glu Phe Asp Asn Glu Lys Pro Ala Ala Val
50 55 60

Val Ala Pro Leu Thr Thr Gly Tyr Thr Val Lys Ile Ser Asn Tyr Gly
65 70 75 80

-continued

Trp Asp Gln Ser Asp Lys Phe Val Lys Ile Tyr Ile Thr Leu Thr Gly
                85                  90                  95

Val His Gln Val Pro Ala Glu Asn Val Gln Val His Phe Thr Glu Arg
            100                 105                 110

Ser Phe Asp Leu Leu Val Lys Asn Leu Asn Gly Lys Asn Tyr Ser Met
        115                 120                 125

Ile Val Asn Asn Leu Leu Lys Pro Ile Ser Val Glu Ser Ser Ser Lys
    130                 135                 140

Lys Val Lys Thr Asp Thr Val Ile Ile Leu Cys Arg Lys Lys Ala Glu
145                 150                 155                 160

Asn Thr Arg Trp Asp Tyr Leu Thr Gln Val Glu Lys Glu Cys Lys Glu
                165                 170                 175

Lys Glu Lys Pro Ser Tyr Asp Thr Glu Ala Asp Pro Ser Glu Gly Leu
            180                 185                 190

Met Asn Val Leu Lys Lys Ile Tyr Glu Asp Gly Asp Asp Asp Met Lys
        195                 200                 205

Arg Thr Ile Asn Lys Ala Trp Val Glu Ser Arg Glu Lys Gln Ala Arg
    210                 215                 220

Glu Asp Thr Glu Phe
225

<210> SEQ ID NO 316
<211> LENGTH: 128
<212> TYPE: PRT
<213> ORGANISM: Rat

<400> SEQUENCE: 316

Arg Ala Glu Phe Gly Thr Ser Gly Glu Met Gly Asn Ala Ala Leu Gly
 1               5                  10                  15

Ala Glu Leu Gly Val Arg Val Leu Leu Phe Val Ala Phe Leu Ala Thr
            20                  25                  30

Glu Leu Leu Pro Pro Phe Gln Arg Arg Ile Gln Pro Glu Glu Leu Trp
        35                  40                  45

Leu Tyr Arg Asn Pro Tyr Val Glu Ala Glu Tyr Phe Pro Thr Gly Pro
    50                  55                  60

Met Phe Val Ile Ala Phe Leu Thr Pro Leu Ser Leu Ile Phe Phe Ala
65                  70                  75                  80

Lys Phe Leu Arg Lys Ala Asp Ala Thr Asp Ser Lys Gln Ala Cys Leu
                85                  90                  95

Ala Ala Ser Leu Ala Leu Ala Leu Asn Gly Val Phe Thr Asn Ile Ile
            100                 105                 110

Lys Leu Ile Val Gly Arg Pro Arg Pro Asp Phe Phe Tyr Arg Cys Phe
        115                 120                 125

<210> SEQ ID NO 317
<211> LENGTH: 75
<212> TYPE: PRT
<213> ORGANISM: Rat

<400> SEQUENCE: 317

Ser Ala Gly Val Met Thr Ala Ala Val Phe Phe Gly Cys Ala Phe Ile
 1               5                  10                  15

Ala Phe Gly Pro Ala Leu Ser Leu Tyr Val Phe Thr Ile Ala Thr Asp
            20                  25                  30

Pro Leu Arg Val Ile Phe Leu Ile Ala Gly Ala Phe Phe Trp Leu Val
        35                  40                  45

-continued

Ser Leu Leu Leu Ser Ser Val Phe Trp Phe Leu Val Arg Val Ile Thr
    50                  55                  60

Asp Asn Arg Asp Gly Pro Val Gln Asn Tyr Leu
65                  70                  75

<210> SEQ ID NO 318
<211> LENGTH: 43
<212> TYPE: PRT
<213> ORGANISM: Human

<400> SEQUENCE: 318

Met Lys Leu Ser Gly Met Phe Leu Leu Leu Ser Leu Ala Leu Phe Cys
 1               5                  10                  15

Phe Leu Thr Gly Val Phe Ser Gln Gly Gly Gln Val Asp Cys Gly Glu
            20                  25                  30

Ser Arg Thr Pro Arg Pro Thr Ala Leu Gly Asn
        35                  40

<210> SEQ ID NO 319
<211> LENGTH: 86
<212> TYPE: PRT
<213> ORGANISM: Mouse

<400> SEQUENCE: 319

Met Leu Gln Gly Pro Ala Pro Ser Cys Phe Trp Val Phe Ser Gly Ile
 1               5                  10                  15

Cys Val Phe Trp Asp Phe Ile Phe Ile Ile Phe Phe Asn Val Leu Ser
            20                  25                  30

Leu Gly Asn Arg Glu Ile Ser Ala Lys Asp Phe Ala Asp Gln Pro Ala
        35                  40                  45

Gly Ala Gln Gly Met Trp Gly Ile Trp Gly His Thr Ile Thr Cys Gly
    50                  55                  60

Leu Ala Pro Gly Ala Lys Pro Cys Ser Leu Lys Arg Glu Gly Pro Asp
65                  70                  75                  80

Leu Leu Ser Phe Pro Pro
                85

<210> SEQ ID NO 320
<211> LENGTH: 60
<212> TYPE: PRT
<213> ORGANISM: Mouse

<400> SEQUENCE: 320

Lys Gly Pro Glu Val Ser Cys Cys Ile Lys Tyr Phe Ile Phe Gly Phe
 1               5                  10                  15

Asn Val Ile Phe Trp Phe Leu Gly Ile Thr Phe Leu Gly Ile Gly Leu
            20                  25                  30

Trp Ala Trp Asn Glu Lys Gly Val Leu Ser Asn Ile Ser Ser Ile Thr
        35                  40                  45

Asp Leu Gly Gly Phe Asp Pro Val Trp Leu Phe Leu
    50                  55                  60

<210> SEQ ID NO 321
<211> LENGTH: 160
<212> TYPE: PRT
<213> ORGANISM: Mouse

<400> SEQUENCE: 321

Ile Arg His Glu Ala Glu Ala Gly Arg His Gln Pro Glu Gln Leu Ala

-continued

```
 1               5                   10                  15

Ala Asp Ser Arg Thr Glu Thr Val Gly Pro Arg Gln Ser Asn Gly Leu
            20                  25                  30

Thr Gly Pro Gly Leu Pro Thr Trp Gln Leu His Pro Val Leu Phe Pro
        35                  40                  45

Glu Leu Val Leu Trp Val Asn Met Val Pro Cys Phe Leu Leu Ser Leu
    50                  55                  60

Leu Leu Leu Val Arg Pro Ala Pro Val Val Ala Tyr Ser Val Ser Leu
65                  70                  75                  80

Pro Ala Ser Phe Leu Glu Glu Val Ala Gly Ser Gly Glu Ala Glu Gly
                85                  90                  95

Ser Ser Ala Ser Ser Pro Ser Leu Leu Pro Pro Arg Thr Pro Ala Phe
            100                 105                 110

Ser Pro Thr Pro Gly Arg Thr Gln Pro Thr Ala Pro Val Gly Pro Val
        115                 120                 125

Pro Pro Thr Asn Leu Leu Asp Gly Ile Val Asp Phe Phe Arg Gln Tyr
    130                 135                 140

Val Met Leu Ile Ala Val Val Gly Ser Leu Thr Phe Leu Ile Ser Ser
145                 150                 155                 160


<210> SEQ ID NO 322
<211> LENGTH: 54
<212> TYPE: PRT
<213> ORGANISM: Mouse

<400> SEQUENCE: 322

Arg Leu Gln Val Asp Thr Ser Gly Ser Lys Val Leu Phe Leu Phe Phe
 1               5                   10                  15

Phe Phe Phe Leu Cys Val Cys Val Leu Val Cys Cys Cys Phe Gly Phe
            20                  25                  30

Pro Gly Thr His Ser Val Asp Gln Ala Ser Pro Lys Leu Arg Asn Leu
        35                  40                  45

Pro Pro Glu Cys Trp Asp
    50


<210> SEQ ID NO 323
<211> LENGTH: 280
<212> TYPE: PRT
<213> ORGANISM: Mouse

<400> SEQUENCE: 323

Leu Asp Ser Arg Ala Cys Arg Ser Thr Leu Val Asp Pro Lys Asn Ser
 1               5                   10                  15

Ala Arg Glu Asn Ile Arg Glu Tyr Val Arg Trp Met Met Tyr Trp Ile
            20                  25                  30

Val Phe Ala Ile Phe Met Ala Ala Glu Thr Phe Thr Asp Ile Phe Ile
        35                  40                  45

Ser Trp Ser Gly Pro Arg Ile Gly Arg Pro Trp Gly Trp Glu Gly Pro
    50                  55                  60

His His His His His Leu Ala Ser Gly Ser His Lys Pro Leu Pro Leu
65                  70                  75                  80

Leu Thr His Arg Phe Pro Phe Tyr Tyr Glu Phe Lys Met Ala Phe Val
                85                  90                  95

Leu Trp Leu Leu Ser Pro Tyr Thr Lys Gly Ala Ser Leu Leu Tyr Arg
            100                 105                 110

Lys Phe Val His Pro Ser Leu Ser Arg His Glu Lys Glu Ile Asp Ala
```

-continued 115 120 125

Cys Ile Val Gln Ala Lys Glu Arg Ser Tyr Glu Thr Met Leu Ser Phe
130 135 140

Gly Lys Arg Ser Leu Asn Ile Ala Ala Ser Ala Ala Val Gln Ala Ala
145 150 155 160

Thr Lys Ser Gln Gly Ala Leu Ala Gly Arg Leu Arg Ser Phe Ser Met
165 170 175

Gln Asp Leu Arg Ser Ile Pro Asp Thr Pro Val Pro Thr Tyr Gln Asp
180 185 190

Pro Leu Tyr Leu Glu Asp Gln Val Pro Arg Arg Arg Pro Pro Ile Gly
195 200 205

Tyr Arg Pro Gly Gly Leu Gln Gly Ser Asp Thr Glu Asp Glu Cys Trp
210 215 220

Ser Asp Asn Glu Ile Val Pro Gln Pro Pro Val Gly Pro Arg Glu Lys
225 230 235 240

Pro Leu Gly Arg Ser Gln Ser Leu Arg Val Val Lys Arg Lys Pro Leu
245 250 255

Thr Arg Glu Gly Thr Ser Arg Ser Leu Lys Val Arg Thr Pro Lys Lys
260 265 270

Ala Met Pro Ser Asp Met Asp Ser
275 280

<210> SEQ ID NO 324
<211> LENGTH: 166
<212> TYPE: PRT
<213> ORGANISM: Rat

<400> SEQUENCE: 324

Ala Leu Arg Arg Val Gly Met Glu Leu Pro Ala Val Asn Leu Lys Val
1 5 10 15

Ile Leu Leu Val His Trp Leu Leu Thr Thr Trp Gly Cys Leu Ala Phe
20 25 30

Ser Gly Ser Tyr Ala Trp Gly Asn Phe Thr Ile Leu Ala Leu Gly Val
35 40 45

Trp Ala Val Ala Gln Arg Asp Ser Val Asp Ala Ile Gly Met Phe Leu
50 55 60

Gly Gly Leu Val Ala Thr Ile Phe Leu Asp Ile Ile Tyr Ile Ser Ile
65 70 75 80

Phe Tyr Ser Ser Val Ala Val Gly Asp Thr Gly Arg Phe Ser Ala Gly
85 90 95

Met Ala Ile Phe Ser Leu Leu Leu Lys Pro Phe Ser Cys Cys Leu Val
100 105 110

Tyr His Met His Arg Glu Arg Gly Gly Glu Leu Pro Leu Arg Ser Asp
115 120 125

Phe Phe Gly Pro Ser Gln Glu His Ser Ala Tyr Gln Thr Ile Asp Ser
130 135 140

Ser Asp Ser Pro Ala Asp Pro Leu Ala Ser Leu Glu Asn Lys Gly Gln
145 150 155 160

Ala Ala Pro Arg Gly Tyr
165

<210> SEQ ID NO 325
<211> LENGTH: 338
<212> TYPE: PRT
<213> ORGANISM: Rat

-continued

<400> SEQUENCE: 325

Ile Arg His Glu Ala Glu Ala Gly Arg His Gln Pro Glu Gln Leu Ala
1 5 10 15

Ala Asp Ser Arg Thr Glu Thr Val Gly Pro Arg Gln Ser Asn Gly Leu
20 25 30

Thr Gly Pro Gly Leu Pro Thr Trp Gln Leu His Pro Val Leu Phe Pro
35 40 45

Glu Leu Val Leu Trp Val Asn Met Val Pro Cys Phe Leu Leu Ser Leu
50 55 60

Leu Leu Leu Val Arg Pro Ala Pro Val Val Ala Tyr Ser Val Ser Leu
65 70 75 80

Pro Ala Ser Phe Leu Glu Glu Val Ala Gly Ser Gly Glu Ala Glu Gly
85 90 95

Ser Ser Ala Ser Ser Pro Ser Leu Leu Pro Pro Arg Thr Pro Ala Phe
100 105 110

Ser Pro Thr Pro Gly Arg Thr Gln Pro Thr Ala Pro Val Gly Pro Val
115 120 125

Pro Pro Thr Asn Leu Leu Asp Gly Ile Val Asp Phe Phe Arg Gln Tyr
130 135 140

Val Met Leu Ile Ala Val Val Gly Ser Leu Thr Phe Leu Ile Met Phe
145 150 155 160

Ile Val Cys Ala Ala Leu Ile Thr Arg Gln Lys His Lys Ala Thr Ala
165 170 175

Tyr Tyr Pro Ser Ser Phe Pro Glu Lys Lys Tyr Val Asp Gln Arg Asp
180 185 190

Arg Ala Gly Gly Pro His Ala Phe Ser Glu Val Pro Asp Arg Ala Pro
195 200 205

Asp Ser Arg Gln Glu Glu Gly Leu Asp Ser Ser Gln Gln Leu Gln Ala
210 215 220

Asp Ile Leu Ala Ala Thr Gln Asn Leu Arg Ser Pro Ala Arg Ala Leu
225 230 235 240

Pro Gly Ser Gly Glu Gly Thr Lys Gln Val Lys Gly Gly Ser Glu Glu
245 250 255

Glu Glu Glu Lys Glu Glu Glu Val Phe Ser Gly Gln Glu Glu Pro Arg
260 265 270

Glu Ala Pro Val Cys Gly Val Thr Glu Glu Lys Pro Glu Val Pro Asp
275 280 285

Glu Thr Ala Ser Ala Glu Ala Glu Gly Val Pro Ala Ala Ser Glu Gly
290 295 300

Gln Gly Glu Pro Glu Gly Ser Phe Ser Leu Ala Gln Glu Pro Gln Gly
305 310 315 320

Ala Ala Gly Pro Ser Glu Arg Ser Cys Ala Cys Asn Arg Ile Ser Pro
325 330 335

Asn Val

<210> SEQ ID NO 326
<211> LENGTH: 347
<212> TYPE: PRT
<213> ORGANISM: Human

<400> SEQUENCE: 326

Ala Trp Ser Arg Pro Arg Tyr Tyr Arg Leu Cys Asp Lys Ala Glu Ala
1 5 10 15

Trp Gly Ile Val Leu Glu Thr Val Ala Thr Ala Gly Val Val Thr Ser

-continued

```
            20                  25                  30

Val Ala Phe Met Leu Thr Leu Pro Ile Leu Val Cys Lys Val Gln Asp
        35                  40                  45

Ser Asn Arg Arg Lys Met Leu Pro Thr Gln Phe Leu Phe Leu Leu Gly
    50                  55                  60

Val Leu Gly Ile Phe Gly Leu Thr Phe Ala Phe Ile Ile Gly Leu Asp
65                  70                  75                  80

Gly Ser Thr Gly Pro Thr Arg Phe Phe Leu Phe Gly Ile Leu Phe Ser
                85                  90                  95

Ile Cys Phe Ser Cys Leu Leu Ala His Ala Val Ser Leu Thr Lys Leu
            100                 105                 110

Val Arg Gly Arg Lys Pro Leu Ser Leu Leu Val Ile Leu Gly Leu Ala
        115                 120                 125

Val Gly Phe Ser Leu Val Gln Asp Val Ile Ala Ile Glu Tyr Ile Val
    130                 135                 140

Leu Thr Met Asn Arg Thr Asn Val Asn Val Phe Ser Glu Leu Ser Ala
145                 150                 155                 160

Pro Arg Arg Asn Glu Asp Phe Val Leu Leu Leu Thr Tyr Val Leu Phe
                165                 170                 175

Leu Met Ala Leu Thr Phe Leu Met Ser Ser Phe Thr Phe Cys Gly Ser
            180                 185                 190

Phe Thr Gly Trp Lys Arg His Gly Ala His Ile Tyr Leu Thr Met Leu
        195                 200                 205

Leu Ser Ile Ala Ile Trp Val Ala Trp Ile Thr Leu Leu Met Leu Pro
    210                 215                 220

Asp Phe Asp Arg Arg Trp Asp Asp Thr Ile Leu Ser Ser Ala Leu Ala
225                 230                 235                 240

Ala Asn Gly Trp Val Phe Leu Leu Ala Tyr Val Ser Pro Glu Phe Trp
                245                 250                 255

Leu Leu Thr Lys Gln Arg Asn Pro Met Asp Tyr Pro Val Glu Asp Ala
            260                 265                 270

Phe Cys Lys Pro Gln Leu Val Lys Lys Ser Tyr Gly Val Glu Asn Arg
        275                 280                 285

Ala Tyr Ser Gln Glu Glu Ile Thr Gln Gly Phe Glu Glu Thr Gly Asp
    290                 295                 300

Thr Leu Tyr Ala Pro Tyr Ser Thr His Phe Gln Leu Gln Asn Gln Pro
305                 310                 315                 320

Pro Gln Lys Glu Phe Ser Ile Pro Arg Ala His Ala Trp Pro Ser Pro
                325                 330                 335

Tyr Lys Asp Tyr Glu Val Lys Lys Glu Gly Ser
            340                 345


<210> SEQ ID NO 327
<211> LENGTH: 141
<212> TYPE: PRT
<213> ORGANISM: Human

<400> SEQUENCE: 327

Lys Asn Ser Lys Cys Leu Leu Phe Trp Cys Arg Lys Ile Val Gly Asn
 1               5                  10                  15

Arg Gln Glu Pro Met Trp Glu Phe Asn Phe Lys Phe Lys Lys Gln Ser
            20                  25                  30

Pro Arg Leu Lys Ser Lys Cys Thr Gly Gly Leu Gln Pro Pro Val Gln
        35                  40                  45
```

-continued

```
Tyr Glu Asp Val His Thr Asn Pro Asp Gln Asp Cys Cys Leu Leu Gln
    50                  55                  60

Val Thr Thr Leu Asn Phe Ile Phe Ile Pro Ile Val Met Gly Met Ile
65                  70                  75                  80

Phe Thr Leu Phe Thr Ile Asn Val Ser Thr Asp Met Arg His His Arg
                85                  90                  95

Val Arg Leu Val Phe Gln Asp Ser Pro Val His Gly Gly Arg Lys Leu
            100                 105                 110

Arg Ser Glu Gln Gly Val Gln Val Ile Leu Asp Gln Cys Thr Ala Phe
        115                 120                 125

Gly Ser Leu Thr Gly Gly Ile Leu Ser Thr His Ser Pro
    130                 135                 140
```

<210> SEQ ID NO 328
<211> LENGTH: 71
<212> TYPE: PRT
<213> ORGANISM: Human

<400> SEQUENCE: 328

```
Arg Glu Arg Thr Ser Leu Glu Phe Phe Val Phe Leu Phe Leu Phe Ile
 1               5                  10                  15

Cys Cys Cys Leu His Ser Gly Gly Leu Gly Gly Val Pro Leu Pro Pro
            20                  25                  30

Phe Pro Pro Gln Ala Gln Arg Gly Glu Gly Pro Gly Lys Trp Met Ser
        35                  40                  45

Pro Pro Leu Pro Pro His Pro Val Val Ala Pro Pro Thr Pro Ser Pro
    50                  55                  60

Ser Arg Gly Cys Val Leu Leu
65                  70
```

<210> SEQ ID NO 329
<211> LENGTH: 109
<212> TYPE: PRT
<213> ORGANISM: Human

<400> SEQUENCE: 329

```
Asp Gly Pro Ser Pro Lys Leu Ala Leu Trp Leu Pro Ser Pro Ala Pro
 1               5                  10                  15

Thr Ala Ala Pro Thr Ala Leu Gly Glu Ala Gly Leu Ala Glu His Ser
            20                  25                  30

Gln Arg Asp Asp Arg Trp Leu Leu Val Ala Leu Leu Val Pro Thr Cys
        35                  40                  45

Val Phe Leu Val Val Leu Leu Ala Leu Gly Ile Val Tyr Cys Thr Arg
    50                  55                  60

Cys Gly Pro His Ala Pro Asn Lys Arg Ile Thr Asp Cys Tyr Arg Trp
65                  70                  75                  80

Val Ile His Ala Gly Ser Lys Ser Pro Thr Glu Pro Met Pro Pro Arg
                85                  90                  95

Gly Ser Leu Thr Gly Val Gln Thr Cys Arg Thr Ser Val
            100                 105
```

<210> SEQ ID NO 330
<211> LENGTH: 155
<212> TYPE: PRT
<213> ORGANISM: Human

<400> SEQUENCE: 330

```
Ser Val Met Ala Ala Gly Leu Phe Gly Leu Ser Ala Arg Arg Leu Leu
```

-continued

```
 1               5                  10                  15

Ala Ala Ala Ala Thr Arg Gly Leu Pro Ala Ala Arg Val Arg Trp Glu
            20                  25                  30

Ser Ser Phe Ser Arg Thr Val Val Ala Pro Ser Ala Val Ala Gly Lys
        35                  40                  45

Arg Pro Pro Glu Pro Thr Thr Pro Trp Gln Glu Asp Pro Glu Pro Glu
    50                  55                  60

Asp Glu Asn Leu Tyr Glu Lys Asn Pro Asp Ser His Gly Tyr Asp Lys
65                  70                  75                  80

Asp Pro Val Leu Asp Val Trp Asn Met Arg Leu Val Phe Phe Phe Gly
                85                  90                  95

Val Ser Ile Ile Leu Val Leu Gly Ser Thr Phe Val Ala Tyr Leu Pro
            100                 105                 110

Asp Tyr Arg Met Lys Glu Trp Ser Arg Arg Glu Ala Glu Arg Leu Val
        115                 120                 125

Lys Tyr Arg Glu Ala Asn Gly Leu Pro Ile Met Glu Ser Asn Cys Phe
    130                 135                 140

Asp Pro Ser Lys Ile Gln Leu Pro Glu Asp Glu
145                 150                 155


<210> SEQ ID NO 331
<211> LENGTH: 299
<212> TYPE: PRT
<213> ORGANISM: Human

<400> SEQUENCE: 331

Met Gly Thr Lys Ala Gln Val Glu Arg Lys Leu Leu Cys Leu Phe Ile
 1               5                  10                  15

Leu Ala Ile Leu Leu Cys Ser Leu Ala Leu Gly Ser Val Thr Val His
            20                  25                  30

Ser Ser Glu Pro Glu Val Arg Ile Pro Glu Asn Asn Pro Val Lys Leu
        35                  40                  45

Ser Cys Ala Tyr Ser Gly Phe Ser Ser Pro Arg Val Glu Trp Lys Phe
    50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
        195                 200                 205

Glu Tyr Ser Cys Glu Ala Arg Asn Gly Tyr Gly Thr Pro Met Thr Ser
    210                 215                 220
```

-continued

Asn Ala Val Arg Met Glu Ala Val Glu Arg Asn Val Gly Val Ile Val
225 230 235 240

Ala Ala Val Leu Val Thr Leu Ile Leu Leu Gly Ile Leu Val Phe Gly
245 250 255

Ile Trp Phe Ala Tyr Ser Arg Gly His Phe Asp Arg Thr Lys Lys Gly
260 265 270

Thr Ser Ser Lys Lys Val Ile Tyr Ser Gln Pro Ser Ala Arg Ser Glu
275 280 285

Gly Glu Phe Lys Gln Thr Ser Ser Phe Leu Val
290 295

<210> SEQ ID NO 332
<211> LENGTH: 299
<212> TYPE: PRT
<213> ORGANISM: Mouse

<400> SEQUENCE: 332

Ala Arg Ala Gly Ala Cys Tyr Cys Pro Ala Gly Phe Leu Gly Ala Asp
1 5 10 15

Cys Ser Leu Ala Cys Pro Gln Gly Arg Phe Gly Pro Ser Cys Ala His
20 25 30

Val Cys Thr Cys Gly Gln Gly Ala Ala Cys Asp Pro Val Ser Gly Thr
35 40 45

Cys Ile Cys Pro Pro Gly Lys Thr Gly Gly His Cys Glu Arg Gly Cys
50 55 60

Pro Gln Asp Arg Phe Gly Lys Gly Cys Glu His Lys Cys Ala Cys Arg
65 70 75 80

Asn Gly Gly Leu Cys His Ala Thr Asn Gly Ser Cys Ser Cys Pro Leu
85 90 95

Gly Trp Met Gly Pro His Cys Glu His Ala Cys Pro Ala Gly Arg Tyr
100 105 110

Gly Ala Ala Cys Leu Leu Glu Cys Ser Cys Gln Asn Asn Gly Ser Cys
115 120 125

Glu Pro Thr Ser Gly Ala Cys Leu Cys Gly Pro Gly Phe Tyr Gly Gln
130 135 140

Ala Cys Glu Asp Thr Cys Pro Ala Gly Phe His Gly Ser Gly Cys Gln
145 150 155 160

Arg Val Cys Glu Cys Gln Gln Gly Ala Pro Cys Asp Pro Val Ser Gly
165 170 175

Arg Cys Leu Cys Pro Ala Gly Phe Arg Gly Gln Phe Cys Glu Arg Gly
180 185 190

Cys Lys Pro Gly Phe Phe Gly Asp Gly Cys Leu Gln Gln Cys Asn Cys
195 200 205

Pro Thr Gly Val Pro Cys Asp Pro Ile Ser Gly Leu Cys Leu Cys Pro
210 215 220

Pro Gly Arg Ala Gly Thr Thr Cys Asp Leu Asp Cys Arg Arg Gly Arg
225 230 235 240

Phe Gly Pro Gly Cys Ala Leu Arg Cys Asp Cys Gly Gly Gly Ala Asp
245 250 255

Cys Asp Pro Ile Ser Gly Gln Cys His Cys Val Asp Ser Tyr Thr Gly
260 265 270

Pro Thr Cys Arg Glu Val Pro Thr Gln Leu Ser Ser Ile Arg Pro Ala
275 280 285

Pro Gln His Ser Ser Ser Lys Ala Met Lys His
290 295

-continued

<210> SEQ ID NO 333
<211> LENGTH: 109
<212> TYPE: PRT
<213> ORGANISM: Mouse

<400> SEQUENCE: 333

Gly Thr Arg Val Gly Thr Pro Tyr Tyr Met Ser Pro Glu Arg Ile His
1               5                   10                  15

Glu Asn Gly Tyr Asn Phe Lys Ser Asp Ile Trp Ser Leu Gly Cys Leu
            20                  25                  30

Leu Tyr Glu Met Ala Ala Leu Gln Ser Pro Phe Tyr Gly Asp Lys Met
        35                  40                  45

Asn Leu Tyr Ser Leu Cys Lys Lys Ile Glu Gln Cys Asp Tyr Pro Pro
    50                  55                  60

Leu Pro Ser Asp His Tyr Ser Glu Glu Leu Arg Gln Leu Val Asn Ile
65                  70                  75                  80

Cys Ile Asn Pro Asp Pro Glu Lys Arg Pro Asp Ile Ala Tyr Val Tyr
                85                  90                  95

Asp Val Ala Lys Arg Met His Ala Cys Thr Ala Ser Thr
            100                 105

<210> SEQ ID NO 334
<211> LENGTH: 787
<212> TYPE: PRT
<213> ORGANISM: Mouse

<400> SEQUENCE: 334

Lys Val Glu Gly Glu Gly Arg Gly Arg Trp Ala Leu Gly Leu Leu Arg
1               5                   10                  15

Thr Phe Asp Ala Gly Glu Phe Ala Gly Trp Glu Lys Val Gly Ser Gly
            20                  25                  30

Gly Phe Gly Gln Val Tyr Lys Val Arg His Val His Trp Lys Thr Trp
        35                  40                  45

Leu Ala Ile Lys Cys Ser Pro Ser Leu His Val Asp Asp Arg Glu Arg
    50                  55                  60

Met Glu Leu Leu Glu Glu Ala Lys Lys Met Glu Met Ala Lys Phe Arg
65                  70                  75                  80

Tyr Ile Leu Pro Val Tyr Gly Ile Cys Gln Glu Pro Val Gly Leu Val
                85                  90                  95

Met Glu Tyr Met Glu Thr Gly Ser Leu Glu Lys Leu Leu Ala Ser Glu
            100                 105                 110

Pro Leu Pro Trp Asp Leu Arg Phe Arg Ile Val His Glu Thr Ala Val
        115                 120                 125

Gly Met Asn Phe Leu His Cys Met Ser Pro Pro Leu Leu His Leu Asp
    130                 135                 140

Leu Lys Pro Ala Asn Ile Leu Leu Asp Ala His Tyr His Val Lys Ile
145                 150                 155                 160

Ser Asp Phe Gly Leu Ala Lys Cys Asn Gly Met Ser His Ser His Asp
                165                 170                 175

Leu Ser Met Asp Gly Leu Phe Gly Thr Ile Ala Tyr Leu Pro Pro Glu
            180                 185                 190

Arg Ile Arg Glu Lys Ser Arg Leu Phe Asp Thr Lys His Asp Val Tyr
        195                 200                 205

Ser Phe Ala Ile Val Ile Trp Gly Val Leu Thr Gln Lys Lys Pro Phe
    210                 215                 220

-continued

```
Ala Asp Glu Lys Asn Ile Leu His Ile Met Met Lys Val Val Lys Gly
225                 230                 235                 240

His Arg Pro Glu Leu Pro Pro Ile Cys Arg Pro Arg Pro Arg Ala Cys
                245                 250                 255

Ala Ser Leu Ile Gly Leu Met Gln Arg Cys Trp His Ala Asp Pro Gln
            260                 265                 270

Val Arg Pro Thr Phe Gln Glu Ile Thr Ser Glu Thr Glu Asp Leu Cys
        275                 280                 285

Glu Lys Pro Asp Glu Glu Val Lys Asp Leu Ala His Glu Pro Gly Glu
    290                 295                 300

Lys Ser Ser Leu Glu Ser Lys Ser Glu Ala Arg Pro Glu Ser Ser Arg
305                 310                 315                 320

Leu Lys Arg Ala Ser Ala Pro Pro Phe Asp Asn Asp Cys Ser Leu Ser
                325                 330                 335

Glu Leu Leu Ser Gln Leu Asp Ser Gly Ile Ser Gln Thr Leu Glu Gly
            340                 345                 350

Pro Glu Glu Leu Ser Arg Ser Ser Ser Glu Cys Lys Leu Pro Ser Ser
        355                 360                 365

Ser Ser Gly Lys Arg Leu Ser Gly Val Ser Ser Val Asp Ser Ala Phe
    370                 375                 380

Ser Ser Arg Gly Ser Leu Ser Leu Ser Phe Glu Arg Glu Ala Ser Thr
385                 390                 395                 400

Gly Asp Leu Gly Pro Thr Asp Ile Gln Lys Lys Lys Leu Val Asp Ala
                405                 410                 415

Ile Ile Ser Gly Asp Thr Ser Arg Leu Met Lys Ile Leu Gln Pro Gln
            420                 425                 430

Asp Val Asp Leu Val Leu Asp Ser Ser Ala Ser Leu Leu His Leu Ala
        435                 440                 445

Val Glu Ala Gly Gln Glu Glu Cys Val Lys Trp Leu Leu Leu Asn Asn
    450                 455                 460

Ala Asn Pro Asn Leu Thr Asn Arg Lys Gly Ser Thr Pro Leu His Met
465                 470                 475                 480

Ala Val Glu Arg Lys Gly Arg Gly Ile Val Glu Leu Leu Leu Ala Arg
                485                 490                 495

Lys Thr Ser Val Asn Ala Lys Asp Glu Asp Gln Trp Thr Ala Leu His
            500                 505                 510

Phe Ala Ala Gln Asn Gly Asp Glu Ala Ser Thr Arg Leu Leu Leu Glu
        515                 520                 525

Lys Asn Ala Ser Val Asn Glu Val Asp Phe Glu Gly Arg Thr Pro Met
    530                 535                 540

His Val Ala Cys Gln His Gly Gln Glu Asn Ile Val Arg Thr Leu Leu
545                 550                 555                 560

Arg Arg Gly Val Asp Val Gly Leu Gln Gly Lys Asp Ala Trp Leu Pro
                565                 570                 575

Leu His Tyr Ala Ala Trp Gln Gly His Leu Pro Ile Val Lys Leu Leu
            580                 585                 590

Ala Lys Gln Pro Gly Val Ser Val Asn Ala Gln Thr Leu Asp Gly Arg
        595                 600                 605

Thr Pro Leu His Leu Ala Ala Gln Arg Gly His Tyr Arg Val Ala Arg
    610                 615                 620

Ile Leu Ile Asp Leu Cys Ser Asp Val Asn Ile Cys Ser Leu Gln Ala
625                 630                 635                 640
```

-continued

```
Gln Thr Pro Leu His Val Ala Ala Glu Thr Gly His Thr Ser Thr Ala
                645                 650                 655

Arg Leu Leu Leu His Arg Gly Ala Gly Lys Glu Ala Leu Thr Ser Glu
            660                 665                 670

Gly Tyr Thr Ala Leu His Leu Ala Ala Gln Asn Gly His Leu Ala Thr
        675                 680                 685

Val Lys Leu Leu Ile Glu Glu Lys Ala Asp Val Met Ala Arg Gly Pro
    690                 695                 700

Leu Asn Gln Thr Ala Leu His Leu Ala Ala Ala Arg Gly His Ser Glu
705                 710                 715                 720

Val Val Glu Glu Leu Val Ser Ala Asp Leu Ile Asp Leu Ser Asp Glu
                725                 730                 735

Gln Gly Leu Ser Ala Leu His Leu Ala Ala Gln Gly Arg His Ser Gln
            740                 745                 750

Thr Val Glu Thr Leu Leu Lys His Gly Ala His Ile Asn Leu Gln Ser
        755                 760                 765

Leu Lys Phe Gln Gly Gly Gln Ser Ser Ala Ala Thr Leu Leu Arg Arg
    770                 775                 780

Ser Lys Thr
785


<210> SEQ ID NO 335
<211> LENGTH: 194
<212> TYPE: PRT
<213> ORGANISM: Mouse

<400> SEQUENCE: 335

Pro Gly Cys Lys Ser Cys Thr Val Cys Arg His Gly Leu Cys Arg Ser
 1               5                  10                  15

Val Glu Lys Asp Ser Val Val Cys Glu Cys His Pro Gly Trp Thr Gly
            20                  25                  30

Pro Leu Cys Asp Gln Glu Ala Arg Asp Pro Cys Leu Gly His Ser Cys
        35                  40                  45

Arg His Gly Thr Cys Met Ala Thr Gly Asp Ser Tyr Val Cys Lys Cys
    50                  55                  60

Ala Glu Gly Tyr Gly Gly Ala Leu Cys Asp Gln Lys Asn Asp Ser Ala
65                  70                  75                  80

Ser Ala Cys Ser Ala Phe Lys Cys His His Gly Gln Cys His Ile Ser
                85                  90                  95

Asp Arg Gly Glu Pro Tyr Cys Leu Cys Gln Pro Gly Phe Ser Gly His
            100                 105                 110

His Cys Glu Gln Glu Asn Pro Cys Met Gly Glu Ile Val Arg Glu Ala
        115                 120                 125

Ile Arg Arg Gln Lys Asp Tyr Ala Ser Cys Ala Thr Ala Ser Lys Val
    130                 135                 140

Pro Ile Met Glu Cys Arg Gly Gly Cys Gly Thr Thr Cys Cys Gln Pro
145                 150                 155                 160

Ile Arg Ser Lys Arg Arg Lys Tyr Val Phe Gln Cys Thr Asp Gly Ser
                165                 170                 175

Ser Phe Val Glu Glu Val Glu Arg His Leu Glu Cys Gly Cys Arg Ala
            180                 185                 190

Cys Ser


<210> SEQ ID NO 336
<211> LENGTH: 274
```

<212> TYPE: PRT
<213> ORGANISM: Human

<400> SEQUENCE: 336

Tyr Arg Tyr Cys Gln His Arg Cys Val Asn Leu Pro Gly Ser Phe Arg
1 5 10 15

Cys Gln Cys Glu Pro Gly Phe Gln Leu Gly Pro Asn Asn Arg Ser Cys
20 25 30

Val Asp Val Asn Glu Cys Asp Met Gly Ala Pro Cys Glu Gln Arg Cys
35 40 45

Phe Asn Ser Tyr Gly Thr Phe Leu Cys Arg Cys His Gln Gly Tyr Glu
50 55 60

Leu His Arg Asp Gly Phe Ser Cys Ser Asp Ile Asp Glu Cys Ser Tyr
65 70 75 80

Ser Ser Tyr Leu Cys Gln Tyr Arg Cys Val Asn Glu Pro Gly Arg Phe
85 90 95

Ser Cys His Cys Pro Gln Gly Tyr Gln Leu Leu Ala Thr Arg Leu Cys
100 105 110

Gln Asp Ile Asp Glu Cys Glu Ser Gly Ala His Gln Cys Ser Glu Ala
115 120 125

Gln Thr Cys Val Asn Phe His Gly Gly Tyr Arg Cys Val Asp Thr Asn
130 135 140

Arg Cys Val Glu Pro Tyr Ile Gln Val Ser Glu Asn Arg Cys Leu Cys
145 150 155 160

Pro Ala Ser Asn Pro Leu Cys Arg Glu Gln Pro Ser Ser Ile Val His
165 170 175

Arg Tyr Met Thr Ile Thr Ser Glu Arg Ser Val Pro Ala Asp Val Phe
180 185 190

Gln Ile Gln Ala Thr Ser Val Tyr Pro Gly Ala Tyr Asn Ala Phe Gln
195 200 205

Ile Arg Ala Gly Asn Ser Gln Gly Asp Phe Tyr Ile Arg Gln Ile Asn
210 215 220

Asn Val Ser Ala Met Leu Val Leu Ala Arg Pro Val Thr Gly Pro Arg
225 230 235 240

Glu Tyr Val Leu Asp Leu Glu Met Val Thr Met Asn Ser Leu Met Ser
245 250 255

Tyr Arg Ala Ser Ser Val Leu Arg Leu Thr Val Phe Val Gly Ala Tyr
260 265 270

Thr Phe

<210> SEQ ID NO 337
<211> LENGTH: 316
<212> TYPE: PRT
<213> ORGANISM: Mouse

<400> SEQUENCE: 337

His Glu Glu Glu Pro Cys Asn Asn Gly Ser Glu Ile Leu Ala Tyr Asn
1 5 10 15

Ile Asp Leu Gly Asp Ser Cys Ile Thr Val Gly Asn Thr Thr Thr His
20 25 30

Val Met Lys Asn Leu Leu Pro Glu Thr Thr Tyr Arg Ile Arg Ile Gln
35 40 45

Ala Ile Asn Glu Ile Gly Val Gly Pro Phe Ser Gln Phe Ile Lys Ala
50 55 60

Lys Thr Arg Pro Leu Pro Pro Ser Pro Pro Arg Leu Glu Cys Ala Ala

-continued 65 70 75 80

Ser Gly Pro Gln Ser Leu Lys Leu Lys Trp Gly Asp Ser Asn Ser Lys
85 90 95

Thr His Ala Ala Gly Asp Met Val Tyr Thr Leu Gln Leu Glu Asp Arg
100 105 110

Asn Lys Arg Phe Ile Ser Ile Tyr Arg Gly Pro Ser His Thr Tyr Lys
115 120 125

Val Gln Arg Leu Thr Glu Phe Thr Cys Tyr Ser Phe Arg Ile Gln Ala
130 135 140

Met Ser Glu Ala Gly Glu Gly Pro Tyr Ser Glu Thr Tyr Thr Phe Ser
145 150 155 160

Thr Thr Lys Ser Val Pro Pro Thr Leu Lys Ala Pro Arg Val Thr Gln
165 170 175

Leu Glu Gly Asn Ser Cys Glu Ile Phe Trp Glu Thr Val Pro Pro Met
180 185 190

Arg Gly Asp Pro Val Ser Tyr Val Leu Gln Val Leu Val Gly Arg Asp
195 200 205

Ser Glu Tyr Lys Gln Val Tyr Lys Gly Glu Glu Ala Thr Phe Gln Ile
210 215 220

Ser Gly Leu Gln Ser Asn Thr Asp Tyr Arg Phe Arg Val Cys Ala Cys
225 230 235 240

Arg Arg Cys Val Asp Thr Ser Gln Glu Leu Ser Gly Ala Phe Ser Pro
245 250 255

Ser Ala Ala Phe Met Leu Gln Gln Arg Glu Val Met Leu Thr Gly Asp
260 265 270

Leu Gly Gly Met Glu Glu Ala Lys Met Lys Gly Met Met Pro Thr Asp
275 280 285

Glu Gln Phe Ala Ala Leu Ile Val Leu Gly Phe Ala Thr Leu Ser Ile
290 295 300

Leu Phe Ala Phe Ile Leu Gln Tyr Phe Leu Met Lys
305 310 315

<210> SEQ ID NO 338
<211> LENGTH: 237
<212> TYPE: PRT
<213> ORGANISM: Mouse

<400> SEQUENCE: 338

Met Leu Ser Leu Arg Ser Leu Leu Pro His Leu Gly Leu Phe Leu Cys
1 5 10 15

Leu Ala Leu His Leu Ser Pro Ser Leu Ser Ala Ser Asp Asn Gly Ser
20 25 30

Cys Val Val Leu Asp Asn Ile Tyr Thr Ser Asp Ile Leu Glu Ile Ser
35 40 45

Thr Met Ala Asn Val Ser Gly Gly Asp Val Thr Tyr Thr Val Thr Val
50 55 60

Pro Val Asn Asp Ser Val Ser Ala Val Ile Leu Lys Ala Val Lys Glu
65 70 75 80

Asp Asp Ser Pro Val Gly Thr Trp Ser Gly Thr Tyr Glu Lys Cys Asn
85 90 95

Asp Ser Ser Val Tyr Tyr Asn Leu Thr Ser Gln Ser Gln Ser Val Phe
100 105 110

Gln Thr Asn Trp Thr Val Pro Thr Ser Glu Asp Val Thr Lys Val Asn
115 120 125

-continued

Leu Gln Val Leu Ile Val Val Asn Arg Thr Ala Ser Lys Ser Ser Val
    130                 135                 140

Lys Met Glu Gln Val Gln Pro Ser Ala Ser Thr Pro Ile Pro Glu Ser
145                 150                 155                 160

Ser Glu Thr Ser Gln Thr Ile Asn Thr Thr Pro Thr Val Asn Thr Ala
                165                 170                 175

Lys Thr Thr Ala Lys Asp Thr Ala Asn Thr Thr Ala Val Thr Thr Ala
            180                 185                 190

Asn Thr Thr Ala Asn Thr Thr Ala Val Thr Thr Ala Lys Thr Thr Ala
        195                 200                 205

Lys Ser Leu Ala Ile Arg Thr Leu Gly Ser Pro Leu Ala Gly Ala Leu
    210                 215                 220

His Ile Leu Leu Val Phe Leu Ile Ser Lys Leu Leu Phe
225                 230                 235

<210> SEQ ID NO 339
<211> LENGTH: 469
<212> TYPE: PRT
<213> ORGANISM: Mouse

<400> SEQUENCE: 339

Met Leu Cys Leu Cys Leu Tyr Val Pro Ile Ala Gly Ala Ala Gln Thr
 1               5                  10                  15

Glu Phe Gln Tyr Phe Glu Ser Lys Gly Leu Pro Ala Glu Leu Lys Ser
            20                  25                  30

Ile Phe Lys Leu Ser Val Phe Ile Pro Ser Gln Glu Phe Ser Thr Tyr
        35                  40                  45

Arg Gln Trp Lys Gln Lys Ile Val Gln Ala Gly Asp Lys Asp Leu Asp
    50                  55                  60

Gly Gln Leu Asp Phe Glu Glu Phe Val His Tyr Leu Gln Asp His Glu
65                  70                  75                  80

Lys Lys Leu Arg Leu Val Phe Lys Ser Leu Asp Lys Lys Asn Asp Gly
                85                  90                  95

Arg Ile Asp Ala Gln Glu Ile Met Gln Ser Leu Arg Asp Leu Gly Val
            100                 105                 110

Lys Ile Ser Glu Gln Gln Ala Glu Lys Ile Leu Lys Ser Met Asp Lys
        115                 120                 125

Asn Gly Thr Met Thr Ile Asp Trp Asn Glu Trp Arg Asp Tyr His Leu
    130                 135                 140

Leu His Pro Val Glu Asn Ile Pro Glu Ile Ile Leu Tyr Trp Lys His
145                 150                 155                 160

Ser Thr Ile Phe Asp Val Gly Glu Asn Leu Thr Val Pro Asp Glu Phe
                165                 170                 175

Thr Val Glu Glu Arg Gln Thr Gly Met Trp Trp Arg His Leu Val Ala
            180                 185                 190

Gly Gly Gly Ala Gly Ala Val Ser Arg Thr Cys Thr Ala Pro Leu Asp
        195                 200                 205

Arg Leu Lys Val Leu Met Gln Val His Ala Ser Arg Ser Asn Asn Met
    210                 215                 220

Cys Ile Val Gly Gly Phe Thr Gln Met Ile Arg Glu Gly Gly Ala Lys
225                 230                 235                 240

Ser Leu Trp Arg Gly Asn Gly Ile Asn Val Leu Lys Ile Ala Pro Glu
                245                 250                 255

Ser Ala Ile Lys Phe Met Ala Tyr Glu Gln Met Lys Arg Leu Val Gly
            260                 265                 270

-continued

```
Ser Asp Gln Glu Thr Leu Arg Ile His Glu Arg Leu Val Ala Gly Ser
        275                 280                 285

Leu Ala Gly Ala Ile Ala Gln Ser Ser Ile Tyr Pro Met Glu Val Leu
    290                 295                 300

Lys Thr Arg Met Ala Leu Arg Lys Thr Gly Gln Tyr Ser Gly Met Leu
305                 310                 315                 320

Asp Cys Ala Arg Arg Ile Leu Ala Lys Glu Gly Val Ala Ala Phe Tyr
                325                 330                 335

Lys Gly Tyr Ile Pro Asn Met Leu Gly Ile Ile Pro Tyr Ala Gly Ile
            340                 345                 350

Asp Leu Ala Val Tyr Glu Thr Leu Lys Asn Thr Trp Leu Gln Arg Tyr
        355                 360                 365

Ala Val Asn Ser Ala Asp Pro Gly Val Phe Val Leu Leu Ala Cys Gly
    370                 375                 380

Thr Ile Ser Ser Thr Cys Gly Gln Leu Ala Ser Tyr Pro Leu Ala Leu
385                 390                 395                 400

Val Arg Thr Arg Met Gln Ala Gln Ala Ser Ile Glu Gly Ala Pro Glu
                405                 410                 415

Val Thr Met Ser Ser Leu Phe Lys Gln Ile Leu Arg Thr Glu Gly Ala
            420                 425                 430

Phe Gly Leu Tyr Arg Gly Leu Ala Pro Asn Phe Met Lys Val Ile Pro
        435                 440                 445

Ala Val Ser Ile Ser Tyr Val Val Tyr Glu Asn Leu Lys Ile Thr Leu
    450                 455                 460

Gly Val Gln Ser Arg
465


<210> SEQ ID NO 340
<211> LENGTH: 99
<212> TYPE: PRT
<213> ORGANISM: Mouse

<400> SEQUENCE: 340

Met Arg Leu Leu Ala Ala Ala Leu Leu Leu Leu Leu Leu Ala Leu Cys
 1               5                  10                  15

Ala Ser Arg Val Asp Gly Ser Lys Cys Lys Cys Ser Arg Lys Gly Pro
            20                  25                  30

Lys Ile Arg Tyr Ser Asp Val Lys Lys Leu Glu Met Lys Pro Lys Tyr
        35                  40                  45

Pro His Cys Glu Glu Lys Met Val Ile Val Thr Thr Lys Ser Met Ser
    50                  55                  60

Arg Tyr Arg Gly Gln Glu His Cys Leu His Pro Lys Leu Gln Ser Thr
65                  70                  75                  80

Lys Arg Phe Ile Lys Trp Tyr Asn Ala Trp Asn Glu Lys Arg Arg Val
                85                  90                  95

Tyr Glu Glu


<210> SEQ ID NO 341
<211> LENGTH: 431
<212> TYPE: PRT
<213> ORGANISM: Mouse

<400> SEQUENCE: 341

Met Asp Ala Arg Trp Trp Ala Val Val Val Leu Ala Thr Leu Pro Ser
 1               5                  10                  15
```

-continued

```
Leu Gly Ala Gly Gly Glu Ser Pro Glu Ala Pro Pro Gln Ser Trp Thr
            20                  25                  30

Gln Leu Trp Leu Phe Arg Phe Leu Leu Asn Val Ala Gly Tyr Ala Ser
        35                  40                  45

Phe Met Val Pro Gly Tyr Leu Leu Val Gln Tyr Leu Arg Arg Lys Asn
    50                  55                  60

Tyr Leu Glu Thr Gly Arg Gly Leu Cys Phe Pro Leu Val Lys Ala Cys
65                  70                  75                  80

Val Phe Gly Asn Glu Pro Lys Ala Pro Asp Glu Val Leu Leu Ala Pro
                85                  90                  95

Arg Thr Glu Thr Ala Glu Ser Thr Pro Ser Trp Gln Val Leu Lys Leu
            100                 105                 110

Val Phe Cys Ala Ser Gly Leu Gln Val Ser Tyr Leu Thr Trp Gly Ile
        115                 120                 125

Leu Gln Glu Arg Val Met Thr Gly Ser Tyr Gly Ala Thr Ala Thr Ser
    130                 135                 140

Pro Gly Glu His Phe Thr Asp Ser Gln Phe Leu Val Leu Met Asn Arg
145                 150                 155                 160

Val Leu Ala Leu Val Val Ala Gly Leu Tyr Cys Val Leu Arg Lys Gln
                165                 170                 175

Pro Arg His Gly Ala Pro Met Tyr Arg Tyr Ser Phe Ala Ser Leu Ser
            180                 185                 190

Asn Val Leu Ser Ser Trp Cys Gln Tyr Glu Ala Leu Lys Phe Val Ser
        195                 200                 205

Phe Pro Thr Gln Val Leu Ala Lys Ala Ser Lys Val Ile Pro Val Met
    210                 215                 220

Met Met Gly Lys Leu Val Ser Arg Arg Ser Tyr Glu His Trp Glu Tyr
225                 230                 235                 240

Leu Thr Ala Gly Leu Ile Ser Ile Gly Val Ser Met Phe Leu Leu Ser
                245                 250                 255

Ser Gly Pro Glu Pro Arg Ser Ser Pro Ala Thr Thr Leu Ser Gly Leu
            260                 265                 270

Val Leu Leu Ala Gly Tyr Ile Ala Phe Asp Ser Phe Thr Ser Asn Trp
        275                 280                 285

Gln Asp Ala Leu Phe Ala Tyr Lys Met Ser Ser Val Gln Met Met Phe
    290                 295                 300

Gly Val Asn Leu Phe Ser Cys Leu Phe Thr Val Gly Ser Leu Leu Glu
305                 310                 315                 320

Gln Gly Ala Leu Leu Glu Gly Ala Arg Phe Met Gly Arg His Ser Glu
                325                 330                 335

Phe Ala Leu His Ala Leu Leu Leu Ser Ile Cys Ser Ala Phe Gly Gln
            340                 345                 350

Leu Phe Ile Phe Tyr Thr Ile Gly Gln Phe Gly Ala Ala Val Phe Thr
        355                 360                 365

Ile Ile Met Thr Leu Arg Gln Ala Ile Ala Ile Leu Leu Ser Cys Leu
    370                 375                 380

Leu Tyr Gly His Thr Val Thr Val Val Gly Gly Leu Gly Val Ala Val
385                 390                 395                 400

Val Phe Thr Ala Leu Leu Leu Arg Val Tyr Ala Arg Gly Arg Lys Gln
                405                 410                 415

Arg Gly Lys Lys Ala Val Pro Thr Glu Pro Pro Val Gln Lys Val
            420                 425                 430
```

-continued

<210> SEQ ID NO 342
<211> LENGTH: 51
<212> TYPE: PRT
<213> ORGANISM: Mouse

<400> SEQUENCE: 342

```
Leu Lys Phe Ser His Pro Cys Leu Glu Asp His Asn Ser Tyr Cys Ile
 1               5                  10                  15

Asn Gly Ala Cys Ala Phe His His Glu Leu Lys Gln Ala Ile Cys Arg
            20                  25                  30

Cys Phe Thr Gly Tyr Thr Gly Gln Arg Cys Glu His Leu Thr Leu Thr
        35                  40                  45

Ser Tyr Ala
    50
```

<210> SEQ ID NO 343
<211> LENGTH: 51
<212> TYPE: PRT
<213> ORGANISM: Mouse

<400> SEQUENCE: 343

```
Leu Lys Phe Ser His Leu Cys Leu Glu Asp His Asn Ser Tyr Cys Ile
 1               5                  10                  15

Asn Gly Ala Cys Ala Phe His His Glu Leu Glu Lys Ala Ile Cys Arg
            20                  25                  30

Cys Phe Thr Gly Tyr Thr Gly Glu Arg Cys Glu His Leu Thr Leu Thr
        35                  40                  45

Ser Tyr Ala
    50
```

<210> SEQ ID NO 344
<211> LENGTH: 95
<212> TYPE: PRT
<213> ORGANISM: Mouse

<400> SEQUENCE: 344

```
Ala Ala Ala Leu Leu Leu Leu Leu Leu Ala Leu Tyr Thr Ala Arg Val
 1               5                  10                  15

Asp Gly Ser Lys Cys Lys Cys Ser Arg Lys Gly Pro Lys Ile Arg Tyr
            20                  25                  30

Ser Asp Val Lys Lys Leu Glu Met Lys Pro Lys Tyr Pro His Cys Glu
        35                  40                  45

Glu Lys Met Val Ile Ile Thr Thr Lys Ser Val Ser Arg Tyr Arg Gly
    50                  55                  60

Gln Glu His Cys Leu His Pro Lys Leu Gln Ser Thr Lys Arg Phe Ile
65                  70                  75                  80

Lys Trp Tyr Asn Ala Trp Asn Glu Lys Arg Arg Val Tyr Glu Glu
                85                  90                  95
```

<210> SEQ ID NO 345
<211> LENGTH: 77
<212> TYPE: PRT
<213> ORGANISM: Mouse

<400> SEQUENCE: 345

```
Ser Lys Cys Lys Cys Ser Arg Lys Gly Pro Lys Ile Arg Tyr Ser Asp
 1               5                  10                  15

Val Lys Lys Leu Glu Met Lys Pro Lys Tyr Pro His Cys Glu Glu Lys
            20                  25                  30
```

-continued

Met Val Ile Val Thr Thr Lys Ser Met Ser Arg Tyr Arg Gly Gln Glu
        35                  40                  45

His Cys Leu His Pro Lys Leu Gln Ser Thr Lys Arg Phe Ile Lys Trp
    50                  55                  60

Tyr Asn Ala Trp Asn Glu Lys Arg Arg Val Tyr Glu Glu
65                  70                  75

<210> SEQ ID NO 346
<211> LENGTH: 77
<212> TYPE: PRT
<213> ORGANISM: Mouse

<400> SEQUENCE: 346

Ser Lys Cys Lys Cys Ser Arg Lys Gly Pro Lys Ile Arg Tyr Ser Asp
 1               5                  10                  15

Val Lys Lys Leu Glu Met Lys Pro Lys Tyr Pro His Cys Glu Glu Lys
            20                  25                  30

Met Val Ile Ile Thr Thr Lys Ser Val Ser Arg Tyr Arg Gly Gln Glu
        35                  40                  45

His Cys Leu His Pro Lys Leu Gln Ser Thr Lys Arg Phe Ile Lys Trp
    50                  55                  60

Tyr Asn Ala Trp Asn Glu Lys Arg Arg Val Tyr Glu Glu
65                  70                  75

<210> SEQ ID NO 347
<211> LENGTH: 215
<212> TYPE: PRT
<213> ORGANISM: Mouse

<400> SEQUENCE: 347

Met Leu Ser Leu Arg Ser Leu Leu Pro His Leu Gly Leu Phe Leu Cys
 1               5                  10                  15

Leu Ala Leu His Leu Ser Pro Ser Leu Ser Ala Ser Asp Asn Gly Ser
            20                  25                  30

Cys Val Val Leu Asp Asn Ile Tyr Thr Ser Asp Ile Leu Glu Ile Ser
        35                  40                  45

Thr Met Ala Asn Val Ser Gly Gly Asp Val Thr Tyr Thr Val Thr Val
    50                  55                  60

Pro Val Asn Asp Ser Val Ser Ala Val Ile Leu Lys Ala Val Lys Glu
65                  70                  75                  80

Asp Asp Ser Pro Val Gly Thr Trp Ser Gly Thr Tyr Glu Lys Cys Asn
                85                  90                  95

Asp Ser Ser Val Tyr Tyr Asn Leu Thr Ser Gln Ser Gln Ser Val Phe
            100                 105                 110

Gln Thr Asn Trp Thr Val Pro Thr Ser Glu Asp Val Thr Lys Val Asn
        115                 120                 125

Leu Gln Val Leu Ile Val Val Asn Arg Thr Ala Ser Lys Ser Ser Val
    130                 135                 140

Lys Met Glu Gln Val Gln Pro Ser Ala Ser Thr Pro Ile Pro Glu Ser
145                 150                 155                 160

Ser Glu Thr Ser Gln Thr Ile Asn Thr Thr Pro Thr Val Asn Thr Ala
                165                 170                 175

Lys Thr Thr Ala Lys Asp Thr Ala Asn Thr Thr Ala Val Thr Thr Ala
            180                 185                 190

Asn Thr Thr Ala Asn Thr Thr Ala Val Thr Thr Ala Lys Thr Thr Ala
        195                 200                 205

-continued

```
Lys Ser Leu Ala Ile Arg Thr
    210                 215


<210> SEQ ID NO 348
<211> LENGTH: 21
<212> TYPE: PRT
<213> ORGANISM: Mouse

<400> SEQUENCE: 348

Gly Tyr Ser Asp Gly Tyr Gln Val Cys Ser Arg Phe Gly Ser Lys Val
 1               5                  10                  15

Pro Gln Phe Leu Asn
            20
```